(12) United States Patent
Jones et al.

(10) Patent No.: US 11,945,797 B2
(45) Date of Patent: *Apr. 2, 2024

(54) 1-CYANO-PYRROLIDINE DERIVATIVES AS DUB INHIBITORS

(71) Applicant: MISSION THERAPEUTICS LIMITED, Cambridge (GB)

(72) Inventors: Alison Jones, Cambridge (GB); Mark Ian Kemp, Cambridge (GB); Martin Lee Stockley, Cambridge (GB); Michael David Woodrow, Cambridge (GB)

(73) Assignee: Mission Therapeutics Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/674,943

(22) Filed: Feb. 18, 2022

(65) Prior Publication Data

US 2022/0177451 A1 Jun. 9, 2022

Related U.S. Application Data

(63) Continuation of application No. 16/087,515, filed as application No. PCT/GB2017/050830 on Mar. 23, 2017, now Pat. No. 11,352,339.

(30) Foreign Application Priority Data

Mar. 24, 2016 (GB) ...................................... 1605059
Jan. 18, 2017 (GB) ...................................... 1700839

(51) Int. Cl.
| | | |
|---|---|---|
| C07D 401/14 | (2006.01) | |
| C07D 403/04 | (2006.01) | |
| C07D 403/14 | (2006.01) | |
| C07D 413/04 | (2006.01) | |
| C07D 413/14 | (2006.01) | |
| C07D 417/14 | (2006.01) | |

(52) U.S. Cl.
CPC ......... C07D 401/14 (2013.01); C07D 403/04 (2013.01); C07D 403/14 (2013.01); C07D 413/04 (2013.01); C07D 413/14 (2013.01); C07D 417/14 (2013.01)

(58) Field of Classification Search
CPC .. C07D 401/14; C07D 403/14; C07D 413/14; C07D 417/14
See application file for complete search history.

(56) References Cited

FOREIGN PATENT DOCUMENTS

| WO | WO 2016192074 | * 12/2016 | |
|---|---|---|---|
| WO | WO-2017093718 A1 | * 6/2017 | .............. A61P 25/00 |
| WO | WO 2017123695 | * 7/2020 | |

* cited by examiner

*Primary Examiner* — Susanna Moore

(57) ABSTRACT

The present invention relates to novel compounds and methods for the manufacture of inhibitors of deubiquitylating enzymes (DUBs). In particular, the invention relates to the inhibition of ubiquitin C-terminal hydrolase 30 or ubiquitin specific peptidase 30 (USP30). The novel compounds have formula (I): (Formula (I)) or are pharmaceutically acceptable salts thereof, wherein: $R^{1a}$, $R^{1b}$, $R^{1c}$, $R^{1d}$, $R^{1e}$ and $R^{1f}$ each independently represent hydrogen, optionally substituted $C_1$-$C_6$ alkyl or optionally substituted $C_3$-$C_4$ cycloalkyl, or $R^{1b}$ and $R^{1c}$ together form an optionally substituted $C_3$-$C_6$ cycloalkyl ring, or $R^{1d}$ and $R^{1e}$ together form an optionally substituted $C_3$-$C_6$ cycloalkyl ring; $R^2$ represents hydrogen or optionally substituted $C_1$-$C_6$ alkyl; A represents an optionally further substituted 5 to 10 membered monocyclic or bicyclic heteroaryl, heterocyclyl or aryl ring; L represents a covalent bond or linker; B represents an optionally substituted 3 to 10 membered monocyclic or bicyclic heterocyclyl, heteroaryl, cycloalkyl or aryl ring; and when -A-L-B is at position x attachment to A is via a carbon ring atom of A, and either: A cannot be triazolopyridazinyl, triazolopyridinyl, imidazotriazinyl, imidazopyrazinyl or pyrrolopyrimidinyl; or B cannot be substituted with phenoxyl; or B cannot be cyclopentyl when L is an oxygen atom.

(I)

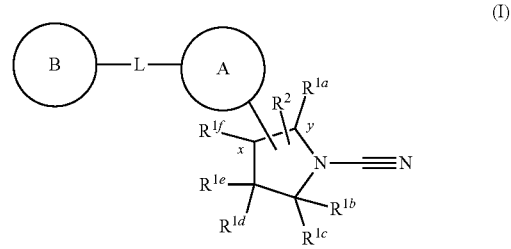

15 Claims, 1 Drawing Sheet

USP30 kinetic assay for high throughput screening of compounds using an isopeptide linked substrate
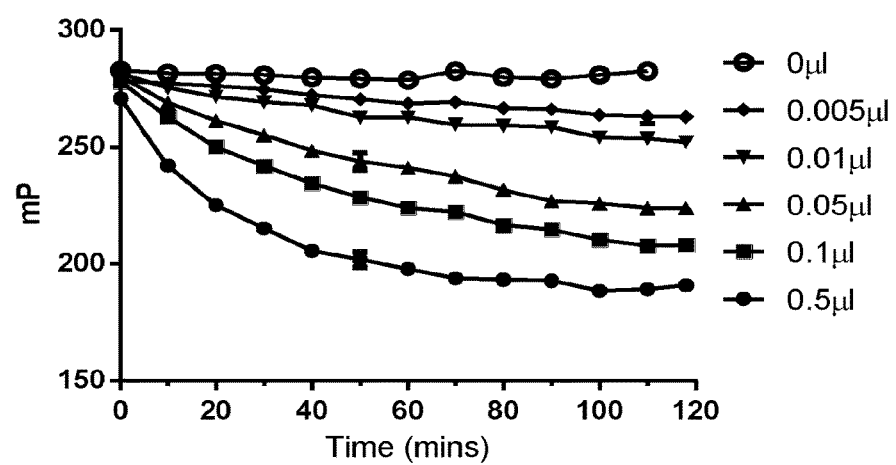

1-CYANO-PYRROLIDINE DERIVATIVES AS DUB INHIBITORS

This application claims priority to and is a continuation of pending U.S. patent application Ser. No. 16/087,515 filed Sep. 21, 2018, which in turn claims priority to and is a National Stage Application of PCT/GB2017/050830, filed Mar. 23, 2017, which claims priority from UK Patent Application No. 1605059.3, filed on Mar. 24, 2016 and UK Patent Application No. 1700839.2, filed on Jan. 18, 2017. The priority of said PCT and UK Patent Applications are claimed. Each of the prior mentioned applications is hereby incorporated by reference herein in its entirety.

The present invention relates to novel compounds and methods for the manufacture of inhibitors of deubiquitylating enzymes (DUBs). In particular, the invention relates to the inhibition of ubiquitin C-terminal hydrolase 30 or ubiquitin specific peptidase 30 (USP30). The invention further relates to the use of DUB inhibitors in the treatment of conditions involving mitochondrial dysfunction and in the treatment of cancer.

BACKGROUND TO THE INVENTION

The listing or discussion of an apparently prior-published document in this specification should not necessarily be taken as an acknowledgement that the document is part of the state of the art or is common general knowledge.

Ubiquitin is a small protein consisting of 76 amino acids that is important for the regulation of protein function in the cell. Ubiquitylation and deubiquitylation are enzymatically mediated processes by which ubiquitin is covalently bound or cleaved from a target protein by deubiquitylating enzymes (DUBs), of which there are approximately 95 DUBs in human cells, divided into sub-families based on sequence homology. The USP family are characterised by their common Cys and His boxes which contain Cys and His residues critical for their DUB activities. The ubiquitylation and deubiquitylation processes have been implicated in the regulation of many cellular functions including cell cycle progression, apoptosis, modification of cell surface receptors, regulation of DNA transcription and DNA repair. Thus, the ubiquitin system has been implicated in the pathogenesis of numerous disease states including inflammation, viral infection, metabolic dysfunction, CNS disorders, and oncogenesis.

Ubiquitin is a master regulator of mitochondrial dynamics. Mitochondria are dynamic organelles whose biogenesis, fusion and fission events are regulated by the post-translational regulation via ubiquitylation of many key factors such as mitofusins. While ubiquitin ligases such as parkin are known to ubiquitylate a number of mitochondrial proteins, until recently, deubiquitylating enzymes remained elusive. USP30 is a 517 amino acid protein which is found in the mitochondrial outer membrane. It is the sole deubiquitylating enzyme bearing a mitochondrial addressing signal and has been shown to deubiquitylate a number of mitochondrial proteins. It has been demonstrated that USP30 opposes parkin-mediated mitophagy and that reduction of USP30 activity can rescue parkin-mediated defects in mitophagy.

Mitochondrial dysfunction can be defined as diminished mitochondrial content (mitophagy or mitochondrial biogenesis), as a decrease in mitochondrial activity and oxidative phosphorylation, but also as modulation of reactive oxygen species (ROS) generation. Hence a role for mitochondrial dysfunctions in a very large number of aging processes and pathologies including but not limited to, neurodegenerative diseases (e.g. Parkinson's disease (PD), Alzheimer's disease, Huntington's disease, Amylotrophic Lateral Sclerosis (ALS), multiple sclerosis), cancer, diabetes, metabolic disorders, cardio-vascular diseases, psychiatric diseases (e.g. Schizophrenia), inflammatory and autoimmune diseases, fibrosis and osteoarthritis.

For example, Parkinson's disease affects around 10 million people worldwide (Parkinson's Disease Foundation) and is characterised by the loss of dopaminergic neurons in the substantia nigra. The exact mechanisms underlying PD are unclear; however mitochondrial dysfunction is increasingly appreciated as a key determinant of dopaminergic neuronal susceptibility in PD and is a feature of both familial and sporadic disease, as well as in toxin-induced Parkinsonism. Parkin is one of a number of proteins that have been implicated with early onset PD. While most PD cases are linked to defects in alpha-synuclein, 10% of Parkinson's cases are linked to specific genetic defects, one of which is in the ubiquitin E3 ligase parkin. Parkin and the protein kinase PTEN-induced putative kinase 1 (PINK1) collaborate to ubiquitylate mitochondrial membrane proteins of damaged mitochondria resulting in mitophagy. Dysregulation of mitophagy results in increased oxidative stress, which has been described as a characteristic of PD. Inhibition of USP30 could therefore be a potential strategy for the treatment of PD. For example, PD patients with parkin mutations leading to reduced activity could be therapeutically compensated by inhibition of USP30.

It has been reported that depletion of USP30 enhances mitophagic clearance of mitochondria and also enhances parkin-induced cell death. USP30 has also been shown to regulate BAX/BAK-dependent apoptosis independently of parkin over expression. Depletion of USP30 sensitises cancer cells to BH-3 mimetics such as ABT-737, without the need for parkin over expression. Thus, an anti-apoptotic role has been demonstrated for USP30 and USP30 is therefore a potential target for anti-cancer therapy.

The ubiquitin-proteasome system has gained interest as a target for the treatment of cancer following the approval of the proteasome inhibitor bortezomib (Velcade®) for the treatment of multiple myeloma. Extended treatment with bortezomib is limited by its associated toxicity and drug resistance. However, therapeutic strategies that target specific aspects of the ubiquitin-proteasome pathway upstream of the proteaseome, such as DUBs, are predicted to be better tolerated. Thus, there is a need for compounds and pharmaceutical compositions to inhibit DUBs such as USP30 for the treatment of indications where DUB activity is observed, including, although not limited to, conditions involving mitochondrial dysfunction and cancer.

SUMMARY OF THE INVENTION

In accordance with a first aspect of the invention there is provided a compound of formula (I)

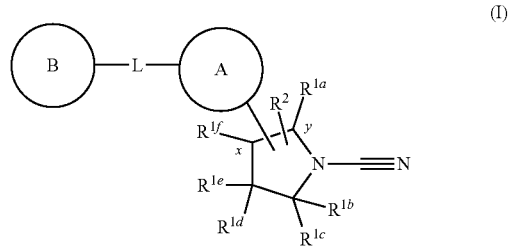

or a pharmaceutically acceptable salt thereof, wherein:

$R^{1a}$, $R^{1b}$, $R^{1c}$, $R^{1d}$, $R^{1e}$ and $R^{1f}$ each independently represent hydrogen, optionally substituted $C_1$-$C_6$ alkyl or optionally substituted $C_3$-$C_4$ cycloalkyl, or $R^{1b}$ and $R^{1c}$ together form an optionally substituted $C_3$-$C_6$ cycloalkyl ring, or $R^{1d}$ and $R^{1e}$ together form an optionally substituted $C_3$-$C_6$ cycloalkyl ring;

$R^2$ represents hydrogen or optionally substituted $C_1$-$C_6$ alkyl;

A represents an optionally further substituted 5 to 10 membered monocyclic or bicyclic heteroaryl, heterocyclyl or aryl ring;

L represents a covalent bond or linker;

B represents an optionally substituted 3 to 10 membered monocyclic or bicyclic heterocyclyl, heteroaryl, cycloalkyl or aryl ring; and when -A-L-B is at position x, attachment to A is via a carbon ring atom of A, and either:

A cannot be triazolopyridazinyl, triazolopyridinyl, imidazotriazinyl, imidazopyrazinyl or pyrrolopyrimidinyl; or B cannot be substituted with phenoxyl; or B cannot be cyclopentyl when L is an oxygen atom.

In one aspect, the invention also relates to pharmaceutical compositions comprising the compounds of the present invention and one or more pharmaceutically acceptable excipients.

In another aspect, the compounds of the invention are useful for the treatment of conditions involving mitochondrial dysfunction and in the treatment of cancer.

BRIEF DESCRIPTION OF THE FIGURES

FIG. 1 is a graph showing proteolytic activity of USP30 measured using a fluorescence polarisation assay. Various volumes of purified USP30 as indicated were incubated with a TAMRA labelled peptide linked to ubiquitin via an isopeptide bond.

DETAILED DESCRIPTION OF THE INVENTION

The definitions and explanations below are for the terms as used throughout this entire document including both the specification and the claims. Reference to compounds as described herein (e.g. a compound of formula (I)), includes reference to formula (I) and formula (II) including any sub-generic embodiments thereof.

Where any group of the compounds of formula (I) have been referred to as optionally substituted, this group may be substituted or unsubstituted. Substitution may be by one or more of the specified substituents which may be the same or different. It will be appreciated that the number and nature of substituents will be selected to avoid any sterically undesirable combinations.

In the context of the present specification, unless otherwise stated an alkyl, alkylene, alkoxy, alkenyl, or alkynyl substituent (or linker) group or an alkyl, alkenyl moiety in a substituent group may be linear or branched. Alkyl, alkylene, alkenyl and alkenylene chains may also include intervening heteroatoms such as oxygen.

$C_x$-$C_y$ alkyl refers to a saturated aliphatic hydrocarbon group having x-y carbon atoms which may be linear or branched. For example $C_1$-$C_6$ alkyl contains from 1 to 6 carbon atoms and includes $C_1$, $C_2$, $C_3$, $C_4$, $C_5$ and $C_6$. "Branched" means that at least one carbon branch point is present in the group. For example, tert-butyl and isopropyl are both branched groups. Examples of $C_1$-$C_6$ alkyl groups include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl. $C_1$-$C_6$ alkyl, $C_1$-$C_4$ alkyl and $C_1$-$C_3$ alkyl within the definitions of $R^{1a}$, $R^{1b}$, $R^{1c}$, $R^{1d}$, $R^{1e}$, $R^{1f}$, $R^2$, $R^{2x}$, $R^{2y}$, $R^3$, $R^4$, $R^5$, $R^6$, $R^7$, $R^9$, $R^{10}$, $R^{11}$, and within the definition of substituents for rings A and B, may be unsubstituted or substituted with one or more of the substituents defined herein. Examples of substituted $C_1$-$C_6$ alkyl therefore include $CF_3$, $CH_2CF_3$, $CH_2CN$, $CH_2OH$ and $CH_2CH_2OH$.

A $C_x$-$C_y$ alkylene group or moiety may be linear or branched and refers to a divalent hydrocarbon group having one less hydrogen atom from $C_x$-$C_y$ alkyl as defined above. $C_1$-$C_6$ alkylene may include intervening heteroatoms such as oxygen, and therefore includes alkyleneoxy groups. Alkyleneoxy as employed herein also extends to embodiments in which the or an oxygen atom (e.g. a single oxygen atom) is located within the alkylene chain, for example $CH_2CH_2OCH_2$ or $CH_2OCH_2$. Examples of $C_1$-$C_6$ alkylene groups include methylene, methyleneoxy, ethylene, ethyleneoxy, n-propylene, n-propyleneoxy, n-butylene, n-butyleneoxy, methylmethylene and dimethylmethylene. Unless stated otherwise, $C_1$-$C_6$ alkylene, $C_1$-$C_4$ alkylene and $C_1$-$C_3$ alkylene within the definitions of $R^8$, $Q^{1a}$, $Q^{1b}$, L may be unsubstituted or substituted with one or more of the substituents defined herein.

$C_2$-$C_6$ alkenyl refers to a linear or branched hydrocarbon chain radical containing at least two carbon atoms and at least one double bond and includes $C_2$-$C_4$ alkenyl. Examples of alkenyl groups include ethenyl, propenyl, 2-propenyl, 1-butenyl, 2-butenyl, 1-hexenyl, 2-methyl-1-propenyl, 1,2-butadienyl, 1,3-pentadienyl, 1,4-pentadienyl and 1-hexadienyl. Unless stated otherwise, $C_2$-$C_6$ alkenyl and $C_2$-$C_4$ alkenyl within the definition of substituents for rings A and B, may be unsubstituted or substituted with one or more of the substituents defined herein.

$C_2$-$C_6$ alkenylene refers to linear or branched hydrocarbon group having one less hydrogen atom from $C_2$-$C_6$ alkenyl as defined above. Examples of $C_2$-$C_6$ alkenylene include ethenylene, propenylene and butenylene. Unless stated otherwise, $C_2$-$C_6$ alkenylene and $C_2$-$C_4$ alkenylene within the definition of $Q^{1a}$, $Q^{1b}$ and L may be unsubstituted or substituted with one or more of the substituents defined herein.

$C_2$-$C_6$ alkynyl refers to a linear or branched hydrocarbon chain radical containing at least two carbon atoms and at least one triple bond. Examples of alkenyl groups include ethynyl, propynyl, 2-propynyl, 1-butynyl, 2-butynyl and 1-hexynyl. Unless specified otherwise, $C_2$-$C_6$ alkynyl, within the definition of substituents for rings A and B, may be unsubstituted or substituted with one or more of the substituents defined herein.

$C_1$-$C_6$ alkoxy refers to a group or part of a group having an —O—$C_x$-$C_y$ alkyl group according to the definition of $C_x$-$C_y$ alkyl above. $C_1$-$C_6$ alkoxy contains from 1 to 6 carbon atoms and includes $C_1$, $C_2$, $C_3$, $C_4$, $C_5$ and $C_6$. Examples of $C_1$-$C_6$ alkoxy include methoxy, ethoxy, propoxy, isopropoxy, butoxy, pentoxy and hexoxy. Alkoxy as employed herein also extends to embodiments in which the or an oxygen atom (e.g. a single oxygen atom) is located within the alkyl chain, for example $CH_2CH_2OCH_3$ or $CH_2OCH_3$. Thus the alkoxy may be linked through carbon to the remainder of the molecule, for example, —$CH_2CH_2OCH_3$, or alternatively, the alkoxy is linked through oxygen to the remainder of the molecule, for example —OC$_{1-6}$ alkyl. In certain instances, the alkoxy may be linked through oxygen to the remainder of the molecule but the alkoxy group contains a further oxygen atom, for example —OCH$_2$CH$_2$OCH$_3$. Unless specified otherwise, C$_1$-C$_6$ alkoxy and C$_1$-C$_3$ alkoxy within the definition of substituents for rings A and B, may be unsubstituted or substituted with one or more of the substituents defined herein. Examples of substituted C$_1$-C$_6$ alkoxy therefore include OCF$_3$, OCHF$_2$, OCH$_2$CF$_3$, CH$_2$CH$_2$OCH$_3$ and CH$_2$CH$_2$OCH$_2$CH$_3$.

The term "halogen" or "halo" refers to chlorine, bromine, fluorine or iodine atoms, in particular chlorine or fluorine atoms.

The term "oxo" means =O.

For the avoidance of doubt it will be understood that the cycloalkyl, heterocyclyl, aryl and heteroaryl rings disclosed herein and within the definitions of R$^{1a}$, R$^{1b}$, R$^{1c}$, R$^{1d}$, R$^{1e}$, R$^{1f}$, R$^{12}$, rings A and B and within the definition of substituents for ring A, do not include any unstable ring structures or, in the case of heteroaryl and heterocyclic ring systems, any O—O, O—S or S—S bonds. The ring systems may be monocyclic or bicyclic. Bicyclic ring systems include bridged, fused and Spiro ring systems. In particular, the bicyclic ring systems described herein are fused ring systems. A substituent if present may be attached to any suitable ring atom which may be a carbon atom or, in the case of heteroaryl and heterocyclic ring systems, a heteroatom. Substitution on a ring may also include a change in the ring atom at the position of the substitution. For example, substitution on a phenyl ring may include a change in the ring atom at the position of substitution from carbon to nitrogen, resulting in a pyridine ring.

"cycloalkyl" refers to a monocyclic saturated or partially unsaturated, non-aromatic ring, wherein all of the ring atoms are carbon, and having the number of ring atoms as indicated. For example C$_3$-C$_{10}$ cycloalkyl refers to a monocyclic or bicyclic hydrocarbon ring containing 3 to 10 carbon atoms. Examples of C$_3$-C$_{10}$ cycloalkyl are cyclopropyl, cyclobutyl, cyclopentyl, cyclohexyl, cycloheptyl, cyclooctyl and decahydronaphthalenyl. Bicyclic cycloalkyl groups include bridged ring systems such as bicycloheptane and bicyclooctane. Unless specified otherwise, cycloalkyl within the definitions of R$^{1a}$, R$^{1b}$, R$^{1c}$, R$^{1d}$, R$^{1e}$, R$^{1f}$, R$^{12}$ ring A and ring B, may be unsubstituted or substituted with one or more of the substituents defined herein.

An "aryl" group/moiety refers to any monocyclic or bicyclic hydrocarbon group comprising at least one aromatic group and having from 5 to 10 carbon atom ring members. Examples of aryl groups include phenyl, naphthyl and tetrahydronaphthalenyl. Bicyclic rings may be fused aromatic rings where both rings are aromatic, for example, naphthalenyl, or where only one ring is aromatic, for example tetrahydronaphthalenyl. Preferred aryl groups are phenyl, naphthyl and tetrahydronaphthalenyl, more preferably phenyl and tetrahydronaphthalenyl, even more preferably phenyl. Unless specified otherwise, aryl within the definitions of R$^{12}$, ring A and Ring B may be unsubstituted or substituted with one or more of the substituents defined herein.

"Heteroaryl" as used herein means a polyunsaturated, monocyclic or bicyclic 5 to 10 membered aromatic moiety containing at least one and up to 5 heteroatoms, particularly 1, 2 or 3 heteroatoms selected from N, O and S, and the remaining ring atoms are carbon atoms, in stable combinations known to the skilled person. Heteroaryl ring nitrogen and sulphur atoms are optionally oxidised, and the nitrogen atom(s) are optionally quaternized. A heteroaryl ring can be a single aromatic ring or a fused bicyclic ring where the bicyclic ring system can be aromatic, or one of the fused rings is aromatic and the other is at least partially saturated. Examples of fused rings where one of the rings is aromatic and the other is at least partially saturated include tetrahydropyridopyrazinyl, tetrahydroquinolinyl and tetrahydroisoquinolinyl. In such instances, attachment of the bicyclic ring to the group it is a substituent of is via the aromatic ring of the bicycle. Attachment of the bicyclic ring to the group it is a substituent of, e.g. the cyanopyrrolidine core, is from the aromatic ring. In one example, a bicyclic heteroaryl is one in which the entire fused ring system is aromatic. A bicyclic heteroaryl can have the at least one heteroatom in either of the fused rings. For example, a bicyclic ring with an aromatic ring fused to a partially saturated ring may contain the at least one heteroatom in the aromatic ring or the partially saturated ring. Attachment of the bicyclic ring to the group it is a substituent of may be via either a heteroatom containing ring or a carbon only containing ring. The point of attachment of heteroaryl to the group it is a substituent of can be via a carbon atom or a heteroatom (e.g. nitrogen). Examples of heteroaryl rings include pyridinyl, pyrazinyl, pyrimidinyl, pyridazinyl, furanyl, thiophenyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydrophyridinyl, dihydropyrrolopyridinyl, quinoxalinyl, dihydrobenzoxazinyl, tetrahydropyridopyrazinyl, tetrahydroquinolinyl and tetrahydroisoquinolinyl. Unless specified otherwise, heteroaryl within the definitions of R$^{12}$, ring A and ring B, may be unsubstituted or substituted with one or more of the substituents defined herein.

"Heterocyclyl" or "heterocyclic" as used herein in describing a ring means, unless otherwise stated, a monocyclic saturated or partially unsaturated, non-aromatic ring or a bicyclic saturated or partially unsaturated ring, wherein the bicyclic ring system is non-aromatic, the mono- or bicyclic ring having, for example, 3 to 10 members, where at least one member and up to 5 members, particularly 1, 2 or 3 members of the ring are heteroatoms selected from N, O and S, and the remaining ring atoms are carbon atoms, in stable combinations known to those of skill in the art. Heterocyclic ring nitrogen and sulphur atoms are optionally oxidised, and the nitrogen atoms(s) are optionally quaternized. As used herein, the heterocyclic ring may be a fused ring to another ring system to form a bicycle, i.e. one or two of the heterocyclic ring carbons is common to an additional ring system. In instances where the heterocylcyl is a bicyclic ring, the second ring can be aromatic, e.g. a fused phenyl, pyridyl, pyrazolyl, or the like. The bicyclic heterocycle can have at least one heteroatom in either of the fused rings. The heterocyclyl may be linked through carbon or a heteroatom to the remainder of the molecule and in instances where the heterocylyl is a bicyclic ring, the link may be via the heteroatom containing ring or the fused ring. In instances where the heterocyclyl is a bicyclic ring where the second ring is aromatic, e.g. tetrahydropyridopyrazinyl, tetrahydroquinolinyl or tetrahydroisoquinolinyl, attachment of the bicyclic ring to the group it is a substituent of, e.g. the cyanopyrrolidine core, is from the heterocyclcyl ring.

Examples of heterocyclyl groups include azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, dihydropyrrolopyridinyl, dihydrobenzoxazinyl, pyrrolopyridinyl, dihydronaphthyridinyl, dihydroisoquinolinyl and tetrahydroisoquinolinyl. Unless specified otherwise, heterocyclyl within the definitions of $R^{12}$, ring A and ring B, may be unsubstituted or substituted with one or more of the substituents defined herein. Examples of substituted heterocyclyl rings include for example 4,5-dihydro-1H-maleimido, tetramethylenesulfoxide and hydantoinyl. When -A-L-B is at position x, ring A cannot be triazolopyridazinyl, triazolopyridinyl, imidazotriazinyl, imidazopyrazinyl or pyrrolopyrimidinyl.

"Optionally substituted" as applied to any group means that the said group may if desired be substituted with one or more substituents (e.g., 1, 2, 3 or 4 substituents) which may be the same or different.

Examples of suitable substituents for "substituted" and "optionally substituted" $C_1$-$C_6$ alkyl (including $C_1$-$C_4$ alkyl, $C_1$-$C_3$ alkyl and $C_1$-$C_2$ alkyl) and $C_1$-$C_6$ alkoxy (including $C_1$-$C_4$ alkoxy, $C_1$-$C_3$ alkoxy and $C_1$-$C_2$ alkoxy) and $C_2$-$C_6$ alkenyl (including $C_2$-$C_4$ alkenyl) and $C_2$-$C_6$ alkynyl (including $C_2$-$C_4$ alkynyl), for example within the definitions of $R^{1a}$, $R^{1b}$, $R^{1c}$, $R^{1d}$, $R^{1e}$, $R^{1f}$, $R^2$, $R^{2x}$, $R^{2y}$, $R^3$, $R^4$, $R^5$, $R^6$, $R^7$, $R^9$, $R^{10}$, $R^{11}$, and within the definition of substituents for ring A and ring B, and $C_1$-$C_6$ alkylene (including $C_1$-$C_3$ alkylene) and $C_2$-$C_6$ alkenylene, for example within the definitions of $R^8$, $Q^{1a}$, $Q^{1b}$ and L include halogen, cyano, oxo, nitro, amino, amido, hydroxy, $C_1$-$C_6$ alkyl or $C_1$-$C_3$ alkyl, $C_1$-$C_6$ alkoxy or $C_1$-$C_3$ alkoxy, aryl, heteroaryl, heterocyclyl, $C_3$-$C_6$ cycloalkyl, $C_{1-3}$ alkylamino, $C_{2-6}$ alkenylamino, di-$C_1$-$C_3$ alkylamino, $C_1$-$C_3$ acylamino, di-$C_1$-$C_3$ acylamino, carboxy, $C_1$-$C_3$ alkoxycarbonyl, carboxamidyl, carbamoyl, mono-$C_{1-3}$ carbamoyl, di-$C_{1-3}$ carbamoyl or any of the above in which a hydrocarbyl moiety is itself substituted by halogen, e.g. fluorine, hydroxyl, cyano, amino, nitro or $SF_5$ (a known mimetic of nitro). In particular, suitable substituents may be selected from halogen, hydroxyl, thiol, cyano, amino, amido, nitro and $SF_5$ (a known mimetic of nitro), in particular, halogen (preferably fluorine or chlorine), hydroxyl and cyano.

Examples of suitable substituents for all remaining "substituted" and "optionally substituted" moieties, including the cycloalkyl, heterocyclyl, aryl and heteroaryl rings, for example within the definitions of $R^{1a}$, $R^{1b}$, $R^{1c}$, $R^{1d}$, $R^{1e}$, $R^{1f}$, $R^{12}$ ring A and ring B and within the definition of substituents for ring A, include halogen, cyano, oxo, nitro, amino, amido, hydroxy, amido, $C_1$-$C_6$ alkyl or $C_1$-$C_3$ alkyl, $C_1$-$C_6$ alkoxy or $C_1$-$C_3$ alkoxy, aryl, heteroaryl, heterocyclyl, $C_3$-$C_6$ cycloalkyl, $C_{1-3}$ alkylamino, $C_{2-6}$ alkenylamino, di-$C_1$-$C_3$ alkylamino, $C_1$-$C_3$ acylamino, di-$C_1$-$C_3$ acylamino, carboxy, $C_1$-$C_3$ alkoxycarbonyl, carboxamidyl, carbamoyl, mono-$C_{1-3}$ carbamoyl, di-$C_{1-3}$ carbamoyl or any of the above in which a hydrocarbyl moiety is itself substituted by halogen, e.g. fluorine, hydroxyl, cyano, amino, amido, nitro or $SF_5$ (a known mimetic of nitro).

Examples of suitable substituents for "substituted" and "optionally substituted" rings include in particular, fluorine, chlorine, oxo, cyano, $C_1$-$C_3$ alkyl, $C_1$-$C_3$ alkoxy, heterocyclyl, cycloalkyl, heteroary or aryl, wherein the alkyl or alkoxy is optionally substituted with one or more (e.g. one, two or three) substituents selected from halogen, hydroxyl, thiol, cyano, amino, amido, nitro and $SF_5$.

Substituted groups thus include for example Br, Cl, F, CN, Me, Et, Pr, Bu, i-Bu, OMe, OEt, OPr, $C(CH_3)_3$, $CH(CH_3)_2$, $CF_3$, $OCF_3$, $C(O)NHCH_3$, cyclopropyl, phenyl, etc. In the case of aryl groups, the substitutions may be in the form of rings from adjacent carbon atoms in the aryl ring, for example cyclic acetals such as O—$CH_2$—O.

In substituted groups containing an oxygen atom such as hydroxy and alkoxy, the oxygen atom can be replaced with sulphur to make groups such as thio (SH) and thio-alkyl (S-alkyl). Optional substituents therefore include groups such as S-methyl. In thio-alkyl groups, the sulphur atom may be further oxidised to make a sulfoxide or sulfone, and thus optional substituents therefore includes groups such as S(O)-alkyl and $S(O)_2$-alkyl.

The term "treat" or "treating" or "treatment" includes prophylaxis and means to ameliorate, alleviate symptoms, eliminate the causation of the symptoms either on a temporary or permanent basis, or to prevent or slow the appearance of symptoms of the named disorder or condition. The compounds of the invention are useful in the treatment of humans and non-human animals.

The dose of the compound is that amount effective to prevent occurrence of the symptoms of the disorder or to treat some symptoms of the disorder from which the patient suffers. By "effective amount" or "therapeutically effective amount" or "effective dose" is meant that amount sufficient to elicit the desired pharmacological or therapeutic effects, thus resulting in effective prevention or treatment of the disorder. Prevention of the disorder is manifested by delaying the onset of the symptoms of the disorder to a medically significant extent. Treatment of the disorder is manifested by a decrease in the symptoms associated with the disorder or an amelioration of the reoccurrence of the symptoms of the disorder.

Pharmaceutically acceptable salts of the compounds of the invention include but are not limited to addition salts (for example phosphates, nitrates, sulphates, borates, acetates, maleates, citrates, fumarates, succinates, methanesulphonates, benzoates, salicylates and hydrohalides), salts derived from organic bases (such as lithium, potassium and sodium), salts of amino acids (such as glycine, alanine, valine, leucine, isoleucine, cysteine, methionine and proline), inorganic bases (such as triethylamine, hydroxide, choline, thiamine and N—N'-diacetylethylenediamine). Other pharmaceutically acceptable salts include ammonium salts, substituted ammonium salts and aluminium salts. Further pharmaceutically acceptable salts include quaternary ammonium salts of the compounds of the invention.

General methods for the production of salts are well known to the person skilled in the art. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Where compounds of the invention exist in different enantiomeric and/or diastereoisomeric forms, the invention relates to these compounds prepared as isomeric mixtures or racemates whether present in an optically pure form or as mixtures with other isomers. Enantiomers differ only in their ability to rotate plane-polarized light by equal amounts in opposite directions and are denoted as the (+)/(S) or (−)/(R) forms respectively. Individual enantiomers or isomers may be prepared by methods known in the art, such as optical resolution of products or intermediates (for example chiral chromatographic separation e.g. chiral HPLC, or an asymmetric synthesis approach). Similarly where compounds of the invention exist as alternative tautomeric forms e.g. keto/enol, amide/imidic acid, the invention relates to the individual tautomers in isolation, and to mixtures of the tautomers in all proportions.

Isotopes

The compounds described herein may contain one or more isotopic substitutions, and a reference to a particular element includes within its scope all isotopes of the element. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O. Examples of isotopes include $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P and $^{35}$S.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment, the compounds contain no radioactive isotopes. Such compounds are preferred for therapeutic use. In another embodiment, however, the compounds may contain one or more radioisotopes. Compounds containing such radioisotopes may be useful in a diagnostic context.

Certain isotopically labelled compounds of formula (I), for example, those incorporating a radioactive isotope, are useful in drug and/or substrate tissue distribution studies. The radioactive isotopes i.e. $^3$H and $^{14}$C are particularly useful for this purpose in view of their ease of incorporation and ready means of detection. Substitution with heavier isotopes i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining receptor occupancy. Isotopically labelled compounds of formula (I) can generally be prepared by conventional techniques known to those skilled in the art or by processes analogous to those described in the accompanying examples and preparations using an appropriate isotopically labelled reagent in place of the non-labelled reagent previously employed.

Crystalline and Amorphous Forms

The compounds of formula (I) may exist in crystalline or amorphous form and some of the crystalline forms may exist as polymorphs, which are included within the scope of the present invention. Polymorphic forms of compounds of formula (I) may be characterised and differentiated using a number of conventional analytical techniques, including, but not limited to, infra-red spectra, Raman spectra, X-ray powder diffraction, differential scanning calorimetry, thermogravimetric analysis and solid state nuclear magnetic resonance.

Accordingly, in further embodiments, the invention provides a compound according to any described embodiments in a crystalline form. The compound may be from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline. The compound may alternatively be in an amorphous form.

The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

The invention relates to any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al., Solid-State Chemistry of Drugs, Second Edition, published by SSCI, Inc of West Lafayette, IN, USA, 1999, ISBN 0-967-06710-3.

The invention relates to pharmaceutically functional derivatives of compounds as defined herein including ester derivatives and/or derivatives that have, or provide for, the same biological function and/or activity as any relevant compound of the invention. Thus, for the purposes of this invention, the term also includes prodrugs of compounds as defined herein.

The term "prodrug" of a relevant compound includes any compound that, following oral or parenteral administration, is metabolised in vivo to form that compound in an experimentally-detectable amount, and within a predetermined time (e.g. within a dosing interval of between 6 and 24 hours (i.e. once to four times daily).

Prodrugs of compounds may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds wherein a hydroxyl, amino, sulfhydryl, carboxyl or carbonyl group in a compound is bonded to any group that may be cleaved in vivo to regenerate the free hydroxyl, amino, sulfhydryl, carboxyl or carbonyl group, respectively.

Examples of prodrugs include, but are not limited to, esters and carbamates of hydroxyl functional groups, ester groups of carboxyl functional groups, N-acyl derivatives and N-Mannich bases. General information on prodrugs may be found e.g. in Bundegaard, H. "Design of Prodrugs" p. 1-92, Elsevier, New York-Oxford (1985).

Compounds of the invention may be metabolised in vivo. Metabolites of compounds of formula (I) are also within the scope of the present invention. The term 'metabolites' refers to all molecules derived from any of the compounds according to the present invention in a cell or organism, preferably mammal. Preferably the term relates to molecules which differ from any molecule which is present in any such cell or organism under physiological conditions.

A treatment defined herein may be applied as a sole therapy of may involve, in addition to the compounds of the invention, conventional surgery or radiotherapy or chemotherapy. Furthermore, compounds of formula (I) can also be used in combination with existing therapeutic agents for the treatment of conditions associated with cancer, including small molecule therapeutics or antibody based therapeutics.

The compounds described herein are characterised by a cyanopyrrolidine core with an aryl or heteroaryl ring attached at position x or y, wherein the aryl or heteroaryl ring is substituted with a further optionally substituted ring, optionally via a linker.

Described herein are compounds of formula (I):

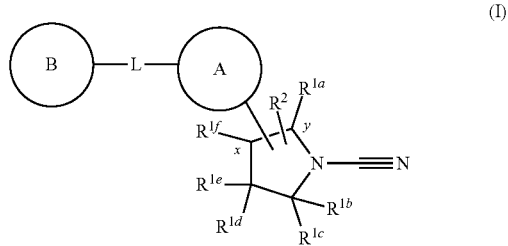

(I)

or a pharmaceutically acceptable salt thereof, wherein:
$R^{1a}$, $R^{1b}$, $R^{1c}$, $R^{1d}$, $R^{1e}$ and $R^{1f}$ each independently represent hydrogen, optionally substituted $C_1$-$C_6$ alkyl or optionally substituted $C_3$-$C_4$ cycloalkyl, or $R^{1b}$ and $R^{1c}$ together form an optionally substituted $C_3$-$C_6$ cycloalkyl ring, or $R^{1d}$ and $R^{1e}$ together form an optionally substituted $C_3$-$C_6$ cycloalkyl ring;

$R^2$ represents hydrogen or optionally substituted $C_1$-$C_6$ alkyl;

A represents an optionally further substituted 5 to 10 membered monocyclic or bicyclic heteroaryl, heterocyclyl or aryl ring;

L represents a covalent bond or linker;

B represents an optionally substituted 3 to 10 membered monocyclic or bicyclic heterocyclyl, heteroaryl, cycloalkyl or aryl ring.

A-L-B may be attached to the cyanopyrrolidine core at position y. Alternatively, -A-L-B is attached to the cyanopyrrolidine core at position x.

In accordance with a first aspect of the invention there is provided a compound of formula (I):

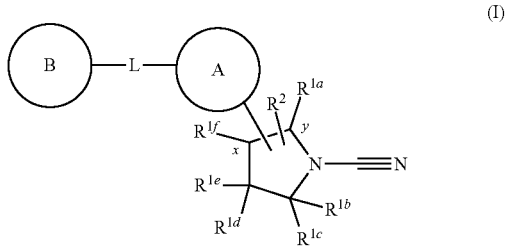

(I)

or a pharmaceutically acceptable salt thereof, wherein:
$R^{1a}$, $R^{1b}$, $R^{1c}$, $R^{1d}$, $R^{1e}$, and $R^{1f}$ each independently represent hydrogen, optionally substituted $C_1$-$C_6$ alkyl or optionally substituted $C_3$-$C_4$ cycloalkyl, or $R^{1b}$ and $R^{1c}$ together form an optionally substituted $C_3$-$C_6$ cycloalkyl ring, or $R^{1d}$ and $R^{1e}$ together form an optionally substituted $C_3$-$C_6$ cycloalkyl ring;

$R^2$ represents hydrogen or optionally substituted $C_1$-$C_6$ alkyl;

A represents an optionally further substituted 5 to 10 membered monocyclic or bicyclic heteroaryl, heterocyclyl or aryl ring;

L represents a covalent bond or linker;

B represents an optionally substituted 3 to 10 membered monocyclic or bicyclic heterocyclyl, heteroaryl, cycloalkyl or aryl ring; and when -A-L-B is at position x, attachment to A is via a carbon ring atom of A, and either:
A cannot be triazolopyridazinyl, triazolopyridinyl, imidazotriazinyl, imidazopyrazinyl or pyrrolopyrimidinyl; or
B cannot be substituted with phenoxyl; or
B cannot be cyclopentyl when L is an oxygen atom.

The compounds may be in the form where -A-L-B is at position y. In such cases the compounds may be of the formula:

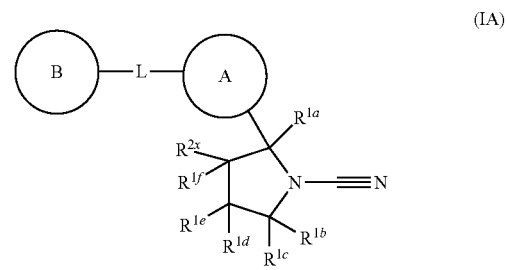

(IA)

or a pharmaceutically acceptable salt thereof, wherein:
$R^{1a}$, $R^{1b}$, $R^{1c}$, $R^{1d}$, $R^{1e}$, and $R^{1f}$ each independently represent hydrogen, optionally substituted $C_1$-$C_6$ alkyl or optionally substituted $C_3$-$C_4$ cycloalkyl, or $R^{1b}$ and $R^{1c}$ together form an optionally substituted $C_3$-$C_6$ cycloalkyl ring, or $R^{1d}$ and $R^{1e}$ together form an optionally substituted $C_3$-$C_6$ cycloalkyl ring;

$R^{2x}$ represents hydrogen or optionally substituted $C_1$-$C_6$ alkyl;

A represents an optionally further substituted 5 to 10 membered monocyclic or bicyclic heteroaryl, heterocyclyl or aryl ring;

L represents a covalent bond or linker;

B represents an optionally substituted 3 to 10 membered monocyclic or bicyclic heterocyclyl, heteroaryl, cycloalkyl or aryl ring.

Alternatively, the compounds may be in the form where -A-L-B is at position x. In such cases the compounds may be of the formula:

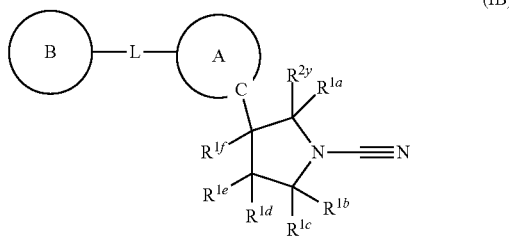

(IB)

or a pharmaceutically acceptable salt thereof, wherein:
$R^{1a}$, $R^{1b}$, $R^{1c}$, $R^{1d}$, $R^{1e}$, and $R^{1f}$ each independently represent hydrogen, optionally substituted $C_1$-$C_6$ alkyl or optionally substituted $C_3$-$C_4$ cycloalkyl, or $R^{1b}$ and $R^{1c}$ together form an optionally substituted $C_3$-$C_6$ cycloalkyl ring, or $R^{1d}$ and $R^{1e}$ together form an optionally substituted $C_3$-$C_6$ cycloalkyl ring;
$R^{2y}$ represents hydrogen or optionally substituted $C_1$-$C_6$ alkyl;
A represents an optionally further substituted 5 to 10 membered monocyclic or bicyclic heteroaryl, heterocyclyl or aryl ring, with the proviso that the ring is not triazolopyridazinyl, triazolopyridinyl, imidazotriazinyl, imidazopyrazinyl or pyrrolopyrimidinyl;
L represents a covalent bond or a linker;
B represents an optionally substituted 3 to 10 membered monocyclic or bicyclic heterocyclyl, heteroaryl, cycloalkyl or aryl ring, with the proviso that either B is not substituted with phenoxyl; or
B is not cyclopentyl when L is an oxygen atom.

In one embodiment, ring A as defined in formula (TB) is not substituted with $NH_2$.

In all cases described herein, $R^{1a}$, $R^{1b}$, $R^{1c}$, $R^{1d}$, $R^{1e}$ and $R^{1f}$ may each independently represent hydrogen, optionally substituted $C_1$-$C_6$ alkyl or optionally substituted $C_3$-$C_4$ cycloalkyl, or $R^{1b}$ together with $R^{1c}$ forms an optionally substituted $C_3$-$C_6$ cycloalkyl ring, or $R^{1d}$ and together with $R^{1e}$ form an optionally substituted $C_3$-$C_6$ cycloalkyl ring. In particular, $R^{1a}$, $R^{1b}$, $R^{1c}$, $R^{1d}$, $R^{1e}$ and $R^{1f}$ may each independently represent hydrogen, methyl, ethyl or cyclopropyl. The alkyl and cycloalkyl within the definitions of $R^{1a}$, $R^{1b}$, $R^{1c}$, $R^{1d}$, $R^{1e}$, and $R^{1f}$ may be unsubstituted or substituted with one or more substituents selected from halogen, hydroxyl, thiol, cyano, amino, amido, nitro and $SF_5$. In particular, the alkyl may be substituted with fluorine.

, $R^{1a}$ may represent hydrogen. $R^{1a}$ may represent $C_1$-$C_6$ alkyl. $R^{1a}$ may represent $C_1$-$C_4$ alkyl. $R^{1a}$ may represent $C_1$-$C_3$ alkyl. $R^{1a}$ may represent $C_1$-$C_2$ alkyl (e.g. methyl or ethyl). $R^{1a}$ may represent methyl or substituted methyl. When $R^{1a}$ represents $C_1$-$C_6$ alkyl, $R^{1b}$, $R^{1c}$, $R^{1d}$, $R^{1e}$ and $R^{1f}$ may each represent hydrogen. In one embodiment, $R^{1a}$ represents methyl and $R^{1b}$, $R^{1c}$, $R^{1d}$, $R^{1e}$ and $R^{1f}$ each represent hydrogen. When -A-L-B is at position y, $R^{1a}$ is preferably hydrogen. When -A-L-B is at position x, $R^{1a}$ may be hydrogen or methyl. The alkyl within the definition of $R^{1a}$ may be unsubstituted or substituted with one or more substituents selected from halogen, hydroxyl, thiol, cyano, amino, amido, nitro and $SF_5$. In particular, the alkyl is optionally substituted with fluorine.

$R^{1b}$ may represent hydrogen. $R^{1b}$ may represent $C_1$-$C_6$ alkyl. $R^{1b}$ may represent $C_1$-$C_4$ alkyl. $R^{1b}$ may represent $C_1$-$C_3$ alkyl. $R^{1b}$ may represent $C_1$-$C_2$ alkyl (e.g. methyl or ethyl). $R^{1b}$ may represent methyl or substituted methyl. When $R^{1b}$ represents $C_1$-$C_6$ alkyl, $R^{1a}$, $R^{1c}$, $R^{1d}$, $R^{1e}$ and $R^{1f}$ may each represent hydrogen. The alkyl within the definition of $R^{1b}$ may be unsubstituted or substituted with one or more substituents selected from halogen, hydroxyl, thiol, cyano, amino, amido, nitro and $SF_5$. In particular, the alkyl is optionally substituted with fluorine.

$R^{1d}$ may represent hydrogen. $R^{1d}$ may represent $C_1$-$C_6$ alkyl. $R^{1d}$ may represent $C_1$-$C_4$ alkyl. $R^{1d}$ may represent $C_1$-$C_3$ alkyl. $R^{1d}$ may represent $C_1$-$C_2$ alkyl (e.g. methyl or ethyl). $R^{1d}$ may represent methyl or substituted methyl. $R^{1d}$ may represent $C_3$-$C_4$ cycloalkyl. $R^{1d}$ may represent cyclopropyl. When $R^{1c}$ represents $C_1$-$C_6$ alkyl or $C_3$-$C_4$ cycloalkyl, $R^{1a}$, $R^{1b}$, $R^{1c}$, $R^{1e}$ and $R^{1f}$ may each represent hydrogen. The alkyl and cycloalkyl within the definition of $R^{1d}$ may be unsubstituted or substituted with one or more substituents selected from halogen, hydroxyl, thiol, cyano, amino, amido, nitro and $SF_5$. In particular, the alkyl or cycloalkyl is optionally substituted with fluorine.

Alternatively, $R^{1b}$ and $R^{1c}$ may together form a cycloalkyl ring. In addition, or alternatively, $R^{1d}$ and $R^{1e}$ may together form a cycloalkyl ring. When $R^{1b}$ and $R^{1e}$ together form a cycloalkyl ring, $R^{1d}$ and $R^{1e}$ may each independently represent hydrogen or optionally substituted $C_1$-$C_6$ alkyl. When $R^{1d}$ and $R^{1e}$ together form a cycloalkyl ring, $R^{1b}$ and $R^{1c}$ may each independently represent hydrogen or optionally substituted $C_1$-$C_6$ alkyl. The cycloalkyl ring within the definitions of, $R^{1b}$, $R^{1c}$, $R^{1d}$ and $R^{1e}$ can contain 3, 4, 5, or 6 carbon ring atoms, in particular 3 or 4 carbon ring atoms. The cycloalkyl ring is attached to the cyanopyrrolidine core as a spiro ring, i.e. they share one ring atom. The cycloalkyl ring may be unsubstituted or substituted with a substituent selected from $C_1$-$C_3$ alkyl, $C_1$-$C_3$ alkoxy, halogen, hydroxyl, thiol, cyano, amino, amido, nitro and $SF_5$, wherein the alkyl and alkoxy may be optionally substituted with halogen.

In a further embodiment, $R^{1a}$ represents methyl. In one embodiment, $R^{1a}$ represents methyl and $R^{1b}$, $R^{1c}$, $R^{1d}$, $R^{1e}$ and $R^{1f}$ each represent hydrogen.

In a further embodiment, $R^{1b}$ represents methyl. In one embodiment, $R^{1b}$ represents methyl and Ria $R^{1c}$, $R^{1d}$, $R^{1e}$ and $R^{1f}$ each represent hydrogen. In a further embodiment, when $R^{1b}$ is other than hydrogen, $R^{1c}$ is hydrogen. When $R^{1c}$ is other than hydrogen, $R^{1b}$ is hydrogen, such that either $R^{1b}$ or $R^{1c}$ must be hydrogen.

In a further embodiment, $R^{1d}$ represents methyl, ethyl or cyclopropyl. In one embodiment, $R^{1d}$ represents methyl and $R^{1a}$, $R^{1b}$, $R^{1c}$, $R^{1e}$ and $R^{1f}$ each represent hydrogen. In one embodiment, $R^{1d}$ represents ethyl and $R^{1a}$, $R^{1b}$, $R^{1c}$, $R^{1e}$ and $R^{1f}$ each represent hydrogen. In one embodiment, $R^{1d}$ represents cyclopropyl and $R^{1a}$, $R^{1b}$, $R^{1c}$, $R^{1e}$, and $R^{1f}$ each represent hydrogen. In a further embodiment, when $R^{1d}$ is other than hydrogen, $R^{1e}$ is hydrogen. When $R^{1e}$ is other than hydrogen, $R^{1d}$ is hydrogen, such that either $R^{1d}$ or $R^{1e}$ must be hydrogen.

In one embodiment, $R^{1a}$, $R^{1b}$, $R^{1c}$, $R^{1d}$, $R^{1e}$ and $R^{1f}$ are each hydrogen.

Each occurrence of $R^2$, $R^{2x}$ or $R^{2y}$ represents hydrogen or optionally substituted $C_1$-$C_6$ alkyl. $R^2$, $R^{2x}$ and $R^{2y}$ may represent hydrogen. $R^2$, $R^{2x}$ and $R^{2y}$ may represent $C_1$-$C_6$ alkyl. $R^2$, $R^{2x}$ and $R^{2y}$ may represent $C_1$-$C_4$ alkyl. $R^2$, $R^{2x}$ and $R^{2y}$ may represent $C_1$-$C_3$ alkyl. $R^2$, $R^{2x}$ and $R^{2y}$ may represent $C_1$-$C_2$ alkyl (e.g. methyl or ethyl). When -A-L-B is at position x, $R^2$ is at position y on the cyanopyrrolidine ring. When -A-L-B is at position y, $R^2$ is at position x on the cyanopyrrolidine ring. When at position x, $R^2$ is referred to as $R^{2x}$. When at position y, $R^2$ is referred to as $R^{2y}$. $R^{2x}$ and $R^{2y}$ have the same definition as $R^2$.

When $R^2$ is at position x and denoted as $R^{2x}$, and $R^{1f}$ is other than hydrogen, $R^{2x}$ is preferably hydrogen. When $R^{2x}$ is other than hydrogen, $R^{1f}$ is preferably hydrogen, such that either $R^{2x}$ or $R^{1f}$ must be hydrogen. When $R^2$ is at position y and denoted as $R^{2y}$, and $R^{1a}$ is other than hydrogen, for example methyl, $R^{2y}$ is preferably hydrogen. When $R^{2y}$ is other than hydrogen, $R^{1a}$ is preferably hydrogen, such that either $R^{2y}$ or $R^{1a}$ must be hydrogen.

In one embodiment, $R^{1a}$, $R^{1b}$, $R^{1c}$, $R^{1d}$, $R^{1e}$, $R^{1f}$ and $R^2$, $R^{2x}$ or $R^{2y}$, are each hydrogen. In another embodiment, $R^{1a}$ is methyl and, $R^{1b}$, $R^{1c}$, $R^{1d}$, $R^{1e}$, $R^{1f}$ and $R^2$, $R^{2x}$ or $R^{2y}$, are each hydrogen. In another embodiment, $R^{1d}$ is methyl and $R^{1a}$, $R^{1b}$, $R^{1c}$, $R^{1e}$, $R^{1f}$ and $R^2$, $R^{2x}$ or $R^{2y}$, are each hydrogen. In yet another embodiment, $R^{1d}$ is ethyl and $R^{1a}$, $R^{1b}$, $R^{1c}$, $R^{1e}$, $R^{1f}$ and $R^2$, $R^{2x}$ or $R^{2y}$ are each hydrogen. In another embodiment, $R^{1d}$ is cyclopropyl and $R^{1a}$, $R^{1b}$, $R^{1c}$, $R^{1e}$, $R^{1f}$ and $R^2$, $R^{2x}$ or $R^{2y}$ are each hydrogen.

One of $R^{1a}$, $R^{1b}$, $R^{1c}$, $R^{1d}$, $R^{1e}$, $R^{1f}$ and $R^2$ may be other than hydrogen, and the remaining are each hydrogen.

Two of $R^{1a}$, $R^{1b}$, $R^{1c}$, $R^{1d}$, $R^{1e}$, $R^{1f}$ and $R^2$ may be other than hydrogen, and the remaining are each hydrogen.

Three of $R^{1a}$, $R^{1b}$, $R^{1c}$, $R^{1d}$, $R^{1e}$, $R^{1f}$ and $R^2$ may be other than hydrogen, and the remaining are each hydrogen.

Four of $R^{1a}$, $R^{1b}$, $R^{1c}$, $R^{1d}$, $R^{1e}$, $R^{1f}$ and $R^2$ may be other than hydrogen, and the remaining are each hydrogen.

Five of $R^{1a}$, $R^{1b}$, $R^{1c}$, $R^{1d}$, $R^{1e}$, $R^{1f}$ and $R^2$ may be other than hydrogen, and the remaining are each hydrogen.

Six of $R^{1a}$, $R^{1b}$, $R^{1c}$, $R^{1d}$, $R^{1e}$, $R^{1f}$ and $R^2$ may be other than hydrogen, and the remaining are each hydrogen.

When one, two, three, four, five or six of $R^{1a}$, $R^{1b}$, $R^{1c}$, $R^{1d}$, $R^{1e}$, $R^{1f}$ and $R^2$ are other than hydrogen, the remaining R groups represent a group in accordance with the definitions above. In particular, one, two, three or four of $R^{1a}$, $R^{1b}$, $R^{1c}$, $R^{1d}$, $R^{1e}$, $R^{1f}$ and $R^2$ may be other than hydrogen and the remaining each represent hydrogen. More particularly, one or two of $R^{1a}$, $R^{1b}$, $R^{1c}$, $R^{1d}$, $R^{1e}$, $R^{1f}$ and $R^2$ may be other than hydrogen and the remaining each represent hydrogen.

The compounds may be in the form where $R^{1a}$, $R^{1b}$, $R^{1c}$, $R^{1d}$, $R^{1e}$, $R^{1f}$ and $R^2$ are each hydrogen. In such cases the compounds may be of the formula:

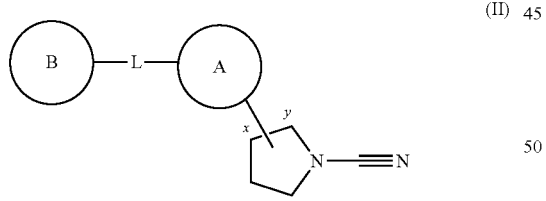

(II)

or a pharmaceutically acceptable salt thereof, wherein:
  A represents an optionally further substituted 5 to 10 membered monocyclic or bicyclic heteroaryl, heterocyclyl or aryl ring;
  L represents an optional linker;
  B represents an optionally substituted 3 to 10 membered monocyclic or bicyclic heterocyclyl, heteroaryl, cycloalkyl or aryl ring; and
  when -A-L-B is at position x, attachment is to a carbon atom of A, and either
  A cannot be triazolopyridazinyl, triazolopyridinyl, imidazotriazinyl, imidazopyrazinyl or pyrrolopyrimidinyl; or
  B cannot be substituted with phenoxyl; or
  B cannot be cyclopentyl when L is an oxygen atom.

In all cases described herein, Ring A represents a 5 to 10 membered (e.g. 5, 6, 7, 8, 9 or 10 membered) monocyclic or fused bicyclic heteroaryl, heterocyclyl or aryl ring which may be optionally substituted. In certain instances, ring A represents a 5 to 10 membered (e.g. 5, 6, 7, 8, 9 or 10 membered) monocyclic or fused bicyclic heteoraryl or aryl ring which may be optionally substituted.

Ring A may represent an optionally substituted 5 or 6 membered monocyclic heteroaryl, heterocylcyl or aryl ring. For example, ring A may represent an optionally substituted 5 or 6 membered heteroaryl or aryl ring.

Alternatively, ring A may represent an optionally substituted 9 or 10 membered bicyclic heteroaryl, heterocyclyl or aryl ring. For example, ring A may represent an optionally substituted 9 or 10 membered bicyclic heteroaryl or aryl ring.

In one embodiment, ring A represents an optionally substituted 5 to 10 membered monocyclic or bicyclic aryl or nitrogen containing heteroaryl, or nitrogen containing heterocyclyl ring. For example, ring A may represent an optionally substituted 5 to 10 membered monocyclic or bicyclic aryl or nitrogen containing heteroaryl ring.

In certain instances, when ring A is attached to the cyanopyrrolidine core at position x, ring A cannot a bicyclic heteroaryl ring containing 3 or 4 nitrogen atoms. For example, ring A cannot be a 9 membered bicyclic heteroaryl ring containing 3 or 4 nitrogen atoms.

In particular, when ring A is attached to the cyanopyrrolidine core at position x, the ring cannot be triazolopyridazinyl, triazolopyridinyl, imidazotriazinyl, imidazopyrazinyl or pyrrolopyrimidinyl. In particular, ring A cannot be any one of the following rings:

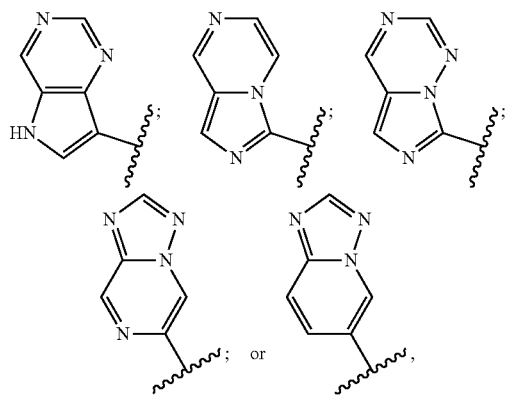

wherein

indicates direct attachment to the cyanopyrrolidine core at position x.

In certain instances, when ring A is attached to the cyanopyrrolidine core at position x, ring A cannot be substituted with $NH_2$. In particular, ring A cannot be substituted with $NH_2$ when ring A is a bicyclic heteroaryl ring. More particularly, ring A cannot be substituted with $NH_2$ when ring A is a bicyclic heteroaryl ring containing 3 or 4 nitrogen atoms. Even more particularly, ring A cannot be substituted with NH$_2$ when ring A is a bicyclic heteroaryl ring selected from triazolopyridazinyl, triazolopyridinyl, imidazotriazinyl, imidazopyrazinyl and pyrrolopyrimidinyl.

When ring A is attached to the cyanopyrrolidine core at position x, attachment is via a carbon ring atom of ring A. When ring A is attached to the cyanopyrrolidine core at position y, attachment can be via a carbon ring atom or a hetero ring atom of ring A. Preferably, attachment is via a hetero ring atom of ring A, in particular, attachment is via a nitrogen ring atom.

Ring A may be selected from azetidinyl, pyrrolidinyl, piperidinyl, azepanyl, diazepanyl, dihydrofuranyl, dioxolanyl, morpholinyl, oxazolidinyl, oxazinanyl, indolinyl, isoindolinyl, piperazinyl, tetrahydrofuranyl, thiomorpholinyl, dihydropyranyl, homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, pyrrolopyridinyl, dihydronaphthyridinyl, dihydroisoquinolinyl, pyridinyl, pyrazinyl, pyrimidinyl, pyridazinyl, furanyl, thiophenyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydrophyridinyl, dihydropyrrolopyridinyl, quinoxalinyl, dihydrobenzoxazinyl, tetrahydropyridopyrazinyl, tetrahydroquinolinyl and tetrahydroisoquinolinyl.

In particular, ring A may be selected from pyridinyl, pyrazinyl, pyrimidinyl, pyridazinyl, furanyl, thiophenyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydrophyridinyl, dihydropyrrolopyridinyl, quinoxalinyl, dihydrobenzoxazinyl, tetrahydropyridopyrazinyl, tetrahydroquinolinyl and tetrahydroisoquinolinyl.

More particularly, ring A is selected from phenyl, pyrimidinyl, pyrazolyl, triazolyl, oxadiazolyl, isoxazolyl, benzimidazolyl, imidazopyridinyl, tetrahydropyridopyrazinyl and benzoxazolyl.

More particularly, ring A is selected from phenyl, pyrimidinyl, pyrazolyl, triazolyl, oxadiazolyl, isoxazolyl, benzimidazolyl, imidazopyridinyl and benzoxazolyl.

Ring A may be further substituted (i.e. in addition to substitution with ring B), with one or more substitutents.

The one or more (e.g. one, two or three) further substituents may be selected from halogen (e.g. fluorine, chlorine or bromine), cyano, oxo, nitro, hydroxyl, —SR$^3$, —NR$^3$R$^4$, —CONR$^3$R$^4$, —NR$^3$COR$^4$, —NR$^3$CONR$^4$R$^5$, —COR$^3$, —C(O)OR$^3$, —SO$_2$R$^3$, —SO$_2$NR$^3$R$^4$, —NR$^3$SO$_2$R$^4$, NR$^3$SO$_2$NR$^4$R$^5$, —NR$^3$C(O)OR$^4$, optionally substituted —C$_1$-C$_6$ alkyl, optionally substituted —C$_1$-C$_6$ alkoxy, optionally substituted —C$_2$-C$_6$ alkenyl, optionally substituted —C$_2$-C$_6$ alkynyl and optionally substituted C$_3$-C$_4$ cycloalkyl.

The one or more (e.g. one, two or three) further substituents may be selected from halogen (e.g. fluorine, chlorine or bromine), cyano, oxo, nitro, hydroxyl, —SR$^3$, —NR$^3$R$^4$, —CONR$^3$R$^4$, —NR$^3$COR$^4$, —NR$^3$CONR$^4$R$^5$, —COR$^3$, —C(O)OR$^3$, —SO$_2$R$^3$, —SO$_2$NR$^3$R$^4$, —NR$^3$SO$_2$R$^4$, NR$^3$SO$_2$NR$^4$R$^5$, —NR$^3$C(O)OR$^4$, —C$_1$-C$_6$ alkyl, —C$_1$-C$_4$ alkyl, —C$_1$-C$_2$ alkyl, —C$_1$-C$_6$ alkoxy, —C$_1$-C$_4$ alkoxy, —C$_1$-C$_2$ alkoxy, —C$_2$-C$_6$ alkenyl, —C$_2$-C$_4$ alkenyl, —C$_2$-C$_6$ alkynyl, —C$_2$-C$_4$ alkynyl and optionally substituted C$_3$-C$_4$ cycloalkyl.

In particular, the further substituents may be selected from halogen (e.g. fluorine, chlorine or bromine), oxo, C$_1$-C$_4$ alkyl (e.g. methyl, ethyl, propyl, tert butyl), —NR$^3$R$^4$ (e.g. amino) and —CONR$^3$R$^4$ (e.g. amido). More particularly, the further substituents are selected from fluorine, oxo, methyl, —NH$_2$ and —CONHMe.

In certain instances, ring A is selected from phenyl, pyrimidinyl, pyrazolyl, triazolyl, oxadiazolyl, isoxazolyl, benzimidazolyl, imidazopyridinyl, tetrahydropyridopyrazinyl and benzoxazolyl and is optionally further substituted with one or more substituents selected from halogen, cyano, oxo, nitro, hydroxyl, —SR$^3$, —NR$^3$R$^4$, —CONR$^3$R$^4$, —NR$^3$COR$^4$, —NR$^3$CONR$^4$R$^5$, —COR$^3$, —C(O)OR$^3$, —SO$_2$R$^3$, —SO$_2$NR$^3$R$^4$, —NR$^3$SO$_2$R$^4$, NR$^3$SO$_2$NR$^4$R$^5$, —NR$^3$C(O)OR$^4$, optionally substituted —C$_1$-C$_6$ alkyl, optionally substituted —C$_1$-C$_6$ alkoxy, optionally substituted —C$_2$-C$_6$ alkenyl, optionally substituted —C$_2$-C$_6$ alkynyl and optionally substituted C$_3$-C$_4$ cycloalkyl.

Ring A may be selected from phenyl, pyrimidinyl, pyrazolyl, triazolyl, oxadiazolyl, isoxazolyl, benzimidazolyl, imidazopyridinyl, tetrahydropyridopyrazinyl and benzoxazolyl and is optionally further substituted with one or more substituents selected from fluorine, oxo, methyl, —NH$_2$ and —CONHMe.

R$^3$, R$^4$ and R$^5$ each independently represent hydrogen, C$_1$-C$_6$ alkyl, C$_1$-C$_4$ alkyl or C$_1$-C$_2$ alkyl.

R$^3$, R$^4$ and R$^5$ may each independently represent hydrogen or C$_1$-C$_2$ alkyl (e.g. methyl or ethyl).

The alkyl within the definition of R$^3$, R$^4$ and R$^5$ may be optionally substituted with halogen, hydroxyl, thiol, cyano, amino, amido, nitro and SF$_5$. In particular, the alkyl may be optionally substituted with fluorine.

Examples of ring A include those shown below:

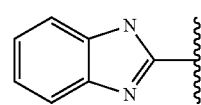

A

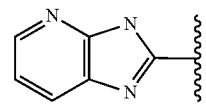

B

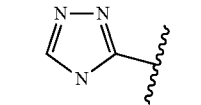

C

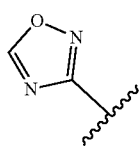

D

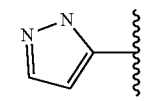

E

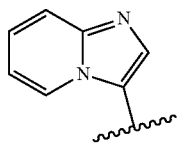

F

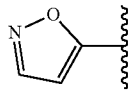

G

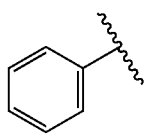

H

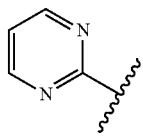

I

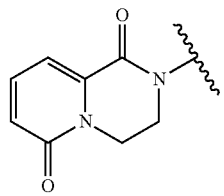

J

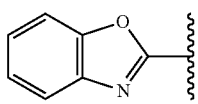

K

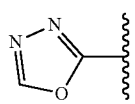

L

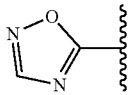

M

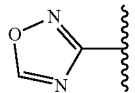

N wherein

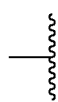

indicates direct attachment to the cyanopyrrolidine core at position x or y. The rings shown above are substituted with -L-B where L is a covalent bond or optional linker and B is an optionally substituted 3 to 10 membered heterocyclyl, heteroaryl, cycloalkyl or aryl ring. Hydrogen atoms attached to ring nitrogen atoms have not been shown. It will be understood by the skilled person which ring nitrogen atoms are suitable for substitution and where not substituted the nitrogen may be bound to a hydrogen atom to complete its valency, where appropriate.

In all cases described herein, L may be selected from a covalent bond, an oxygen atom, a sulphur atom, —$OR^8$—, —SO—, —$SO_2$—, —CO—, —C(O)O—, $C_0$-$C_3$ alkylene-$CONR^6$—$C_0$-$C_3$ alkylene-, —$C_0$-$C_3$ alkylene-$NR^6$—$C_0$-$C_3$ alkylene, —$C_0$-$C_3$ alkylene-$NR^6$CO—$C_0$-$C_3$ alkylene, —$C_0$-$C_3$ alkylene-$NR^6CONR^7$—$C_0$-$C_3$ alkylene, —$C_0$-$C_3$ alkylene-$SO_2NR^6$—$C_0$-$C_3$ alkylene, —$C_0$-$C_3$ alkylene-$NR^6SO_2$—$C_0$-$C_3$ alkylene, —$C_0$-$C_3$ alkylene-$NR^6SO_2NR^7$—$C_0$-$C_3$ alkylene, —$C_0$-$C_3$ alkylene-$NR^6$C(O)O—$C_0$-$C_3$ alkylene, —$C_0$-$C_3$ alkylene-$NR^6C(O)OR^7$—$C_0$-$C_3$ alkylene, optionally substituted —$C_1$-$C_6$ alkylene or optionally substituted —$C_2$-$C_6$ alkenylene.

L may be selected from a covalent bond, a sulphur atom, —$OR^8$—, —SO—, —$SO_2$—, —CO—, —C(O)O—, $C_0$-$C_3$ alkylene-$CONR^6$—$C_0$-$C_3$ alkylene-, —$C_0$-$C_3$ alkylene-$NR^6$—$C_0$-$C_3$ alkylene, —$C_0$-$C_3$ alkylene-$NR^6$CO—$C_0$-$C_3$ alkylene, —$C_0$-$C_3$ alkylene-$NR^6CONR^7$—$C_0$-$C_3$ alkylene, —$C_0$-$C_3$ alkylene-$SO_2NR^6$—$C_0$-$C_3$ alkylene, —$C_0$-$C_3$ alkylene-$NR^6SO_2$—$C_0$-$C_3$ alkylene, —$C_0$-$C_3$ alkylene-$NR^6SO_2NR^7$—$C_0$-$C_3$ alkylene, —$C_0$-$C_3$ alkylene-$NR^6$C(O)O—$C_0$-$C_3$ alkylene, —$C_0$-$C_3$ alkylene-$NR^6C(O)OR^7$—$C_0$-$C_3$ alkylene, optionally substituted —$C_1$-$C_6$ alkylene or optionally substituted —$C_2$-$C_6$ alkenylene.

In particular, L may be selected from a covalent bond or —$C_0$-$C_3$ alkylene-$NR^6$C(O)—$C_0$-$C_3$ alkylene. L may represent a covalent bond. Alternatively, L may represent —$C_0$-$C_3$ alkylene-$NR^6$C(O)—$C_0$-$C_3$ alkylene, for example, —$C_0$-$C_3$ alkylene-$NR^6$C(O)—, —$NR^6$C(O)— or —$NR^6$C(O)—$C_0$-$C_3$ alkylene. L may represent —$NR^6$C(O)—, e.g. —NHCO—. Alternatively, L may represent —NHC(O)-methylene.

In certain instances, L is not an oxygen atom when ring B is cyclopentyl. In particular, when -A-L-B is at position x, e.g. for compounds of formula (IIB), L cannot be an oxygen atom when B is cyclopentyl, in particular an unsubstituted cyclopentyl.

$R^6$ and $R^7$ each independently represent hydrogen, $C_1$-$C_6$ alkyl, $C_1$-$C_4$ alkyl or $C_1$-$C_2$ alkyl. In particular, $R^6$ and $R^7$ each independently represent hydrogen or $C_1$-$C_2$ alkyl. The alkyl within the definition of $R^6$ and $R^7$ may be optionally substituted with halogen, hydroxyl, thiol, cyano, amino, amido, nitro and $SF_5$. In particular, the optional substituents may be selected from fluorine and hydroxyl.

$R^8$ represents $C_1$-$C_6$ alkylene, $C_1$-$C_4$ alkylene, $C_1$-$C_2$ alkylene, $C_2$-$C_6$ alkenylene or $C_2$-$C_4$ alkenylene. In particular, $R^8$ represents $C_1$-$C_2$ alkylene. The alkylene and alkenylene within the definition of $R^8$ may be optionally substituted with halogen, hydroxyl, thiol, cyano, amino, amido, nitro and $SF_5$. In particular, the optional substituents may be selected from fluorine and hydroxyl.

In all cases described herein, B represents an optionally substituted monocyclic or bicyclic 3 to 10 membered (e.g. 3, 4, 5, 6, 7, 8, 9 or 10 membered) heterocyclyl, heteroaryl, cycloalkyl or aryl ring.

B may represent an optionally substituted 3 to 6 membered monocyclic heterocyclyl, heteroaryl, cycloalkyl or awl ring. B may represent an optionally substituted 5 or 6 membered monocyclic heterocyclyl, heteroaryl, cycloalkyl or aryl ring.

Alternatively, B may represent an optionally substituted 9 or 10 membered bicyclic heterocyclyl, heteroaryl or aryl ring.

B may represent an optionally substituted monocyclic or bicyclic 5 to 10 membered aryl or nitrogen containing heteroaryl or heterocyclyl ring.

B may be selected from phenyl, naphthyl, naphthalenyl, tetrahydronaphthalenyl, pyridinyl, pyrazinyl, pyrimidinyl, pyridazinyl, furanyl, thiophenyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, quinoxalinyl, dihydrobenzoxazinyl, dihydropyrrolopyridinyl, tetrahydropyridopyrazinyl, cyclopropyl, cyclobutyl, cyclopentyl, cyclohexyl, cycloheptyl, cyclooctyl, decahydronaphthalenyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, dihydrobenzoxazinyl, pyrrolopyridinyl, dihydroisoquinolinyl, dihydronaphthyridinyl, and tetrahydroisoquinolinyl.

More particularly, B is selected from phenyl, pyridinyl, pyrimidinyl, pyrazinyl, pyridazinyl, azetidinyl, indazolyl, quinolinyl, benzothiazolyl, pyrazolyl, isoxazolyl, piperidinyl, pyrrolidinyl, imidazopyridinyl, benzoimidazolyl, imidazolyl and naphthalenyl.

In particular, B is selected from phenyl, pyridinyl, pyrazinyl, pyridazinyl, indazolyl, quinolinyl, benzothiazolyl, pyrazolyl, pyrazinyl, pyridazinyl, isoxazolyl, piperidinyl, pyrrolidinyl, imidazopyridinyl, benzoimidazolyl, imidazolyl and naphthalenyl. More particularly, B is selected from pyridinyl, pyrazinyl, pyridazinyl and phenyl.

In certain instances, B is not cyclopropanyl. In particular, B cannot be cyclopropyl when L is an oxygen atom. More particularly, when -A-L-B is at position x, e.g. for compounds of formula (IIB), B cannot be cyclopropyl when L is an oxygen atom. Even more particularly, B cannot be unsubstituted cyclopropyl when L is an oxygen atom.

In all cases described herein, B may be unsubstituted or substituted with one or more non-ring substituents and/or ring substituents. When B is substituted with a ring substituent, generally B will be substituted with only one ring. However, when -A-L-B is attached to the cyanopyrrolidine ring at position x, e.g. for compounds of formula (IIB), ring B cannot be substituted with phenoxyl, i.e. $-Q^{1a}$-O-$Q^{1b}$-$R^{12}$ wherein $Q^{1a}$ and $Q^{1b}$ are both a covalent bond and $R^{12}$ is phenyl.

B may be unsubstituted or substituted with one or more substituent selected from halogen, cyano, oxo, nitro, hydroxyl, —$SR^9$, optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, -$Q^{1a}$-$R^{12}$, -$Q^{1a}$-O-$Q^{1b}$-$R^{12}$, $Q^{1a}$-S-$Q^{1b}$-$R^{12}$, $Q^{1a}$-SO-$Q^{1b}$-$R^{12}$, -$Q^{1a}$-$NR^9CONR^{10}R^{11}$, -$Q^{1a}$-$NR^9CONR^{10}$-$Q^{1b}$-$R^{12}$, -$Q^{1a}$-$NR^9R^{10}$, -$Q^{1a}$-$NR^9$-$Q^{1b}$-$R^{12}$, -$Q^{1a}$-$COR^9$, -$Q^{1a}$-CO-$Q^{1b}$-$R^{12}$—, -$Q^{1a}$-$NR^9COR^{10}$, -$Q^{1a}$-$NR^9CO$-$Q^{1b}R^{12}$, -$Q^{1a}$-$NR^9C(O)OR^{10}$, -$Q^{1a}$-$NR^9C(O)O$-$Q^{1b}$-$R^{12}$—, -$Q^{1a}$-$SO_2R^9$, -$Q^{1a}$-$SO_2$-$Q^{1b}$-$R^{12}$, -$Q^{1a}$-$CONR^9R^{10}$, -$Q^{1a}$-$CONR^9$-$Q^{1b}$-$R^{12}$, -$Q^{1a}$-$CO_2R^9$, -$Q^{1a}$-$CO_2$-$Q^{1b}$-$R^{12}$, -$Q^{1a}$-$SO_2NR^9R^{10}$, -$Q^{1a}$-$SO_2NR^9$-$Q^{1b}$-$R^{12}$, -$Q^{1a}$-$NR^9SO_2R^{10}$, -$Q^{1a}$-$NR^9SO_2$-$Q^{1b}$-$R^{12}$, -$Q^{1a}$-$NR^9SO_2NR^{10}R^{11}$ and -$Q^{1a}$-$NR^9SO_2NR^{10}$-$Q^{1b}$-$R^{12}$, with the proviso that when -A-L-B is attached to the cyanopyrrolidine ring at position x, ring B cannot be substituted with phenoxyl.

The non-ring substituents may be selected from halogen, cyano, oxo, nitro, hydroxyl, —$SR^9$, optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, -$Q^{1a}$-$NR^9CONR^{10}R^{11}$, -$Q^{1a}$-$NR^9R^{10}$, -$Q^{1a}$-$COR^9$, -$Q^{1a}$-$NR^9COR^{10}$, —$Q^{1a}$-$NR^9C(O)OR^{10}$, -$Q^{1a}$-$SO_2R^9$, -$Q^{1a}$-$CONR^9R^{10}$, -$Q^{1a}$-$CO_2R^9$, -$Q^{1a}$-$SO_2NR^9R^{10}$, -$Q^{1a}$-$NR^9SO_2R^{10}$ and —$Q^{1a}$-$NR^9SO_2NR^{10}R^{11}$.

The ring substituents may be selected from -$Q^{1a}$-$R^{12}$, -$Q^{1a}$-O-$Q^{1b}$-$R^{12}$, $Q^{1a}$-S-$Q^{1b}$-$R^{12}$, $Q^{1a}$-SO-$Q^{1b}$-$R^{12}$, -$Q^{1a}$-$NR^9CONR^{10}$-$Q^{1b}$-$R^{12}$, -$Q^{1a}$-$NR^9$-$Q^{1b}$-$R^{12}$—, -$Q^{1a}$-CO-$Q^{1b}$-$R^{12}$—, -$Q^{1a}$-$NR^9CO$-$Q^{1b}$-$R^{12}$, -$Q^{1a}$-$NR^9C(O)O$-$Q^{1b}$-$R^{12}$—, -$Q^{1a}$-$SO_2$-$Q^{1b}$-$R^{12}$, -$Q^{1a}$-$CONR^9$-$Q^{1b}$-$R^{12}$, -$Q^{1a}$-$CO_2$-$Q^{1b}$-$R^{12}$, -$Q^{1a}$-$SO_2NR^9$-$Q^{1b}$-$R^{12}$, -$Q^{1a}$-$NR^9SO_2$-$Q^{1b}$-$R^{12}$ and -$Q^{1a}$-$NR^9SO_2NR^{10}$-$Q^{1b}$-$R^{12}$.

B may be substituted with one or more substituents are selected from halogen, cyano, nitro, $C_1$-$C_6$ alkyl, $C_1$-$C_4$ alkyl, $C_1$-$C_2$ alkyl, $C_1$-$C_6$ alkoxy, $C_1$-$C_4$ alkoxy, $C_1$-$C_2$ alkoxy, -$Q^{1a}$-$CONR^9R^{10}$-$Q^{1a}$-$NR^9COR^{10}$, -$Q^{1a}$-$R^{12}$, -$Q^{1a}$-O-$Q^{1b}$-$R^{12}$, -$Q^{1a}$-$CONR^9$-$Q^{1b}$-$R^{12}$ and -$Q^{1a}$-$SO_2$-$Q^{1b}$-$R^{12}$.

In particular, B may be substituted with one or more substituents selected from halogen, cyano, $C_1$-$C_6$ alkyl, $C_1$-$C_4$ alkyl, $C_1$-$C_2$ alkyl, $C_1$-$C_6$ alkoxy, $C_1$-$C_4$ alkoxy, $C_1$-$C_2$ alkoxy, -$Q^{1a}$-$CONR^9R^{10}$, -$Q^{1a}$-$NR^9COR^{10}$-$Q^{1a}$-$R^{12}$, -$Q^{1a}$-O-$Q^{1b}$-$R^{12}$, -$Q^{1a}$-$CONR^9$-$Q^{1b}$-$R^{12}$-$Q^{1a}$-$SO_2$-$Q^{1b}$-$R^{12}$.

More particularly, B may be substituted with one or more non-ring substituents selected from fluorine, chlorine, bromine, cyano, nitro, methyl, butyl, methoxy, $OCF_3$, O-propyl, —$CONHMe$, $CONH_2$ and —$NHCOMe$.

More particularly, B may be substituted with one or more non-ring substituents selected from fluorine, chlorine, bromine, cyano, methyl, butyl, methoxy, $OCF_3$, O-propyl, —$CONHMe$, $CONH_2$ and —$NHCOMe$.

In one embodiment, B is unsubstituted. In another embodiment, B is substituted with a ring.

$Q^{1a}$ and $Q^{1b}$ each independently represent a covalent bond, $C_1$-$C_6$ alkylene, $C_1$-$C_4$ alkylene, $C_1$-$C_2$ alkylene, $C_2$-$C_6$ alkenylene or $C_2$-$C_4$ alkenylene. The alkylene and alkenylene within the definition of $Q^{1a}$ and $Q^{1b}$ may be optionally substituted with halogen, hydroxyl, thiol, cyano, amino, amido, nitro and $SF_5$. In particular, the optional substituents may be selected from fluorine and hydroxyl.

$R^9$, $R^{10}$ and $R^{11}$ each independently represent hydrogen, $C_1$-$C_6$ alkyl, $C_1$-$C_4$ alkyl or $C_1$-$C_2$ alkyl. The alkyl within the definition of $R^9$, $R^{10}$ and $R^{11}$ may be optionally substituted with halogen, hydroxyl, thiol, cyano, amino, amido, nitro and $SF_5$. In particular, the optional substituents may be selected from fluorine and hydroxyl.

$R^{12}$ represents a 3 to 10 membered heterocyclyl, heteroaryl, aryl or cycloalkyl ring. $R^{12}$ may be a 3 to 6 membered or 5 to 6 membered heterocyclyl, heteroaryl, aryl or cycloalkyl ring.

$R^{12}$ may be optionally substituted with one or more (e.g. one, two or three) substituents selected from halogen (e.g. fluorine, chlorine or bromine), cyano, oxo, nitro, hydroxyl, —$SR^3$, —$NR^3R^4$, —$CONR^3R^4$, —$NR^3COR^4$, —$NR^3CONR^4R^5$, —$COR^3$, —$C(O)OR^3$, —$SO_2R^3$, —$SO_2NR^3R^4$, —$NR^3SO_2R^4$, $NR^3SO_2NR^4R^5$, —$NR^3C(O)$ OR$^4$, optionally substituted —C$_1$-C$_6$ alkyl, optionally substituted —C$_1$-C$_6$ alkoxy, optionally substituted —C$_2$-C$_6$ alkenyl, optionally substituted —C$_2$-C$_6$ alkynyl and optionally substituted C$_3$-C$_4$ cycloalkyl.

R$^3$, R$^4$ and R$^5$ each independently represent hydrogen, C$_1$-C$_6$ alkyl, C$_1$-C$_4$ alkyl or C$_1$-C$_2$ alkyl.

R$^3$, R$^4$ and R$^5$ may each independently represent hydrogen or C$_1$-C$_2$ alkyl (e.g. methyl or ethyl).

The alkyl within the definition of R$^3$, R$^4$ and R$^5$ may be optionally substituted with halogen, hydroxyl, thiol, cyano, amino, amido, nitro and SF$_5$. In particular, the alkyl may be optionally substituted with fluorine.

For example, the R$^{12}$ ring may be unsubstituted or substituted with halogen, nitro, —NR$^3$R$^4$, —SO$_2$NR$^3$R$^4$, C$_1$-C$_3$ alkyl or C$_1$-C$_3$ alkoxy, —S(O)$_2$R$^3$, C(O)OR$^3$, wherein the alkyl or alkoxy is optionally substituted with halogen, and wherein R$^3$ and R$^4$ each independently represent hydrogen or C$_1$-C$_2$ alkyl.

The ring may be substituted with one or more substituents selected from halogen, cyano, oxo, nitro, amino, hydroxy, amido, C$_1$-C$_6$ alkyl or C$_1$-C$_3$ alkyl, C$_1$-C$_6$ alkoxy or C$_1$-C$_3$ alkoxy, or C$_3$-C$_4$ cycloalkyl. In particular, R$^{12}$ may be unsubstituted or substituted with halogen, amido, C$_1$-C$_3$ alkyl or C$_1$-C$_3$ alkoxy, wherein the alkyl or alkoxy is optionally substituted with halogen.

More particularly, R$^{12}$ may be unsubstituted or substituted with fluorine, chlorine, methyl, methoxy, OCF$_3$, cyano, nitro, CONH$_2$, CONHMe, S(O)$_2$N(Me$_2$), S(O)$_2$Me and C(O)OMe.

R$^{12}$ may be selected from phenyl, morpholinyl, pyrimidinyl, pyrazolyl, pyrrolidinyl, pyridinyl, isoxazolyl, imidazolyl, piperazinyl, indolyl, indazolyl, furanyl, thiophenyl, dihydroisoquinolinyl and piperidinyl.

In particular, R$^{12}$ may be selected from phenyl, morpholinyl, pyrimidinyl, pyrazolyl, pyrrolidinyl, pyridinyl, isoxazolyl, imidazolyl, piperazinyl, dihydroisoquinolinyl and piperidinyl.

In one embodiment, B is unsubstituted, mono-substituted, bi-substituted or tri-substituted. In particular B is unsubstituted, mono-substituted or bi-substituted. B may be unsubstituted. B may be monosubstituted. B may be bi-substituted.

In certain instances, B is selected from phenyl, morpholinyl, pyrimidinyl, pyrazolyl, pyrrolidinyl, pyridinyl, isoxazolyl, imidazolyl, piperazinyl and piperidinyl which is either unsubstituted or substituted with one or more substituents selected from halogen, cyano, oxo, nitro, hydroxyl, —SR$^9$, optionally substituted C$_1$-C$_6$ alkyl, optionally substituted C$_1$-C$_6$ alkoxy, optionally substituted C$_2$-C$_6$ alkenyl, optionally substituted C$_2$-C$_6$ alkynyl, -Q$^{1a}$-R$^{12}$, -Q$^{1a}$-O-Q$^{1b}$-R$^{12}$, Q$^{1a}$-S-Q$^{1b}$-R$^{12}$, Q$^{1a}$-SO-Q$^{1b}$-R$^{12}$, -Q$^{1a}$-NR$^9$CONR$^{10}$R$^{11}$, -Q$^{1a}$-NR$^9$CONR$^{10}$-Q$^{1b}$R$^{12}$, -Q$^{1a}$-NR$^9$R$^{10}$, -Q$^{1a}$-NR$^9$-Q$^{1b}$-R$^{12}$—, -Q$^{1a}$-COR$^9$, —Q$^{1a}$-CO-Q$^{1b}$-R$^{12}$—, -Q$^{1a}$-NR$^9$COR$^{10}$, -Q$^{1a}$-NR$^9$CO-Q$^{1b}$-R$^{12}$, -Q$^{1a}$-NR$^9$C(O)OR$^{10}$, -Q$^{1a}$-NR$^9$C(O)O-Q$^{1b}$-R$^{12}$—, -Q$^{1a}$-SO$_2$R$^9$, -Q$^{1a}$-SO$_2$-Q$^{1c}$R$^{12}$, -Q$^{1a}$-CONR$^9$R$^{10}$, -Q$^{1a}$-CONR$^9$-Q$^{1b}$-R$^{12}$, -Q$^{1a}$-CO$_2$R$^9$, -Q$^{1a}$-CO$_2$-Q$^{1b}$-R$^{12}$, -Q$^{1a}$-SO$_2$NR$^9$R$^{10}$, -Q$^{1a}$-SO$_2$NR$^9$-Q$^{1b}$-R$^{12}$, -Q$^{1a}$-NR$^9$SO$_2$R$^{10}$, -Q$^{1a}$-NR$^9$SO$_2$-Q$^{1b}$-R$^{12}$, -Q$^{1a}$-NR$^9$SO$_2$NR$^{10}$R$^{11}$ and -Q$^{1a}$-NR$^9$SO$_2$NR$^{10}$-Q$^{1b}$-R$^{12}$.

B may represent a ring selected from phenyl, morpholinyl, pyrimidinyl, pyrazolyl, pyrrolidinyl, pyridinyl, isoxazolyl, imidazolyl, piperazinyl and piperidinyl which is either unsubstituted or substituent with one or more substituents selected from halogen, cyano, C$_1$-C$_6$ alkyl, C$_1$-C$_4$ alkyl, C$_1$-C$_2$ alkyl, C$_1$-C$_6$ alkoxy, C$_1$-C$_4$ alkoxy, C$_1$-C$_2$ alkoxy, -Q$^{1a}$-CONR$^9$R$^{10}$, -Q$^{1a}$-NR$^9$COR$^{10}$, -Q$^{1a}$-R$^{12}$, -Q$^{1a}$-O-Q$^{1b}$-R$^{12}$, -Q$^{1a}$-CONR$^9$-Q$^{1b}$-R$^{12}$, -Q$^{1a}$-SO$_2$-Q$^{1b}$-R$^{12}$.

The present invention further relates to compounds of formula (I), or a pharmaceutically acceptable salt thereof, wherein:
R$^{1a}$, R$^{1b}$, R$^{1c}$, R$^{1d}$, R$^{1e}$ and R$^{1f}$ each independently represent hydrogen, optionally substituted C$_1$-C$_6$ alkyl or optionally substituted C$_3$-C$_4$ cycloalkyl;
R$^2$ represents hydrogen;
Ring A is as defined herein;
L represents a covalent bond or —C$_0$-C$_3$ alkylene-NR$^6$C(O)—C$_0$-C$_3$ alkylene;
Ring B is as defined herein.

The present invention further relates to compounds of formula (IA), or a pharmaceutically acceptable salt thereof, wherein:
R$^{1a}$, R$^{1b}$, R$^{1c}$, R$^{1d}$, R$^{1e}$ and R$^{1f}$ each independently represent hydrogen, optionally substituted C$_1$-C$_6$ alkyl or optionally substituted C$_3$-C$_4$ cycloalkyl;
R$^{2x}$ represents hydrogen;
Ring A represents an optionally further substituted 5 to 10 membered monocyclic or bicyclic heteroaryl or aryl ring;
L represents a covalent bond;
Ring B represents an optionally substituted 3 to 10 membered monocyclic or bicyclic heterocyclyl, heteroaryl, cycloalkyl or aryl ring.

In particular, ring A represents an optionally further substituted 5 to 10 membered nitrogen containing monocyclic or bicyclic heteroaryl ring.

The present invention further relates to compounds of formula (IB), or a pharmaceutical acceptable salt thereof, wherein:
R$^{1a}$, R$^{1b}$, R$^{1c}$, R$^{1d}$, R$^{1e}$ and R$^{1f}$ each independently represent hydrogen, optionally substituted C$_1$-C$_6$ alkyl or optionally substituted C$_3$-C$_4$ cycloalkyl;
R$^{2x}$ represents hydrogen;
Ring A represents an optionally further substituted 5 to 10 membered monocyclic or bicyclic heteroaryl or aryl ring, wherein the ring cannot be triazolopyridazinyl, triazolopyridinyl, imidazotriazinyl, imidazopyrazinyl or pyrrolopyrimidinyl;
L represents a covalent bond or —C$_0$-C$_3$ alkylene-NR$^6$C(O)—C$_0$-C$_3$ alkylene;
Ring B represents an optionally substituted 3 to 10 membered monocyclic or bicyclic heterocyclyl, heteroaryl, cycloalkyl or aryl ring, with the proviso that ring B is not substituted with phenoxyl.

Examples of novel compounds of formula (I) include:
3-(3-(3-cyanophenyl)-1H-pyrazol-5-yl)pyrrolidine-1-carbonitrile
3-(3-(4-cyanophenyl)-1H-pyrazol-5-yl)pyrrolidine-1-carbonitrile
5-(5-(1-cyanopyrrolidin-3-yl)-1H-pyrazol-3-yl)-N-methylpicolinamide
4-(5-(1-cyanopyrrolidin-3-yl)-1H-pyrazol-3-yl)benzamide
3-(3-(4-(4-methylpiperazin-1-yl)phenyl)-1H-pyrazol-5-yl)pyrrolidine-1-carbonitrile
3-(5-(1-cyanopyrrolidin-3-yl)-1H-pyrazol-3-yl)benzamide
N-(3-(5-(1-cyanopyrrolidin-3-yl)-1H-pyrazol-3-yl)phenyl)acetamide
3-(5-(1-cyanopyrrolidin-3-yl)-1H-pyrazol-3-yl)-N,N-dimethylbenzamide
N-(4-(5-(1-cyanopyrrolidin-3-yl)-1H-pyrazol-3-yl)phenyl)acetamide
3-(3-(4-(morpholinosulfonyl)phenyl)-1H-pyrazol-5-yl)pyrrolidine-1-carbonitrile 3-(3-(2-methylpyridin-4-yl)-1H-pyrazol-5-yl)pyrrolidine-1-carbonitrile
3-(3-(3-(piperidin-1-yl)phenyl)-1H-pyrazol-5-yl)pyrrolidine-1-carbonitrile
3-(3-(3-(morpholinosulfonyl)phenyl)-1H-pyrazol-5-yl)pyrrolidine-1-carbonitrile
3-(3-([1,1'-biphenyl]-3-yl)-1H-pyrazol-5-yl)pyrrolidine-1-carbonitrile
3-(3-([1,1'-biphenyl]-3-yl)-4-fluoro-1H-pyrazol-5-yl)pyrrolidine-1-carbonitrile
(R)-3-(3-([1,1'-biphenyl]-3-yl)-4-fluoro-1H-pyrazol-5-yl)pyrrolidine-1-carbonitrile
(S)-3-(3-([1,1'-biphenyl]-3-yl)-4-fluoro-1H-pyrazol-5-yl)pyrrolidine-1-carbonitrile
3-(5-(naphthalen-2-yl)-1H-pyrazol-3-yl)pyrrolidine-1-carbonitrile
trans-3-(3-([1,1'-biphenyl]-3-yl)-1H-pyrazol-5-yl)-4-methylpyrrolidine-1-carbonitrile
trans-3-(3-([1,1'-biphenyl]-3-yl)-1H-pyrazol-5-yl)-4-methylpyrrolidine-1-carbonitrile: Enantiomer 1
trans-3-(3-([1,1'-biphenyl]-3-yl)-1H-pyrazol-5-yl)-4-methylpyrrolidine-1-carbonitrile: Enantiomer 2
trans-3-(3-([1,1'-biphenyl]-3-yl)-4-fluoro-1H-pyrazol-5-yl)-4-methylpyrrolidine-1-carbonitrile: Enantiomer 1
trans-3-(3-([1,1'-biphenyl]-3-yl)-4-fluoro-1H-pyrazol-5-yl)-4-methylpyrrolidine-1-carbonitrile: Enantiomer 2
trans-3-(3-([1,1'-biphenyl]-3-yl)-1-methyl-1H-pyrazol-5-yl)-4-methylpyrrolidine-1-carbonitrile
trans-3-(5-([1,1'-biphenyl]-3-yl)-1-methyl-1H-pyrazol-3-yl)-4-methylpyrrolidine-1-carbonitrile
3-(3-(3-(pyridin-3-yl)phenyl)-1H-pyrazol-5-yl)pyrrolidine-1-carbonitrile
4-(3-([1,1'-biphenyl]-3-yl)-1H-pyrazol-5-yl)-2-methylpyrrolidine-1-carbonitrile
3-(3-(3-(pyridin-4-yl)phenyl)-1H-pyrazol-5-yl)pyrrolidine-1-carbonitrile
3-(3-(4'-chloro-[1,1'-biphenyl]-3-yl)-1H-pyrazol-5-yl)pyrrolidine-1-carbonitrile
3-(3-(4'-methoxy-[1,1'-biphenyl]-3-yl)-1H-pyrazol-5-yl)pyrrolidine-1-carbonitrile
3-(5-(3-(1-methyl-1H-pyrazol-4-yl)phenyl)-1H-pyrazol-3-yl)pyrrolidine-1-carbonitrile
3-(5-(3-(pyridin-2-yl)phenyl)-1H-pyrazol-3-yl)pyrrolidine-1-carbonitrile
3-(5-(3-(isoxazol-4-yl)phenyl)-1H-pyrazol-3-yl)pyrrolidine-1-carbonitrile
3-(5-(3-(1-methyl-1H-imidazol-4-yl)phenyl)-1H-pyrazol-3-yl)pyrrolidine-1-carbonitrile
3-(5-([1,1'-biphenyl]-4-yl)-1H-pyrazol-3-yl)pyrrolidine-1-carbonitrile
3-(5-(5-phenylpyridin-3-yl)-1H-pyrazol-3-yl)pyrrolidine-1-carbonitrile
3-(5-(6-phenylpyridin-2-yl)-1H-pyrazol-3-yl)pyrrolidine-1-carbonitrile
3-(5-(2-phenylpyridin-4-yl)-1H-pyrazol-3-yl)pyrrolidine-1-carbonitrile
3-(5-(4-phenylpyridin-2-yl)-1H-pyrazol-3-yl)pyrrolidine-1-carbonitrile
3-(5-(6-phenylpyridin-3-yl)-1H-pyrazol-3-yl)pyrrolidine-1-carbonitrile
3-(5-(6-phenylpyridin-2-methylphenyl)-1H-pyrazol-3-yl)pyrrolidine-1-carbonitrile: Enantiomer 1
3-(5-(6-phenylpyridin-2-yl)-1H-pyrazol-3-yl)pyrrolidine-1-carbonitrile: Enantiomer 2
trans-3-(3-([1,1'-biphenyl]-3-yl)-1H-pyrazol-5-yl)-4-ethylpyrrolidine-1-carbonitrile
trans-3-(3-([1,1'-biphenyl]-3-yl)-1H-pyrazol-5-yl)-4-ethylpyrrolidine-1-carbonitrile: Enantiomer 1
trans-3-(3-([1,1'-biphenyl]-3-yl)-1H-pyrazol-5-yl)-4-ethylpyrrolidine-1-carbonitrile: Enantiomer 2
trans-3-(3-([1,1'-biphenyl]-3-yl)-1H-pyrazol-5-yl)-4-cyclopropylpyrrolidine-1-carbonitrile
3-(3-([2,3'-bipyridin]-4-yl)-1H-pyrazol-5-yl)pyrrolidine-1-carbonitrile
trans-3-methyl-4-(3-(pyridin-4-yl)-1H-pyrazol-5-yl)pyrrolidine-1-carbonitrile
trans-3-methyl-4-(3-phenyl-1H-pyrazol-5-yl)pyrrolidine-1-carbonitrile
N-(3-(1-cyanopyrrolidin-3-yl)-1H-pyrazol-5-yl)benzamide
N-(3-(1-cyanopyrrolidin-3-yl)-1H-pyrazol-5-yl)-2-phenylacetamide
3-(5-(2-oxo-6-phenyl-1,2-dihydropyridin-3-yl)-1,2,4-oxadiazol-3-yl)pyrrolidine-1-carbonitrile
3-(5-(2-phenylquinolin-4-yl)-1,2,4-oxadiazol-3-yl)pyrrolidine-1-carbonitrile
3-(5-(benzo[d]thiazol-6-yl)-1,2,4-oxadiazol-3-yl)pyrrolidine-1-carbonitrile
3-(5-([1,1'-biphenyl]-3-yl)-1,2,4-oxadiazol-3-yl)pyrrolidine-1-carbonitrile
3-(5-(2-methylquinolin-6-yl)-1,2,4-oxadiazol-3-yl)pyrrolidine-1-carbonitrile
3-(5-(3-chloro-5-(trifluoromethoxy)phenyl)-1,2,4-oxadiazol-3-yl)pyrrolidine-1-carbonitrile
3-(5-(4-methoxyquinolin-2-yl)-1,2,4-oxadiazol-3-yl)pyrrolidine-1-carbonitrile
3-(5-(2-(benzyloxy)phenyl)-1,2,4-oxadiazol-3-yl)pyrrolidine-1-carbonitrile
3-(5-(4-bromophenyl)-1,2,4-oxadiazol-3-yl)pyrrolidine-1-carbonitrile
3-(5-(4-morpholinophenyl)-1,2,4-oxadiazol-3-yl)pyrrolidine-1-carbonitrile
3-(5-(4-((R)-3-methoxypyrrolidin-1-yl)phenyl)-1,2,4-oxadiazol-3-yl)pyrrolidine-1-carbonitrile
(R)-3-(5-(4-phenylpyridin-2-yl)-1,2,4-oxadiazol-3-yl)pyrrolidine-1-carbonitrile
(R)-3-(5-(1-(pyrimidin-2-yl)piperidin-4-yl)-1,2,4-oxadiazol-3-yl)pyrrolidine-1-carbonitrile
(R)-3-(5-(2-(3,4-dihydroisoquinolin-2(1H)-yl)pyridin-4-yl)-1,2,4-oxadiazol-3-yl)pyrrolidine-1-carbonitrile
3-(5-(4-(1-methyl-1H-pyrazol-4-yl)phenyl)-1,2,4-oxadiazol-3-yl)pyrrolidine-1-carbonitrile
2-(5-([1,1'-biphenyl]-4-yl)-1,2,4-oxadiazol-3-yl)pyrrolidine-1-carbonitrile
2-(5-([1,1'-biphenyl]-3-yl)-1,2,4-oxadiazol-3-yl)pyrrolidine-1-carbonitrile
3-(5-(1-phenylpyrrolidin-3-yl)-1,2,4-oxadiazol-3-yl)pyrrolidine-1-carbonitrile
(R)-3-(5-(4-fluoro-3-(1-methyl-1H-pyrazol-4-yl)phenyl)-1,2,4-oxadiazol-3-yl)pyrrolidine-1-carbonitrile
(R)-3-(5-(3-methoxy-4-(1-methyl-1H-pyrazol-4-yl)phenyl)-1,2,4-oxadiazol-3-yl)pyrrolidine-1-carbonitrile
3-(6-(3-cyanophenyl)-1H-benzo[d]imidazol-2-yl)pyrrolidine-1-carbonitrile
3-(6-(2-(benzyloxy)phenyl)-1H-benzo[d]imidazol-2-yl)pyrrolidine-1-carbonitrile
4-(2-(1-cyanopyrrolidin-3-yl)-1H-benzo[d]imidazol-6-yl)benzamide
4-(2-(1-cyanopyrrolidin-3-yl)-1H-benzo[d]imidazol-6-yl)-N-methylbenzamide
3-(6-(2-fluoro-5-methylphenyl)-1H-benzo[d]imidazol-2-yl)pyrrolidine-1-carbonitrile
3-(6-(6-isopropoxypyridin-3-yl)-1H-benzo[d]imidazol-2-yl)pyrrolidine-1-carbonitrile 3-(6-(1-isobutyl-1H-pyrazol-4-yl)-1H-benzo[d]imidazol-2-yl)pyrrolidine-1-carbonitrile
N-benzyl-4-(2-(1-cyanopyrrolidin-3-yl)-1H-benzo[d]imidazol-6-yl)benzamide
3-(6-(pyridin-4-yl)-3H-imidazo[4,5-b]pyridin-2-yl)pyrrolidine-1-carbonitrile
(S)-3-(6-(pyridin-4-yl)-3H-imidazo[4,5-b]pyridin-2-yl)pyrrolidine-1-carbonitrile
(R)-3-(6-(pyridin-4-yl)-3H-imidazo[4,5-b]pyridin-2-yl)pyrrolidine-1-carbonitrile
3-(6-phenyl-3H-imidazo[4,5-b]pyridin-2-yl)pyrrolidine-1-carbonitrile
3-(6-(4-cyanophenyl)-3H-imidazo[4,5-b]pyridin-2-yl)pyrrolidine-1-carbonitrile
3-(6-(3-cyanophenyl)-3H-imidazo[4,5-b]pyridin-2-yl)pyrrolidine-1-carbonitrile
3-(6-(6-methoxypyridin-3-yl)-3H-imidazo[4,5-b]pyridin-2-yl)pyrrolidine-1-carbonitrile
3-(6-(1H-indazol-5-yl)-3H-imidazo[4,5-b]pyridin-2-yl)pyrrolidine-1-carbonitrile
3-(6-(1H-pyrazol-4-yl)-3H-imidazo[4,5-b]pyridin-2-yl)pyrrolidine-1-carbonitrile
3-(2-(1-cyanopyrrolidin-3-yl)-3H-imidazo[4,5-b]pyridin-6-yl)-N-methylbenzamide
3-(6-(4-cyanophenyl)-3H-imidazo[4,5-b]pyridin-2-yl)pyrrolidine-1-carbonitrile: Enantiomer 1
3-(6-(4-cyanophenyl)-3H-imidazo[4,5-b]pyridin-2-yl)pyrrolidine-1-carbonitrile: Enantiomer 2
3-(2-(1-cyanopyrrolidin-3-yl)-3H-imidazo[4,5-b]pyridin-6-yl)-N-methylbenzamide: Enantiomer 1
3-(2-(1-cyanopyrrolidin-3-yl)-3H-imidazo[4,5-b]pyridin-6-yl)-N-methylbenzamide: Enantiomer 2
(S)-2-(6-phenyl-1H-benzo[d]imidazol-2-yl)pyrrolidine-1-carbonitrile
3-(5-phenyl-1H-benzo[d]imidazol-2-yl)pyrrolidine-1-carbonitrile
(S)-2-(1-methyl-5-phenyl-1H-benzo[d]imidazol-2-yl)pyrrolidine-1-carbonitrile
3-(5-phenyl-3H-imidazo[4,5-b]pyridin-2-yl)pyrrolidine-1-carbonitrile
3-(7-phenyl-3H-imidazo[4,5-b]pyridin-2-yl)pyrrolidine-1-carbonitrile
3-(5-methyl-6-phenyl-3H-imidazo[4,5-b]pyridin-2-yl)pyrrolidine-1-carbonitrile
3-(7-methyl-6-phenyl-3H-imidazo[4,5-b]pyridin-2-yl)pyrrolidine-1-carbonitrile
3-(3-methyl-6-phenyl-3H-imidazo[4,5-b]pyridin-2-yl)pyrrolidine-1-carbonitrile
trans-3-methyl-4-(6-phenyl-3H-imidazo[4,5-b]pyridin-2-yl)pyrrolidine-1-carbonitrile: Enantiomer 1
trans-3-methyl-4-(6-phenyl-3H-imidazo[4,5-b]pyridin-2-yl)pyrrolidine-1-carbonitrile: Enantiomer 2
trans-3-methyl-4-(5-phenyl-1H-benzo[d]imidazol-2-yl)pyrrolidine-1-carbonitrile: Enantiomer 1
3-(5-(pyridin-2-yl)-4H-1,2,4-triazol-3-yl)pyrrolidine-1-carbonitrile
3-(5-phenyl-4H-1,2,4-triazol-3-yl)pyrrolidine-1-carbonitrile
3-(5-(1H-benzo[d]imidazol-6-yl)-4H-1,2,4-triazol-3-yl)pyrrolidine-1-carbonitrile
3-(5-(imidazo[1,2-a]pyridin-6-yl)-4H-1,2,4-triazol-3-yl)pyrrolidine-1-carbonitrile
3-(5-(4-phenylpyridin-2-yl)-4H-1,2,4-triazol-3-yl)pyrrolidine-1-carbonitrile
3-(5-(6-phenylpyridin-2-yl)-4H-1,2,4-triazol-3-yl)pyrrolidine-1-carbonitrile
3-(3-([1,1'-biphenyl]-3-yl)-1H-1,2,4-triazol-5-yl)pyrrolidine-1-carbonitrile
3-(3-([1,1'-biphenyl]-4-yl)-1H-1,2,4-triazol-5-yl)pyrrolidine-1-carbonitrile
trans-3-methyl-4-(3-phenyl-1H-1,2,4-triazol-5-yl)pyrrolidine-1-carbonitrile
trans-3-(3-([1,1'-biphenyl]-3-yl)-1H-1,2,4-triazol-5-yl)-4-methylpyrrolidine-1-carbonitrile
trans-3-(3-([1,1'-biphenyl]-3-yl)-1H-1,2,4-triazol-5-yl)-4-methylpyrrolidine-1-carbonitrile: Enantiomer 1
trans-3-(3-([1,1'-biphenyl]-3-yl)-1H-1,2,4-triazol-5-yl)-4-methylpyrrolidine-1-carbonitrile: Enantiomer 2
3-(3-([1,1'-biphenyl]-3-yl)isoxazol-5-yl)pyrrolidine-1-carbonitrile
3-(3-([1,1'-biphenyl]-3-yl)isoxazol-5-yl)pyrrolidine-1-carbonitrile: Enantiomer 1
3-(3-([1,1'-biphenyl]-3-yl)isoxazol-5-yl)pyrrolidine-1-carbonitrile: Enantiomer 2
3-(6-oxo-5-phenyl-1,6-dihydropyrimidin-2-yl)pyrrolidine-1-carbonitrile
(R)-3-(7-(4-methyl-1H-imidazol-1-yl)-1,6-dioxo-1,3,4,6-tetrahydro-2H-pyrido[1,2-a]pyrazin-2-yl)pyrrolidine-1-carbonitrile
(S)-2-(1-cyanopyrrolidin-2-yl)-N-methyl-6-phenylbenzo[d]oxazole-4-carboxamide
3-(2-amino-[1,1'-biphenyl]-3-yl)pyrrolidine-1-carbonitrile
3-(7-phenylimidazo[1,2-a]pyridin-3-yl)pyrrolidine-1-carbonitrile
3-(7-(3,5-dimethylisoxazol-4-yl)imidazo[1,2-a]pyridin-3-yl)pyrrolidine-1-carbonitrile
3-(3-(3-cyanophenyl)-1H-pyrazol-5-yl)pyrrolidine-1-carbonitrile
3-(3-(4-cyanophenyl)-1H-pyrazol-5-yl)pyrrolidine-1-carbonitrile
5-(5-(1-cyanopyrrolidin-3-yl)-1H-pyrazol-3-yl)-N-methylpicolinamide
4-(5-(1-cyanopyrrolidin-3-yl)-1H-pyrazol-3-yl)benzamide
3-(3-(4-(4-methylpiperazin-1-yl)phenyl)-1H-pyrazol-5-yl)pyrrolidine-1-carbonitrile
3-(5-(1-cyanopyrrolidin-3-yl)-1H-pyrazol-3-yl)benzamide
N-(3-(5-(1-cyanopyrrolidin-3-yl)-1H-pyrazol-3-yl)phenyl)acetamide
3-(5-(1-cyanopyrrolidin-3-yl)-1H-pyrazol-3-yl)-N,N-dimethylbenzamide
N-(4-(5-(1-cyanopyrrolidin-3-yl)-1H-pyrazol-3-yl)phenyl)acetamide
3-(3-(4-(morpholinosulfonyl)phenyl)-1H-pyrazol-5-yl)pyrrolidine-1-carbonitrile
3-(3-(2-methylpyridin-4-yl)-1H-pyrazol-5-yl)pyrrolidine-1-carbonitrile
3-(3-(3-(piperidin-1-yl)phenyl)-1H-pyrazol-5-yl)pyrrolidine-1-carbonitrile
3-(3-(3-(morpholinosulfonyl)phenyl)-1H-pyrazol-5-yl)pyrrolidine-1-carbonitrile
3-(3-([1,1'-biphenyl]-3-yl)-1H-pyrazol-5-yl)pyrrolidine-1-carbonitrile
3-(3-([1,1'-biphenyl]-3-yl)-4-fluoro-1H-pyrazol-5-yl)pyrrolidine-1-carbonitrile
(R)-3-(3-([1,1'-biphenyl]-3-yl)-4-fluoro-1H-pyrazol-5-yl)pyrrolidine-1-carbonitrile
(S)-3-(3-([1,1'-biphenyl]-3-yl)-4-fluoro-1H-pyrazol-5-yl)pyrrolidine-1-carbonitrile
3-(5-(naphthalen-2-yl)-1H-pyrazol-3-yl)pyrrolidine-1-carbonitrile
trans-3-(3-([1,1'-biphenyl]-3-yl)-1H-pyrazol-5-yl)-4-methylpyrrolidine-1-carbonitrile
trans-3-(3-([1,1'-biphenyl]-3-yl)-1H-pyrazol-5-yl)-4-methylpyrrolidine-1-carbonitrile: Enantiomer 1 trans-3-(3-([1,1'-biphenyl]-3-yl)-1H-pyrazol-5-yl)-4-methylpyrrolidine-1-carbonitrile: Enantiomer 2
trans-3-(3-([1,1'-biphenyl]-3-yl)-4-fluoro-1H-pyrazol-5-yl)-4-methylpyrrolidine-1-carbonitrile: Enantiomer 1
trans-3-(3-([1,1'-biphenyl]-3-yl)-4-fluoro-1H-pyrazol-5-yl)-4-methylpyrrolidine-1-carbonitrile: Enantiomer 2
trans-3-(3-([1,1'-biphenyl]-3-yl)-1-methyl-1H-pyrazol-5-yl)-4-methylpyrrolidine-1-carbonitrile
trans-3-(5-([1,1'-biphenyl]-3-yl)-1-methyl-1H-pyrazol-3-yl)-4-methylpyrrolidine-1-carbonitrile
3-(3-(3-(pyridin-3-yl)phenyl)-1H-pyrazol-5-yl)pyrrolidine-1-carbonitrile
4-(3-([1,1'-biphenyl]-3-yl)-1H-pyrazol-5-yl)-2-methylpyrrolidine-1-carbonitrile
3-(3-(3-(pyridin-4-yl)phenyl)-1H-pyrazol-5-yl)pyrrolidine-1-carbonitrile
3-(3-(4'-chloro-[1,1'-biphenyl]-3-yl)-1H-pyrazol-5-yl)pyrrolidine-1-carbonitrile
3-(3-(4'-methoxy-[1,1'-biphenyl]-3-yl)-1H-pyrazol-5-yl)pyrrolidine-1-carbonitrile
3-(5-(3-(1-methyl-1H-pyrazol-4-yl)phenyl)-1H-pyrazol-3-yl)pyrrolidine-1-carbonitrile
3-(5-(3-(pyridin-2-yl)phenyl)-1H-pyrazol-3-yl)pyrrolidine-1-carbonitrile
3-(5-(3-(isoxazol-4-yl)phenyl)-1H-pyrazol-3-yl)pyrrolidine-1-carbonitrile
3-(5-(3-(1-methyl-1H-imidazol-4-yl)phenyl)-1H-pyrazol-3-yl)pyrrolidine-1-carbonitrile
3-(5-([1,1'-biphenyl]-4-yl)-1H-pyrazol-3-yl)pyrrolidine-1-carbonitrile
3-(5-(5-phenylpyridin-3-yl)-1H-pyrazol-3-yl)pyrrolidine-1-carbonitrile
3-(5-(6-phenylpyridin-2-yl)-1H-pyrazol-3-yl)pyrrolidine-1-carbonitrile
3-(5-(2-phenylpyridin-4-yl)-1H-pyrazol-3-yl)pyrrolidine-1-carbonitrile
3-(5-(4-phenylpyridin-2-yl)-1H-pyrazol-3-yl)pyrrolidine-1-carbonitrile
3-(5-(6-phenylpyridin-3-yl)-1H-pyrazol-3-yl)pyrrolidine-1-carbonitrile
3-(5-(6-phenylpyridin-2-yl)-1H-pyrazol-3-yl)pyrrolidine-1-carbonitrile: Enantiomer 1
3-(5-(6-phenylpyridin-2-yl)-1H-pyrazol-3-yl)pyrrolidine-1-carbonitrile: Enantiomer 2
trans-3-(3-([1,1'-biphenyl]-3-yl)-1H-pyrazol-5-yl)-4-ethylpyrrolidine-1-carbonitrile
trans-3-(3-([1,1'-biphenyl]-3-yl)-1H-pyrazol-5-yl)-4-ethylpyrrolidine-1-carbonitrile: Enantiomer 1
trans-3-(3-([1,1'-biphenyl]-3-yl)-1H-pyrazol-5-yl)-4-ethylpyrrolidine-1-carbonitrile: Enantiomer 2
trans-3-(3-([1,1'-biphenyl]-3-yl)-1H-pyrazol-5-yl)-4-cyclopropylpyrrolidine-1-carbonitrile
3-(3-([2,3'-bipyridin]-4-yl)-1H-pyrazol-5-yl)pyrrolidine-1-carbonitrile
trans-3-methyl-4-(3-(pyridin-4-yl)-1H-pyrazol-5-yl)pyrrolidine-1-carbonitrile trans-3-methyl-4-(3-phenyl-1H-pyrazol-5-yl)pyrrolidine-1-carbonitrile
N-(3-(1-cyanopyrrolidin-3-yl)-1H-pyrazol-5-yl)benzamide
N-(3-(1-cyanopyrrolidin-3-yl)-1H-pyrazol-5-yl)-2-phenylacetamide
3-(5-(2-oxo-6-phenyl-1,2-dihydropyridin-3-yl)-1,2,4-oxadiazol-3-yl)pyrrolidine-1-carbonitrile
3-(5-(2-phenylquinolin-4-yl)-1,2,4-oxadiazol-3-yl)pyrrolidine-1-carbonitrile
3-(5-(benzo[d]thiazol-6-yl)-1,2,4-oxadiazol-3-yl)pyrrolidine-1-carbonitrile
3-(5-([1,1'-biphenyl]-3-yl)-1,2,4-oxadiazol-3-yl)pyrrolidine-1-carbonitrile
3-(5-(2-methylquinolin-6-yl)-1,2,4-oxadiazol-3-yl)pyrrolidine-1-carbonitrile
3-(5-(3-chloro-5-(trifluoromethoxy)phenyl)-1,2,4-oxadiazol-3-yl)pyrrolidine-1-carbonitrile
3-(5-(4-methoxyquinolin-2-yl)-1,2,4-oxadiazol-3-yl)pyrrolidine-1-carbonitrile
3-(5-(2-(benzyloxy)phenyl)-1,2,4-oxadiazol-3-yl)pyrrolidine-1-carbonitrile
3-(5-(4-bromophenyl)-1,2,4-oxadiazol-3-yl)pyrrolidine-1-carbonitrile
3-(5-(4-morpholinophenyl)-1,2,4-oxadiazol-3-yl)pyrrolidine-1-carbonitrile
3-(5-(4-((R)-3-methoxypyrrolidin-1-yl)phenyl)-1,2,4-oxadiazol-3-yl)pyrrolidine-1-carbonitrile
(R)-3-(5-(4-phenylpyridin-2-yl)-1,2,4-oxadiazol-3-yl)pyrrolidine-1-carbonitrile
(R)-3-(5-(1-(pyrimidin-2-yl)piperidin-4-yl)-1,2,4-oxadiazol-3-yl)pyrrolidine-1-carbonitrile
(R)-3-(5-(2-(3,4-dihydroisoquinolin-2(1H)-yl)pyridin-4-yl)-1,2,4-oxadiazol-3-yl)pyrrolidine-1-carbonitrile
3-(5-(4-(1-methyl-1H-pyrazol-4-yl)phenyl)-1,2,4-oxadiazol-3-yl)pyrrolidine-1-carbonitrile
2-(5-([1,1'-biphenyl]-4-yl)-1,2,4-oxadiazol-3-yl)pyrrolidine-1-carbonitrile
2-(5-([1,1'-biphenyl]-3-yl)-1,2,4-oxadiazol-3-yl)pyrrolidine-1-carbonitrile
3-(5-(1-phenylpyrrolidin-3-yl)-1,2,4-oxadiazol-3-yl)pyrrolidine-1-carbonitrile
(R)-3-(5-(4-fluoro-3-(1-methyl-1H-pyrazol-4-yl)phenyl)-1,2,4-oxadiazol-3-yl)pyrrolidine-1-carbonitrile
(R)-3-(5-(3-methoxy-4-(1-methyl-1H-pyrazol-4-yl)phenyl)-1,2,4-oxadiazol-3-yl)pyrrolidine-1-carbonitrile
3-(6-(3-cyanophenyl)-1H-benzo[d]imidazol-2-yl)pyrrolidine-1-carbonitrile
3-(6-(2-(benzyloxy)phenyl)-1H-benzo[d]imidazol-2-yl)pyrrolidine-1-carbonitrile
4-(2-(1-cyanopyrrolidin-3-yl)-1H-benzo[d]imidazol-6-yl)benzamide
4-(2-(1-cyanopyrrolidin-3-yl)-1H-benzo[d]imidazol-6-yl)-N-methylbenzamide
3-(6-(2-fluoro-5-methylphenyl)-1H-benzo[d]imidazol-2-yl)pyrrolidine-1-carbonitrile
3-(6-(6-isopropoxypyridin-3-yl)-1H-benzo[d]imidazol-2-yl)pyrrolidine-1-carbonitrile
3-(6-(1-isobutyl-1H-pyrazol-4-yl)-1H-benzo[d]imidazol-2-yl)pyrrolidine-1-carbonitrile
N-benzyl-4-(2-(1-cyanopyrrolidin-3-yl)-1H-benzo[d]imidazol-6-yl)benzamide
3-(6-(pyridin-4-yl)-3H-imidazo[4,5-b]pyridin-2-yl)pyrrolidine-1-carbonitrile
(S)-3-(6-(pyridin-4-yl)-3H-imidazo[4,5-b]pyridin-2-yl)pyrrolidine-1-carbonitrile
(R)-3-(6-(pyridin-4-yl)-3H-imidazo[4,5-b]pyridin-2-yl)pyrrolidine-1-carbonitrile
3-(6-phenyl-3H-imidazo[4,5-b]pyridin-2-yl)pyrrolidine-1-carbonitrile
3-(6-(4-cyanophenyl)-3H-imidazo[4,5-b]pyridin-2-yl)pyrrolidine-1-carbonitrile
3-(6-(3-cyanophenyl)-3H-imidazo[4,5-b]pyridin-2-yl)pyrrolidine-1-carbonitrile
3-(6-(6-methoxypyridin-3-yl)-3H-imidazo[4,5-b]pyridin-2-yl)pyrrolidine-1-carbonitrile
3-(6-(1H-indazol-5-yl)-3H-imidazo[4,5-b]pyridin-2-yl)pyrrolidine-1-carbonitrile 3-(6-(1H-pyrazol-4-yl)-3H-imidazo[4,5-b]pyridin-2-yl)pyrrolidine-1-carbonitrile 3-(2-(1-cyanopyrrolidin-3-yl)-3H-imidazo[4,5-b]pyridin-6-yl)-N-methylbenzamide 3-(6-(4-cyanophenyl)-3H-imidazo[4,5-b]pyridin-2-yl)pyrrolidine-1-carbonitrile: Enantiomer 1

3-(6-(4-cyanophenyl)-3H-imidazo[4,5-b]pyridin-2-yl)pyrrolidine-1-carbonitrile: Enantiomer 2

3-(2-(1-cyanopyrrolidin-3-yl)-3H-imidazo[4,5-b]pyridin-6-yl)-N-methylbenzamide: Enantiomer 1

3-(2-(1-cyanopyrrolidin-3-yl)-3H-imidazo[4,5-b]pyridin-6-yl)-N-methylbenzamide: Enantiomer 2

(S)-2-(6-phenyl-1H-benzo[d]imidazol-2-yl)pyrrolidine-1-carbonitrile 3-(5-phenyl-1H-benzo[d]imidazol-2-yl)pyrrolidine-1-carbonitrile (S)-2-(1-methyl-5-phenyl-1H-benzo[d]imidazol-2-yl)pyrrolidine-1-carbonitrile 3-(5-phenyl-3H-imidazo[4,5-b]pyridin-2-yl)pyrrolidine-1-carbonitrile 3-(7-phenyl-3H-imidazo[4,5-b]pyridin-2-yl)pyrrolidine-1-carbonitrile 3-(5-methyl-6-phenyl-3H-imidazo[4,5-b]pyridin-2-yl)pyrrolidine-1-carbonitrile 3-(7-methyl-6-phenyl-3H-imidazo[4,5-b]pyridin-2-yl)pyrrolidine-1-carbonitrile 3-(3-methyl-6-phenyl-3H-imidazo[4,5-b]pyridin-2-yl)pyrrolidine-1-carbonitrile trans-3-methyl-4-(6-phenyl-3H-imidazo[4,5-b]pyridin-2-yl)pyrrolidine-1-carbonitrile: Enantiomer 1 trans-3-methyl-4-(6-phenyl-3H-imidazo[4,5-b]pyridin-2-yl)pyrrolidine-1-carbonitrile: Enantiomer 2 trans-3-methyl-4-(5-phenyl-1H-benzo[d]imidazol-2-yl)pyrrolidine-1-carbonitrile: Enantiomer 1

3-(5-(pyridin-2-yl)-4H-1,2,4-triazol-3-yl)pyrrolidine-1-carbonitrile 3-(5-phenyl-4H-1,2,4-triazol-3-yl)pyrrolidine-1-carbonitrile 3-(5-(1H-benzo[d]imidazol-6-yl)-4H-1,2,4-triazol-3-yl)pyrrolidine-1-carbonitrile 3-(5-(imidazo[1,2-a]pyridin-6-yl)-4H-1,2,4-triazol-3-yl)pyrrolidine-1-carbonitrile 3-(5-(4-phenylpyridin-2-yl)-4H-1,2,4-triazol-3-yl)pyrrolidine-1-carbonitrile 3-(5-(6-phenylpyridin-2-yl)-4H-1,2,4-triazol-3-yl)pyrrolidine-1-carbonitrile 3-(3-([1,1'-biphenyl]-3-yl)-1H-1,2,4-triazol-5-yl)pyrrolidine-1-carbonitrile 3-(3-([1,1'-biphenyl]-4-yl)-1H-1,2,4-triazol-5-yl)pyrrolidine-1-carbonitrile trans-3-methyl-4-(3-phenyl-1H-1,2,4-triazol-5-yl)pyrrolidine-1-carbonitrile trans-3-(3-([1,1'-biphenyl]-3-yl)-1H-1,2,4-triazol-5-yl)-4-methylpyrrolidine-1-carbonitrile trans-3-(3-([1,1'-biphenyl]-3-yl)-1H-1,2,4-triazol-5-yl)-4-methylpyrrolidine-1-carbonitrile: Enantiomer 1 trans-3-(3-([1,1'-biphenyl]-3-yl)-1H-1,2,4-triazol-5-yl)-4-methylpyrrolidine-1-carbonitrile: Enantiomer 2

3-(3-([1,1'-biphenyl]-3-yl)isoxazol-5-yl)pyrrolidine-1-carbonitrile 3-(3-([1,1'-biphenyl]-3-yl)isoxazol-5-yl)pyrrolidine-1-carbonitrile: Enantiomer 1

3-(3-([1,1'-biphenyl]-3-yl)isoxazol-5-yl)pyrrolidine-1-carbonitrile: Enantiomer 2

3-(6-oxo-5-phenyl-1,6-dihydropyrimidin-2-yl)pyrrolidine-1-carbonitrile (R)-3-(7-(4-methyl-1H-imidazol-1-yl)-1,6-dioxo-1,3,4,6-tetrahydro-2H-pyrido[1,2-a]pyrazin-2-yl)pyrrolidine-1-carbonitrile (S)-2-(1-cyanopyrrolidin-2-yl)-N-methyl-6-phenylbenzo[d]oxazole-4-carboxamide 3-(2-amino-[1,1'-biphenyl]-3-yl)pyrrolidine-1-carbonitrile 3-(7-phenylimidazo[1,2-a]pyridin-3-yl)pyrrolidine-1-carbonitrile 3-(7-(3,5-dimethylisoxazol-4-yl)imidazo[1,2-a]pyridin-3-yl)pyrrolidine-1-carbonitrile (S)-2-(5-(3-cyanophenyl)benzo[d]oxazol-2-yl)pyrrolidine-1-carbonitrile (S)-6-(2-(1-cyanopyrrolidin-2-yl)benzo[d]oxazol-5-yl)picolinonitrile (S)-2-(6-(3-cyanophenyl)benzo[d]oxazol-2-yl)pyrrolidine-1-carbonitrile (S)-2-(5-(3-ethylphenyl)benzo[d]oxazol-2-yl)pyrrolidine-1-carbonitrile (S)-2-(6-(3-ethylphenyl)benzo[d]oxazol-2-yl)pyrrolidine-1-carbonitrile (S)-2-(1-cyanopyrrolidin-2-yl)-6-(3-ethylphenyl)-N-methylbenzo[d]oxazole-4-carboxamide (S)-6-(2-(1-cyanopyrrolidin-2-yl)benzo[d]oxazol-6-yl)picolinonitrile (S)-2-(5-(3-(trifluoromethoxy)phenyl)benzo[d]oxazol-2-yl)pyrrolidine-1-carbonitrile (S)-2-(5-(3-methyl-1H-indazol-6-yl)benzo[d]oxazol-2-yl)pyrrolidine-1-carbonitrile (S)-2-(5-(1-methyl-1H-indazol-5-yl)benzo[d]oxazol-2-yl)pyrrolidine-1-carbonitrile (S)-2-(5-(3-nitrophenyl)benzo[d]oxazol-2-yl)pyrrolidine-1-carbonitrile (S)-2-(5-(3-cyano-2-fluorophenyl)benzo[d]oxazol-2-yl)pyrrolidine-1-carbonitrile (S)-2-(5-(3-cyano-5-fluorophenyl)benzo[d]oxazol-2-yl)pyrrolidine-1-carbonitrile (S)—N-benzyl-3-(2-(1-cyanopyrrolidin-2-yl)benzo[d]oxazol-5-yl)-4-methylbenzenesulfonamide 2-(5-([1,1'-biphenyl]-3-yl)-1,3,4-oxadiazol-2-yl)pyrrolidine-1-carbonitrile (S)-2-(3-([1,1'-biphenyl]-3-yl)-1,2,4-oxadiazol-5-yl)pyrrolidine-1-carbonitrile 2-(5-(6-phenylpyridin-2-yl)-1,2,4-oxadiazol-3-yl)pyrrolidine-1-carbonitrile 2-(5-(3-(1-methyl-1H-pyrazol-5-yl)phenyl)-1,2,4-oxadiazol-3-yl)pyrrolidine-1-carbonitrile 2-(5-(3-(2-methoxypyridin-4-yl)phenyl)-1,2,4-oxadiazol-3-yl)pyrrolidine-1-carbonitrile 2-(5-(3'-cyano-2'-fluoro-[1,1'-biphenyl]-3-yl)-1,2,4-oxadiazol-3-yl)pyrrolidine-1-carbonitrile 2-(5-(5'-cyano-2'-methoxy-[1,1'-biphenyl]-3-yl)-1,2,4-oxadiazol-3-yl)pyrrolidine-1-carbonitrile 2-(5-(3-(3,5-dimethylisoxazol-4-yl)phenyl)-1,2,4-oxadiazol-3-yl)pyrrolidine-1-carbonitrile 2-(5-(3-(1-methyl-1H-pyrazol-4-yl)phenyl)-1,2,4-oxadiazol-3-yl)pyrrolidine-1-carbonitrile 3'-(3-(1-cyanopyrrolidin-2-yl)-1,2,4-oxadiazol-5-yl)-[1,1'-biphenyl]-4-carboxamide 3'-(3-(1-cyanopyrrolidin-2-yl)-1,2,4-oxadiazol-5-yl)-N,N-dimethyl-[1,1'-biphenyl]-3-sulfonamide 2-(5-(3-(1-methyl-1H-indazol-5-yl)phenyl)-1,2,4-oxadiazol-3-yl)pyrrolidine-1-carbonitrile 2-(5-(3-(pyridin-3-yl)phenyl)-1,2,4-oxadiazol-3-yl)pyrrolidine-1-carbonitrile 2-(5-(4'-(methylsulfonyl)-[1,1'-biphenyl]-3-yl)-1,2,4-oxadiazol-3-yl)pyrrolidine-1-carbonitrile 2-(5-(3-(6-methylpyridin-3-yl)phenyl)-1,2,4-oxadiazol-3-yl)pyrrolidine-1-carbonitrile
2-(5-(2'-cyano-[1,1'-biphenyl]-3-yl)-1,2,4-oxadiazol-3-yl)pyrrolidine-1-carbonitrile
methyl 3'-(3-(1-cyanopyrrolidin-2-yl)-1,2,4-oxadiazol-5-yl)-[1,1'-biphenyl]-2-carboxylate
2-(5-(4'-nitro-[1,1'-biphenyl]-3-yl)-1,2,4-oxadiazol-3-yl)pyrrolidine-1-carbonitrile
2-(5-(3-(6-methoxypyridin-3-yl)phenyl)-1,2,4-oxadiazol-3-yl)pyrrolidine-1-carbonitrile
2-(5-(3-(pyrimidin-5-yl)phenyl)-1,2,4-oxadiazol-3-yl)pyrrolidine-1-carbonitrile
2-(5-(3-(furan-3-yl)phenyl)-1,2,4-oxadiazol-3-yl)pyrrolidine-1-carbonitrile
2-(5-(3'-nitro-[1,1'-biphenyl]-3-yl)-1,2,4-oxadiazol-3-yl)pyrrolidine-1-carbonitrile
2-(5-(3-(2-methoxypyridin-3-yl)phenyl)-1,2,4-oxadiazol-3-yl)pyrrolidine-1-carbonitrile
2-(5-(3'-cyano-5'-fluoro-[1,1'-biphenyl]-3-yl)-1,2,4-oxadiazol-3-yl)pyrrolidine-1-carbonitrile
2-(5-(3-(5-methylpyridin-3-yl)phenyl)-1,2,4-oxadiazol-3-yl)pyrrolidine-1-carbonitrile
2-(5-(3-(7-methyl-1H-indol-2-yl)phenyl)-1,2,4-oxadiazol-3-yl)pyrrolidine-1-carbonitrile
2-(5-(3-(5-cyanothiophen-2-yl)phenyl)-1,2,4-oxadiazol-3-yl)pyrrolidine-1-carbonitrile
2-(5-(2-phenylpyridin-4-yl)-1,2,4-oxadiazol-3-yl)pyrrolidine-1-carbonitrile
2-(5-(2-(3-(trifluoromethoxy)phenyl)pyridin-4-yl)-1,2,4-oxadiazol-3-yl)pyrrolidine-1-carbonitrile
2-(5-(2-(4-(trifluoromethoxy)phenyl)pyridin-4-yl)-1,2,4-oxadiazol-3-yl)pyrrolidine-1-carbonitrile
3-(4-(3-(1-cyanopyrrolidin-2-yl)-1,2,4-oxadiazol-5-yl)pyridin-2-yl)benzamide
3-(4-(3-(1-cyanopyrrolidin-2-yl)-1,2,4-oxadiazol-5-yl)pyridin-2-yl)-N-methylbenzamide
2-(5-(4-(3-cyanophenyl)pyridin-2-yl)-1,2,4-oxadiazol-3-yl)pyrrolidine-1-carbonitrile
4'-(3-(1-cyanopyrrolidin-2-yl)-1,2,4-oxadiazol-5-yl)-[2,2'-bipyridine]-4-carbonitrile
(S)-2-(5-(4'-cyano-[1,1'-biphenyl]-3-yl)-1,2,4-oxadiazol-3-yl)pyrrolidine-1-carbonitrile
(S)-2-(5-(6-(4-cyanophenyl)pyridin-2-yl)-1,2,4-oxadiazol-3-yl)pyrrolidine-1-carbonitrile
(S)-2-(5-(4-(4-cyanophenyl)pyridin-2-yl)-1,2,4-oxadiazol-3-yl)pyrrolidine-1-carbonitrile
(S)-2-(5-(2-(4-cyanophenyl)pyridin-4-yl)-1,2,4-oxadiazol-3-yl)pyrrolidine-1-carbonitrile
(S)-2-(5-(7-cyanonaphthalen-2-yl)-1,2,4-oxadiazol-3-yl)pyrrolidine-1-carbonitrile
7-(3-(1-cyanopyrrolidin-2-yl)-1,2,4-oxadiazol-5-yl)quinoline-2-carbonitrile
4'-(3-(1-cyanopyrrolidin-2-yl)-1,2,4-oxadiazol-5-yl)-[2,2'-bipyridine]-6-carbonitrile
(S)-4-(3-(1-cyanopyrrolidin-2-yl)-1,2,4-oxadiazol-5-yl)-[2,4'-bipyridine]-2'-carbonitrile
(S)-2'-(3-(1-cyanopyrrolidin-2-yl)-1,2,4-oxadiazol-5-yl)-[4,4'-bipyridine]-2-carbonitrile
(S)-6-(3-(1-cyanopyrrolidin-2-yl)-1,2,4-oxadiazol-5-yl)-[2,4'-bipyridine]-2'-carbonitrile
2-(5-(2-(3-(trifluoromethoxy)phenyl)pyrimidin-4-yl)-1,2,4-oxadiazol-3-yl)pyrrolidine-1-carbonitrile
(S)-2-(5-(2-(4-cyanophenyl)pyrimidin-4-yl)-1,2,4-oxadiazol-3-yl)pyrrolidine-1-carbonitrile
(S)-2-(5-(2-(3-cyanophenyl)pyrimidin-4-yl)-1,2,4-oxadiazol-3-yl)pyrrolidine-1-carbonitrile
(S)-1-(4-(3-(1-cyanopyrrolidin-2-yl)-1,2,4-oxadiazol-5-yl)pyrimidin-2-yl)-1H-pyrazole-4-carbonitrile
(S)-4-(4-(3-(1-cyanopyrrolidin-2-yl)-1,2,4-oxadiazol-5-yl)pyrimidin-2-yl)picolinonitrile
2-(5-(6-(3-cyanophenyl)pyrimidin-4-yl)-1,2,4-oxadiazol-3-yl)pyrrolidine-1-carbonitrile
(S)-1-(3-(3-(1-cyanopyrrolidin-2-yl)-1,2,4-oxadiazol-5-yl)phenyl)-1H-pyrazole-4-carbonitrile
(S)-1-(2-(3-(1-cyanopyrrolidin-2-yl)-1,2,4-oxadiazol-5-yl)pyridin-4-yl)-1H-pyrazole-4-carbonitrile
(S)-1-(6-(3-(1-cyanopyrrolidin-2-yl)-1,2,4-oxadiazol-5-yl)pyridin-2-yl)-1H-pyrazole-4-carbonitrile
(S)-1-(4-(3-(1-cyanopyrrolidin-2-yl)-1,2,4-oxadiazol-5-yl)pyridin-2-yl)-1H-pyrazole-4-carbonitrile
3-(5-(5-phenylpyridin-2-yl)-1H-pyrazol-3-yl)pyrrolidine-1-carbonitrile
3-(3-(5-(pyrimidin-2-yl)pyridin-2-yl)-1H-pyrazol-5-yl)pyrrolidine-1-carbonitrile
3-(4-fluoro-3-(6-(piperidin-1-yl)pyridin-2-yl)-1H-pyrazol-5-yl)pyrrolidine-1-carbonitrile
3-(3-(3-(3-cyanophenyl)azetidin-1-yl)-1,2,4-oxadiazol-5-yl)pyrrolidine-1-carbonitrile
3-(3-(3-(4-cyanophenyl)azetidin-1-yl)-1,2,4-oxadiazol-5-yl)pyrrolidine-1-carbonitrile
3-(3-(2-phenylpyridin-4-yl)-1H-1,2,4-triazol-5-yl)pyrrolidine-1-carbonitrile
(S)-2-(5-(2-(3-cyanophenyl)pyridin-4-yl)-1,2,4-oxadiazol-3-yl)pyrrolidine-1-carbonitrile
(S)-5-(4-(3-(1-cyanopyrrolidin-2-yl)-1,2,4-oxadiazol-5-yl)pyrimidin-2-yl)picolinonitrile
(S)-1-(6-(3-(1-cyanopyrrolidin-2-yl)-1,2,4-oxadiazol-5-yl)pyrazin-2-yl)-1H-pyrazole-4-carbonitrile
(S)-4-(6-(3-(1-cyanopyrrolidin-2-yl)-1,2,4-oxadiazol-5-yl)pyrazin-2-yl)picolinonitrile
(S)-4-(5-(3-(1-cyanopyrrolidin-2-yl)-1,2,4-oxadiazol-5-yl)pyridazin-3-yl)picolinonitrile.
or pharmaceutically acceptable salts thereof.

According to a further aspect of the invention there is provided a process for the preparation of a compound of formula (I) or a pharmaceutically acceptable salt thereof comprising the steps of reacting an amine of formula (III) with cyanogen bromide to form N—CN compounds:

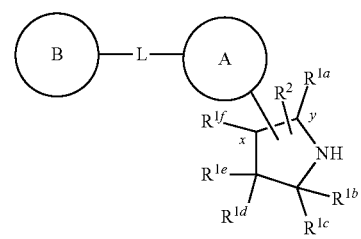

(III)

Where $R^{1a}$, $R^{1b}$, $R^{1c}$, $R^{1d}$, $R^{1e}$ and $R^{1f}$ each independently represent hydrogen, optionally substituted $C_1$-$C_6$ alkyl or optionally substituted $C_3$-$C_4$ cycloalkyl, or $R^{1b}$ and $R^{1c}$ together form an optionally substituted $C_3$-$C_6$ cycloalkyl ring, or $R^{1d}$ and $R^{1e}$ together form an optionally substituted $C_3$-$C_6$ cycloalkyl ring;

$R^2$ represents hydrogen or optionally substituted $C_1$-$C_6$ alkyl;

A represents an optionally further substituted 5 to 10 membered monocyclic or bicyclic heteroaryl, heterocyclyl or aryl ring;

L represents a covalent bond or linker;

B represents an optionally substituted 3 to 10 membered monocyclic or bicyclic heterocyclyl, heteroaryl, cycloalkyl or aryl ring; and when -A-L-B is at position x, attachment to A is via a carbon ring atom of A, and either:

A cannot be triazolopyridazinyl, triazolopyridinyl, imidazotriazinyl, imidazopyrazinyl or pyrrolopyrimidinyl; or B cannot be substituted with phenoxyl; or B cannot be cyclopentyl when L is an oxygen atom.

According to a further aspect of the invention there is provided a pharmaceutical composition comprising a compound of the invention.

Pharmaceutical compositions of this invention comprise any of the compounds of the invention combined with any pharmaceutically acceptable carrier, adjuvant or vehicle. Examples of pharmaceutically acceptable carriers, are known to those skilled in the art and include but are not limited to preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may be in the form of, for example, tablets, capsules, powders, granules, elixirs, lozenges, suppositories, syrups and liquid preparations including suspensions and solutions. The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms.

The compounds of the invention may be used in the treatment of disorders and diseases related to DUB inhibition, particularly USP30 and Cezanne 1 inhibition.

Conditions Involving Mitochondrial Dysfunction

The compounds of the invention can be used in the treatment of disorders or diseases having a component relating to mitochondrial dysfunction, particularly disorders or diseases linked to DUB activity. More particularly, disorders or diseases link to USP30 activity.

The compounds described herein may be used in the manufacture of a medicament for the treatment of conditions involving mitochondrial dysfunction.

In a further aspect of the invention there is provided a method of treatment or prevention of a condition involving mitochondrial dysfunction, the method comprising administering a pharmaceutically effective amount of a compound of the invention or a pharmaceutical composition thereof to an individual diagnosed with a condition involving mitochondrial dysfunction.

Mitochondrial dysfunctions result from defects of the mitochondria, which are specialized compartments present in every cell of the body except red blood cells. When mitochondria fail, less and less energy is generated within the cell and cell injury or even cell death will follow. If this process is repeated throughout the body the life of the subject in whom this is happening is severely compromised. Diseases of the mitochondria appear most often in organs that are very energy demanding such as the brain, heart, liver, skeletal muscles, kidney and the endocrine and respiratory system.

The condition involving mitochondrial dysfunction may be selected from a condition involving a mitophagy defect, a condition involving a mutation in mitochondrial DNA, a condition involving mitochondrial oxidative stress, a condition involving a defect in mitochondrial membrane potential, mitochondrial biogenesis, a condition involving a defect in mitochondrial shape or morphology, and a condition involving a lysosomal storage defect.

In particular, the condition involving mitochondrial dysfunction may be selected from a neurodegenerative disease; multiple sclerosis (MS), mitochondrial myopathy, encephalopathy, lactic acidosis, and stroke-like episodes (MELAS) syndrome; Leber's hereditary optic neuropathy (LHON); cancer; neuropathy, ataxia, retinitis pigmentosa-maternally inherited Leigh syndrome (NARP-MILS); Danon disease; diabetes; diabetic nephropathy; metabolic disorders; heart failure; ischemic heart disease leading to myocardial infarction; psychiatric diseases, for example schizophrenia; multiple sulfatase deficiency (MSD); mucolipidosis II (ML II); mucolipidosis III (ML III); mucolipidosis IV (ML IV); GM1-gangliosidosis (GM1); neuronal ceroid-lipofuscinoses (NCL1); Alpers disease; Barth syndrome; Beta-oxidation defects; carnitine-acyl-carnitine deficiency; carnitine deficiency; creatine deficiency syndromes; co-enzyme Q10 deficiency; complex 1 deficiency; complex 11 deficiency; complex III deficiency; complex IV deficiency; complex V deficiency; COX deficiency; chronic progressive external ophthalmoplegia syndrome (CPEO); CPT I deficiency; CPT II deficiency; glutaric aciduria type II; Kearns-Sayre syndrome; lactic acidosis; long-chain acyl-CoA dehydrogenase deficiency (LCHAD); Leigh disease or syndrome; lethal infantile cardiomyopathy (LIC); Luft disease; glutaric aciduria type II; medium-chain acyl-CoA dehydrogenase deficiency (MCAD); myoclonic epilepsy and ragged-red fiber (MERRF) syndrome; mitochondrial cytopathy; mitochondrial recessive ataxia syndrome; mitochondrial DNA depletion syndrome; myoneurogastointestinal disorder and encephalopathy; Pearson syndrome; pyruvate dehydrogenase deficiency; pyruvate carboxylase deficiency; POLG mutations; medium/short-chain 3-hydroxyacyl-CoA dehydrogenase (M/SCHAD) deficiency; very long-chain acyl-CoA dehydrogenase (VLCAD) deficiency; and age-dependent decline in cognitive function and muscle-strength.

The condition involving mitochondrial dysfunction may be a CNS disorder, for example a neurodegenerative disease.

Neurodegenerative diseases include, but are not limited to, Parkinson's disease, Alzheimer's disease, amyotrophic lateral sclerosis (ALS), Huntington's disease, ischemia, stroke, dementia with Lewy bodies, and frontotemporal dementia.

In a particular embodiment, the compounds of the invention are useful in the treatment of Parkinson's disease, including, but not limited to, PD related to mutations in α-synuclein, parkin and PINK1, autosomal recessive juvenile Parkinson's disease (AR-JP) where parkin is mutated.

The compounds of the invention or pharmaceutical compositions thereof as described herein may be combined with one or more additional agents when used for the treatment of conditions involving mitochondrial dysfunction. The compounds may be combined with one or more additional agents selected from levodopa, a dopamine agonist, a monoamino oxygenase (MAO) B inhibitor, a catechol O-methyltransferase (COMT) inhibitor, an anticholinergic, riluzole, amantadine, a cholinesterase inhibitor, memantine, tetrabenazine, an antipsychotic, diazepam, clonazepam, an antidepressant, and an anti-convulsant.

Cancer

Compounds of the invention also have use in the treatment of cancer and more particularly in the treatment of cancer linked to DUB activity, especially USP30 or Cezanne 1 activity.

The compounds as described herein may also be used in the manufacture of a medicament for the treatment of a cancer. In a further aspect of the invention there is provided a method of treatment or prevention of a cancer, the method comprising administering a pharmaceutically effective amount of a compound of the invention or a pharmaceutical composition thereof to an individual suffering from a cancer.

The compounds of the invention also have use in the treatment of cancer linked to mitochondrial dysfunction.

In one embodiment, the compounds of the invention have use in the treatment of cancer where apoptotic pathways are dysregulated and more particularly where proteins of the BCL-2 family are mutated, or over or under expressed.

References to "cancer" or "tumour" include but are not limited to breast, ovarian, prostate, lung, kidney, gastric, colon, testicular, head and neck, pancreas, brain, melanoma, bone or other cancers of tissue organs and cancers of the blood cells such as lymphomas and leukaemias. Particular cancers include lymphoma, multiple myeloma, colorectal cancer, and non-small cell lung carcinoma.

The compounds of the invention or pharmaceutical compositions thereof as described herein may be combined with one or more additional agents when used for the treatment of cancer. The compounds may be combined with an additional anti-tumour therapeutic agent, for example chemotherapeutic drugs or inhibitors of other regulatory proteins. In one embodiment the additional anti-tumour therapeutic agent is a BH-3 mimetic. In a further embodiment BH-3 mimetics may be selected from but not limited to one or more of ABT-737, ABT-199, ABT-263, and Obatoclax. In a further embodiment the additional anti-tumour agent is a chemotherapeutic agent. Chemotherapeutic agents may be selected from but not limited to, olaparib, mitomycin C, cisplatin, carboplatin, oxaliplatin, ionizing radiation (IR), camptothecin, irinotecan, topotecan, temozolomide, taxanes, 5-fluoropyrimidines, gemcitabine, and doxorubicin.

Dosage Forms

For treating a mitochondrial dysfunction disorder, the pharmaceutical compositions of the invention may be designed for administration by the oral, parenteral or mucosal route and the choice or the specific form of composition is dependent on the administration route. Thus for oral administration the composition may be in the form, for example, of tablets, lozenges, dragees, films, powders, elixirs, syrups, liquid preparations including dispersions, suspensions, emulsions, solutions or sprays, cachets, granules, capsules, etc. For administration to mucosa the composition may be in the form of sprays, inhalants, dispersions, suspensions, emulsions, solutions, gels, patches, films, ointments, creams, lotions, suppositories etc. For parenteral administration the composition is in the form of a liquid preparation such as a solution, dispersion, emulsion or suspension including liposome compositions.

For treating a CNS disorder, the compounds of the invention must have the ability to pass across the blood-brain barrier. As such, such compounds have the ability to enter the central nervous system of a patient. Alternatively, the pharmaceutical compositions of the present invention can bypass the blood brain barrier through use of compositions and methods known in the art for bypassing the blood brain barrier or can be injected directly into the brain. Suitable areas for injection include the cerebral cortex, cerebellum, midbrain, brainstem, hypothalamus, spinal cord and ventricular tissue, and areas of the PNS including the carotid body and the adrenal medulla. Further dosage forms include those suitable for oral delivery including, but not limited to tablets, dragees, powders, elixirs, syrups, liquid preparations including suspensions, sprays, inhalants, tablets, lozenges, emulsions, solutions, cachets, granules and capsules. For parenteral administration, preparations include sterile aqueous, aqueous-organic, and organic solutions, suspensions and emulsions.

For treating a cancer, the pharmaceutical compositions of the invention may be administered in any effective manner suitable for targeting cancer cells, for example orally in any orally acceptable dosage form including, but not limited to tablets, dragees, powders, elixirs, syrups, liquid preparations including suspensions, sprays, inhalants, tablets, lozenges, emulsions, solutions, cachets, granules and capsules. Preparations according to the invention for parenteral administration include sterile aqueous, aqueous-organic, and organic solutions, suspensions and emulsions.

Such dosage forms are prepared according to techniques known in the art of pharmaceutical formulation. When in the form of sprays or inhalants the pharmaceutical compositions may be administered nasally. Suitable formulations for this purpose are known to those skilled in the art.

The pharmaceutical compositions of the invention may be administered by injection and may be in the form of a sterile liquid preparation for injection, including liposome preparations. The pharmaceutical compositions of the invention may also be in the form of suppositories for rectal administration. These are formulated so that the pharmaceutical composition is solid at room temperature and liquid at body temperature to allow release of the active compound.

The dosages may be varied depending upon the requirements of the patient, the severity of the condition being treated, and the compound being employed. Determination of the proper dosage for a particular situation is within the remit of the person skilled in the skill of the art. Generally, treatment is initiated with smaller dosages which are less than the optimal dose of the compound. Thereafter the dosage is increased by small increments until the optimum effect under the circumstances is reached.

The magnitude of an effective dose of a compound will, of course, vary with the nature of the severity of the condition to be treated and with the particular compound and its route of administration. The selection of appropriate dosages is within the ability of one of ordinary skill in this art, without undue burden. The daily dose range is about 101 µg to about 100 mg per kg body weight of a human and non-human animal and in general may be around 10 µg to 30 mg per kg body weight per dose. The above dose may be given from one to three times per day.

Synthetic Methodologies

Compounds of the invention may be prepared via a variety of synthetic routes. Exemplary routes to certain compounds of the invention are shown below. Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art. Those skilled in the art appreciate that, where appropriate, the individual transformations within a scheme can be completed in a different order. The following schemes describe general synthetic methods whereby intermediate and target compounds of the present invention may be prepared. Additional representative compounds and stereoisomers, racemic mixtures, diastereomers and enantiomers thereof can be synthesized using the intermediates prepared in accordance to the general schemes and other materials, compounds and reagents known to those skilled in the art. All such compounds, stereoisomers, racemic mixtures, diastereomers and enantiomers thereof are intended to be encompassed within the scope of the present invention.

All the compounds were characterised by either liquid chromatography-mass spectroscopy (LCMS) or $^1$H NMR or both.

Abbreviations

ABPR Automated back pressure regulator
BOC Tert-butoxycarbonyl
br Broad (NMR signal)
BuLi n-Butyllithium
CDI 1,1'-Carbonyldiimidazole
d Doublet (NMR signal)
dba Dibenzylideneacetone
DCM Dichloromethane
DEA Diethylamine
DIAD Diethyl azodicarboxylate
DIPEA Diisopropylethylamine
DME 1,2-Dimethoxyethane
DMF N,N-Dimethylformamide
DMSO Dimethylsulphoxide
dppf 1,1'-Bis(diphenylphosphino)ferrocene
EDCI N-(3-Dimethylaminopropyl)-N'-ethylcarbodiimide hydrochloride
ES Electrospray
EtOAc Ethyl acetate
EtOH Ethanol
h Hour(s)
HATU 1-[Bis(dimethylamino)methylene]-1H-1,2,3-triazolo[4,5-b]pyridinium 3-oxide hexafluorophosphate
HOBt Hydroxybenzotriazole
HPLC High-performance liquid chromatography
IPA Isopropyl alcohol
LCMS Liquid chromatography-mass spectrometry
m Multiplot (NMR signal)
min minutes
MeCN Acetonitrile
MeOH Methanol
PPh3 Triphenylphosphine
PE Petroleum Ether
RT Retention time
rt Room temperature
s Singlet (NMR signal)
SFC Supercritical Fluid Chromatography
t Triplet (NMR signal)
TBTU O-(Benzotriazol-1-yl)-N,N,N',N'-tetramethyluronium tetrafluoroborate
TLC Thin layer chromatography
TEA Triethylamine
TFA Trifluoroacetic acid
THF Tetrahydrofuran
Xantphos 4,5-Bis(diphenylphosphino)-9,9-dimethylxanthene
X-Phos 2-Dicyclohexylphosphino-2',4',6'-triisopropylbiphenyl LCMS Methods

| Method A | | |
|---|---|---|
| Column | X-bridge C18, 50 × 4.6 mm, 3.51 μm or equivalent | |
| Mobile Phase | (A) 0.1% Ammonia in water; (B) 0.1% Ammonia in MeCN | |
| Flow Rate | 1.0 ml/min | |
| Gradient | Time (min) | % B |
| | 0.01 | 5 |
| | 5.00 | 90 |
| | 5.80 | 95 |
| | 7.20 | 95 |
| | 7.21 | 5 |
| | 10.00 | 5 |

| Method B | | |
|---|---|---|
| Column | BEH C18, 50 × 2.1 mm, 1.71 μm or equivalent | |
| Mobile Phase | (A) 5 mM Ammonium acetate + 0.1% Formic acid in water (B) 0.1% Formic acid in MeCN | |
| Flow Rate | 0.45 ml/min | |
| Gradient | Time (min) | % B |
| | 0.01 | 2 |
| | 0.50 | 2 |
| | 5.00 | 90 |
| | 6.00 | 95 |
| | 7.00 | 95 |
| | 7.01 | 2 |
| | 8.00 | 2 |

| Method C | | |
|---|---|---|
| Column | BEH C18, 50 × 2.1 mm, 1.7 μm or equivalent | |
| Mobile Phase | (A) 5 mM Ammonium acetate + 0.1% Formic acid in water (B) 0.1% Formic acid in MeCN | |
| Flow Rate | 0.55 ml/min | |
| Gradient | Time (min) | % B |
| | 0.01 | 5 |
| | 0.40 | 5 |
| | 0.80 | 35 |
| | 1.20 | 55 |
| | 2.50 | 100 |
| | 3.30 | 100 |
| | 3.31 | 5 |
| | 4.00 | 5 |

| Method D | | |
|---|---|---|
| Column | Agilent TC-C18, 50 × 2.1 mm, 5 μm or equivalent | |
| Mobile Phase | (A) 0.04% TFA in water; (B) 0.02% TFA in MeCN | |
| Flow Rate | 1 ml/min | |
| Gradient | Time (min) | %B |
| | 0.1 | 10 |
| | 5.00 | 90 |
| | 7.00 | 100 |
| | 11.00 | 100 |
| | 11.01 | 10 |
| | 12.00 | 10 |

| Method E | | |
|---|---|---|
| Column | X-Bridge C18, 250 × 4.6 mm, 5 μm or equivalent | |
| Mobile Phase | (A) 10mM Ammonium acetate in water; (B) MeCN | |
| Flow Rate | 1 ml/min | |
| Gradient | Time (min) | % B |
| | 0.1 | 10 |
| | 10 | 40 |
| | 20 | 70 |
| | 25 | 90 |
| | 30 | 90 |
| | 30.01 | 10 |

| Method F | | |
|---|---|---|
| Column | X-Bridge C18, 250 × 4.6 mm, 5 μm or equivalent | |
| Mobile Phase | (A) 0.1% Ammonia in water; (B) 0.1% Ammonia in MeCN | |
| Flow Rate | 1 ml/min | |
| Gradient | Time (min) | % B |
| | 0.01 | 5 |
| | 5.00 | 5 |
| | 10.00 | 30 |
| | 15.00 | 30 |
| | 25.00 | 60 |
| | 30.00 | 90 |
| | 35.00 | 90 |
| | 35.01 | 5 |
| | 40.00 | 5 |

| Method G | | |
|---|---|---|
| Column | X-Bridge C18, 250 × 4.6 mm, 5 μm or equivalent | |
| Mobile Phase | (A) 0.04% TFA in water; (B) 0.02% TFA in MeCN | |
| Flow Rate | 1 ml/min | |
| Gradient | Time (min) | % B |
| | 0.01 | 5 |
| | 5.00 | 5 |
| | 10.00 | 30 |
| | 15.00 | 30 |
| | 25.00 | 60 |
| | 30.00 | 90 |
| | 35.00 | 90 |
| | 35.01 | 5 |
| | 40.00 | 5 |

| Method H | | |
|---|---|---|
| Column | Agilent TC-C18, 50 × 2.1 mm, 5 μm or equivalent | |
| Mobile Phase | (A) 0.04% TFA in water; (B) 0.02% TFA in MeCN | |
| Flow Rate | 0.8 ml/min | |
| Gradient | Time (min) | % B |
| | 0.00 | 1 |
| | 0.40 | 1 |
| | 3.40 | 100 |
| | 4.00 | 100 |
| | 4.01 | 1 |
| | 4.50 | 1 |

| Method I | | |
|---|---|---|
| Column | XBridge ShieldRP18, 50 × 2.1 mm, 5 um or equivalent | |
| Mobile Phase | (A) 0.05% Ammonia in water; (B) MeCN | |
| Flow Rate | 0.80 ml/min | |
| Gradient | Time (min) | %B |
| | 0.00 | 0 |
| | 0.40 | 5 |
| | 3.40 | 100 |
| | 4.00 | 100 |
| | 4.01 | 5 |
| | 4.50 | 5 |

| Method J | | |
|---|---|---|
| Column | Agilent TC-C18, 50 × 2.1 mm, 5 μm | |
| Mobile Phase | (A) 0.04% TFA in water; (B) 0.02% TFA in MeCN | |
| Flow Rate | 0.8 ml/min | |
| Gradient | Time (min) | % B |
| | 0 | 0 |
| | 0.4 | 0 |
| | 3.4 | 100 |
| | 4 | 100 |
| Temperature | 40° C. | |

| Method K | | |
|---|---|---|
| Column | Agilent TC-C18, 50 × 2.1 mm, 5 μm or equivalent | |
| Mobile Phase | (A) 0.04% TFA in water; (B) 0.02% TFA in MeCN | |
| Flow Rate | 0.80 ml/min | |
| Gradient | Time (min) | % B |
| | 0.01 | 10 |
| | 3.40 | 100 |
| | 4.00 | 100 |
| | 4.01 | 10 |
| | 4.50 | 10 |

| Chiral HPLC Method Y | | |
|---|---|---|
| Column | Chiralpak IC, 250 × 4.6 mm, 51 μm or equivalent | |
| Mobile Phase | (A) 0.1% TFA in hexane; (B) 0.1% TFA in IPA | |
| Flow Rate | 1.0 ml/min | |
| Gradient | Time (min) | % B |
| | 0.01 | 20 |
| | 3.0 | 20 |
| | 5.0 | 55 |
| | 15.0 | 70 |
| | 25.0 | 70 |

| Chiral HPLC Method Z | | |
|---|---|---|
| Column | Chiralpak ID, 250 × 4.6 mm, 5 μm or equivalent | |
| Mobile Phase | (A) 0.1% DEA in hexane; (B) 0.1% DEA in EtOH | |
| Flow Rate | 1.0 ml/min | |
| Gradient | Time (min) | % B |
| | 0.01 | 20 |
| | 3.0 | 20 |

-continued

Chiral HPLC Method Z

| | |
|---|---|
| 5.0 | 55 |
| 15.0 | 85 |
| 25.0 | 85 | reaction mixture was concentrated. The residue was purified by flash silica gel chromatography (ISCO®; 220 g Sepa-Flash® Silica Flash Column, eluent of 0~5% MeOH/DCM gradient @ 65 ml/min) to get tert-butyl 3-(3-hydroxy-1H-pyrazol-5-yl) pyrrolidine-1-carboxylate (31.6 mmol). $^1$H NMR (400 MHz, DMSO-d6) δ ppm 10.52 (brs, 2H), 5.29 (s, 1H), 3.60-3.56 (m, 1H), 3.39-3.33 (m, 1H), 3.28-3.13 (m, 3H), 2.14-2.11 (m, 1H), 1.92-1.85 (m, 1H), 1.40 (s, 9H).

Scheme 1

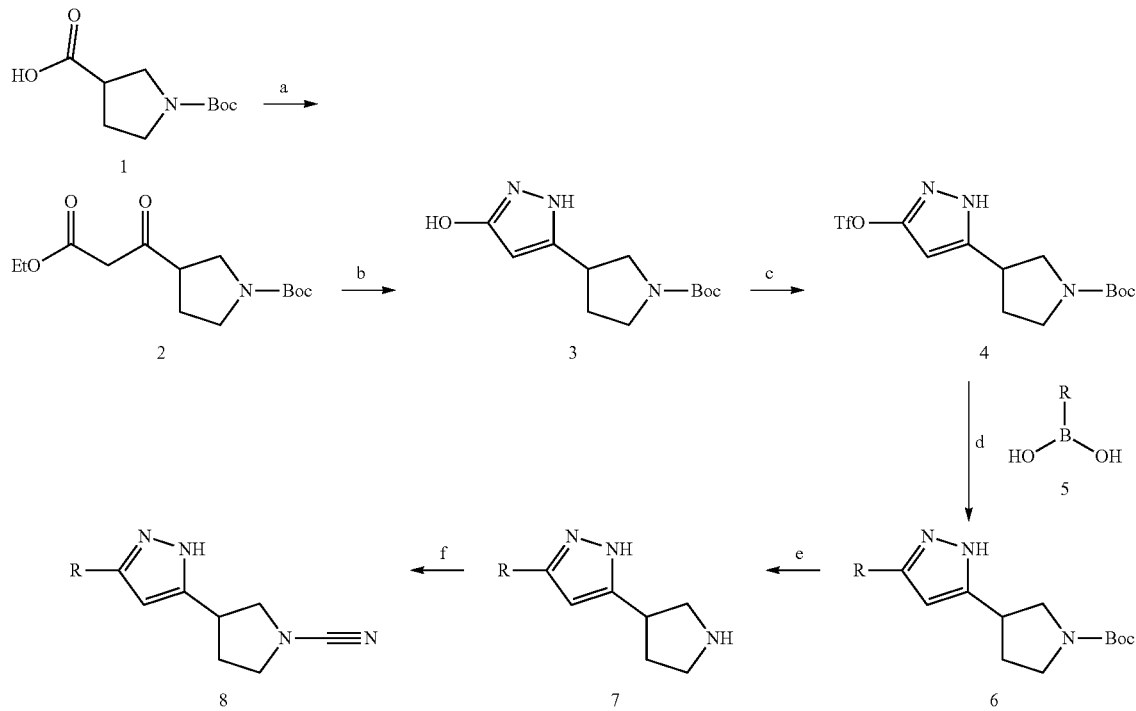

Reagents and conditions: a) 3-ethoxy-3-oxo-propanoic acid, CDI, i-PrMgCl, THF, 0-40° C., 34 h; b) anhydrous hydrazine, EtOH, rt, 2 h; c) N,N-Bis(trifluoromethylsulfonyl)aniline, DIPEA, DCM, rt to 40° C., 4 h; d) Pd(dppf)Cl$_2$, dppf, K$_3$PO$_4$, 1,4-dioxane, water, 110° C., 16 h; e) HCl/EtOAc, rt, 2 h; f) cyanogen bromide, NaHCO$_3$, EtOH, rt, 16 h.

Step a. (i) A mixture of 1-(tert-butoxycarbonyl) pyrrolidine-3-carboxylic (62.92 mmol) acid in THF (100 ml) was added CDI (111.5 mmol), the reaction mixture was stirred at rt for 16 h to yield a crude intermediate. (ii) A solution of 3-ethoxy-3-oxo-propanoic acid (139.4 mmol) in THF (100 ml) was cooled to 0° C. under N$_2$ and then i-PrMgCl (278.8 mmol) was added dropwise at this temperature. After addition the mixture was stirred at 0° C. for 30 min, rt for 30 min and 40° C. for 30 min. (iii) The solution from part (ii) was cooled to 0° C. and treated with the solution from part (i), and the mixture was stirred at rt for 16 h. The reaction mixture was cooled to 0° C. and ice-cool 1.0 M H$_3$PO$_4$ (400 ml) was added to the mixture. After 5 min, the mixture was extracted with EtOAc (3×400 ml). The combined organic extracts were washed with saturation NaHCO$_3$ (400 ml) and brine (400 ml) dried over MgSO$_4$, filtered and concentrated to give the crude tert-butyl 3-(3-ethoxy-3-oxopropanoyl)-pyrrolidine-1-carboxylate (101.63 mmol), which was used for the next step without further purification.

Step b. To a solution of tert-butyl 3-(3-ethoxy-3-oxopropanoyl)pyrrolidine-1-carboxylate (70.1 mmol) in EtOH (300 ml), anhydrous hydrazine (77.1 mmol) was added dropwise, the reaction mixture was stirred at rt for 2 h. The Step c. To a stirred solution of tert-butyl 3-(3-hydroxy-1H-pyrazol-5-yl)pyrrolidine-1-carboxylate (31.58 mmol) and DIPEA (94.74 mmol) in DCM (80 ml) was added N,N-bis(trifluoromethylsulfonyl)aniline at rt, and then the reaction mixture was heated to 40° C. and stirred for 4 h. The reaction mixture was concentrated under reduced pressure to give a residue. The residue was purified by flash silica gel chromatography (ISCO®; 220 g SepaFlash® Silica Flash Column, eluent of 20-30% EtOAc/PE gradient at 70 ml/min) to provide tert-butyl 3-(3-(((trifluoromethyl)-sulfonyl)oxy)-1H-pyrazol-5-yl)pyrrolidine-1-carboxylate (22.06 mmol). $^1$H NMR (400 MHz, DMSO-d6) δ ppm 13.07 (s, 1H), 6.23 (s, 1H), 3.70-3.65 (m, 1H), 3.45-3.20 (m, 4H), 2.20-2.18 (m, 1H), 1.99-1.92 (m, 1H), 1.40 (s, 9H).

Step d. To a solution of Compound 5 (0.2 mmol), tert-butyl 3-(3-(((trifluoromethyl)sulfonyl)oxy)-1H-pyrazol-5-yl)-pyrrolidine-1-carboxylate (0.2 mmol) and K$_3$PO$_4$ (0.6 mmol, 3 eq) in 1,4-dioxane (1 ml) and water (0.2 ml) were added Pd(dppf)Cl$_2$ (0.2 eq) and dppf (0.2 eq) at it under nitrogen. The reaction mixture was stirred at 110° C. for 16 h. The resulting mixture was concentrated under reduced pressure. The resulting residue was purified by preparative TLC (PE/EtOAc=3:1) yielding Compound 6.

Step e. To a solution of Compound 6 in EtOAc (1 ml) was added 4 M HCl/EtOAc (1 ml). The reaction mixture was stirred at it for 2 h. The resulting mixture was concentrated under reduced pressure. The residue Compound 7 was used for the next step directly without further purification.

Step f. To a solution of Compound 7 in EtOH (2 ml) was added cyanogen bromide (0.2 mmol) and NaHCO₃ (0.6 mmol). The reaction mixture was stirred at rt for 16 h. The resulting mixture was concentrated under reduced pressure. The crude was purified by preparative reverse phase HPLC (A: 0.078% CH₃COONH₄ in water, B: MeCN) to afford the desired Compound 8.

Compounds in Table 1 were synthesised using the method as exemplified by Scheme 1.

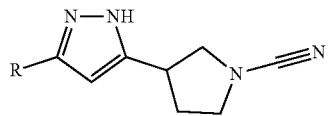

TABLE 1

| Ex | R | Name | LCMS Method | LCMS RT (min) | MS (ES+) |
|---|---|---|---|---|---|
| 1 | (3-cyanophenyl) | 3-(3-(3-Cyanophenyl)-1H-pyrazol-5-yl)pyrrolidine-1-carbonitrile | H | 2.34 | 264 |
| 2 | (4-cyanophenyl) | 3-(3-(4-Cyanophenyl)-1H-pyrazol-5-yl)pyrrolidine-1-carbonitrile | H | 2.30 | 264 |
| 3 | (N-methylpicolinamide) | 5-(5-(1-cyanopyrrolidin-3-yl)-1H-pyrazol-3-yl)-N-methylpicolinamide | I | 1.92 | 297 |
| 4 | (4-carbamoylphenyl) | 4-(5-(1-Cyanopyrrolidin-3-yl)-1H-pyrazol-3-yl)benzamide | I | 1.51 | 282 |
| 5 | (4-(4-methylpiperazin-1-yl)phenyl) | 3-(3-(4-(4-Methylpiperazin-1-yl)phenyl)-1H-pyrazol-5-yl)pyrrolidine-1-carbonitrile | H | 1.89 | 337 |
| 6 | (3-carbamoylphenyl) | 3-(5-(1-Cyanopyrrolidin-3-yl)-1H-pyrazol-3-yl)benzamide | I | 1.95 | 282 |
| 7 | (3-acetamidophenyl) | N-(3-(5-(1-Cyanopyrrolidin-3-yl)-1H-pyrazol-3-yl)phenyl)acetamide | I | 1.76 | 296 |

TABLE 1-continued

| Ex | R | Name | LCMS Method | LCMS RT (min) | MS (ES+) |
|---|---|---|---|---|---|
| 8 | (3-dimethylcarbamoyl-phenyl) | 3-(5-(1-cyanopyrrolidin-3-yl)-1H-pyrazol-3-yl)-N,N-dimethylbenzamide | I | 1.79 | 310 |
| 9 | (4-acetamidophenyl) | N-(4-(5-(1-Cyanopyrrolidin-3-yl)-1H-pyrazol-3-yl)phenyl)acetamide | I | 1.69 | 296 |
| 10 | (4-(morpholinosulfonyl)phenyl) | 3-(3-(4-(Morpholinosulfonyl)phenyl)-1H-pyrazol-5-yl)pyrrolidine-1-carbonitrile | I | 2.02 | 388 |
| 11 | (2-methylpyridin-4-yl) | 3-(3-(2-Methylpyridin-4-yl)-1H-pyrazol-5-yl)pyrrolidine-1-carbonitrile | I | 2.02 | 254 |
| 12 | (3-(piperidin-1-yl)phenyl) | 3-(3-(3-(Piperidin-1-yl)phenyl)-1H-pyrazol-5-yl)pyrrolidine-1-carbonitrile | H | 1.91 | 322 |
| 13 | (3-(morpholinosulfonyl)phenyl) | 3-(3-(3-Morpholinosulfonyl)phenyl)-1H-pyrazol-5-yl)pyrrolidine-1-carbonitrile | I | 2.29 | 388 |

Example 14 3-(3-([1,1'-Biphenyl]-3-yl)-1H-pyrazol-5-yl)pyrrolidine-1-carbonitrile

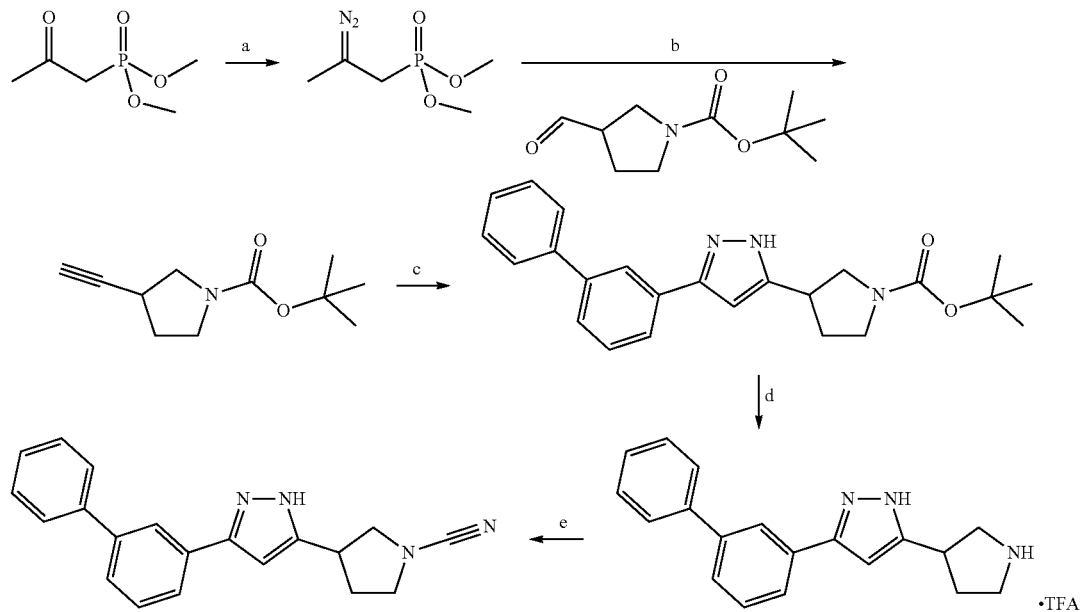

Step a. To a suspension of sodium hydride (60% dispersion in mineral oil, 2.1 g, 53.0 mmol) in THF (125 ml) was drop wise added a solution of dimethyl (2-oxopropyl)phosphonate (CAS Number 4202 14-6; 8 g, 48.2 mmol) in THF (125 ml) at 0° C. The reaction mixture was stirred at 0° C. for 1 h. 4-Methylbenzenesulfonyl azide (CAS Number 941-55-9; 10 g, 51.0 mmol) was added to the reaction mixture at 0° C. The reaction mixture was stirred at 0° C. for 1 h. The resulting reaction mixture was filtered through celite hyflow and the resulting filtrate was concentrated under reduced pressure. The resulting residue was purified by flash chromatography (4-5% EtOAc in hexane) yielding dimethyl (1-diazo-2-oxopropyl)phosphonate (6.0 g, 31.2 mmol). LCMS: Method C, 1.234 min, MS: ES+193.09; $^1$H NMR (400 MHz, CDCl$_3$) δ ppm 3.89 (s, 3H), 3.85 (s, 3H), 2.29 (s, 3H).

Step b. To a solution of 3-formyl-pyrrolidine-1-carboxylic acid tert-butyl ester (CAS Number 59379 02-1; 1 g, 5.02 mmol) in MeOH (20 ml) were added K$_2$CO$_3$ (1.38 g, 10.0 mmol), dimethyl (1-diazo-2-oxopropyl)phosphonate (1.15 g, 6.02 mmol) and silica (60-120 mesh, 2 g) at 0° C. The reaction mixture was stirred at rt for 2 h. The resulting reaction mixture was combined with one other batch prepared by an identical method on the same scale. The resulting reaction mixture was filtered under vacuum and the resulting filtrate was concentrated under reduced pressure. The resulting residue was purified by flash chromatography (4-5% EtOAc in hexane) yielding tert-butyl 3-ethynylpyrrolidine-1-carboxylate (1.2 g, 6.150 mmol). LCMS: Method C, 2.189 min, MS: ES+196.3; $^1$H NMR (400 MHz, CDCl$_3$) δ ppm 3.45-3.71 (m, 2H), 3.23-3.40 (m, 2H), 2.92-2.991 (m, 1H), 2.10-2.20 (m, 2H), 1.91-2.00 (m, 1H), 1.47 (s, 9H).

Step c. A solution of biphenyl-3-carboxaldehyde (CAS Number 1204-60-0; 0.2 g, 1.097 mmol) and 4-methylbenzenesulfonohydrazide (CAS Number 1576-35-8; 0.204 g, 1.097 mmol) in MeCN (10 ml) was stirred at rt for 2 h. 5 M NaOH (0.23 ml, 1.10 mmol) was added to the reaction mixture at rt. The reaction mixture was stirred at rt for 20 min. Tert-butyl 3-ethynylpyrrolidine-1-carboxylate (0.43 g, 2.19 mmol) was added to the reaction mixture at rt. The reaction mixture was heated at 50° C. for 15 h. The resulting reaction mixture was cooled to rt and poured into water (20 ml). The obtained mixture was extracted with EtOAc (3×20 ml). The combined organic phase was collected, dried over Na$_2$SO$_4$, filtered and concentrated under reduced pressure. The resulting residue was purified by flash chromatography (35% EtOAc in hexane) yielding tert-butyl 3-(3-([1,1'-biphenyl]-3-yl)-1H-pyrazol-5-yl)pyrrolidine-1-carboxylate (0.105 g, 0.269 mmol). LCMS: Method C, 2.667 min, MS: ES+390.4; $^1$H NMR (400 MHz, DMSO-d6, 80° C.) δ ppm 12.78-13.08 (m, 1H), 8.04 (S, 1H), 7.68-7.81 (m, 3H), 7.53-7.63 (m, 1H), 7.48-7.55 (m, 3H), 7.40 (t, J=7.2 Hz, 1H), 6.72 (s, 1H), 3.63-3.71 (m, 1H), 3.32-3.45 (m, 4H), 2.24-2.35 (m, 1H), 1.99-2.03 (m, 1H), 1.421 (s, 9H).

Step d. To a solution of tert-butyl 3-(3-([1,1'-biphenyl]-3-yl)-1H-pyrazol-5-yl)pyrrolidine-1-carboxylate (0.1 g, 0.256 mmol) in DCM (10 ml) was added TFA (0.5 ml) at rt. The reaction mixture was stirred at rt for 5 h. The resulting reaction mixture was concentrated under reduced pressure to yield 3-([1,1'-biphenyl]-3-yl)-5-(pyrrolidin-3-yl)-1H-pyrazole TFA salt (0.11 g, quantitative). This material was directly used for the next step without further purification.

Step e. To a solution of 3-([1,1'-biphenyl]-3-yl)-5-(pyrrolidin-3-yl)-1H-pyrazole TFA salt (0.1 g, 0.248 mmol) in THF (3 ml) was added K$_2$CO$_3$ (0.14 g, 0.992 mmol) at rt. The resulting reaction mixture was stirred at rt for 15 min. Cyanogen bromide (0.04 g, 0.372 mmol) was added to the reaction mixture at rt. The reaction mixture was stirred at rt for 30 min. The resulting reaction mixture was poured into water (25 ml) and extracted with EtOAc (3×25 ml). The combined organic phase was dried over Na$_2$SO$_4$, filtered and concentrated under reduced pressure. The resulting residue was purified by flash chromatography (50% EtOAc in hexane) yielding the title compound (0.075 g, 0.238 mmol). LCMS: Method B, 4.360 min, MS: ES+315; $^1$H NMR (400 MHz, DMSO-d6, 80° C.) δ ppm 12.70-13.02 (m, 1H), 8.03

(s, 1H), 7.70-7.78 (m, 3H), 7.58-7.63 (m, 1H), 7.47-7.55 (m, 3H), 7.40 (t, J=7.2 Hz, 1H), 6.71 (s, 1H), 3.71-3.81 (m, 1H), 3.45-3.61 (m, 4H), 2.25-2.38 (m, 1H), 2.04 2.18 (m, 1H).

Example 15 3-(3-([1,1'-Biphenyl]-3-yl)-4-fluoro-1H-pyrazol-5-yl)pyrrolidine-1-carbonitrile

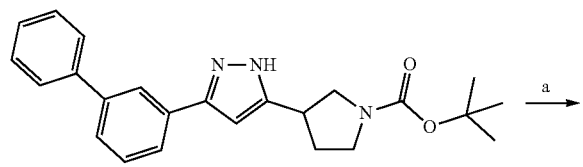

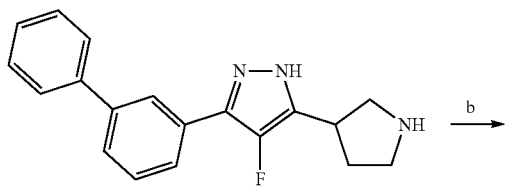

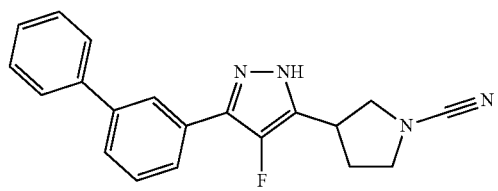

Step a. A solution of tert-butyl 3-(3-([1,1'-biphenyl]-3-yl)-1H-pyrazol-5-yl)pyrrolidine-1-carboxylate (Example 14, step c) (0.26 g, 0.67 mmol) and 1-chloromethyl-4-fluoro-1,4-diazoniabicyclo[2.2.2]octane bis(tetrafluoroborate) (CAS Number 140681-55-6; 0.24 g, 0.67 mmol) in MeCN (5 ml) was heated in microwave at 90° C. for 1 h. The resulting reaction mixture was cooled to rt and concentrated under reduced pressure yielding 3-([1,1'-biphenyl]-3-yl)-4-fluoro-5-(pyrrolidin-3-yl)-1H-pyrazole (0.49 g, quantitative). LCMS: Method C, 1.945 min, MS: ES+308.23. This material was used for the next step without further purification.

Step b. The title compound was synthesised from the intermediate above using a procedure similar to that described for Example 14, step e. LCMS: Method A, 4.944 min, MS: ES+333.14; $^1$H NMR (400 MHz, DMSO-d6, 80° C.) δ ppm 12.81-13.11 (m, 1H), 7.98 (s, 1H), 7.49-7.73 (m, 7H), 7.40-7.43 (m, 1H), 3.71-3.80 (m, 1H), 3.47-3.61 (m, 4H), 2.30-2.33 (m, 1H), 2.11-2.17 (m, 1H).

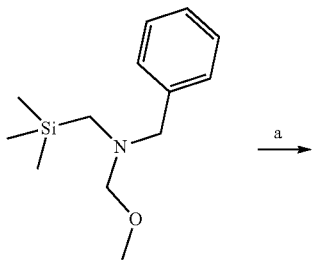

The obtained racemic material was subjected to enantiomeric separation by preparative chiral HPLC, using 0.1% DEA in hexane and 0.1% DEA in EtOH to provide the following enantiomers (absolute stereochemistry was not determined):

Example 16 3-(3-([1,1'-Biphenyl]-3-yl)-4-fluoro-1H-pyrazol-5-yl)pyrrolidine-1-carbonitrile: Enantiomer 1

LCMS: Method A, 5.028 min, MS: ES+333.08; Chiral SFC: CHIRALPAK IF 250×4.6 mm 5 μm, mobile phase: (A) Liquid carbon dioxide; (B) MeOH, column flow was 4.0 ml/min and ABPR was 150 bar, isocratic gradient of 50% B over 12 min, RT 7.7 min; $^1$H NMR (400 MHz, DMSO-d6) δ ppm 12.86-13.20 (m, 1H), 7.98 (s, 1H), 7.66-7.72 (m, 4H), 7.57-7.60 (m, 1H), 7.49-7.53 (m, 2H), 7.41-7.43 (m, 1H), 3.76-3.80 (m, 1H), 3.49-3.61 (m, 4H), 2.28-2.33 (m, 1H), 2.08-2.13 (m, 1H).

Example 17 3-(3-([1,1'-Biphenyl]-3-yl)-4-fluoro-1H-pyrazol-5-yl)pyrrolidine-1-carbonitrile: Enantiomer 2

LCMS: Method A, 5.019 min, MS: ES+333.08; Chiral SFC: CHIRALPAK IF 250×4.6 mm 5 μm, mobile phase: (A) Liquid carbon dioxide; (B) MeOH, column flow was 4.0 ml/min and ABPR was 150 bar, isocratic gradient of 50% B over 12 min, RT 5.17 min; $^1$H NMR (400 MHz, DMSO-d6) δ ppm 12.86-13.20 (m, 1H), 7.98 (s, 1H), 7.66-7.72 (m, 4H), 7.57-7.60 (m, 1H), 7.49-7.53 (m, 2H), 7.39-7.43 (m, 1H), 3.76-3.80 (m, 1H), 3.47-3.61 (m, 4H), 2.26-2.33 (m, 1H), 2.08-2.13 (m, 1H).

Example 18 3-(3-(Naphthalen-2-yl)-1H-pyrazol-5-yl)pyrrolidine-1-carbonitrile

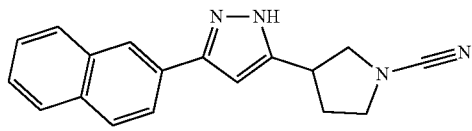 [SMILES: N#CN1CCC(c2cc(-c3ccc4ccccc4c3)n[nH]2)C1]

The title compound was synthesised using a procedure similar to that described for Example 14. LCMS: Method B, 4.174 min, MS: ES+289.19; $^1$H NMR (400 MHz, DMSO-d6) δ ppm 12.89-13.24 (m, 1H), 8.28 (s, 1H), 7.92-8.08 (m, 4H), 7.52 (br s, 2H), 6.79 (s, 1H), 3.74-3.78 (m, 1H), 3.42 3.53 (m, 4H), 2.29-2.33 (m, 1H), 1.99-2.12 (m, 1H).

Example 19 Trans-3-(3-([1,1'-biphenyl]-3-yl)-1H-pyrazol-5-yl)-4-methylpyrrolidine-1-carbonitrile

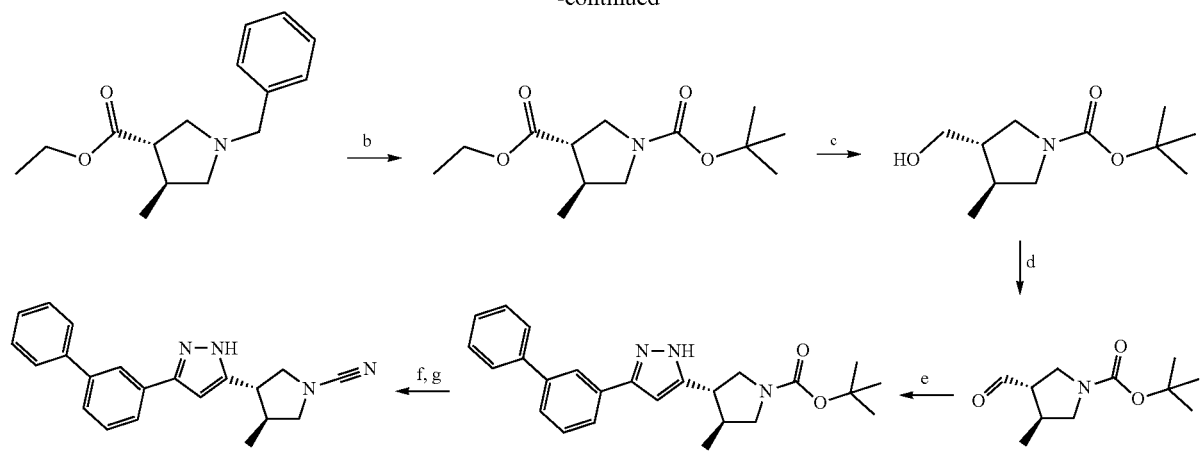

Step a. A solution of ethyl crotonate (CAS Number 623-70-1; 2.0 g, 17.5 mmol) and N-benzyl-O-ethyl-N-((trimethylsilyl)methyl)hydroxylamine (CAS Number 93102-05-7; 4.5 g, 19.3 mmol) in toluene (40 ml) was stirred at it for 5 min. TFA (1.9 g, 17.54 mmol) was added drop wise to the reaction mixture at rt. The reaction mixture was stirred at 50° C. for 16 h. The resulting reaction mixture was poured into water (100 ml) and basified with solid NaHCO$_3$. The resulting mixture was extracted with EtOAc (2×180 ml). The combined organic phase was dried over Na$_2$SO$_4$, filtered and concentrated under reduced pressure. The resulting residue was purified by column chromatography (9% EtOAc in hexane) yielding trans ethyl 1-benzyl-4-methylpyrrolidine-3-carboxylate (2.5 g, 10.121 mmol). LCMS: Method C, 1.503 min, MS: ES+248.33; $^1$H NMR (400 MHz, CDCl$_3$) δ ppm 7.24-7.36 (m, 5H), 4.12-4.15 (m, 2H), 3.57-3.74 (m, 2H), 2.77-2.92 (m, 3H), 2.48-2.59 (m, 2H), 2.21-2.26 (m, 1H), 1.27 (t, J=6.4 Hz, 3H), 1.16 (d, J=6.4 Hz, 3H).

Step b. To a solution of trans ethyl 1-benzyl-4-methylpyrrolidine-3-carboxylate (2.5 g, 10.121 mmol) in EtOH (30 ml) were added polymethyl hydrosiloxane (2.5 g, 1.0 w/w), 20% Pd(OH)$_2$ on carbon (dry basis) (1.25 g, 0.5 w/w) and BOC anhydride (4.4 g, 20.24 mmol) at 0° C. The reaction mixture was stirred at rt for 1.5 h. The resulting reaction mixture was carefully filtered through celite hyflow and the filtrate was concentrated under reduced pressure. The resulting residue was purified by column chromatography (9% EtOAc in hexane) yielding trans 1-(tert-butyl) 3-ethyl 4-methylpyrrolidine-1,3-dicarboxylate (2.2 g, 8.56 mmol). LCMS: Method C, 2.277 min, MS: ES+202.2 (M-56); $^1$H NMR (400 MHz, CDCl$_3$) δ ppm 4.15-4.21 (m, 2H), 3.61-3.77 (m, 2H), 3.47-3.55 (m, 1H), 2.89-2.97 (m, 1H), 2.57-2.67 (m, 1H), 2.44-2.53 On, 1H), 1.47 (s, 9H), 1.27-1.31 (m, 3H), 1.23 (t, J=5.2 Hz, 3H).

Step c. To a stirred solution of trans 1-(tert-butyl) 3-ethyl 4-methylpyrrolidine-1,3-dicarboxylate (2.0 g, 7.78 mmol) in THF (20 ml) was added lithium aluminium hydride (1 M in THF) (3.89 ml, 3.89 mmol) drop wise at 0° C. The resulting reaction mixture was stirred at rt for 16 h. The reaction mixture was poured into EtOAc (100 ml) and then diluted with water (100 ml). The resulting reaction mixture was filtered through a celite bed. The organic phase was separated and aqueous phase was re-extracted with EtOAc (50 ml). The combined organic phase was dried over Na$_2$SO$_4$, filtered and concentrated under reduced pressure to provide trans tert-butyl 3-(hydroxymethyl)-4-methylpyrrolidine-1-carboxylate (1.59 g, 7.39 mmol). This material was used directly in the next step without further purification. LCMS: Method C, 1.792 min, MS: ES+160.14 (M-56); $^1$H NMR (400 MHz, DMSO-d6) δ ppm 4.61-4.64 (m, 1H), 3.28-3.31 (m, 1H), 3.35-3.51 (m, 3H), 2.99 (q, J=8.8 Hz, 1H), 2.76 (q, J=10.8 Hz, 1H), 1.88-1.96 (m, 1H), 1.77-1.83 (m, 1H), 1.34 (s, 9H), 0.96 (d, J=6.4 Hz, 3H).

Step d. To a stirred solution of trans tert-butyl 3-(hydroxymethyl)-4-methylpyrrolidine-1-carboxylate (1.59 g, 7.39 mmol) in DCM (20 ml) was added Dess-Martin periodinane (6.29 g, 14.79 mmol) portion wise at 0° C. The reaction mixture was stirred at rt for 48 h. The resulting reaction mixture was filtered through celite hyflow, washed with DCM (50 ml) the filtrate was concentrated under vacuum. The resulting residue was purified by column chromatography (8% EtOAc in hexane) yielding trans tert-butyl 3-formyl-4-methylpyrrolidine-1-carboxylate (0.87 g, 4.08 mmol). LCMS: Method C, 1.720 min, MS: ES+158.14 (M-56).

Step e. A mixture of trans tert-butyl 3-formyl-4-methylpyrrolidine-1-carboxylate (0.35 g, 1.643 mmol) and p-toluene sulphonyl hydrazine (CAS Number 1576-35-8; 0.305 g, 1.643 mmol) in MeCN (10 ml) was stirred at rt for 2 h. Sodium hydroxide (0.131 g, 3.286 mmol) was added to the reaction mixture at it. The reaction mixture was stirred at rt for 20 min. A solution of 1-ethynyl-3-phenylbenzene (CAS Number 58650-11-6; 0.872 g, 4.929 mmol) in MeCN (2 ml) was added drop wise to the above reaction mixture at rt. The reaction mixture was heated at 80° C. for 16 h. The resulting reaction mixture was cooled to rt, poured into water (200 ml) and extracted with EtOAc (2×100 ml). The combined organic phase was dried over Na$_2$SO$_4$, filtered and concentrated under reduced pressure. The resulting residue was purified by column chromatography (30% EtOAc in hexane) yielding trans tert-butyl 3-(3-([1,1'-biphenyl]-3-yl)-1H-pyrazol-5-yl)-4-methyl pyrrolidine-1-carboxylate (0.19 g, 0.471 mmol). LCMS: Method C, 2.744 min, MS: ES+404.65; $^1$H NMR (400 MHz, DMSO-6) δ ppm 13.13 (s, 1H), 8.06 (s, 1H), 7.72-7.80 (m, 3H), 7.48-7.62 (m, 4H), 7.40 (s, 1H), 6.78 (s, 1H), 3.62-3.74 (m, 2H), 3.34-3.36 (m, 1H), 2.92-2.97 (m, 2H), 2.32-2.33 (m, 1H), 1.41 (d, J=4.8 Hz, 9H), 0.98 (s, 3H).

Steps f, g. The title compound was synthesised from the intermediate above using a procedure similar to that described for Example 14, steps d, e. LCMS: Method A, 4.808 min, MS: ES+329.08; ¹H NMR (400 MHz, DMSO-d6) δ ppm 13.18 (s, 1H), 8.05 (s, 1H), 7.70-7.80 (m, 3H), 7.56-7.65 (m, 1H), 7.45-7.53 (m, 3H), 7.37-7.42 (m, 1H), 6.80 (s, 1H), 3.78-4.04 (m, 1H), 3.68-3.72 (m, 1H), 3.52-3.57 (m, 1H), 3.10-3.14 (m, 1H), 3.02-3.07 (m, 1H), 2.33-2.37 (m, 1H), 1.00 (s, 3H).

The obtained racemic material was subjected to enantiomeric separation by Chiral SFC: CHIRALPAK AD-H 250× 21.0 mm, 5 μm, mobile phase: (A) Liquid carbon dioxide; (B) MeOH, column flow was 60.0 ml/min and ABPR was 100 bar which yielded the following enantiomers (absolute stereochemistry was not determined):

Example 20 Trans-3-(3-([1,1'-biphenyl]-3-yl)-1H-pyrazol-S yl)-4-methylpyrrolidine-1-carbonitrile: Enantiomer 1

LCMS: Method A, 4.906 min, MS: ES+329.02; Chiral SFC: CHIRALART SA 250×4.6 mm 5 μm, mobile phase: (A) Liquid carbon dioxide; (B) 0.1% DEA in MeOH, column flow was 4.0 ml/min and ABPR was 150 bar, 5% to 50% B over 5 min, followed by isocratic gradient of 50% B over 5 min, RT 6.2 min; ¹H NMR (400 MHz, DMSO-d6) δ ppm 13.18 (s, 1H), 8.05 (s, 1H), 7.72-7.80 (m, 3H), 7.49-7.65 (m, 4H), 7.37-7.45 (m, 1H), 6.80 (s, 1H), 3.78-3.82 (m, 1H), 3.68-3.72 (m, 1H), 3.53-3.57 (m, 1H), 3.02-3.14 (m, 2H), 2.32-2.40 (m, 1H), 1.02 (d, J=6.0 Hz, 3H).

Example 21 Trans-3-(3-([1,1'-biphenyl]-3-yl)-1H-pyrazol-5-yl)-4-methylpyrrolidine-1-carbonitrile: Enantiomer 2

LCMS: Method A, 4.906 min, MS: ES+329.02; Chiral SFC: CHIRALART SA 250×4.6 mm 5 μm, mobile phase: (A) Liquid carbon dioxide; (B) 0.1% DEA in MeOH, column flow was 4.0 ml/min and ABPR was 1.50 bar, 5% to 50% B over 5 min, followed by isocratic gradient of 50% B over 5 min, RT 6.61 min; ¹H NMR (400 MHz, DMSO-d6) δ ppm 13.19 (s, 1H), 8.05 (s, 1H), 7.72-7.77 (m, 3H), 7.49-7.65 (m, 4H), 7.37-7.43 (m, 1H), 6.80 (s, 1H), 3.78-3.82 (m, 1H), 3.68-3.72 (m, 1H), 3.50-3.57 (m, 1H), 3.02-3.12 (m, 2H), 2.33-2.37 (m, 1H), 1.02 (d, J=4.8 Hz, 3H).

Trans-3-(3-([1,1-biphenyl]-3-yl)-1H-pyrazol-5-yl)-4-methylpyrrolidine-1-carbonitrile

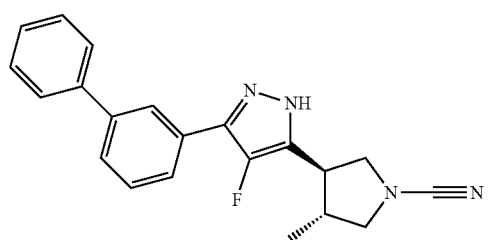 [SMILES: C[C@H]1CN(C#N)C[C@@H]1c1[nH]nc(-c2cccc(-c3ccccc3)c2)c1F]

The title compound was synthesised from tert-butyl 3-(3-([1,1'-biphenyl]-3-yl)-1H-pyrazol-5-yl)-4-methylpyrrolidine-1-carboxylate (Example 19, step e) using a procedure similar to that described for Example 15. The obtained racemic material was subjected to enantiomeric separation by preparative chiral HPLC to provide the following enantiomers (absolute stereochemistry was not determined):

Example 22 Trans-3-(3-([1,1'-biphenyl]-3-yl)-1H-pyrazol-5-yl)-4-methylpyrrolidine-1-carbonitrile: Enantiomer 1

LCMS: Method A, 5.243 min, MS: ES+347.18; Chiral SFC: CHIRALART SA 250×4.6 mm 5 μm, mobile phase: (A) Liquid carbon dioxide; (B) 0.1% DEA in MeOH, column flow was 3.0 ml/min and ABPR was 130 bar, isocratic gradient of 35% B over 10 min, RT 3.78 min.

Example 23 Trans-3-(3-([1,1'-biphenyl]-3-yl)-1H-pyrazol-5-yl)-4-methylpyrrolidine-1-carbonitrile: Enantiomer 2

LCMS: Method A, 5.282 min, MS: ES+347.11; Chiral SFC: CHIRALART SA 250×4.6 mm 5 μm, mobile phase: (A) Liquid carbon dioxide; (B) 0.1% DEA in MeOH, column flow was 3.0 ml/min and ABPR was 130 bar, isocratic gradient of 35% B over 10 min, RT 4.7 min.

Example 24 Trans tert-butyl 3-(3-([1,1'-biphenyl]-3-yl)-1-methyl-1H-pyrazol-5-yl)-4-methyl-pyrrolidine-1-carboxylate

Example 25 Trans tert-butyl 3-(5-([1,1'-biphenyl]-3-yl)-1-methyl-1H-pyrazol-3-yl)-4-methyl-pyrrolidine-1-carboxylate

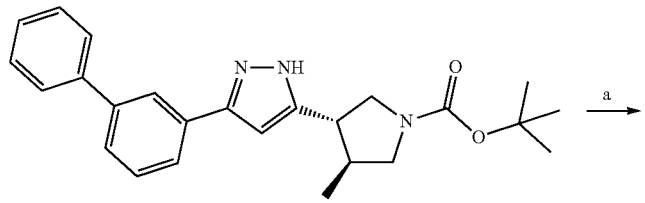

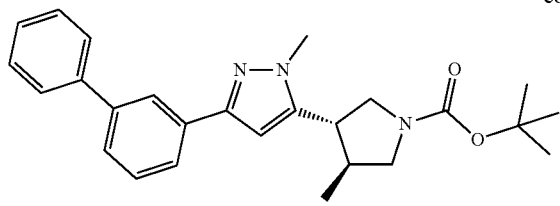
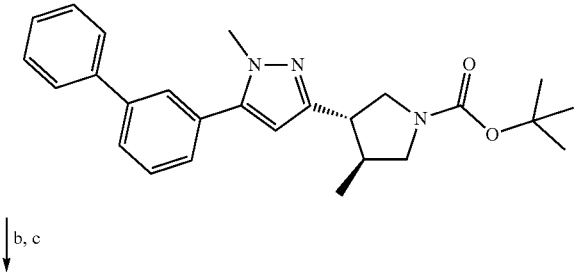

↓ b, c

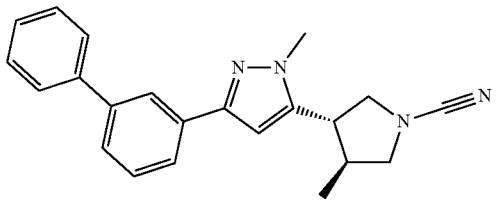

Example 24

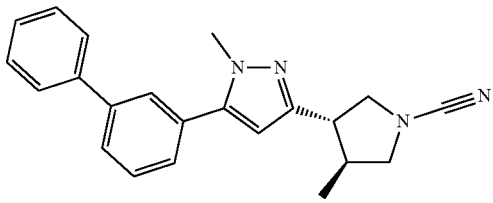

Example 25

Step a. To a stirred solution of tert-butyl 3-(3-([1,1'-biphenyl]-3-yl)-1H-pyrazol-5-yl)-4-methylpyrrolidine-1-carboxylate (Example 19, step e; 0.14 g, 0.347 mmol) in THF (6 ml) was added sodium hydride (60% dispersion; 0.042 g, 1.042 mmol) at 0° C. The reaction mixture was stirred at 60° C. for 2 h. The reaction mixture was cooled to rt. A solution of methyl iodide (0.148 g, 1.042 mmol) in THF (1 ml) was added to the reaction mixture and stirred for 2 h. The resulting reaction mixture was diluted with EtOAc (15 ml) and quickly poured into water (100 ml). The organic phase was separated and aqueous phase was re-extracted with EtOAc (2×25 ml). The combined organic phase was dried over $Na_2SO_4$, filtered and concentrated under reduced pressure yielding a mixture of trans tert-butyl 3-(5-([1,1'-biphenyl]-3-yl)-1-methyl-1H-pyrazol-3-yl)-4-methylpyrrolidine-1-carboxylate and trans tert-butyl 3-(3-([1,1'-biphenyl]-3-yl)-1-methyl-1H-pyrazol-5-yl)-4-methylpyrrolidine-1-carboxylate (0.15 g, quantitative). This material was used directly to the next step without further purification. LCMS: Method C, 2.987 min, 3.038 min, MS: ES+417.2.

Steps b, c. The title compound was synthesised from the intermediate above using a procedure similar to that described for Example 14, steps d, e. The mixture of regioisomers was separated by preparative HPLC to afford:

Example 24 LCMS: Method A, 5.109 min, MS: ES+343.05; $^1$H NMR (400 MHz, DMSO-d6) δ ppm 8.02 (s, 1H), 7.76 (d, J=8.0 Hz, 1H), 7.71 (d, J=7.2 Hz, 2H), 7.57 (d, J=8.0 Hz, 1H), 7.46-7.51 (m, 3H), 7.37-7.41 (m, 1H), 6.86 (s, 1H), 3.92 (t, J=8.4 Hz, 1H), 3.85 (s, 3H), 3.72-3.76 (m, 1H), 3.32-3.34 (m, 1H), 3.22-3.29 (m, 2H), 3.12-3.16 (m, 1H), 1.03 (d, J=6.8 Hz, 3H).

Example 25 LCMS: Method A, 5.184 min, MS: ES+343.05; $^1$H NMR (400 MHz, DMSO-d6) δ ppm 7.71-7.77 (m, 4H), 7.59 (t, J=7.6 Hz, 1H), 7.47-7.53 (m, 3H), 7.38-7.42 (m, 1H), 6.48 (s, 1H), 3.86 (s, 3H), 3.78 (t, J=8.4 Hz, 1H), 3.68 (t, J=8.4 Hz, 1H), 3.51 (t, J=9.2 Hz, 1H), 3.10 (t, J=9.2 Hz, 1H), 2.95-3.02 (m, 1H), 2.33-2.37 (m, 1H), 1.01 (d, J=6.4 Hz, 3H).

Scheme 2

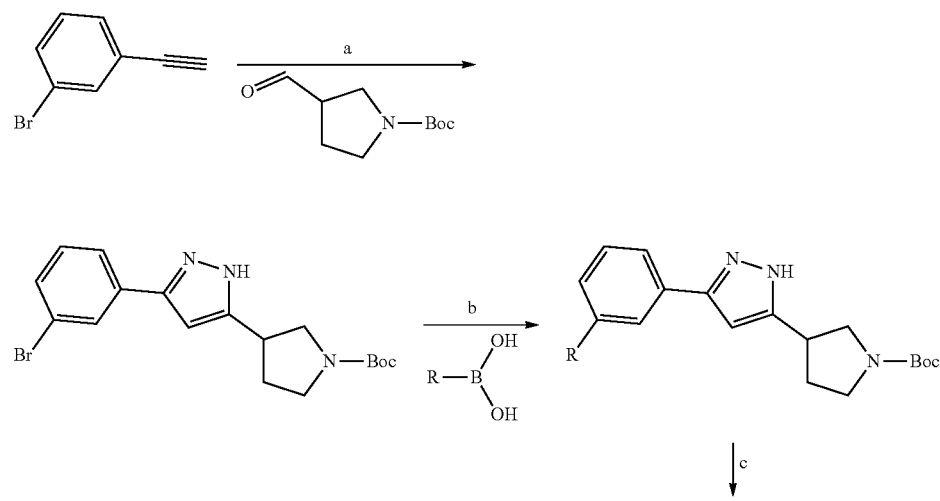

↓ c

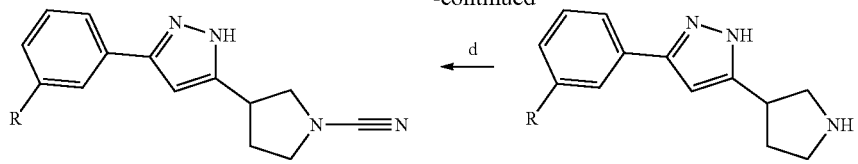

Reagents and conditions: a) (i) 1-BOC-pyrrolidine-3-carboxaldehyde, p-toluene sulphonyl hydrazine, MeCN, rt, 2 h (ii) NaOH, rt, 20 min (iii) alkyne, 80° C., 16 h; b) Cs₂CO₃, Pd(PPh₃)₄, THF, water, 100° C., 16 h; c) TFA/DCM, rt, 1 h; d) cyanogen bromide, K₂CO₃, THF, rt, 1 h.

Example 26 3-(3-(3-(Pyridin-3-yl)phenyl)-1H-pyrazol-5-yl)pyrrolidine-1-carbonitrile (Prepared according to Scheme 2)

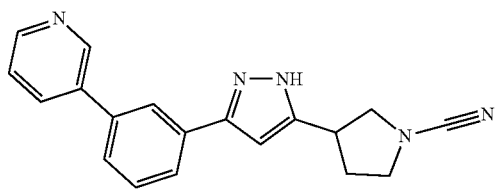 [SMILES: N#CN1CCC(c2cc(-c3cccc(-c4cccnc4)c3)n[nH]2)C1]

Step a. A mixture 1-BOC-pyrrolidine-3-carboxaldehyde (CAS Number 59379-02-1; 0.36 g, 1.81 mmol) and p-toluene sulphonyl hydrazine (CAS Number 1576-35-8; 0.336 g, 1.81 mmol) in MeCN (10 ml) was stirred at rt for 2 h. Sodium hydroxide (0.144 g, 3.62 mmol) was added to the reaction mixture at rt. The reaction mixture was stirred at rt for 20 min. A solution of 1-bromo-3-ethynylbenzene (CAS Number 766-81-4; 0.491 g, 2.71 mmol) in MeCN (2 ml) was added drop wise to the reaction mixture at rt. The reaction mixture was heated at 80° C. for 16 h. The resulting reaction mixture was cooled to rt, poured into water (200 ml) and extracted with EtOAc (2×30 ml). The combined organic phase was dried over Na₂SO₄, filtered and concentrated under reduced pressure. The resulting residue was purified by column chromatography (35% EtOAc in hexane) yielding tert-butyl 3-(3-(3-bromo-phenyl)-1H-pyrazol-5-yl)pyrrolidine-1-carboxylate (0.45 g, 1.15 mmol). LCMS: Method A, 5.240 min, MS: ES+392.0, 394.0; ¹H NMR (400 MHz, DMSO-d6) δ ppm 12.89 (s, 1H), 7.96 (s, 1H), 7.72-7.80 (m, 1H), 7.33-7.53 (m, 2H), 6.70 (d, J=17.2, 1H), 3.69-3.73 (m, 1H), 3.40-3.44 (m, 2H), 3.25-3.29 (m, 2H), 2.15-2.30 (m, 1H), 1.94-2.03 (m, 1H), 1.41 (s, 9H).

Step b. To a stirred solution of tert-butyl 3-(3-(3-bromophenyl)-1H-pyrazol-5-yl)pyrrolidine-1-carboxylate (0.15 g, 0.384 mmol) in THF:water (4:1; 10 ml) was added Cs₂CO₃ (0.374 g, 1.151 mmol) at rt. The reaction mixture was degassed for 10 min before addition of pyridine-3-boronic acid (CAS Number 1692-25-7; 0.094 g, 0.767 mmol) and Pd(PPh₃)₄ (0.022 g, 0.019 mmol). The reaction mixture was heated at 100° C. for 16 h. The resulting reaction mixture was cooled to rt, poured into water (50 ml) and extracted with EtOAc (3×50 ml). The combined organic phase was dried over Na₂SO₄, filtered and concentrated under reduced pressure. The resulting residue was purified by column chromatography (neutral aluminium oxide; column packed in hexane and EtOAc gradually increased to 100%) yielding tert-butyl 3-(3-(3-(pyridin-3-yl)phenyl)-1H-pyrazol-5-yl)pyrrolidine-1-carboxylate (0.18 g, quantitative). LCMS: Method C, 2.044 min, MS: ES+391.30; ¹H NMR (400 MHz, DMSO-d6) δ ppm 12.78 (br s, 1H), 8.97 (s, 1H), 8.60 (d, J=3.6 Hz, 1H), 8.15 (d, J=8.0 Hz, 1H), 8.10 (s, 1H), 7.81 (d, J=6.8 Hz, 1H), 7.66 (d, J=7.6 Hz, 1H), 7.51-7.56 (m, 2H), 6.77 (s, 1H), 3.65-3.73 (m, 1H), 3.43-3.50 (m, 2H), 3.27-3.32 (m, 2H), 2.20-2.28 (m, 1H), 2.02-2.06 (m, 1H), 1.42 (s, 9H).

Steps c, d. The title compound was synthesized from the intermediate above using a procedure similar to that described for Example 14, steps d, e. LCMS: Method A, 3.658 min, MS: ES+315.98; ¹H NMR (400 MHz, DMSO-d6) δ ppm 13.18 (s, 1H), 8.98 (d, J=18.0 Hz, 1H), 8.61 (s, 1H), 8.10-8.18 (m, 2H), 7.64-7.87 (m, 2H), 7.53-7.60 (m, 2H), 6.82 (s, 1H), 3.71-3.80 (m, 1H), 3.41-3.57 (m, 4H), 2.23-2.33 (m, 1H), 2.03-2.10 (m, 1H).

Example 27 4-(3-([1,1'-Biphenyl]-3-yl)-1H-pyrazol-5-yl)-2-methylpyrrolidine-1-carbonitrile

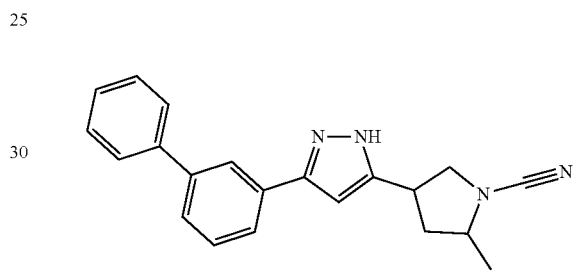

The title compound was synthesised using a procedure similar to that described for Example 26 using tert-butyl 4-formyl-2-methylpyrrolidine-1-carboxylate (CAS Number 1374657-82-5). LCMS: Method E, 5.25 min, MS: ES+352.01; ¹H NMR (400 MHz, DMSO-d6) δ ppm 8.15 (d, J=8.4 Hz, 1H), 7.70 (t, J=6.0 Hz, 1H), 7.62-7.63 (m, 2H), 7.53-7.56 (m, 1H), 7.46 (t, J=8.0 Hz, 1H), 7.38 (d, J=8.0 Hz, 1H), 4.23 (t, J=8.8 Hz, 2H), 3.57-3.67 (m, 2H), 3.44-3.49 (m, 3H), 3.23 (t, J=8.4 Hz, 2H), 1.18-2.25 (m, 1H), 2.05-2.12 (m, 1H).

Compounds in Table 2 were synthesised using the procedure as exemplified by Example 26.

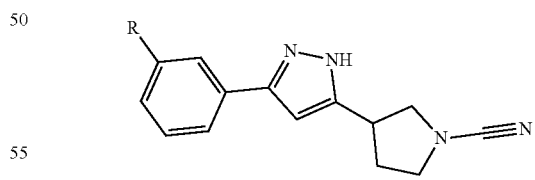

Compounds in Table 3 were synthesised using the procedure as exemplified by Example 26.

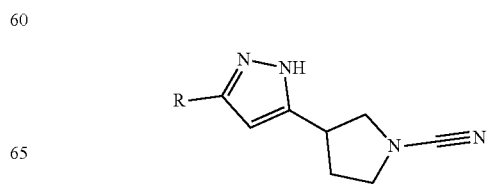

TABLE 2

| Ex | R | Name | LCMS Method | LCMS RT (min) | MS (ES+) | $^1$H NMR (400 MHz, DMSO-d6) δ ppm |
|---|---|---|---|---|---|---|
| 28 | 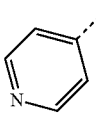 | 3-(3-(3-(Pyridin-4-yl)phenyl)-1H-pyrazol-5-yl)pyrrolidine-1-carbonitrile | A | 3.594 | 315.98 | 12.86-13.22 (m, 1 H), 8.68 (s, 2 H), 8.17 (s, 1 H), 7.70-7.79 (m, 4 H), 7.58-7.63 (m, 1 H), 6.48 (s, 1 H), 3.76 (s, 1 H), 3.43-3.52 (m, 4 H), 2.28-2.32 (m, 1 H), 1.91-2.09 (m, 1 H). |
| 29 | 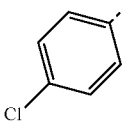 | 3-(3-(4'-Chloro-[1,1'-biphenyl]-3-yl)-1H-pyrazol-5-yl)pyrrolidine-1-carbonitrile | A | 5.001 | 348.98 | 12.85-13.18 (m, 1 H), 8.05 (s, 1 H), 7.71-7.80 (m, 3 H), 7.56-7.63 (m, 4 H), 6.78 (s, 1 H), 3.74-3.77 (m, 1 H), 3.45-3.54 (m, 4 H), 2.28-2.33 (m, 1 H), 2.01-2.09 (m, 1 H). |
| 30 | 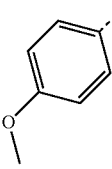 | 3-(3-(4'-Methoxy-[1,1'-biphenyl]-3-yl)-1H-pyrazol-5-yl)pyrrolidine-1-carbonitrile | A | 4.574 | 344.98 | 12.82-13.15 (m, 1 H), 7.99 (s, 1 H), 7.44-7.71 (m, 6 H), 7.05-7.07 (m, 1 H), 6.75 (s, 1 H), 3.85 (s, 3 H), 3.73-3.77 (m, 1 H), 3.45-3.56 (m, 4 H), 2.24-2.33 (m, 1 H), 2.02-2.07 (m, 1 H). |
| 31 |  | 3-(5-(3-(1-Methyl-1H-pyrazol-4-yl)phenyl)-1H-pyrazol-3-yl)pyrrolidine-1-carbonitrile | A | 3.557 | 319.04 | 12.80-13.08 (m, 1 H), 8.19 (d, J = 6.0 Hz, 1 H), 7.90-7.94 (m, 2 H), 7.35-7.61 (m, 3 H), 6.71 (s, 1 H), 3.88 (s, 3 H), 3.73-3.77 (m, 1 H), 3.413-3.56 (m, 4 H) 2.24-2.33 (m, 1 H), 2.06-2.08 (m, 1 H). |
| 32 | 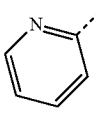 | 3-(5-(3-(Isoxazol-4-yl)phenyl)-1H-pyrazol-3-yl)pyrrolidine-1-carbonitrile | B | 3.291 | 316.00 | 12.86-13.20 (m, 1 H), 8.71 (d, J = 4.4 Hz, 1 H), 8.43-8.49 (m, 1 H), 7.79-8.05 (m, 4 H), 7.51-7.56 (m, 1 H), 7.40 (s, 1 H), 6.76 (s, 1 H), 3.74-3.76 (m, 1 H), 3.47-3.60 (m, 4 H), 2.29-2.33 (m, 1 H), 2.01-2.08 (m, 1 H). |
| 33 | 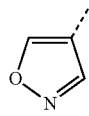 | 3-(5-(3-(Isoxazol-4-yl)phenyl)-1H-pyrazol-3-yl)pyrrolidine-1-carbonitrile | B | 3.627 | 306.52 | 12.86-13.13 (m, 1 H), 9.51 (d, J = 6.5 Hz, 1 H), 9.23 (s, 1 H), 8.08 (s, 1 H), 7.61-7.76 (m, 2 H), 7.46-7.51 (m, 1 H), 6.74 (s, 1 H), 3.73-3.77 (m, 1 H), 3.34-3.51 (m, 4 H), 2.28-2.33 (m, 1 H), 2.05-2.08 (m, 1 H). |
| 34 | 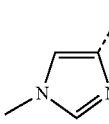 | 3-(5-(3-(1-Methyl-1H-imidazol-4-yl)phenyl)-1H-pyrazol-3-yl)pyrrolidine-1-carbonitrile | A | 3.402 | 319.24 | 12.79-13.09 (s, 1 H), 8.10-8.16 (m, 1 H), 7.52-7.66 (m, 4 H), 7.35-7.40 (m, 1 H), 6.66 (s, 1 H), 3.71-3.80 (m, 2 H), 3.70 (s, 3H), 3.41-3.49 (m, 3 H), 2.25-2.33 (m, 1 H), 2.03-2.08 (m, 1 H). |

TABLE 3

| Ex | R | Name | Alkyne CAS Number | LCMS Method | LCMS RT (min) | MS (ES+) | $^1$H NMR (400 MHz, DMSO-d6) δ ppm |
|---|---|---|---|---|---|---|---|
| 35 | 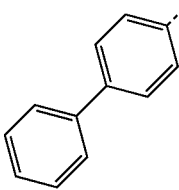 | 3-(5-([1,1'-Biphenyl]-4-yl)-1H-pyrazol-3-yl)pyrrolidine-1-carbonitrile | 766-96-1 | B | 4.436 | 315.25 | 12.83-13.14 (m, 1 H), 7.81-7.85 (m, 2 H), 7.71-7.73 (m, 4 H), 7.48 (t, J = 7.2 Hz, 2 H), 7.36-7.39 (m, 1 H), 6.69 (s, 1 H), 3.73-3.76 (m, 1 H), 3.48-3.52 (m, 4 H), 2.28-2.33 (m, 1 H), 2.07-2.11 (m, 1 H). |
| 36 | 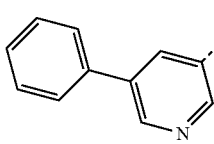 | 3-(5-(5-Phenylpyridin-3-yl)-1H-pyrazol-3-yl)pyrrolidine-1-carbonitrile | 866683-52-5 | B | 3.562 | 316.10 | 13.03-13.33 (m, 1 H), 8.95-9.00 (m, 1 H), 8.80-8.85 (m, 1 H), 8.36-8.42 (m, 1 H), 7.79-7.81 (m, 2 H), 7.46-7.54 (m, 3 H), 6.91 (s, 1 H), 3.77-3.79 (m, 1 H), 3.37-3.57 (m, 4 H), 2.28-2.33 (m, 1 H), 2.07-2.11 (m, 1 H). |

TABLE 3-continued

| Ex | R | Name | Alkyne CAS Number | LCMS Method | LCMS RT (min) | MS (ES+) | $^1$H NMR (400 MHz, DMSO-d6) δ ppm |
|---|---|---|---|---|---|---|---|
| 37 | | 3-(5-(6-Phenylpyridin-2-yl)-1H-pyrazol-3-yl)pyrrolidine-1-carbonitrile | 445468-63-3 | A | 4.349 | 316.11 | 12.99-13.39 (m, 1 H), 8.31-8.33 (m, 1 H), 8.18-8.23 (m, 1 H), 7.89-7.96 (m, 2 H), 7.74-7.75 (m, 1 H), 7.46-7.54 (m, 3 H), 6.90 (s, 1 H), 3.76-3.79 (m, 1 H), 3.42-3.59 (m, 4 H), 2.27-233 (m, 1 H), 2.01-2.14 (m, 1 H). |
| 38 | | 3-(5-(2-Phenylpyridin-4-yl)-1H-pyrazol-3-yl)pyrrolidine-1-carbontrile | 1196156-17-8 | A | 4.670 | 315.98 | 13.13-13.50 (m, 1 H), 8.66-8.71 (m, 1 H), 8.27-8.31 (m, 1 H), 8.16 (br s, 2H), 7.67-7.73 (m, 1 H), 7.48-7.52 (m, 3 H), 7.01-7.05 (m, 1 H), 3.77-3.79 (m, 1 H), 3.50-3.58 (m, 4 H), 2.30-2.35 (m, 1 H), 2.06-2.08 (m, 1 H). |
| 39 | | 3-(5-(6-Phenylpyridin-2-yl)-1H-pyrazol-3-yl)pyrrolidine-1-carbonitrile | 1196155-22-2 | A | 4.106 | 316.05 | 13.011-13.36 (m, 1 H), 8.60-8.66 (m, 1 H), 8.17 (s, 1 H), 7.82-7.91 (m, 2 H), 7.55-7.67 (m, 4 H), 6.79-6.99 (m, 1 H), 3.71-3.75 (m, 1 H), 3.50-3.52 (m, 4 H), 2.26-2.33 (m, 1 H), 2.02-2.10 (m, 1H). |
| 40 | | 3-(5-(2-Phenylpyridin-4-yl)-1H-pyrazol-3-yl)pyrrolidine-1-carbonitrile | 569672-28-2 | A | 4.017 | 316.05 | 12.99-13.30 (m, 1 H), 9.04-9.08 (m, 1 H), 8.00-8.23 (m, 4 H), 7.44-7.52 (m, 3 H), 6.80-6.83 (m, 1 H), 3.74-3.81 (m, 1 H), 3.43-3.60 (m, 4 H), 2.27-2.33 (m, 1 H), 2.03-2.11 (m, 1 H). |

The racemic Example 37 was subjected to enantiomeric separation by preparative chiral HPLC to provide the following enantiomers (absolute stereochemistry was not determined):

Example 41 3-(5-(6-Phenylpyridin-2-yl)-1H-pyrazol-3-yl)pyrrolidine-1-carbonitrile: Enantiomer 1

LCMS: Method A, 4.502 min, MS: ES+315.98; Chiral SFC: CHIRALART SA 250×4.6 mm 5 μm, mobile phase: (A) Liquid carbon dioxide; (B) IPA, column flow was 4.0 ml/min and ABPR was 150 bar, isocratic gradient of 40% B over 15 min, RT 9.01 min; $^1$H NMR (400 MHz, DMSO-d6) δ ppm 13.10-13.40 (m, 1H), 8.27 (br s, 2H), 7.92-7.94 (m, 2H), 7.81 (br s, 1H), 7.45-7.54 (m, 3H), 6.90 (s, 1H), 3.76-3.77 (m, 1H), 3.47-3.56 (m, 4H), 2.28-2.33 (m, 1H), 2.07-2.12 (m, 1H).

Example 42 3-(5-(6-Phenylpyridin-2 yl)-1H-pyrazol-3 yl)pyrrolidine-1-carbonitrile: Enantiomer 2

LCMS: Method A, 4.471 min, MS: ES+315.98; Chiral SFC: CHIRALART SA 250×4.6 mm 5 μm, mobile phase: (A) Liquid carbon dioxide; (B) IPA, column flow was 4.0 ml/min and ABPR was 150 bar, isocratic gradient of 40% B over 15 min, RT 10.43 min; $^1$H NMR (400 MHz, DMSO-d6) δ ppm 13.10-13.40 (m, 1H), 8.27 (br s, 2H), 7.92-7.94 (m, 2H), 7.81 (br s, 1H), 7.45-7.54 (m, 3H), 6.90 (s, 1H), 3.76-3.77 (m, 1H), 3.47-3.56 (m, 4H), 2.28-2.33 (m, 1H), 2.07-2.12 (m, 1H).

Example 43 trans-3-(3-([1,1'-biphenyl]-3 yl)-1H-pyrazol-5-yl)-4-ethylpyrrolidine-1-carbonitrile

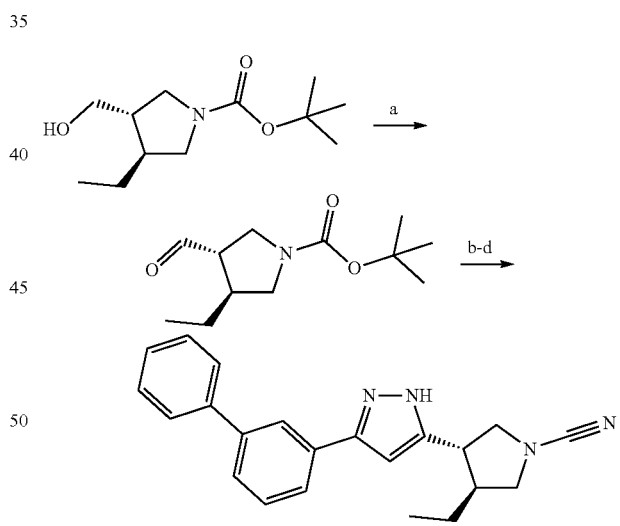

Step a. To a stirred solution of trans tert-butyl 3-ethyl-4-(hydroxymethyl)pyrrolidine-1-carboxylate (0.425 g, 1.86 mmol) in DCM (8 ml) was added Dess-Martin periodinane (3.9 g, 9.28 mmol) portion wise at 0° C. under nitrogen atmosphere. The reaction mixture was stirred at rt for 16 h. The resulting reaction mixture was filtered through a celite bed and washed with DCM (20 ml). The filtrate was poured into saturated NaHCO$_3$ solution (20 ml). The organic phase was separated and washed with water (20 ml). The organic phase was dried over Na$_2$SO$_4$, filtered and concentrated under reduced pressure. The resulting residue was purified by column chromatography (58% EtOAc in hexane) yielding trans tert-butyl 3-ethyl-4-formylpyrrolidine-1-carboxylate (0.182 g, 1.064 mmol). LCMS: Method C, 1.941 min, MS: ES+172.1.

Steps b-d. The title compound was synthesized from the intermediate above using a procedure similar to that described for Example 19, steps e-g. LCMS: Method B, 4.787 min, MS: ES+343.88; $^1$H NMR (400 MHz, DMSO-6) δ ppm 12.86-13.17 (m, 1H), 8.05 (s, 1H), 7.72-7.77 (m, 3H), 7.48-7.63 (m, 4H), 7.40-7.42 (m, 1H), 6.80 (s, 1H), 3.43-3.82 (m, 3H), 3.05-3.20 (m, 2H), 2.22-2.33 (m, 1H), 1.51-1.55 (m, 1H), 1.23-1.34 (m, 1H), 0.78-0.86 (m, 3H). The obtained racemic material was subjected to enantiomeric separation by preparative chiral HPLC to provide the following enantiomers (absolute stereochemistry was not determined):

Example 44 Trans-3-(3-([1,1'-biphenyl]-3-yl)-1H-pyrazol-5-yl)-4-ethylpyrrolidine-1-carbonitrile: Enantiomer 1

LCMS: Method B, 4.803 min, MS: ES+343.51; $^1$H NMR (400 MHz, DMSO-d6) δ ppm 12.86-13.17 (m, 1H), 8.05 (s, 1H), 7.73-7.75 (m, 3H), 7.59 (d, J=7.6 Hz, 1H), 7.48-7.53 (m, 3H), 7.38-7.41 (m, 1H), 6.76 (s, 1H), 3.43-3.82 (m, 3H), 3.05-3.20 (m, 2H), 2.22-2.33 (m, 1H), 1.51-1.55 (m, 1H), 1.23-1.34 (m, 1H), 0.83-0.87 (m, 3H).

Example 45 Trans-3-(3-([1,1'-biphenyl]-3 yl)-1H-pyrazol-5 yl)-4-ethylpyrrolidine-1-carbonitrile: Enantiomer 2

LCMS: Method B, 4.575 min, MS: ES+343.51; Chiral SFC: CHIRALART SA 250×4.6 mm 5 μm, mobile phase: (A) Liquid carbon dioxide; (B) MeOH, column flow was 3.0 ml/min and ABPR was 150 bar, isocratic gradient of 30% B over 20 min, RT 8.65 min; $^1$H NMR (400 MHz, DMSO-d6) δ ppm 12.86-13.17 (m, 1H), 8.05 (s, 1H), 7.73-7.75 (m, 3H), 7.61 (d, J=7.6 Hz, 1H), 7.48-7.53 (m, 3H), 7.38-7.42 (m, 1H), 6.79 (s, 1H), 3.77-3.82 (m, 1H), 3.70-3.74 (m, 1H), 3.50-3.55 (m, 1H), 3.11-3.20 (m, 2H), 2.23-2.33 (m, 1H), 1.50-1.56 (m, 1H), 1.23-1.34 (m, 1H), 0.84 (t, J=7.6 Hz, 3H).

Example 46 Trans-3-(3-([1,1'-biphenyl]-3 yl)-1H-pyrazol-5 yl)-4-cyclopropylpyrrolidine-1-carbonitrile

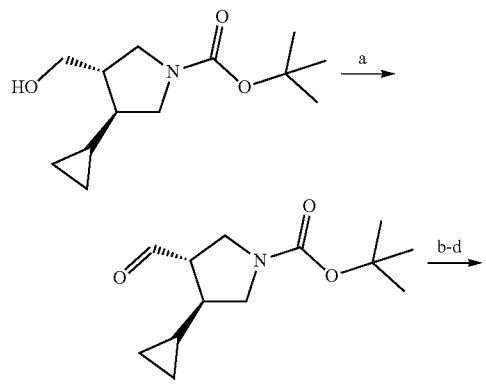

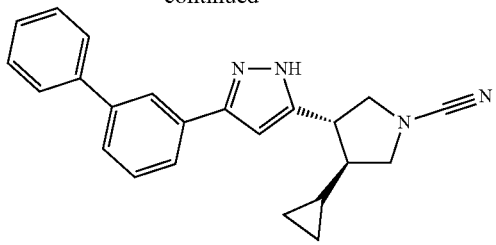

Step a. To a stirred solution of tert-butyl 3-cyclopropyl-4-(hydroxymethyl)pyrrolidine-1-carboxylate (0.065 g, 0.270 mmol) in DCM (3 ml) was added Dess-Martin periodinane (0.572 g, 1.348 mmol) portion wise at 0° C. The reaction mixture was stirred at rt for 8 h. Excess Dess-Martin periodinane (1.71 g, 4.046 mmol) was added to the reaction mixture and then stirred at rt for 16 h. The reaction mixture was filtered through celite bed and the filtrate was concentrated under vacuum. The resulting residue was purified by column chromatography (2% MeOH in DCM) yielding trans tert-butyl 3-cyclopropyl-4-formylpyrrolidine-1-carboxylate (0.04 g, 0.167 mmol). $^1$H NMR (400 MHz, DMSO-d6) δ ppm 9.59 (s, 1H), 3.39-3.51 (m, 4H), 3.02-3.09 (m, 2H), 1.74-1.85 (m, 1H), 1.39 (s, 9H), 0.77-0.83 (m, 1H), 0.19-0.21 (m, 1H) 0.03-0.15 (s, 1H).

Steps b-d. The title compound was synthesized from the intermediate above using a procedure similar to that described for Example 19, steps e-g. LCMS: Method B, 4.839 min, MS: ES+355.2; $^1$H NMR (400 MHz, DMSO-6) δ ppm 13.14-12.84 (m, 1H), 8.05 (s, 1H), 7.71-7.80 (m, 3H), 7.48-7.58 (m, 4H), 7.39-7.41 (m, 1H), 6.78 (s, 1H), 3.79-3.84 (m, 1H), 3.62-3.67 (m, 1H), 3.50-3.56 (m, 1H), 3.24-3.31 (m, 2H), 1.76-1.89 (m, 1H), 1.34-1.46 (m, 1H), 0.78-0.86 (m, 1H), 0.34-0.36 (m, 2H), 0.07-0.12 (m, 2H). Duplication of peaks observed in NMR thus material is a mixture of tautomers.

Example 47 3-(3-([2,3'-Bipyridin]-4-yl)-1H-pyrazol-5-yl)pyrrolidine-1-carbonitrile

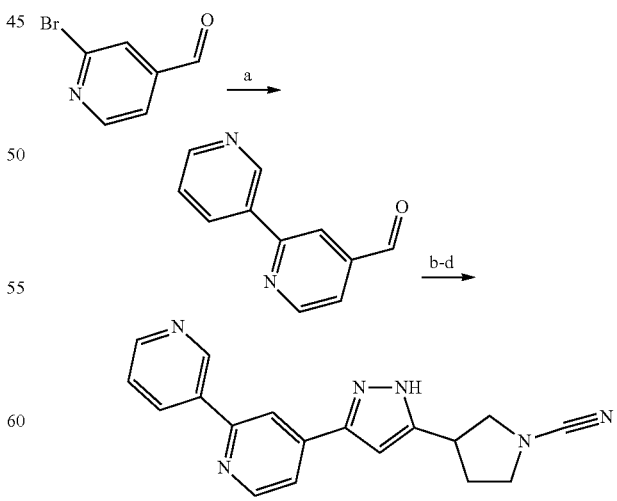

Step a. To a solution of 2-bromoisonicotinaldehyde (CAS Number 118289-17-1; 0.6 g, 3.243 mmol) and pyridin-3-ylboronic acid (CAS Number 1692-25-7; 0.59 g, 4.864 mmol) in 1,4-dioxane (9 ml) was added a solution of Na₂CO₃ (0.68 g, 6.486 mmol) in water (1 ml) at rt. The reaction mixture was degassed for 20 min before addition of PdCl₂(dppf) (0.23 g, 0.324 mmol) at rt. The resulting reaction mixture was heated at 100° C. for 3 h. The resulting reaction mixture was cooled to rt, poured into water (50 ml) and extracted with EtOAc (3×50 ml). The combined organic phase was dried over Na₂SO₄, filtered and concentrated under reduced pressure. The residue was purified by flash chromatography (2% MeOH in DCM) to yielding [2,3'-bipyridine]-4-carbaldehyde (0.22 g, 1.195 mmol). MS: ES+185.0; ¹H NMR (400 MHz, DMSO-d6) δ ppm 10.17 (s, 1H), 9.34 (d, J=1.6 Hz, 1H), 9.0 (d, J=4.8 Hz, 1H), 8.69 (d, J=4.8 Hz, 1H), 8.50 (s, 1H), 8.53 (s, 1H), 7.83 (d, J=5.2 Hz, 1H), 7.51 7.59 (m, 1H).

Steps b-d. The title compound was synthesized from the intermediate above using a procedure similar to that described for Example 14, steps c-e. LCMS: Method A, 3.213 min, MS: ES+317.31; ¹H NMR (400 MHz, DMSO-d6+1 drop TFA) δ ppm 9.59 (s, 1H), 9.23 (d, J=7.6 Hz, 1H), 9.00 (d, J=5.2 Hz, 1H), 8.81 (d, J=5.2 Hz, 1H), 8.60 (s, 1H), 8.18 (t, J=7.2 Hz, 1H), 7.98 (d, J=4.8 Hz, 1H), 7.05 (s, 1H), 3.78 (t, J=8.8 Hz, 1H), 3.43-3.61 (m, 4H), 3.31-2.33 (m, 1H), 2.03-2.08 (m, 1H).

Example 194 3-(5-(5-Phenylpyridin-2-yl)-1H-pyrazol-3-yl)pyrrolidine-1-carbonitrile mmol) in THF (5 ml) was added dropwise to the reaction mixture at 0° C. The reaction mixture was stirred at 0° C. for 3 h. The resulting reaction mixture was filtered through a celite bed and the filtrate was concentrated under reduced pressure to yield dimethyl(1-diazo-2-oxopropyl)phosphonate (1.23 g). LCMS: Method C, 1.273 min, MS: ES+193.09. The material was used in step c without further purification.

Step b. To a mixture of 5-bromo-2-pyridinecarboxaldehyde (0.700 g, 3.76 mmol) and phenylboronic acid (0.551 g, 4.52 mmol) in toluene:MeOH:water (2:0.2:1, 16 ml) was added Na₂CO₃ (0.997 g, 9.41 mmol) at rt. The reaction mixture was degassed for 30 min before addition of Pd(PPh₃)₄ (0.217 g, 0.188 mmol). The reaction mixture was heated at 80° C. for 1 h. The reaction mixture was cooled to rt, diluted with water (25 ml) and extracted with EtOAc (2×25 ml). The combined organic phase was dried over Na₂SO₄, filtered and concentrated under reduced pressure. The residue was purified by flash column chromatography (6% EtOAc in hexane) to yield 5-phenylpicolinaldehyde (0.440 g, 2.40 mmol). MS: ES+184, ¹H NMR (400 MHz, CDCl₃) δ ppm 10.16 (s, 1H), 9.04-9.04 (m, 1H), 8.06-8.10 (m, 2H), 7.66-7.68 (m, 2H), 7.485-7.579 (m, 3H).

Step c. To a stirred solution of 5-phenylpicolinaldehyde (0.435 g, 2.38 mmol) in MeOH (15 ml) was added K₂CO₃ (0.656 g, 4.75 mmol) at 0° C. A solution of dimethyl

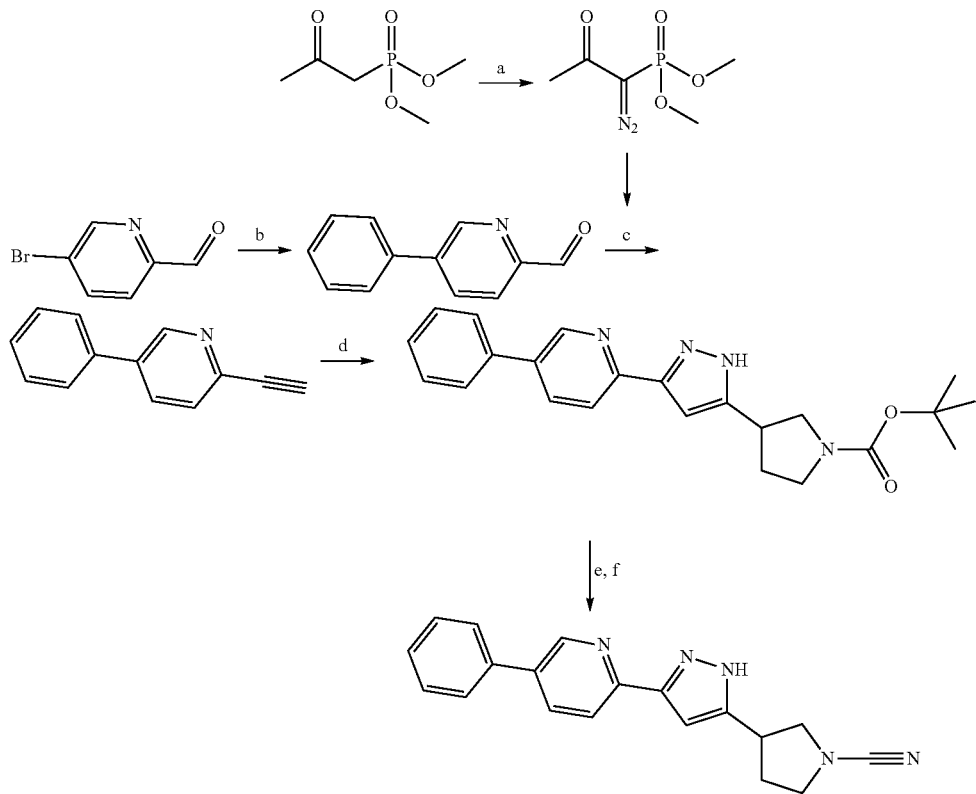

Step a. To a stirred suspension of NaH (60% dispersion in oil; 0.265 g, 6.63 mmol) in THF (20 ml) was added dropwise a solution of dimethyl-2-oxopropylphosphonate (1.000 g, 6.024 mmol) in THF (5 ml) at 0° C. under an inert atmosphere. The resulting reaction mixture was stirred at 0° C. for 1 h. A solution of p-toluenesulfonylazide (1.18 g, 6.02

(1-diazo-2-oxopropyl)phosphonate (prepared in step a; 0.684 g, 3.565 mmol) in MeOH (5 ml) was added to the reaction mixture at 0° C. The reaction mixture was stirred at rt for 2.5 h. Silica gel (1.0 g) was added to the reaction mixture at rt. The reaction mixture was stirred at rt for 30 min. The mixture was concentrated under reduced pressure and the residue was purified by flash column chromatography (7% EtOAc in hexane) to yield 2-ethynyl-5-phenylpyridine (0.300 g, 1.68 mmol). LCMS: Method C, 2.191 min, MS: ES+180.40; ¹H NMR (400 MHz, DMSO-d6) δ ppm 8.91 (d, J=1.6 Hz, 1H), 8.12 (dd, J=8.0, 2.4 Hz, 1H), 7.76-7.78 (m, 2H), 7.66 (d, J=8.0 Hz, 1H), 7.51-7.54 (m, 2H), 7.45-7.47 (m, 1H), 4.40 (s, 1H).

Step d. To a stirred solution of 1-BOC-3-pyrrolidinecarbaldehyde (0.265 g, 1.33 mmol) in MeCN (10 ml) was added p-toluenesulfonyl hydrazide (0.247 g, 1.33 mmol) at rt. The reaction mixture was stirred at rt for 2 h. NaOH (0.106 g, 2.66 mmol) was added to a reaction mixture at rt. The reaction mixture was stirred at rt for 30 min before addition of 2-ethynyl-5-phenylpyridine (0.286 g, 1.597 mmol). The reaction mixture was heated at 80° C. for 18 h. The resulting reaction mixture was cooled to rt, diluted with water (20 ml) and extracted with EtOAc (2×20 ml). The combined organic phase was dried over Na₂SO₄, filtered and concentrated under reduced pressure. The residue was purified by flash column chromatography (60% EtOAc in hexane) yielding tert-butyl 3-(3-(5-phenylpyridin-2-yl)-1H-pyrazol-5-yl)pyrrolidine-1-carboxylate (0.440 g, 1.14 mmol). LCMS: Method C, 2.379 min, MS: ES+391.30; ¹H NMR (400 MHz, DMSO-d6) δ ppm 13.05 (s, 1H), 8.89-8.92 (m, 1H), 8.15 (d, J=8.4 Hz, 1H), 7.96 (s, 1H), 7.77-7.78 (m, 2H), 7.50-7.53 (m, 2H), 7.41-7.45 (m, 1H), 6.77 (brs, 1H), 3.67-3.71 (m, 1H), 3.40-3.45 (m, 4H), 2.21-2.24 (m, 1H), 2.01-2.04 (m, 1H), 1.41 (s, 9H).

Steps e, f. The title compound was synthesised from the intermediate above using a procedure similar to that described for Example 14, steps d, e. LCMS: Method B, 3.809 min, MS: ES+316.20; ¹H NMR (400 MHz, DMSO-d6) δ ppm 12.99-13.37 (m, 1H), 8.90 (s, 1H), 8.09-8.16 (m, 1H), 7.92 7.95 (m, 1H), 7.77-7.79 (m, 2H), 7.50-7.54 (m, 2H), 7.42-7.45 (m, 1H), 6.82-6.85 (m, 1H), 3.72-3.76 (m, 1H), 3.41-3.54 (m, 4H), 2.21-2.33 (m, 1H), 2.02-2.09 (m, 1H).

Example 195 3-(3-(5-(Pyrimidin-2-yl)pyridin-2-yl)-1H-pyrazol-5-yl)pyrrolidine-1-carbonitrile

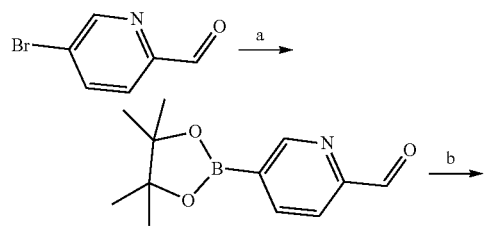

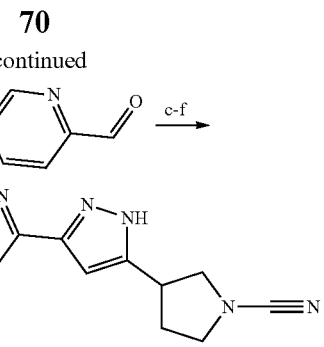

Step a. To a stirred solution of 5-bromo-2-pyridinecarboxaldehyde (5.00 g, 26.9 mmol) in THF (50 ml) was added bis(pinacolato)diboron (10.23 g, 40.3 mmol) and potassium acetate (7.91 g, 80.6 mmol) at rt. The reaction mixture was degassed for 30 min before addition of Pd₂(dba)₃ (1.230 g, 1.34 mmol) and X-phos (1.28 g, 26.88 mmol) at rt. The reaction mixture was heated at 75° C. for 5 h. The resulting reaction mixture was cooled to rt, filtered through celite bed and washed with EtOAc (2×100 ml). The combined filtrate was concentrated under reduced pressure yielding 5-(4,4,5,5-tetramethyl-1,3,2-dioxaborolan-2-yl)picolinaldehyde (15.2 g). This material was directly used for the next step without further purification. MS: ES+152 (M-82).

Step b. To a mixture of 5-(4,4,5,5-tetramethyl-1,3,2-dioxaborolan-2-yl)picolinaldehyde (15.00 g, 64.4 mmol) and 2-chloropyrimidine (3.680 g, 32.2 mmol) in 1,4-dioxane: water (4:1, 96 ml) was added K₂CO₃ (26.65 g, 19.3 mmol) at rt. The reaction mixture was degassed for 30 min before addition of PdCl₂(dppf) (1.170 g, 1.61 mmol) at rt. The reaction mixture was heated at 80° C. for 2 h. The resulting reaction mixture was cooled to rt, diluted with water (200 ml) and extracted with EtOAc (2×250 ml). The combined organic phase was dried over Na₂SO₄, filtered and concentrated under reduced pressure. The residue was purified by flash column chromatography (30% EtOAc in hexane) yielding 5-(pyrimidin-2-yl)picolinaldehyde (1.510 g, 8.11 mmol). LCMS: Method A, 2.724 min, MS: ES+184

Steps c-f. The title compound was synthesised from the intermediate above using a procedure similar to that described for Example 194, steps c-f LCMS: Method A, 3.181 min, MS: ES+318.06; ¹H NMR (400 MHz, DMSO-d6) δ ppm 13.11-13.51 (m, 1H), 9.50-9.54 (m, 1H), 8.95-8.98 (m, 2H), 8.69-8.76 (m, 1H), 7.96-8.11 (m, 1H), 7.50-7.54 (m, 1H), 6.84-6.94 (m, 1H), 3.72-3.80 (m, 1H), 3.45-3.59 (m, 4H), 2.24-2.33 (m, 1H), 2.04-2.09 (m, 1H).

Example 196 3-(4-Fluoro-3-(6-(piperidin-1-yl)pyridin-2-yl)-1H-pyrazol-5-yl)pyrrolidine-1-carbonitrile

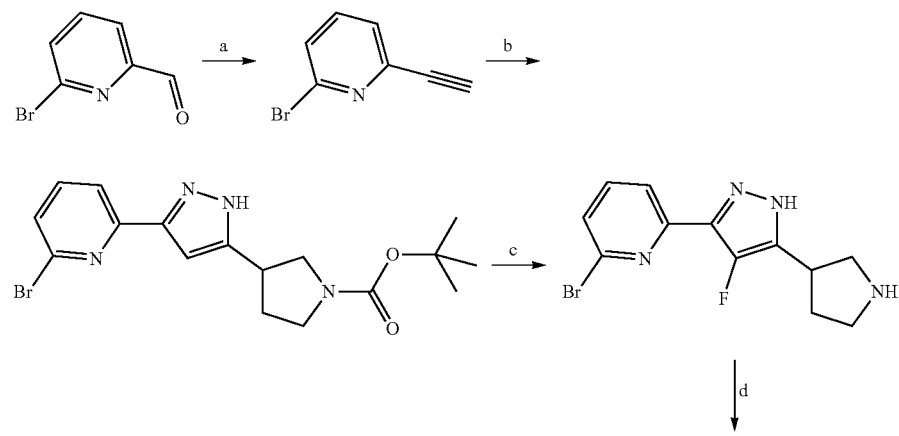

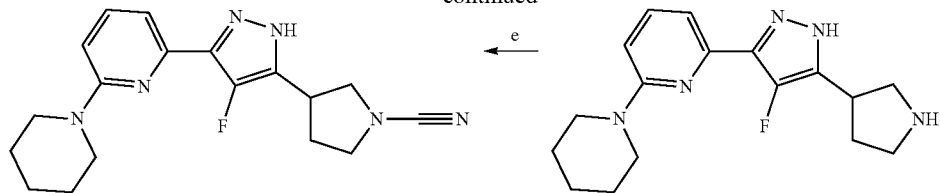

Step a. To a solution of 6-bromo-2-formylpyridine (0.700 g, 3.76 mmol) in MeOH (7 ml) was added K₂CO₃ (1.030 g, 7.52 mmol) at 0° C. Dimethyl(1-diazo-2-oxopropyl)phosphonate (prepared according to Example 90942, step a; 0.890 g, 4.70 mmol) was added to the reaction mixture at 0° C. The reaction mixture was stirred at rt for 1 h. The resulting reaction mixture was combined with one other batch prepared on the same scale by an identical method. The reaction mixture was filtered through celite bed and washed with MeOH (10 ml). The combined filtrate was concentrated under reduced pressure yielding 2-bromo-6-ethynylpyridine (2.50 g). This material was directly used for the next step without any further purification. LCMS: Method C, 1.73 min, MS: ES+182.0, 184.0

Step b. To a solution of 1-BOC-pyrrolidine-3-carboxaldehyde (1.000 g, 5.025 mmol) in MeCN (10 ml) was added p-tolunesulfonyl hydrazide (0.934 g, 5.025 mmol) at rt. The reaction mixture was stirred at rt for 1 h. NaOH solution (0.603 g, 15.075 mmol) in water (2 ml) was added to the reaction mixture at rt. The reaction mixture was stirred at rt for 30 min before addition of 2-bromo-6-ethynylpyridine (1.097 g, 6.030 mmol). The reaction mixture was heated at 80° C. for 5 h. The resulting mixture was cooled to it and poured into water (50 ml). The resulting mixture was extracted with EtOAc (3×25 ml). The combined organic phase was dried over Na₂SO₄, filtered and concentrated under reduced pressure. The residue was purified by flash chromatography (40% EtOAc in hexane) yielding tert-butyl 3-(3-(6-bromopyridin-2-yl)-1H-pyrazol-5-yl)pyrrolidine-1-carboxylate (1.100 g, 2.79 mmol). LCMS: Method C, 2.65 min, MS: ES+393.20, 395.20

Step c. To a solution of tert-butyl 3-(3-(6-bromopyridin-2-yl)-1H-pyrazol-5-yl)pyrrolidine-1-carboxylate (0.350 g, 0.892 mmol) in MeCN (10 ml) was added Selectfluor (0.395 g, 1.12 mmol) in a microwave tube at rt. The reaction mixture was irradiated at 90° C. under microwave condition for 45 min. The resulting mixture was combined with two other batches prepared on the same scale by an identical method. The combined reaction mixture was concentrated under reduced pressure yielding 2-bromo-6-(4-fluoro-5-(pyrrolidin-3-yl)-1H-pyrazol-3-yl)pyridine (2.100 g). This material was directly used for the next step without any further purification. LCMS: Method C, 1.77 min, MS: ES+311.0, 313.0

Step d. To a solution 2-bromo-6-(4-fluoro-5-(pyrrolidin-3-yl)-1H-pyrazol-3-yl)pyridine (0.590 g, 1.90 mmol) in 1,4-dioxane (10 ml) was added piperidine (1.61 g, 19.0 mmol) and K₃PO₄ (2.010 g, 9.48 mmol) at rt. The reaction mixture was heated 110° C. for 36 h. The resulting mixture was cooled to it, filtered and washed with DCM (20 ml). The combined filtrate was concentrated under reduced pressure. The crude material was triturated with diethyl ether (2×5 ml) and concentrated under reduced pressure yielding 2-(4-fluoro-5-(pyrrolidin-3-yl)-1H-pyrazol-3-yl)-6-(piperidin-1-yl)pyridine (1.300 g). This material was directly used for the next step without any further purification. LCMS: Method C, 1.608 min, MS: ES+316.53 [M+1].

Step e. To a solution 2-(4-fluoro-5-(pyrrolidin-3-yl)-1H-pyrazol-3-yl)-6-(piperidin-1-yl)pyridine (0.597 g, 1.895 mmol) in THF (5 ml) was added K₂CO₃ (0.328 g, 2.38 mmol) at 0° C. Cyanogen bromide (0.084 g, 0.793 mmol) was added to the reaction mixture at 0° C. The reaction mixture was stirred at rt for 1 h. The resulting mixture was poured into water (25 ml) and extracted with EtOAc (2×20 ml). The combined organic phase was washed with brine solution (10 ml), dried over Na₂SO₄, filtered and concentrated under reduced pressure. The residue was purified by preparative TLC (10% MeOH in DCM) yielding the title compound (0.015 g, 0.044 mmol). LCMS: Method A, 5.491 min, MS: ES+341.0 [M+1].

Example 48 Trans-3-methyl-4-(3-(pyridin-4-yl)-1H-pyrazol-5-yl)pyrrolidine-1-carbonitrile

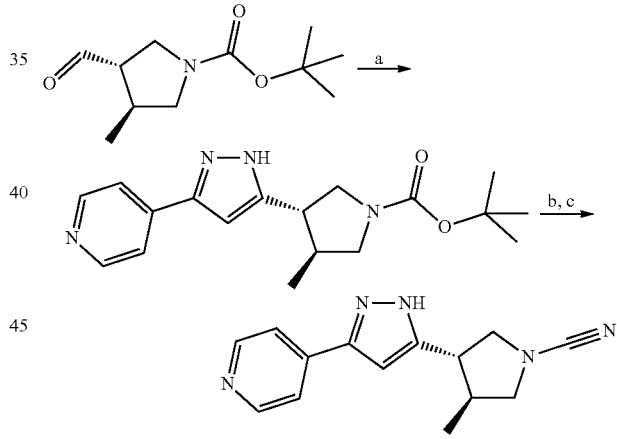

Step a. A mixture of trans tert-butyl 3-formyl-4-methylpyrrolidine-1-carboxylate (Example 19, step d) (0.10 g, 0.47 mmol) and p-toluenesulfonyl hydrazide (CAS Number 1576-35-8; 0.09 g, 0.47 mmol) in MeCN (15 ml) was stirred at rt for 2 h. 5 M NaOH solution (0.1 g, 2.34 mmol) was added to the reaction mixture at it and stirred for 25 min. 4-Ethynylpyridine hydrochloride (0.20 g, 1.41 mmol) was added to the reaction mixture at rt. The reaction mixture was heated at 50° C. for 24 h. The resulting reaction mixture was combined with two other batches prepared on the same scale by an identical method. The resulting reaction mixture was diluted with water (100 ml) and extracted with EtOAc (3×100 ml). The combined organic phase was dried over Na₂SO₄, filtered and concentrated under reduced pressure. The resulting residue was purified by flash chromatography (5% MeOH in DCM) yielding trans tert-butyl 3-methyl-4-

(3-(pyridin-4-yl)-1H-pyrazol-5-yl)pyrrolidine-1-carboxylate (0.25 g, 0.761 mmol). LCMS: Method C, 1.665 min, MS: ES+329.34.

Step b. To a solution of trans tert-butyl 3-methyl-4-(3-(pyridin-4-yl)-1H-pyrazol-5-yl)pyrrolidine-1-carboxylate (0.25 g, 0.761 mmol) in DCM (3 ml) was added TFA (0.5 ml) at rt. The reaction mixture was stirred at it for 2 h. The resulting reaction mixture was concentrated under reduced pressure. The obtained residue was azeotropically distilled with DCM (5 ml) and finally dried under high vacuum to yield trans 4-(5-(4-methylpyrrolidin-3-yl)-1H-pyrazol-3-yl)pyridine TFA salt (0.3 g, quantitative). This material was used directly for the next step without further purification.

Step c. To a solution of trans 4-(5-(4-methylpyrrolidin-3-yl)-1H-pyrazol-3-yl)pyridine TFA salt (0.30 g, 0.877 mmol) in THF (10 ml) was added K$_2$CO$_3$ (0.35 g, 2.631 mmol) at rt. Cyanogen bromide (0.12 g, 1.052 mmol) was added to the reaction mixture at it. The reaction mixture was stirred at it for 30 min. The resulting reaction mixture was poured into saturated NaHCO$_3$ solution (50 ml) and extracted with EtOAc (2×35 ml). The combined organic phase was washed with brine (2×30 ml), dried over Na$_2$SO$_4$, filtered and concentrated under reduced pressure. The resulting residue was purified by flash chromatography (5-7% MeOH in DCM) yielding the title compound (0.025 g, 0.098 mmol). LCMS: Method A, 3.045 min, MS: ES+253.93; $^1$H NMR (400 MHz, DMSO-d6, 80° C.) δ ppm 12.95-13.28 (m, 1H), 8.56-8.63 (m, 2H), 7.69-7.74 (m, 2H), 6.77-6.79 (m, 1H), 3.79-3.84 (m, 1H), 3.69-3.73 (m, 1H), 3.48-3.53 On 1H), 3.11-3.18 (m, 2H), 2.33-2.38 (m, 1H), 1.04-1.05 (m, 3H).

Example 49 Trans-3-methyl-4-(3-phenyl-1H-pyrazol-5-yl)pyrrolidine-1-carbonitrile

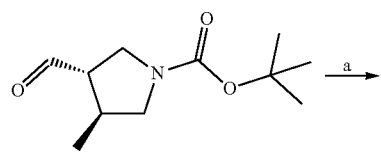

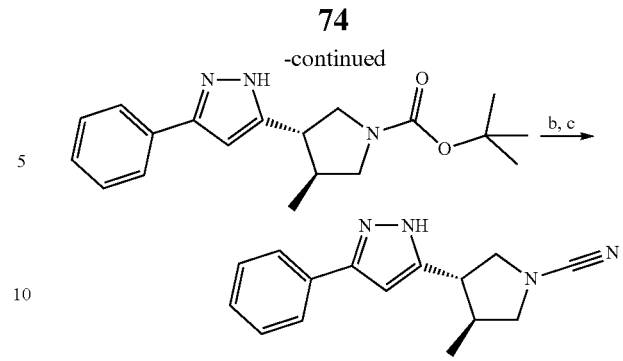

Step a. A mixture of trans tert-butyl 3-formyl-4-methylpyrrolidine-1-carboxylate (Example 19, step d) (0.20 g, 0.94 mmol) and p-toluenesulfonyl hydrazide (CAS Number 1576-35-8; 0.18 g, 0.94 mmol) in MeCN (15 ml) was stirred at rt for 2 h. 5 M NaOH solution (0.04 g, 0.94 mmol) was added to the reaction mixture at rt and stirred for 2.5 min. Phenylacetylene (0.28 g, 2.81 mmol) was added to the reaction mixture at rt. The reaction mixture was heated at 60° C. for 72 h. The resulting reaction mixture was diluted with water (50 ml) and extracted with EtOAc (3×50 ml). The combined organic phase was washed with brine (40 ml) and dried over Na$_2$SO$_4$, filtered and concentrated under reduced pressure. The resulting residue was purified by flash chromatography (20% EtOAc in hexane) yielding trans tert-butyl 3-methyl-4-(3-phenyl-1H-pyrazol-5-yl)pyrrolidine-1-carboxylate (0.19 g, 0.580 mmol). LCMS: Method C, 2.301 min, MS: ES+328.25

Steps b, c. The title compound was synthesised from the intermediate above using a procedure similar to that described for Example 14, steps d, e. LCMS: Method A, 4.024 min, MS: ES+252.9; $^1$H NMR (400 MHz, DMSO-d6, 80° C.) δ ppm 12.64-12.87 (m, 1H), 7.74 (d, J=6.8 Hz, 2H), 7.41 (t, J=7.2 Hz, 2H), 7.30-7.33 (m, 1H), 6.58 (s, 1H), 3.79 (t, J=8.8 Hz, 1H), 3.67-3.71 (m, 1H), 3.53 (t, J=9.2 Hz, 1H), 3.06-311 (m, 2H), 2.32-2.39 (m, 1H), 1.05 (d, J=6.4 Hz, 3H).

Example 50 N-(3-(1-Cyanopyrrolidin-3-yl)-1H-pyrazol-5-yl)benzamide

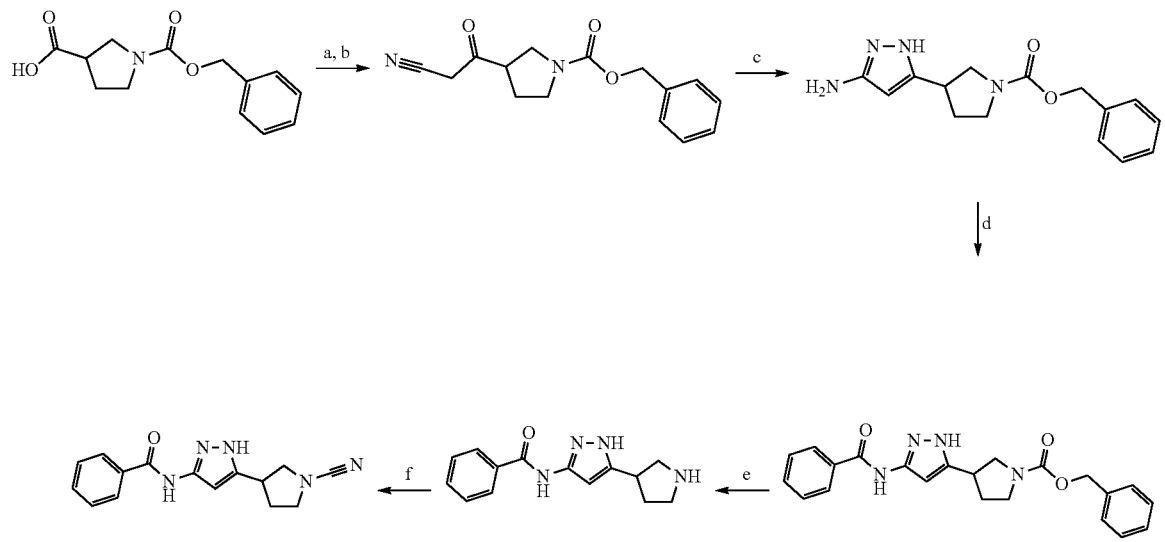

Step a. To a stirred solution of 1-((benzyloxy)carbonyl)pyrrolidine-3-carboxylic acid (CAS Number 188527-21-1; 2.0 g, 8.03 mmol) and methyl iodide (2.27 g, 16.05 mmol) in DMF (20 ml) was added KHCO$_3$ (1.6 g, 16.05 mmol) at rt. The reaction mixture was stirred at rt for 5 h. The resulting reaction mixture was poured into cold water (400 ml) and extracted with EtOAc (2×100 ml). The combined organic phase was separated, dried over Na$_2$SO$_4$, filtered and concentrated under reduced pressure. The resulting crude material was purified by flash chromatography (25% EtOAc in hexane) yielding 1-benzyl 3-methyl pyrrolidine-1,3-dicarboxylate (2.0 g, 7.604 mmol). LCMS: Method C, 2.029 min, MS: ES+264.3; $^1$H NMR (400 MHz, CDCl$_3$) δ ppm 7.31-7.39 (m, 5H), 5.15 (d, J=1.6 Hz, 2H), 3.73 (s, 3H), 3.54-3.70 (m, 3H), 3.44-3.49 (m, 1H), 3.06-3.12 (m, 1H), 2.15-2.19 (m, 2H).

Step b. To a stirred solution of MeCN (0.374 g, 9.125 mmol) in dry THF (20 ml) was added n-BuLi (1.6 M in hexane; 4.75 ml, 7.60 mmol) drop wise at −78° C. under nitrogen atmosphere. The reaction mixture was stirred at −78° C. for 10 min. A solution of 1-benzyl 3-methyl pyrrolidine-1,3-dicarboxylate (2.0 g, 7.60 mmol) in dry THF (ml) was added to the reaction mixture drop wise at −78° C. The reaction mixture was stirred at −78° C. for 1 h. The reaction mixture was warmed to −20° C. and stirred for 3 h. The resulting reaction mixture was poured into water (300 ml), acidified with 2 M HCl (pH 3) and extracted with EtOAc (2×100 ml). The combined organic phase was separated, dried over Na$_2$SO$_4$, filtered and concentrated under reduced pressure. The resulting crude material was purified by flash chromatography (62% EtOAc in hexane) yielding benzyl 3-(2-cyanoacetyl)pyrrolidine-1-carboxylate (1.2 g, 4.41 mmol). LCMS: Method C, 1.947 min, MS: ES+271.28; $^1$H NMR (400 MHz, CDCl$_3$) δ ppm 7.33-7.38 (m, 5H), 5.15 (s, 2H), 3.67-3.74 (m, 2H), 3.49-3.59 (m, 4H), 3.40-3.46 (m, 1H), 2.06-2.25 (m, 2H).

Step c. A mixture of benzyl 3-(2-cyanoacetyl)pyrrolidine-1-carboxylate (0.6 g, 2.21 mmol) and hydrazine hydrate (0.11 g, 2.21 mmol) in EtOH (10 ml) was heated at 80° C. for 4 h. The resulting reaction mixture was cooled to it and concentrated under vacuum. The resulting crude material was purified by flash chromatography (10% MeOH in DCM) yielding benzyl 3-(5-amino-1H-pyrazol-3-yl)pyrrolidine-1-carboxylate (0.45 g, 1.573 mmol). LCMS: Method C, 1.668 min, MS: ES+287.33; $^1$H NMR (400 MHz, DMSO-d6) δ ppm 11.21 (br s, 1H), 7.30-7.40 (m, 5H), 5.22 (br s, 1H), 5.07 (s, 2H), 4.57 (br s, 2H), 3.63-3.67 (m, 1H), 3.40-3.50 (m, 2H), 3.25-3.33 (m, 2H), 2.10-2.20 (m, 1H), 1.87-1.95 (m, 1H).

Step d. To a stirred solution of ethyl benzoate (0.225 g, 1.5 mmol) and benzyl 3-(5-amino-1H-pyrazol-3-yl)pyrrolidine-1-carboxylate (0.257 g, 0.257 mmol) in THF (12 ml) was added trimethylaluminium (2 M in toluene) (1.57 ml, mmol) at rt. The reaction mixture was heated at 80° C. for 16 h. The resulting reaction mixture was cooled to rt, diluted with MeOH (20 ml) and acidified using 2 M HCl solution. The reaction mixture was extracted with EtOAc (3×40 ml). The resulting crude material was purified by flash chromatography (neutral aluminium oxide; 5% MeOH in DCM) benzyl 3-(5-benzamido-1H-pyrazol-3-yl)pyrrolidine-1-carboxylate (0.15 g, 0.385 mmol). LCMS: Method C, 2.011 min, MS: ES+391.54; $^1$H NMR (400 MHz, DMSO-d6) δ ppm 12.34 (br s, 1H), 10.75 (br s, 1H), 7.98 (d, J=7.6 Hz, 2H), 7.47-7.56 (m, 3H), 7.37-7.38 (m, 3H), 7.31-7.33 (m, 2H), 6.52 (br s, 1H), 5.09 (s, 2H), 3.73-3.82 (m, 1H), 3.34-3.50 (m, 3H), 2.22-2.33 (m, 1H), 1.96-2.05 (m, 1H), 1.23-1.29 (m, 1H), 0.85-0.95 (m, 1H).

Step e. To a stirred solution of benzyl 3-(5-benzamido-1H-pyrazol-3-yl)pyrrolidine-1-carboxylate (0.15 g, 0.385 mmol) in DCM:MeOH (1:1; 30 ml) was carefully added 10% dry Pd/C at rt. The reaction mixture was purged with hydrogen at rt for 3.5 h. The reaction mixture was filtered through celite hyflow and the filtrate was distilled under vacuum to yield N-(3-(pyrrolidin-3-yl)-1H-pyrazol-5-yl)benzamide (0.1 g, 0.390 mmol). LCMS: Method A, 3.526 min, MS: ES+257.12; $^1$H NMR (400 MHz, DMSO-d6) δ ppm 12.49 (br s, 1H), 10.88 (br s, 1H), 9.10 (br s, 1H), 7.99 (dd, J=1.2 Hz, 8.4 Hz, 2H), 7.48-7.60 (m, 3H), 6.63 (br s, 1H), 3.49-3.60 (m, 3H), 3.23-3.27 (m, 2H), 2.28-2.49 (m, 1H), 1.97-2.02 (m, 1H).

Step f. To a stirred solution of N-(3-(pyrrolidin-3-yl)-1H-pyrazol-5-yl)benzamide (0.09 g, 0.351 mmol) in THF:DMF (7:0.5 ml) was added K$_2$CO$_3$ (0.145 g, 1.054 mmol) at −78° C. The reaction mixture was stirred at −78° C. for 5 min. Cyanogen bromide (0.037 g, 0.351 mmol) was added to the reaction mixture at −78° C. The reaction mixture was stirred at −78° C. for 1.5 h. The resulting reaction mixture was poured into water (100 ml) and extracted with EtOAc (3×35 ml). The combined organic phase was separated, dried over Na$_2$SO$_4$, filtered and concentrated under reduced pressure. The resulting crude material was purified by flash chromatography (neutral aluminium oxide; 80% EtOAc in hexane). The obtained material was further purified by flash chromatography (neutral aluminium oxide; 3% MeOH in DCM) yielding N-(3-(1-cyanopyrrolidin-3-yl)-1H-pyrazol-5-yl)benzamide (0.033 g, 0.117 mmol). LCMS: Method A, 3.263 min, MS: ES+282.12; $^1$H NMR (400 MHz, DMSO-d6) δ ppm 12.37 (s, 1H), 10.77 (s, 1H), 7.98 (d, J=7.2 Hz, 2H), 7.49-7.56 (m, 3H), 6.57 (s, 1H), 3.74 (t, J=8.0 Hz, 1H), 3.44-3.53 (m, 3H), 3.37-3.41 (m, 1H), 2.22-2.28 (m, 1H), 1.98-2.04 (m, 1H).

Example 51 3-(5-(Imidazo[1,2-a]pyridin-6-yl)-4H-1,2,4-triazol-3-yl)pyrrolidine-1-carbonitrile

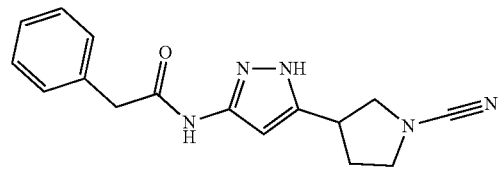 [SMILES: N#CN1CCC(c2cc(NC(=O)Cc3ccccc3)n[nH]2)C1]

The title compound was synthesised using a procedure similar to that described for Example 50. LCMS: Method A, 3.352 min, MS: ES+296.09; $^1$H NMR (400 MHz, DMSO-d6) δ ppm 12.25 (s, 1H), 10.58 (s, 1H), 7.22-7.31 (m, 5H), 6.37 (s, 1H), 3.64-3.71 (m, 1H), 3.58 (s, 2H), 3.40-3.51 (m, 3H), 3.30-3.32 (m, 1H), 2.19-2.23 (m, 1H), 1.89-1.99 (m, 1H).

Scheme 3

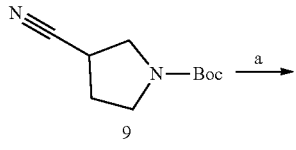

-continued

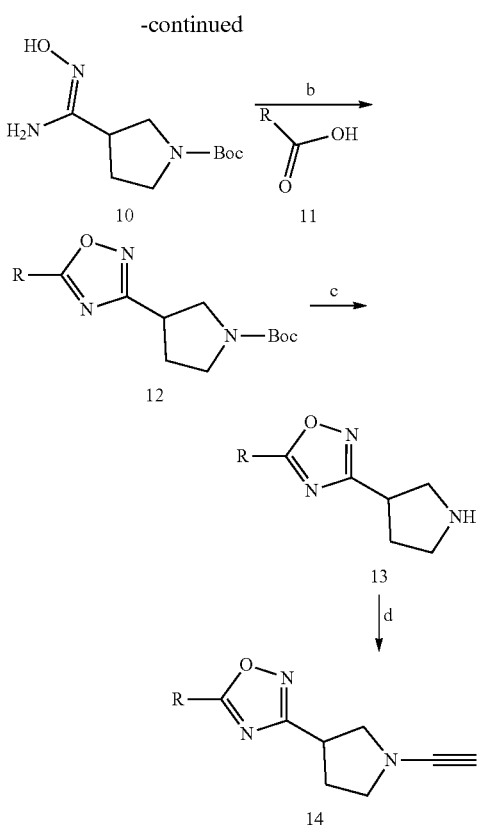

Reagents and conditions: a) K₂CO₃, EtOH, NH₂OH·HCl, rt 3 h; b) HATU, DIPEA, DMF, 120° C., 19 h; c) HCl/EtOAc, rt 2 h; d) cyanogen bromide, NaHCO₃, EtOH, rt, 16 h.

Step a. To a solution of 1-BOC-3-cyanopyrrolidine (CAS Number 476493-40-0; 2.80 g, 14.2 mmol), hydroxylamine hydrochloride (1.98 g, 28.4 mmol) and K₂CO₃ (3.92 g, 28.4 mmol) in absolute EtOH (50 ml) was heated under reflux for 3 h and then stirred at rt overnight and filtered. Evaporation of the filtrate provided tert-butyl 3-(N'-hydroxycarbamimidoyl)-pyrrolidine-1-carboxylate (2.50 g, crude) as a white oil and used in the next step without further purification.

Step b. To a solution of tert-butyl 3-(N'-hydroxycarbamimidoyl)-pyrrolidine-1-carboxylate (0.2 mmol), HATU (0.4 mmol) and DIPEA (0.6 mmol) were dissolved in DMF (1 ml) under nitrogen. Compound 11 (0.2 mmol) was added to the reaction mixture. The reaction mixture was stirred at 120° C. for 19 h. The resulting mixture was concentrated under reduced pressure. The resulting residue was purified by preparative TLC (PE/EtOAc=1:1) yielding Compound 12.

Step c. To a solution of Compound 12 in EtOAc (1 ml) was added HCl/EtOAc (4 M, 1 ml). The reaction mixture was stirred at rt for 2 h. The resulting mixture was concentrated under reduced pressure. The residue Compound 13 was used for the next step directly without further purification.

Step d. To a solution of Compound 13 in EtOH (2 ml) was added cyanogen bromide (0.2 mmol) and NaHCO₃ (0.6 mmol). The reaction mixture was stirred at rt for 16 h. The resulting mixture was concentrated under reduced pressure. The crude was purified by preparative reverse phase HPLC (A: 0.078% CH₃COONH₄ in water, B: MeCN) to provide Compound 14.

Compounds in Table 4 were synthesised using the method as exemplified by Scheme 3.

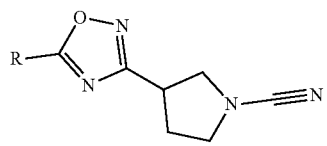

TABLE 4

| Ex | R | Name | LCMS Method | LCMS RT (min) | MS (ES+) |
|---|---|---|---|---|---|
| 52 | ![phenyl-dihydropyridinone] | 3-(5-(2-Oxo-6-phenyl-1,2-dihydropyridin-3-yl)-1,2,4-oxadiazol-3-yl)pyrrolidine-1-carbonitrile | I | 1.85 | 334 |
| 53 | ![2-phenylquinolin-4-yl] | 3-(5-(2-Phenylquinolin-4-yl)-1,2,4-oxadiazol-3-yl)pyrrolidine-1-carbonitrile | I | 3.39 | 368 |
| 54 | ![benzothiazol-6-yl] | 3-(5-(Benzo[d]thiazol-6-yl)-1,2,4-oxadiazol-3-yl)pyrrolidine-1-carbonitrile | I | 2.53 | 298 |

TABLE 4-continued

| Ex | R | Name | LCMS Method | LCMS RT (min) | MS (ES+) |
|---|---|---|---|---|---|
| 55 | | 3-(5-([1,1'-Biphenyl]-3-yl)-1,2,4-oxadiazol-3-yl)pyrrolidine-1-carbonitrile | H | 3.25 | 317 |
| 56 | | 3-(5-(2-Methylquinolin-6-yl)-1,2,4-oxadiazol-3-yl)pyrrolidine-1-carbonitrile | H | 2.07 | 306 |
| 57 | | 3-(5-(3-Chloro-5-(trtfluoromethoxy)phenyl)-1,2,4-oxadiazol-3-yl)pyrrolidine-1-carbonitrile | H | 3.32 | 359 |
| 58 | | 3-(5-(4-Methoxyquinolin-2-yl)-1,2,4-oxadiazol-3-yl)pyrrolidine-1-carbonitrile | H | 2.79 | 322 |
| 59 | | 3-(5-(2-(Benzyloxy)phenyl)-1,2,4-oxadiazol-3-yl)pyrrolidine-1-carbonitrile | H | 3.15 | 347 |

Example 60 3-(5-(4-Bromophenyl)-1,2,4-oxadiazol-3-yl)pyrrolidine-1-carbonitrile

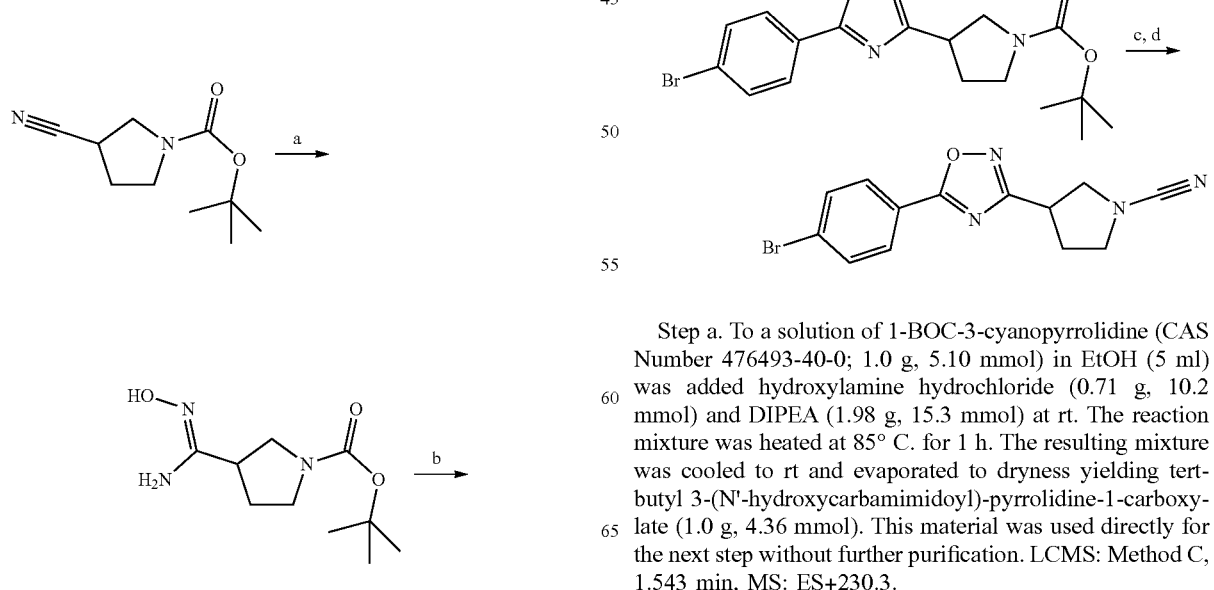

Step a. To a solution of 1-BOC-3-cyanopyrrolidine (CAS Number 476493-40-0; 1.0 g, 5.10 mmol) in EtOH (5 ml) was added hydroxylamine hydrochloride (0.71 g, 10.2 mmol) and DIPEA (1.98 g, 15.3 mmol) at rt. The reaction mixture was heated at 85° C. for 1 h. The resulting mixture was cooled to rt and evaporated to dryness yielding tert-butyl 3-(N'-hydroxycarbamimidoyl)-pyrrolidine-1-carboxylate (1.0 g, 4.36 mmol). This material was used directly for the next step without further purification. LCMS: Method C, 1.543 min, MS: ES+230.3.

Step b. To a solution of 4-bromobenzoic acid (0.6 g, 2.98 mmol) in DMF (8 ml) was added CDI (0.531 g, 3.28 mmol) and stirred at rt for 30 min. Tert-butyl 3-(N'-hydroxycarbamimidoyl)-pyrrolidine-1-carboxylate (1.72 g, 7.46 mmol) was added to the reaction mixture and stirred for 30 min at rt. Additional CDI (0.531 g, 3.28 mmol) was added to the reaction mixture and then heated at 120° C. for 1.2 h. The resulting reaction mixture was cooled to rt and poured into ice cold water (100 ml). The obtained mixture was extracted with EtOAc (3×150 ml). The combined organic phase was dried over $Na_2SO_4$, filtered and concentrated under reduced pressure. The obtained residue was purified using column chromatography (15% EtOAc in hexane) yielding tert-butyl 3-(5-(4-bromophenyl)-1,2,4-oxadiazol-3-yl)pyrrolidine-1-carboxylate (0.85 g, 2.15 mmol). LCMS: Method A, 5.863 min, MS: ES+339.86 (M-56); $^1$H NMR (400 MHz, DMSO-d6) δ ppm 8.02-8.04 (d, J=8.4 Hz, 2H), 7.84-7.86 (d, J=1.60 Hz, 2H), 3.68-3.72 (m, 2H), 3.41-3.53 (m, 4H), 3.34-3.38 (m, 1H), 2.28-2.33 (m, 1H), 2.11-2.15 (m, 1H), 1.43 (s, 9H).

Steps c, d. The title compound was synthesised from the intermediate above using a procedure similar to that described for Example 14, steps d, e. LCMS: Method A, 4.832 min, MS: ES+318.84; $^1$H NMR (400 MHz, DMSO-d6) δ ppm 8.04 (d, J=8.8 Hz, 2H), 7.86 (d, J=8.4 Hz, 2H), 3.76-3.84 (m, 2H), 3.60-3.63 (m, 1H), 3.51-3.57 (m, 2H), 2.32-2.37 (m, 1H), 2.16-2.22 (m, 1H).

Example 61 3-(5-(4 Morpholinophenyl)-1,2,4-oxadiazol-3-yl)pyrrolidine-1-carbonitrile

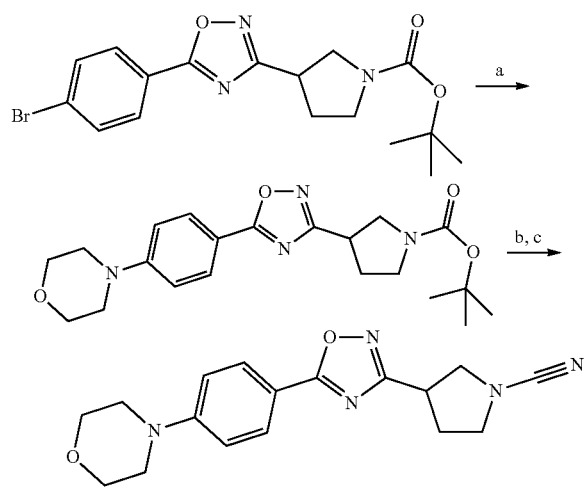

Step a. A solution of tert-butyl 3-(5-(4-bromophenyl)-1,2,4-oxadiazol-3-yl)pyrrolidine-1-carboxylate (Example 60, steps a, b; 0.2 g, 0.51 mmol) and morpholine (1.5 ml) was stirred at 140° C. for 34 h. The resulting reaction mixture was cooled to rt and poured into water (50 ml). The mixture was acidified using a 5 M HCl solution. The obtained solid precipitates were filtered and washed with hot water (50 ml). The solid was dried under vacuum yielding tert-butyl 3-(5-(4-morpholinophenyl)-1,2,4-oxadiazol-3-yl)pyrrolidine-1-carboxylate (0.1 g, 0.249 mmol). LCMS: Method C, 2.424 min, MS: ES+401.42

Steps b, c. The title compound was synthesised from the intermediate above using a procedure similar to that described for Example 14, steps d, e. Method A, 4.050 min, MS: ES+325.96; $^1$H NMR (400 MHz, DMSO-d6) δ ppm 7.92 (d, J=8.8 Hz, 2H), 7.11 (d, J=8.8 Hz, 2H), 3.67-3.81 (m, 6H), 3.50-3.61 (m, 3H), 3.31-3.34 (m, 4H), 2.28-2.36 (m, 1H), 2.12-2.21 (m, 1H).

Example 62 3-(5-(4-((R)-3 Methoxypyrrolidin-1-yl)phenyl)-1,2,4-oxadiazol-3-yl)pyrrolidine-1-carbonitrile

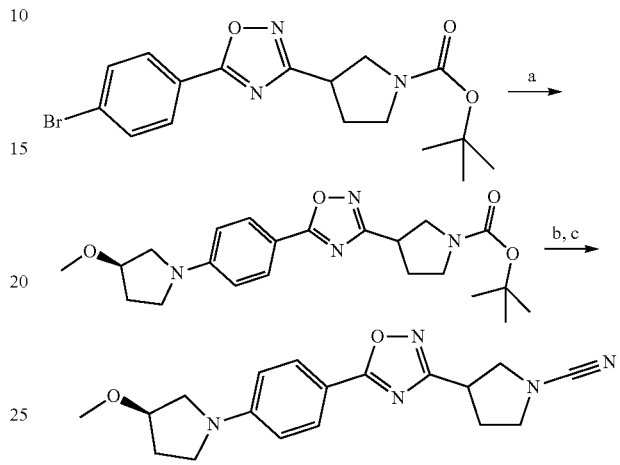

Step a. To a solution of tert-butyl 3-(5-(4-bromophenyl)-1,2,4-oxadiazol-3-yl)pyrrolidine-1-carboxylate (Example 60, steps a, b; 0.350 g, 0.88 mmol) in dry toluene (5 ml) were added (R)-3-methoxypyrrolidine hydrochloride (CAS Number 474707-30-7; 0.181 g, 1.32 mmol) and $Cs_2CO_3$ (0.717 g, 2.20 mmol) at rt under nitrogen atmosphere. The reaction mixture was degassed for 10 min at it before addition of $Pd_2(dba)_3$ (0.040 g, 0.044 mmol) and Xantphos (0.015 g, 0.026 mmol). The reaction mixture was heated at 110° C. for 16 h. The resulting mixture was cooled to rt, poured into water (100 ml) and extracted with EtOAc (3×100 ml). The combined organic phase was separated and concentrated under reduced pressure. The residue was purified by flash chromatography (5% MeOH in DCM) yielding tert-butyl 3-(5-(4-((R)-3-methoxypyrrolidin-1-yl)phenyl)-1,2,4-oxadiazol-3-yl)-pyrrolidine-1-carboxylate (0.4 g, 0.964 mmol). LCMS: Method C, 2.695 min, MS: ES+359.65 (M-56).

Steps b, c. The title compound was synthesised from the intermediate above using a procedure similar to that described for Example 14, steps d, e. LCMS: Method B, 4.224 min, MS: ES+310.51; 1H NMR (400 MHz, DMSO-d6) δ ppm 7.87 (d, J=8.8 Hz, 2H), 6.69 (d, J=9.2 Hz, 2H), 4.09-4.14 (m, 1H), 3.76-3.80 (m, 1H), 3.65-3.71 (m, 1H), 3.47-3.51 (m, 4H), 3.36-3.45 (m, 3H), 3.28 (s, 3H), 2.27-2.35 (m, 1H), 2.05-2.20 (m, 3H).

Example 63 (R)-3-(5-(4-Phenylpyridin-2-yl)-1,2,4-oxadiazol-3-yl)pyrrolidine-1-carbonitrile

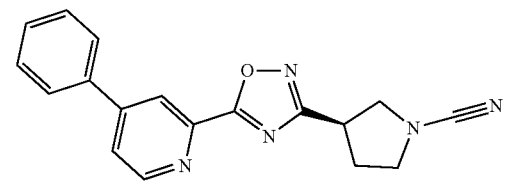 [SMILES: N#CN1CC[C@@H](c2noc(-c3cc(-c4ccccc4)ccn3)n2)C1]

The title compound was synthesised using a procedure similar to that described for Example 60, using 4-phenyl-2-pyridinecarboxylic acid (CAS Number 52565-56-7) in step b. LCMS: Method A, 4.326 min, MS: ES+318.04; ¹H NMR (400 MHz, DMSO-d6) δ ppm 8.88 (d, J=4.8 Hz, 1H), 8.48 (d, J=1.2 Hz, 1H), 8.06 (dd, J=2 Hz, 5.2 Hz, 1H), 7.91-7.94 (m, 2H), 7.53-7.61 (m, 3H), 3.80-3.87 m, 2H), 3.60-3.69 (m, 1H), 3.52-3.59 (m, 2H), 2.35-2.45 (m, 1H), 2.21-2.33 (m, 1H).

Example 64 (R)-3-(5-(1-(Pyrimidin-2 yl)piperidin-4 yl)-1,2,4-oxadiazol-3 yl)pyrrolidine-1-carbonitrile

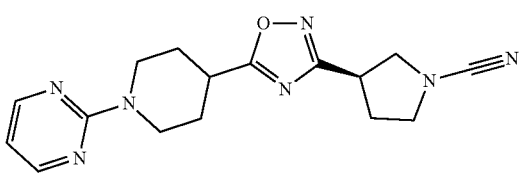 [SMILES: N#CN1CC[C@@H](c2noc(C3CCN(c4ncccn4)CC3)n2)C1]

The title compound was synthesised using a procedure similar to that described for Example 60, using 1-(2-pyrimidinyl)piperidine-4-carboxylic acid (CAS Number 303144-44-7) in step b. LCMS: Method A, 3.748 min, MS: ES+326.09; ¹H NMR (400 MHz, DMSO-d6) δ ppm 8.37 (d, J=4.4 Hz, 2H), 6.61-6.64 (t, J=4.4 Hz, 1H), 4.55-4.60 (m, 2H), 3.73-3.77 (m, 1H), 3.64-3.68 (m, 1H), 3.47-3.53 (m, 3H), 3.35-3.41 (m, 1H), 3.14-3.20 (m, 2H), 2.26-2.30 (m, 1H), 2.04-2.13 (m, 3H), 1.68-1.71 (m, 2H).

Example 65 (R)-3-(5-(2-(3,4-Dihydroisoquinolin-2(1H)-yl)pyridin-4-yl)-1,2,4-oxadiazol-3-yl)pyrrolidine-1-carbonitrile and dried under high vacuum yielding 2-bromoisonicotinic acid (0.246 g, 1.22 mmol). LCMS: Method C, 1.650 min, MS: ES+202.10, 204.10 Step b. To a solution of tert-butyl (R)-3-cyanopyrrolidine-1-carboxylate (CAS Number 132945-76-7; 1.00 g, 5.10 mmol) in EtOH (5.6 ml) were added NH₂OH·HCl (0.709 g, 10.20 mmol) and DIPEA (1.97 g, 15.3 mmol) at rt. The reaction mixture was heated to 85° C. and stirred at rt for 1 h. The reaction mixture was cooled to rt and concentrated under reduced pressure yielding tert-butyl (R,Z)-3-(N'-hydroxycarbamimidoyl)pyrrolidine-1-carboxylate (1.000 g, 4.367 mmol). LCMS: Method C, 1.542 min, MS: ES+230.35

Step c. To a solution of 2-bromoisonicotinic acid (0.215 g, 1.064 mmol) in DMF (7 ml) was added CDI (0.192 g, 1.170 mmol) at rt. The reaction mixture was stirred at rt for 30 min. Tert-butyl (R)-3-(N'-hydroxycarbamimidoyl)pyrrolidine-1-carboxylate (0.613 g, 2.665 mmol) and CDI (0.192 g, 1.170 mmol) were added to the reaction mixture. The reaction mixture was heated to 12.5° C. for 1 h. The reaction mixture was cooled to rt and diluted with water (20 ml). The resulting mixture was extracted with EtOAc (4×10 ml). The combined organic phase was dried over Na₂SO₄, filtered and concentrated under reduced pressure. The resulting residue was purified by column chromatography (20% EtOAc in hexane) yielding tert-butyl (R)-3-(5-(2-bromopyridin-4-yl)-1,2,4-oxadiazol-3-yl)pyrrolidine-1-carboxylate (0.230 g, 0.582 mmol). LCMS: Method C, 2.65 min, MS: ES+339.34, 341.30 (M-56).

Step d. To a solution of tert-butyl (R)-3-(5-(2-bromopyridin-4-yl)-1,2,4-oxadiazol-3-yl)pyrrolidine-1-carboxylate (0.190 g, 0.482 mmol) in DMF (7 ml) was added K₂CO₃ (0.133 g, 0.963 mmol) at rt. The reaction mixture was stirred at rt for 30 min and then treated with 1,2,3,4-tetrahydroisoquinoline (0.084 g, 0.631 mmol). The reaction mixture was

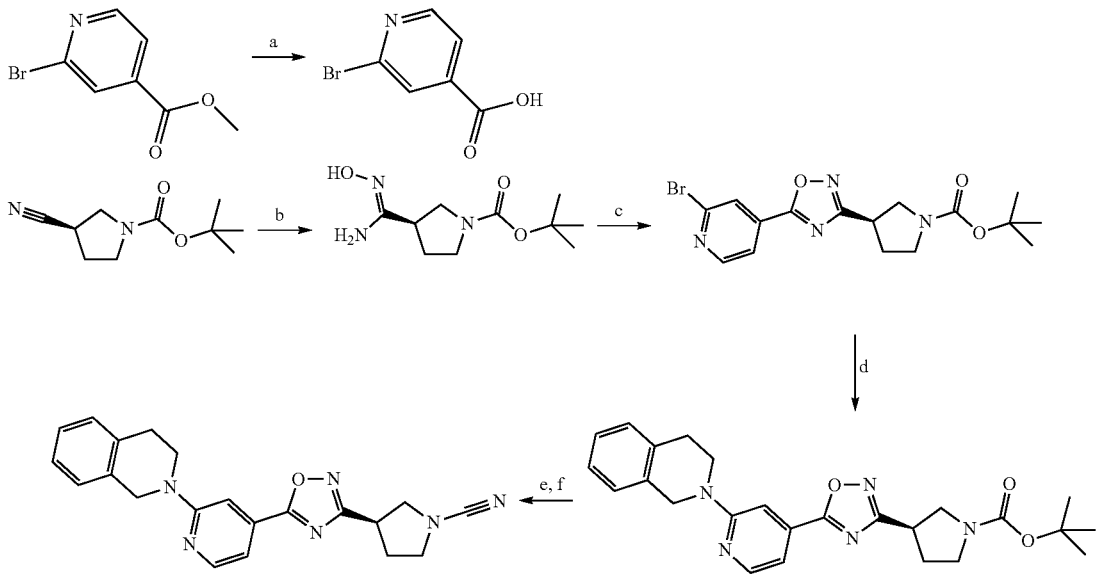

Step a. To a solution of methyl 2-bromoisonicotinate (0.300 g, 1.39 mmol) in THF:water (1:1, 8.9 ml) was added LiOH·H₂O (0.233 g, 5.55 mmol) at rt. The reaction mixture was stirred at rt for 16 h. The resulting reaction mixture was acidified with concentrated HCl (1 ml) and stirred for 10 min at rt. The obtained precipitates were collected by filtration heated to 120° C. for 6 h. The reaction mixture was cooled to rt and poured into water (10 ml). The resulting mixture was extracted with EtOAc (4×10 ml). The combined organic phase was dried over Na₂SO₄, filtered and concentrated under reduced pressure yielding tert-butyl (R)-3-(5-(2-(3,4-dihydroisoquinolin-2(1H)-yl)pyridin-4-yl)-1,2,4-oxadiazol- 3-yl)pyrrolidine-1-carboxylate (0.200 g, 0.446 mmol). LCMS: Method C, 3.005 min, MS: ES+448.51

Steps e, f. The title compound was synthesised from the intermediate above using a procedure similar to that described for Example 14, steps d, e. LCMS: Method D, 7.268 min, MS: ES+373.05; ¹H NMR (400 MHz, DMSO-d6) δ ppm 8.40 (d, J=5.2 Hz, 1H), 7.40 (s, 1H), 7.30-7.31 (m, 1H), 7.21 7.22 (m, 4H), 4.78 (s, 2H), 3.85 (t, J=7.2 Hz, 2H), 3.79-3.82 (m, 2H), 3.63-3.65 (m, 1H), 3.53 3.57 (m, 2H), 2.92-2.95 (t, J=6.0 Hz, 2H), 2.33-2.39 (m, 1H), 2.18-2.24 (m, 1H).

Example 66 3-(5-(4-(1-Methyl-1H-pyrazol-4-yl)phenyl)-1,2,4-oxadiazol-3-yl)pyrrolidine-1-carbonitrile

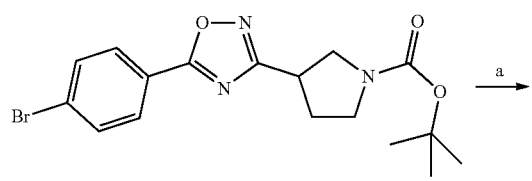

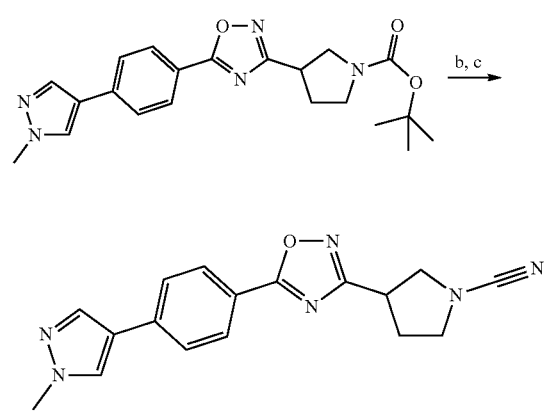

Step a. To a solution of tert-butyl 3-(5-(4-bromophenyl)-1,2,4-oxadiazol-3-yl)pyrrolidine-1-carboxylate (Example 60, steps a, b; 0.250 g, 0.634 mmol) in toluene:EtOH:water (1:0.5:0.5, 4 ml) was added 1-methyl-4-(4,4,5,5-tetramethyl-1,3,2-dioxaborolan-2-yl)-1H-pyrazole (CAS Number 761446-44-0; 0.197 g, 0.947 mmol) followed by NaHCO₃ (0.213 g, 2.535 mmol) at rt. The resulting reaction mixture was degassed for 10 min before addition of PdCl₂(dppf) (0.040 g, 0.054 mmol). The reaction mixture was heated at 110° C. for 8 h. The resulting reaction mixture was cooled to rt, poured into water (100 ml) and extracted with EtOAc (3×100 ml). The combined organic phase was dried over Na₂SO₄, filtered and concentrated under reduced pressure. The obtained residue was purified by flash chromatography (100% EtOAc) yielding tert-butyl 3-(5-(4-bromophenyl)-1,2,4-oxadiazol-3-yl)pyrrolidine-1-carboxylate (0.100 g, 0.253 mmol). LCMS: Method C, 2.316 min, MS: ES+396.50

Steps b, c. The title compound was synthesised from the intermediate above using a procedure similar to that described for Example 14, steps d, e. LCMS: Method A, 3.842 min, MS: ES+320.97; ¹H NMR (400 MHz, DMSO-d6) δ ppm 8.35 (s, 1H), 8.07 (d, J=8.4 Hz, 2H), 8.03 (s, 1H), 7.83 (d, J=8.4 Hz, 2H), 3.89 (s, 3H), 3.75-3.84 (m, 2H), 3.59-3.64 (m, 1H), 3.52-3.57 (m, 2H), 2.33-2.37 (m, 1H), 2.17-2.22 (m, 1H).

Example 67 2-(5-([1,1'-Biphenyl]-4-yl)-1,2,4-oxadiazol-3-yl)pyrrolidine-1-carbonitrile

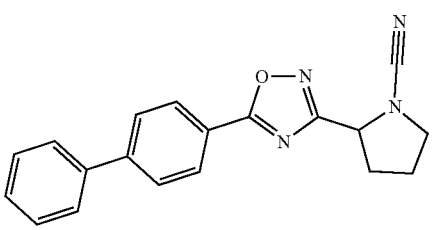 [SMILES: N#CN1CCCC1c1noc(-c2ccc(-c3ccccc3)cc2)n1]

The title compound was synthesised using a procedure similar to that described for Example 66. LCMS: Method A, 4.016 min, MS: ES+350.97; ¹H NMR (400 MHz, DMSO-d6) δ ppm 8.30 (s, 1H), 8.05 (s, 1H), 7.87 (d, J=8.0 Hz, 1H), 7.69-7.71 (m, 1H), 7.66 (s, 1H), 4.01 (s, 3H), 3.90 (s, 3H), 3.75-3.84 (m, 2H), 3.62-3.65 (m, 1H), 3.52-3.57 (m, 2H), 2.33-2.38 (m, 1H), 2.18-2.22 (m, 1H).

Example 68 2-(5-([1,1'-Biphenyl]-3 yl)-1,2,4-oxadiazol-3 yl)pyrrolidine-1-carbonitrile

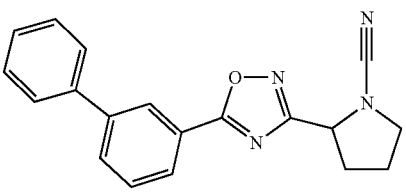 [SMILES: N#CN1CCCC1c1noc(-c2cccc(-c3ccccc3)c2)n1]

The title compound was synthesised using a procedure similar to that described for Example 66. LCMS: Method A, 4.016 min, MS: ES+350.97; ¹H NMR (400 MHz, DMSO-d6) δ ppm 8.30 (s, 1H), 8.05 (s, 1H), 7.87 (d, J=8.0 Hz, 1H), 7.69-7.71 (m, 1H), 7.66 (s, 1H), 4.01 (s, 3H), 3.90 (s, 3H), 3.75-3.84 (m, 2H), 3.62-3.65 (m, 1H), 3.52-3.57 (m, 2H), 2.33-2.38 (m, 1H), 2.18-2.22 (m, 1H).

Example 69 3-(5-(1-Phenylpyrrolidin-3 yl)-1,2,4-oxadiazol-3 yl)pyrrolidine-1-carbonitrile

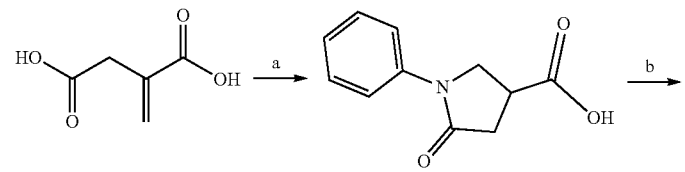

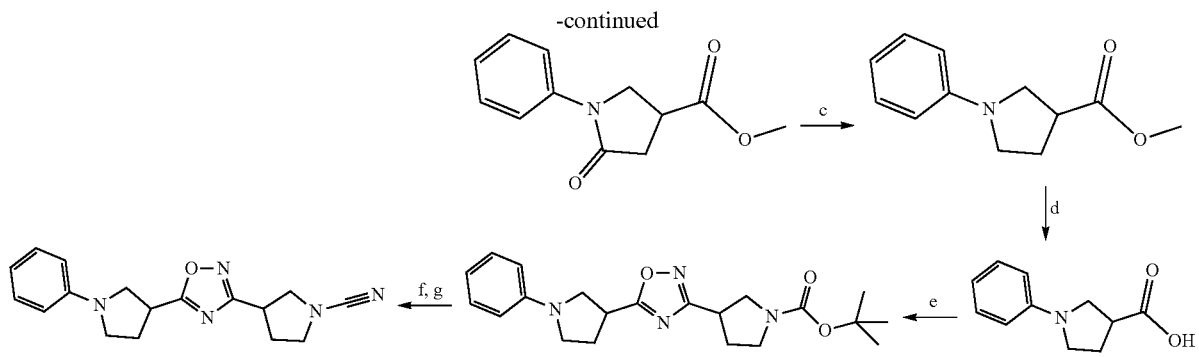

Step a. To a mixture of 2-methylenesuccinic acid (CAS Number 97-65-4; 5 g, 38.45 mmol) in water (9 ml) was added aniline (3 g, 31.9 mmol) at rt. The reaction mixture was heated at 115° C. for 30 h. The resulting mixture was cooled to rt and poured into 6 M NaOH solution (10 ml). The obtained mixture was stirred at rt for 15 min and the resulting solid precipitates collected by vacuum filtration and the filtrate was acidified using 6 M HCl. The resulting solid precipitates were filtered and dried under vacuum to yield 5-oxo-1-phenylpyrrolidine-3-carboxylic acid (6.5 g, 31.7 mmol). LCMS: Method C, 1.701 min, MS: ES+206.18; $^1$H NMR (400 MHz, DMSO-d6) δ ppm 12.79 (s, 1H), 7.63 7.66 (m, 2H), 7.35-7.39 (m, 2H), 7.12-7.16 (t, 1H), 4.03-4.08 (m, 1H), 3.94-3.98 (m, 1H), 3.32-3.39 (m, 1H), 2.76-2.83 (m, 1H), 2.66-2.77 (m, 1H).

Step b. To a solution of 5-oxo-1-phenylpyrrolidine-3-carboxylic acid (3 g, 14.629 mmol) in MeOH (20 ml) was added thionyl chloride (1.51 ml, 21.94 mmol) at 0° C. The reaction mixture was stirred at rt for 1.5 h. The resulting reaction mixture was concentrated under reduced pressure to yield methyl 5-oxo-1-phenylpyrrolidine-3-carboxylate (2.5 g, 11.41 mmol). LCMS: Method C, 1.907 min, MS: ES+221.24. The material was used for the next step without purification.

Step c. To a solution of methyl 5-oxo-1-phenylpyrrolidine-3-carboxylate (1 g, 4.566 mmol) in THF (4 ml) was added solution of 9-borabicyclo[3.3.1]nonane, 0.5 M in THF (18 ml) at rt. The reaction mixture was stirred at rt for 16 h. The resulting reaction mixture was concentrated under reduced pressure. The obtained residue was purified using column chromatography (50-70% EtOAc in hexane) to yield methyl 1-phenylpyrrolidine-3-carboxylate (0.3 g, 1.462 mmol). LCMS: Method C, 2.441 min, MS: ES+207.13

Step d. To a solution of methyl 1-phenylpyrrolidine-3-carboxylate (0.3 g, 1.462 mmol) in THF (3 ml) was added solution of LiOH·H$_2$O (0.307 g, 7.31 mmol) in water (3 ml) at rt. The reaction mixture was stirred at rt for 16 h. The resulting reaction mixture was concentrated under vacuum, acidified using 1 M HCl solution up to pH 3. The resulting mixture was extracted with EtOAc (3×100 ml). The combined organic phase was dried over Na$_2$SO$_4$, filtered and concentrated under reduced pressure. The obtained residue was yielding 1-phenylpyrrolidine-3-carboxylic acid (0.2 g, 1.046 mmol). This material was used directly for the next step without further purification.

Step e. To a solution of 1-phenylpyrrolidine-3-carboxylic acid (0.2 g, 1.04 mmol) in DMF (3 ml) was added CDI (0.186 g, 1.15 mmol) at rt. The reaction mixture was stirred at it for 30 min. Tert-butyl 3-(N'-hydroxycarbamimidoyl) pyrrolidine-1-carboxylate (Example 60, step a; 0.6 g, 2.61 mmol) and CDI (0.186 g, 1.15 mmol) were added to the reaction mixture. The reaction mixture was heated at 120° C. for 45 min. The resulting reaction mixture was cooled to it and poured into chilled water (150 ml) and extracted with EtOAc (3×100 ml). The combined organic phase was dried over Na$_2$SO$_4$, filtered and concentrated under reduced pressure. The obtained residue was purified using column chromatography (15% EtOAc in hexane) to yielding tert-butyl 3-(5-(1-phenylpyrrolidin-3-yl)-1,2,4-oxadiazol-3-yl)pyrrolidine-1-carboxylate (0.1 g, 0.260 mmol). LCMS: Method C, 2.808 min, MS: ES+385.60

Steps f, g. The title compound was synthesised from the intermediate above using a procedure similar to that described for Example 14, steps d, e. LCMS: Method B, 4.450 min, MS: ES+310.51; $^1$H NMR (400 MHz, DMSO-d6) δ ppm 7.19 (t, J=8.4 Hz, 2H), 6.62-6.69 (m, 3H), 3.91-3.94 (m, 1H), 3.70-3.83 (m, 2H), 3.56-3.69 (m, 5H), 3.41-3.54 (m, 2H), 2.51-2.60 (m, 1H), 2.48-2.33 (m, 2H), 2.24-2.30 (m 1H).

Example 70 (R)-3-(5-(4-Fluoro-3-(1-methyl-1H-pyrazol-4-yl)phenyl)-1,2,4-oxadiazol-3-yl)pyrrolidine-1-carbonitrile

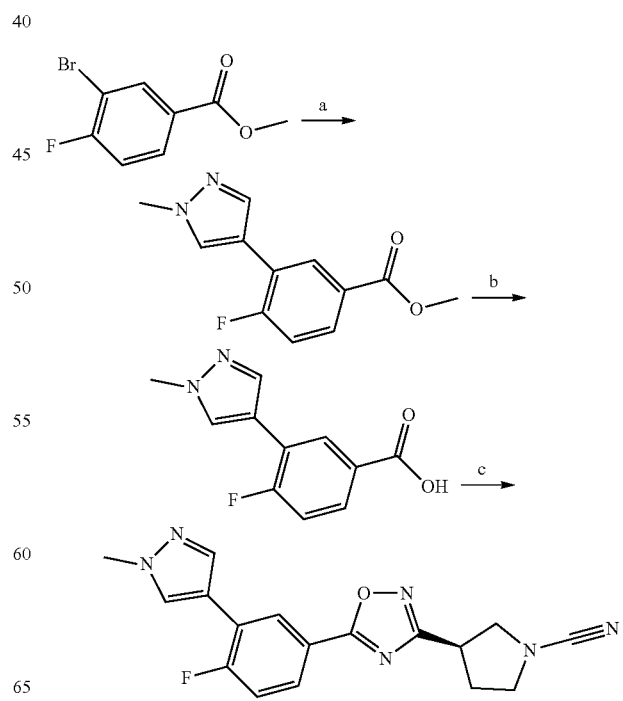

Step a. To a solution of methyl 3-bromo-4-fluorobenzoate (CAS Number 82702-31-6; 0.5 g, 2.14 mmol) and 1-methyl-4-(4,4,5,5-tetramethyl-1,3,2-dioxaborolan-2-yl)-1H-pyrazole (CAS Number 761446-44-0; 0.639 g, 3.22 mmol) in DMF:water (7:3, 10 ml) was added Na$_2$CO$_3$ (0.682 g, 6.43 mmol) at rt. The resulting reaction mixture was degassed for 15 min before addition of Pd(dppf)Cl$_2$ (0.078 g, 0.107 mmol). The reaction mixture was heated at 120° C. in a microwave for 1 h. The resulting reaction mixture was cooled to rt and poured into water (100 ml). The obtained mixture was extracted with EtOAc (2×50 ml). The combined organic phase was dried over Na$_2$SO$_4$, filtered and concentrated under reduced pressure. The obtained residue was purified using column chromatography (3.5% MeOH in DCM) yielding methyl 4-fluoro-3-(1-methyl-1H-pyrazol-4-yl) benzoate (0.3 g, 1.28 mmol). LCMS: Method C, 2.092 min, MS: ES+235.35.

Step b. To a solution of methyl 4-fluoro-3-(1-methyl-1H-pyrazol-4-yl)benzoate (0.6 g, 2.564 mmol) in THF (5 ml) was added a solution of LiOH·H$_2$O (0.753 g, 17.95 mmol) in water (5 ml) at rt. The reaction mixture was stirred at rt for 16 h. The resulting reaction mixture was concentrated under vacuum and the obtained residue was diluted with water (50 ml). The obtained mixture was acidified using 1 M HCl solution up to pH 3. The resulting solid precipitates were collected by filtration and dried under reduced pressure to yield 4-fluoro-3-(1-methyl-1H-pyrazol-4-yl)benzoic acid (0.3 g, 1.36 mmol). LCMS: Method C, 1.819 min, MS: ES+221.29. This material was used for the next step without purification.

Steps c-e. The title compound was synthesised from the intermediate above using a procedure similar to that described for Example 60, steps b-d. LCMS: Method B, 4.450 min, MS: ES+310.51; $^1$H NMR (400 MHz, DMSO-d6) δ ppm 8.46 (dd, J=2.4, 7.2 Hz, 1H), 8.18 (s, 1H), 8.02-8.06 (m, 1H), 8.01 (s, 1H), 7.42 (m, 1H), 3.99 (s, 3H), 3.85-3.88 (m, 1H), 3.76-3.81 (m, 2H), 3.62-3.68 (m, 2H), 2.42-2.46 (m, 1H), 2.36-2.39 (m, 1H).

Example 71 (R)-3-(5-(3 Methoxy-4-(1-methyl-1H-pyrazol-4-yl)phenyl)-1,2,4-oxadiazol-3-yl)pyrrolidine-1-carbonitrile

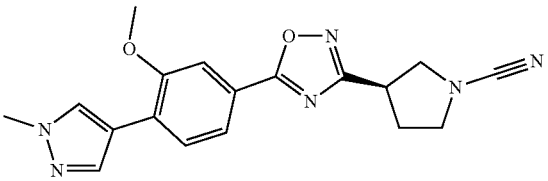 [SMILES: COc1cc(-c2nc([C@@H]3CCN(C#N)C3)no2)ccc1-c1cnn(C)c1]

The title compound was synthesised using a procedure similar to that described for Example 70, using methyl 4-bromo-3-methoxybenzoate (CAS Number 17100-63-9). LCMS: Method A, 4.016 min, MS: ES+350.97; $^1$H NMR (400 MHz, DMSO-d6) δ ppm 8.30 (s, 1H), 8.05 (s, 1H), 7.87 (d, J=8.0 Hz, 1H), 7.69-7.71 (m, 1H), 7.66 (s, 1H), 4.01 (s, 3H), 3.90 (s, 3H), 3.75-3.84 (m, 2H), 3.62-3.65 (m, 1H), 3.52-3.57 (m, 2H), 2.33-2.38 (m, 1H), 2.18-2.22 (m, 1H).

Example 197 3-(3-(3-(3-Cyanophenyl)azetidin-1-yl)-1,2,4-oxadiazol-5-yl)pyrrolidine-1-carbonitrile

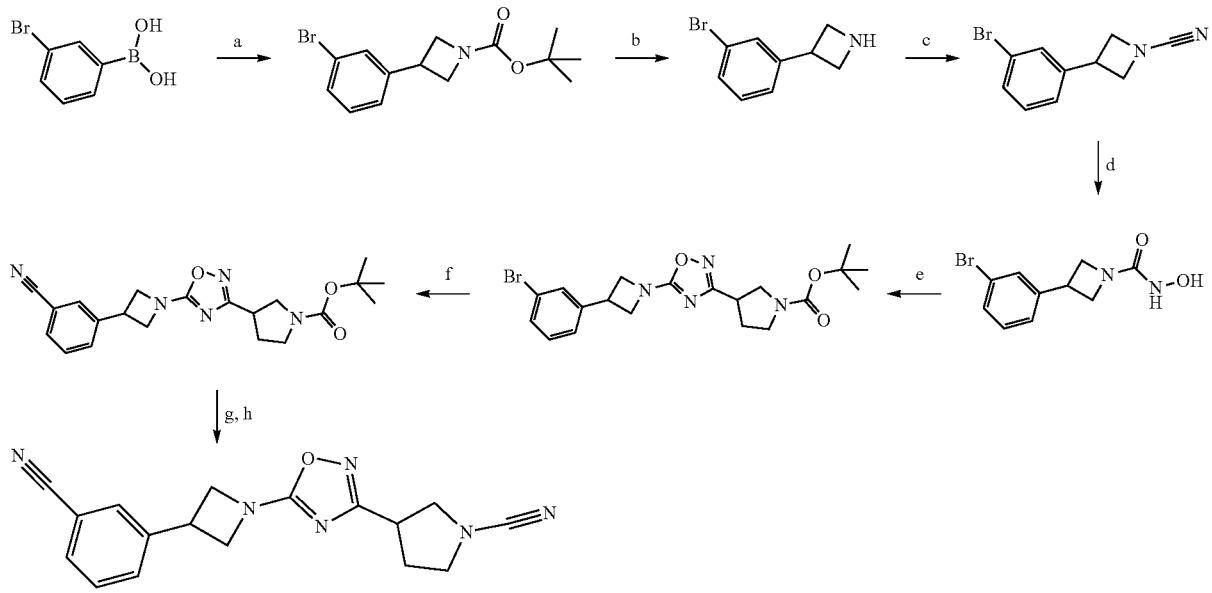

Step a. To a solution of (3-bromophenyl)boronic acid (2.830 g, 14.13 mmol) in IPA (20 ml) was added NiI$_2$ (0.132 g, 0.423 mmol) and trans-2-aminocyclohexanol HCl (0.064 g, 0.423 mmol) at rt. A solution of NaHMDS (1M in THF) (14 ml, 14 mmol) was added dropwise to the reaction mixture at rt. The reaction mixture was degassed for 30 min before addition of tert-butyl-3-iodoazitidine-1-carboxylate (CAS Number 254454-54-1; 2.00 g, 7.06 mmol). The reaction mixture was heated at 90° C. for 2 h. The resulting mixture was concentrated under reduced pressure and diluted with water (100 ml). The resulting mixture was extracted with EtOAc (2×100 ml). The combined organic phases were dried over Na$_2$SO$_4$ and evaporated under reduced pressure. The residue was purified by flash chromatography (5% EtOAc in hexane) yielding tert-butyl 3-(3-bromophenyl)azetidine-1-carboxylate (1.780 g, 5.705 mmol). LCMS: Method C, 2.455 min, MS: ES+312.00, 314.00

Step b. To a solution of tert-butyl 3-(3-bromophenyl)azetidine-1-carboxylate (1.70 g, 5.45 mmol) in DCM (50 ml) was added TFA (8.5 ml) at 0° C. The reaction mixture was stirred at rt for 2 h. The resulting mixture was concentrated under reduced pressure and co-distilled with DCM (3×100 ml). The residue was triturated with n-pentane (2×10 ml) and dried under high vacuum yielding 3-(3-bromophenyl)azetidine TFA Salt (2.55 g). This material is directly used for the next step without any further purification. LCMS: Method C, 1.394 min, MS: ES+212.20, 214.20

Step c. To a solution of 3-(3-bromophenyl)azetidine TFA Salt (2.50 g, 7.67 mmol) in TT-IF (25 ml) was added $K_2CO_3$ (3.170 g, 27.3 mmol). The reaction mixture was stirred at rt for 10 min, cooled to 0° C. and treated with cyanogen bromide (0.812 g, 7.67 mmol). The reaction mixture was stirred at rt for 1 h. The resulting mixture was poured into water (100 ml) and extracted with EtOAc (2×100 ml). The combined organic phases were dried over $Na_2SO_4$ and evaporated under reduced pressure. The residue was purified by flash chromatography (80% EtOAc in hexane) yielding 3-(3-bromophenyl)-azetidine-1-carbonitrile (1.050 g, 4.43 mmol). LCMS: Method C, 2.072 min, MS: ES+237.10, 239.10

Step d. To a solution of (3-(3-bromophenyl)azetidine-1-carbonitrile (1.00 g, 4.22 mmol) in EtOH (8 ml) was added $NaHCO_3$ (1.41 g, 16.9 mmol) and $NH_2OH \cdot HCl$ (0.586 g, 8.43 mmol) at rt. The reaction mixture was heated at 80° C. for 2 h. The resulting reaction mixture was cooled to rt, filtered over celite and washed with EtOH (5 ml). The combined filtrate was evaporated under reduced pressure yielding 3-(3-bromophenyl)-N'-hydroxyazetidine-1-carboximidamide (1.00 g, 3.70 mmol). This material was used for the next step without further purification. LCMS: Method C, 1.520 min, MS: ES+270.30, 272.30

Step e. To a solution of 1-(tert-butoxycarbonyl)pyrrolidine-3-carboxylic acid (0.665 g, 3.09 mmol) in DMF (8 ml) was added CDI (1.002 g, 6.182 mmol) at rt in a microwave tube. The reaction mixture was stirred at rt for 30 min before addition of 3-(3-bromophenyl)-N'-hydroxyazetidine-1-carboximidamide (1.000 g, 3.703 mmol). The reaction mixture was heated at 120° C. for 30 min under microwave irradiation. The resulting mixture was cooled to rt, poured into water (100 ml) and extracted with EtOAc (3×50 ml). The combined organic phases were dried over $Na_2SO_4$ and evaporated under reduced pressure. The residue was purified by flash chromatography (15% EtOAc in hexane) yielding tert-butyl 3-(3-(3-bromophenyl)azetidin-1-yl)-1,2,4-oxadiazol-5-yl)pyrrolidine-1-carboxylate (0.490 g, 1.090 mmol). LCMS: Method A, 5.146 min, MS: ES+449.0, 451.0

Step f. To a solution of tert-butyl 3-(3-(3-(3-bromophenyl)azetidin-1-yl)-1,2,4-oxadiazol-5-yl)-pyrrolidine-1-carboxylate (0.480 g, 1.07 mmol) in NMP (3 ml) were added zinc dust (0.035 g, 0.534 mmol), $Zn(CN)_2$ (0.313 g, 2.67 mmol) and tri-tert-butyl phosphonium tetrafluoroborate (0.062 g, 0.213 mmol) at rt in a microwave tube. The reaction mixture was degassed for 20 min before addition of $Pd_2(dba)_3$ (0.195 g, 0.213 mmol). The reaction mixture was heated at 155° C. for 1 h under microwave irradiation. The resulting mixture was cooled to rt, poured into ice cold water (60 ml) and extracted with EtOAc (3×50 ml). The combined organic phase was dried over $Na_2SO_4$, filtered and evaporated under reduced pressure. The residue was purified by flash chromatography (80% EtOAc in hexane) yielding tert-butyl 3-(3-(3-(3-cyanophenyl)azetidin-1-yl)-1,2,4-oxadiazol-5-yl)pyrrolidine-1-carboxylate (0.118 g, 0.298 mmol). LCMS: Method C, 2.167 min, MS: ES+396.50

Steps g, h. The title compound was synthesised from the intermediate above using a procedure similar to that described for Example 14, steps d, e. LCMS: Method B, 3.689 min, MS: ES+321.38; $^1$H NMR (400 MHz, DMSO-d6) δ ppm 7.92 (s, 1H), 7.74-7.78 (m, 2H), 7.58 (t, J=8.0 Hz, 1H), 4.35 4.39 (m, 2H), 4.05-4.14 (m, 1H), 4.00-4.03 (m, 2H), 3.75-3.80 (m, 2H), 3.59-3.62 (m, 1H), 3.47-3.51 (m, 2H), 2.30-2.35 (m, 1H), 2.12-2.18 (m, 1H).

Example 198 3-(3-(3-(4-Cyanophenyl)azetidin-1-yl)-1,2,4-oxadiazol-5-yl)pyrrolidine-1-carbonitrile

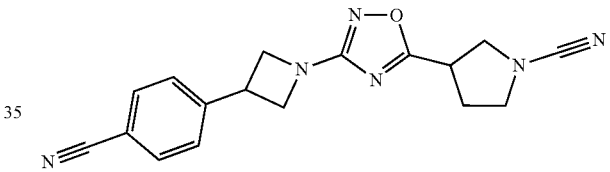

The title compound was synthesised using a procedure similar to that described for Example 198. LCMS: Method B, 3.581 min, MS: ES+321.28; $^1$H NMR (400 MHz, DMSO-d6) δ ppm 7.85 (d, J=8.4 Hz, 2H), 7.62 (d, J=8.0 Hz, 2H), 4.38-4.42 (m, 2H), 4.13-4.16 (m, 1H), 3.97-4.01 (m, 2H), 3.76-3.78 (m, 2H), 3.56-3.61 (m, 1H), 3.47-3.50 (m, 2H), 2.29-2.33 (m, 1H), 2.11-2.16 (m, 1H).

Scheme 4

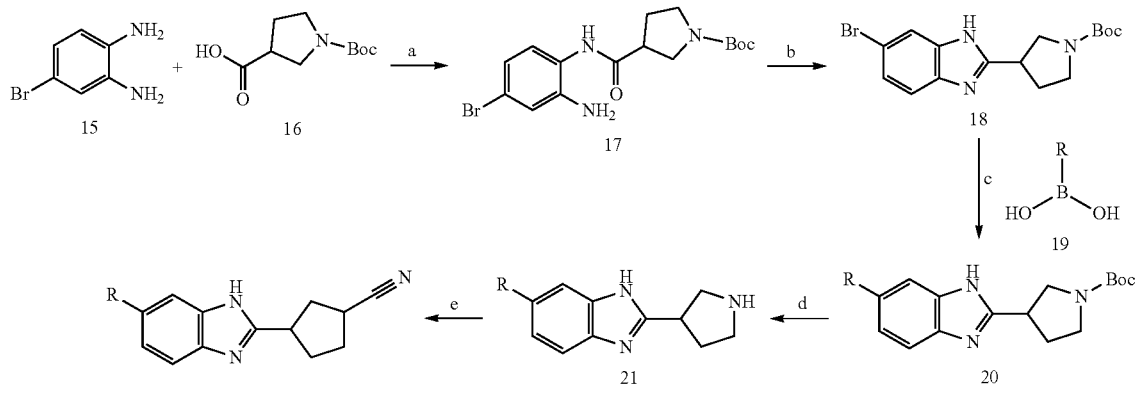

Reagents and conditions: a) EDCI, DCM, rt 16 h b) Acetic acid, 60° C., 16 h; c) Pd(PPh$_3$)$_4$, K$_2$CO$_3$, 1,4-dioxane, water, 100° C., 16 h; d) HCL/EtOAc, 2 h; e) cyanogen bromide, NaHCO$_3$, EtOH, rt, 16 h.

Step a. To a solution of 4-bromobenzene-1,2-diamine (10.00 g, 53.46 mmol) in DCM (240 ml) was added EDCI (11.27 g, 58.8 mmol). The mixture was stirred at rt for 16 h. The reaction mixture was partitioned between DCM (100 ml) and water (200 ml). The organic phase was separated, washed with brine (200 ml), dried over Na₂SO₄, filtered and concentrated under reduced pressure to give a residue. The residue was purified by flash silica gel chromatography (ISCO®; 220 g SepaFlash® Silica Flash Column, eluent of 35-65% EtOAc/PE gradient at 60 ml/min) to provide tert-butyl 3-((2-amino-4-bromophenyl)carbamoyl)-pyrrolidine-1-carboxylate (9.10 g, 16.34 mmol, 30.57% yield, 69% purity) as a brown solid. MS: ES+385.2.

Step b. Tert-butyl 3-[(2-amino-4-bromo-phenyl)carbamoyl]pyrrolidine-1-carboxylate (9.10 g, 23.68 mmol) was dissolved in acetic acid (15 ml) The mixture was stirred at 60° C. for 16 h. LCMS indicated the starting material was consumed completely. The mixture was concentrated under reduced pressure to give a residue. The residue was purified by preparative HPLC to provide tert-butyl 3-(6-bromo-1H-benzo[d]imidazol-2-yl)pyrrolidine-1-carboxylate (1.60 g, 4.32 mmol, 18.26% yield, 99% purity) as a white solid. MS: ES+367.2

Step c. To a solution of tert-butyl 3-(6-bromo-1H-benzo[d]imidazol-2-yl)pyrrolidine-1-carboxylate (0.2 mmol), Compound 19 (0.2 mmol) and K₂CO₃ (0.6 mmol) in 1,4-dioxane (1 ml) and water (0.2 ml) was added Pd(PPh₃)₄ (0.2 eq) at rt under nitrogen. The reaction mixture was stirred at 100° C. for 16 h. The resulting mixture was concentrated under reduced pressure. The resulting residue was purified by preparative TLC (50% EtOAc/PE) to provide Compound 20.

Step d. To a solution of Compound 20 in EtOAc (1 ml) was added HCl/EtOAc (4 M, 1 ml). The reaction mixture was stirred at rt for 2 h. The resulting mixture was concentrated under reduced pressure. The residue Compound 21 was used for the next step directly without further purification.

Step e. To a solution of Compound 21 in EtOH (2 ml) was added cyanogen bromide (0.2 mmol) and NaHCO₃ (0.6 mmol). The reaction mixture was stirred at rt for 16 h. The resulting mixture was concentrated under reduced pressure. The crude was purified by preparative reverse phase HPLC (A: 0.078% CH₃COONH₄ in water, B: MeCN) to provide Compound 22.

Compounds in Table 5 were synthesised using the method as exemplified by Scheme 4.

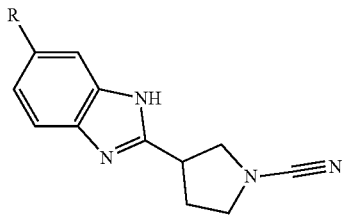

TABLE 5

| Ex | R1 | Name | LCMS Method | LCMS RT (min) | MS (ES+) |
|---|---|---|---|---|---|
| 72 | 3-cyanophenyl | 3-(6-(3-Cyanophenyl)-1H-benzo[d]imidazol-2-yl)pyrrolidine-1-carbonitrile | 2.61 | J | 314 |
| 73 | 2-(benzyloxy)phenyl | 3-(6-(2-(Benzyloxy)phenyl)-1H-benzo[d]imidazol-2-yl)pyrrolidine-1-carbonitrile | 2.22 | K | 395 |
| 74 | 4-carbamoylphenyl | 4-(2-(1-Cyanopyrrolidin-3-yl)-1H-benzo[d]imidazol-6-yl)benzamide | 1.83 | H | 332 |

TABLE 5-continued

| Ex | R1 | Name | LCMS Method | LCMS RT (min) | MS (ES+) |
|---|---|---|---|---|---|
| 75 | | 4-(2-(1-Cyanopyrrolidin-3-yl)-1H-benzo[d]imidazol-6-yl)-N-methylbenzamide | 1.92 | H | 346 |
| 76 | | 3-(6-(2-Fluoro-5-methylphenyl)-1H-benzo[d]imidazol-2-yl)pyrrolidine-1-carbonitrile | 2.18 | K | 321 |
| 77 | | 3-(6-(6-Isopropoxypyridin-3-yl)-1H-benzo[d]imidazol-2-yl)pyrrolidine-1-carbonitrile | 2.38 | J | 348 |
| 78 | | 3-(6-(1-Isobutyl-1H-pyrazol-4-yl)-1H-benzo[d]intidazol-2-yl)pyrrolidine-1-carbonitrile | 2.41 | H | 335 |
| 79 | | N-Benzyl-4-(2-(1-cyanopyrrolidin-3-yl)-1H-benzo[d]imidazol-6-yl)benzamide | 2.09 | H | 422 |

Scheme 5

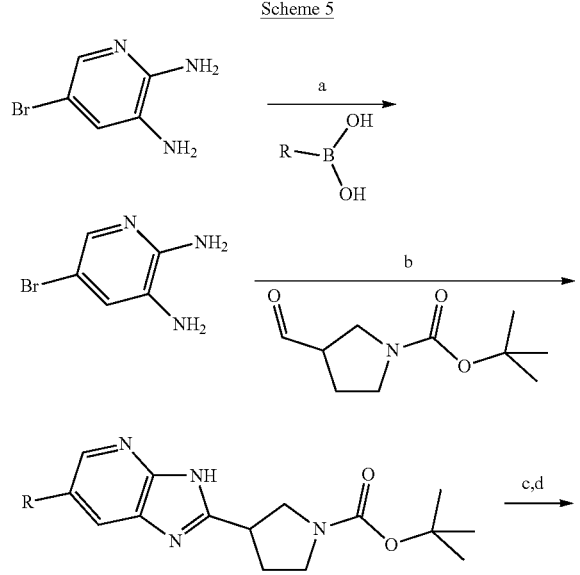

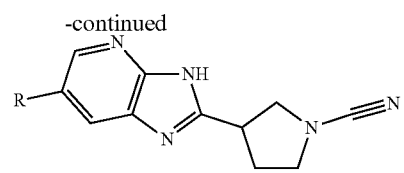

Reagents and conditions: a) NaHCO₃, Pd(PPh₃)₄, 1,4-dioxane, water, 80° C., 16 h; b) sodium metabisulphite, DMF, 120° C., 4 h; c) TFA/DCM, rt, 1 h; d) cyanogen bromide, K₂CO₃, THF, rt, 1 h.

Example 80 3-(6-(Pyridin-4-yl)-3H-imidazo[4,5-b]pyridin-2-yl)pyrrolidine-1-carbonitrile (Prepared according to Scheme 5)

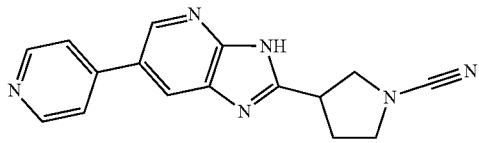 [SMILES: N#CN1CCC(c2nc3cc(-c4ccncc4)cnc3[nH]2)C1]

Step a. To a stirred solution of 2,3-diamino-5-bromopyridine (CAS Number 38875-53-5; 0.5 g, 2.66 mmol) in 1,4-dioxane:water (3:1; 8 ml) was added $Na_2CO_3$ (0.56 g, 5.32 mmol) at rt. The reaction mixture was degassed for 15 min before addition of pyridine-4-boronic acid (CAS Number 1692-15 5; 0.39 g, 3.19 mmol) and $Pd(PPh_3)_4$ (0.15 g, 0.133 mmol). The reaction mixture was heated at 80° C. for 16 h. The resulting mixture was cooled to rt, poured into water (300 ml) and extracted with EtOAc (2×200 ml). The combined organic phase was separated, dried over $Na_2SO_4$, filtered and concentrated under reduced pressure. The residue was purified by flash chromatography (10% MeOH in DCM) yielding [3,4'-bipyridine]-5,6-diamine (0.525 g, quantitative). LCMS: Method A, 2.292 min, MS: ES+187.10; $^1H$ NMR (400 MHz, DMSO-d6) δ ppm 8.50 (dd, J=2.0 Hz, 4.8 Hz, 2H), 7.80 (d, J=2.4 Hz, 1H), 7.51 (dd, J=1.6 Hz, 4.8 Hz, 2H), 7.10 (d, J=2.4 Hz, 1H), 5.88 (br s, 2H), 4.93 (br s, 2H).

Step b. To a stirred solution of [3,4'-bipyridine]-5,6-diamine (0.25 g, 1.344 mmol) and 1-BOC-pyrrolidine-3-carboxaldehyde (0.27 g, 1.344 mmol) in DMF (5 ml) was added sodium metabisulfite (0.255 g, 1.344 mmol) at rt. The reaction mixture was heated at 120° C. for 4 h. The resulting reaction mixture was cooled to rt, poured into water (300 ml) and extracted with EtOAc (2×150 ml). The combined organic phase was separated, dried over $Na_2SO_4$, filtered and concentrated under reduced pressure yielding tert-butyl 3-(6-(pyridin-4-yl)-3H-imidazo[4,5-b]pyridin-2-yl)pyrrolidine-1-carboxylate (0.45 g, 1.232 mmol). This material was used directly to the next step without further purification. LCMS: Method C, 1.568 min, MS: ES+366.14.

Steps c, d. The title compound was synthesised from the intermediate above using a procedure similar to that described for Example 14, steps d, e. The crude material was purified by preparative HPLC:YMC Actus Triart C18 250× 20 mm, 5 μm, mobile phase: (A) 0.1% formic acid in water and (B) 100% MeCN, flow rate 17.0 ml/min to provide the title compound: 3-(6-(pyridin-4-yl)-3H-imidazo[4,5-b]pyridin-2-yl)pyrrolidine-1-carbonitrile (0.024 g, 0.083 mmol). LCMS: Method B, 2.079 min, MS: ES+291.24; $^1H$ NMR (400 MHz, DMSO-d6) δ ppm 8.76 (d, J=2.0 Hz, 1H), 8.65 (d, J=6.0 Hz, 2H), 8.47 (br s, 1H), 8.38 (d, J=2.0 Hz, 1H), 7.82 (dd, J=1.6 Hz, 4.8 Hz, 2H), 3.79-3.87 (m, 3H), 3.51-3.56 (m, 2H), 2.35-2.41 (m, 1H), 2.27-2.35 (m, 1H).

The obtained racemic material was subjected to enantiomeric separation by preparative chiral HPLC: CHIRALPAK AD-H 250×20.0 mm, 5 μm, mobile phase: (A) 100% hexane; (B) IPA:MeCN (50:50), column flow was 15.0 ml/min which yielded the following enantiomers (absolute stereochemistry was not determined):

Example 81 3-(6-(Pyridin-4-yl)-3H-imidazo[4,5-b]pyridin-2-yl)pyrrolidine-1-carbonitrile: Enantiomer 1

LCMS: Method B, 2.198 min, MS: ES+291.28; Chiral SFC: CHIRALPAK TA 250×4.6 mm 5 μm, mobile phase: (A) Liquid carbon dioxide; (B) MeOH, column flow was 3.0 ml/min and ABPR was 130 bar, isocratic gradient of 40% B over 20 min, RT 9.55 min; $^1H$ NMR (400 MHz, DMSO-d6) δ ppm 8.75 (d, J=2.0 Hz, 1H), 8.65 (dd, J=2.0 Hz, 4.8 Hz, 2H), 8.36 (s, 1H), 7.82 (dd, J=1.6 Hz, 4.4 Hz, 2H), 3.79-3.85 (m, 3H), 3.53-3.58 (m, 2H), 2.29-2.41 (m, 2H).

Example 82 3-(6-(Pyridin-4 yl)-3H-imidazo[4,5-b]pyridin-2 yl)pyrrolidine-1-carbonitrile: Enantiomer 2

LCMS: Method B, 2.210 min, MS: ES+291.28; Chiral SFC: CHIRALPAK IA 250×4.6 mm 5 μm, mobile phase: (A) Liquid carbon dioxide; (B) MeOH, column flow was 3.0 ml/min and ABPR was 130 bar, isocratic gradient of 40% B over 20 min, 17.25 min; $^1H$ NMR (400 MHz, DMSO-d6) δ ppm 8.75 (d, J=2.4 Hz, 1H), 8.65 (dd, J=1.6 Hz, 4.4 Hz, 2H), 8.36 (d, J=2.0 Hz, 1H), 7.82 (dd, J=1.6 Hz, 4.4 Hz, 2H), 3.76-3.87 (m, 3H), 3.48-3.60 (m, 2H), 2.27-2.43 (m, 2H).

Compounds in Table 6 were synthesised using the general method as exemplified by Example 80, Scheme 5.

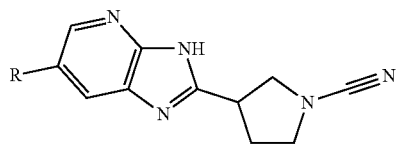

TABLE 6

| Ex | R | Name | LCMS Method | LCMS RT (min) | MS (ES+) | $^1H$ NMR (400 MHz, DMSO-d6) δ ppm |
|---|---|---|---|---|---|---|
| 83 | 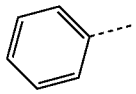 | 3-(6-Phenyl-3H-imidazo[4,5-b]pyridin-2-yl)pyrrolidine-1-carbonitrile | A | 3.32 | 290.1 | 12.83-13.11 (m, 1 H), 8.58-8.63 (m, 1 H), 8.01-8.25 (s, 1 H), 7.74 (d, J = 7.2 Hz, 2 H), 7.48-7.52 (t, J = 27.2 Hz, 2 H), 7.38-7.41 (m, 1 H), 3.75-3.97 (m, 3 H), 3.48-3.66 (m, 2H), 2.36-2.44 (m, 2 H). |
| 84 | 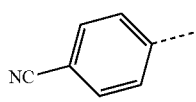 | 3-(6-(4-Cyanophenyl)-3H-imidazo[4,5-b]pyridin-2-yl)pyrrolidine-1-carbonitrile | B | 3.37 | 315.2 | 12.89-13.21 (m, 1 H), 8.67-8.75 (m, 1 H), 8.39 (s, 1 H), 7.94-8.00 (m, 4 H), 3.77-3.84 (m, 3 H), 3.50-3.59 (m, 2 H), 2.26-2.47 (m, 2 H). |
| 85 | 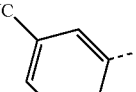 | 3-(6-(3-Cyanophenyl)-3H-imidazo[4,5-b]pyridin-2-yl)pyrrolidine-1-carbonitrile | A | 3.039 | 314.91 | 13.18-13.25 (m, 1 H), 8.68 (s, 1 H), 8.27-8.34 (m, 2 H), 8.12 (d, J = 7.6 Hz, 1 H), 7.85 (d, J = 8.0 Hz, 1 H), 7.68-7.76 (m, 1 H), 3.80-3.93 (m, 3 H), 3.54-3.56 (m, 2 H), 2.29-2.37 (m, 2 H). |

TABLE 6-continued

| Ex | R | Name | LCMS Method | LCMS RT (min) | MS (ES+) | $^1$H NMR (400 MHz, DMSO-d6) δ ppm |
|---|---|---|---|---|---|---|
| 86 | 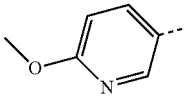 | 3-(6-(6-Methoxypyridin-3-yl)-3H-imidazo[4,5-b]pyridin-2-yl)pyrrolidine-1-carbonitrile | A | 2.737 | 321.03 | 12.83-13.15 (m, 1 H), 8.54-8.58 (m, 2 H), 8.19 (d, J = 2 Hz, 1 H), 8.08-8.11 (m, 1 H), 6.94 (d, J = 8.8 Hz, 1 H), 3.91 (s, 3 H), 3.76-3.84 (m, 3 H), 3.54-3.59 (m, 2 H), 2.26-2.40 (m, 2 H). |
| 87 | 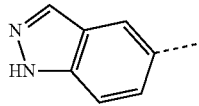 | 3-(6-(1H-Indazol-5-yl)-3H-imidazo[4,5-b]pyridin-2-yl)pyrrolidine-1-carbonitrile | A | 2.605 | 330.02 | 13.14 (s, 1 H), 12.74-13.06 (m, 1 H), 8.59-8.68 (m, 1 H), 8.08-8.25 (m, 3 H), 7.71-7.73 (m, 1 H), 7.64-7.67 (m, 1 H), 3.76-3.86 (m, 3 H), 3.50-3.62 (m, 2 H), 2.27-2.44 (m, 2 H). |
| 88 | 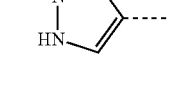 | 3-(6-(1H-Pyrazol-4-yl)-3H-imidazo[4,5-b]pyridin-2-yl)pyrrolidine-1-carbonitrile | A | 2.222 | 280.00 | 8.96 (d, J = 1.6 Hz, 1 H), 8.59 (d, J = 1.6 Hz, 1 H), 8.35 (s, 2 H), 3.95-4.01 (m, 1 H), 3.87-3.91 (m, 1 H), 3.76-3.79 (m, 1 H), 3.49-3.64 (m, 2 H), 2.43-2.48 (m, 1 H), 2.28-2.35 (m, 1 H). |
| 89 | 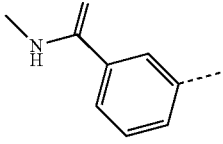 | 3-(2-(1-Cyanopyrrolidin-3-yl)-3H-imidazo[4,5-b]pyridin-6-yl)-N-methylbenzamide | B | 2.602 | 347.26 | 13.15 (s, 1 H), 8.66 (S, 1 H), 8.60 (br s, 1 H), 8.35 (s, 1), 8.20 (br, s, 1 H), 7.90 (d, J = 7.6 Hz, 1 H), 7.84 (d, J = 7.2 Hz, 1 H), 7.58 (t, J = 7.6 Hz, 1 H), 3.80-3.89 (m, 3 H), 3.53-3.62 (m, 2 H), 2.83 (d, J = 4.4 Hz, 3 H), 2.37-2.40 (m, 1 H), 2.27-2.32 (m, 1 H). |

The racemic Example 84 was subjected to enantiomeric separation by preparative chiral HPLC to provide the following enantiomers (absolute stereochemistry was not determined):

Example 90 3-(6-(4-Cyanophenyl)-3H-imidazo[4,5-b]pyridin-2-yl)pyrrolidine-1-carbonitrile: Enantiomer 1

LCMS: Method B, 3.291 min, MS: ES-313.25; Chiral SFC: CHIRALPAK IC 250×4.6 mm 5 μm, mobile phase: (A) Liquid carbon dioxide; (B) MeOH, column flow was 3.0 ml/min and ABPR was 130 bar, isocratic gradient of 45% B over 10 min, RT 5.07 min; $^1$H NMR (400 MHz, CDCl$_3$) δ ppm 12.83-13.15 (m, 1H), 8.70 (s, 1H), 8.33 (br s, 1H), 7.94-8.00 (m, 4H), 3.74-3.87 (m, 3H), 3.50 3.57 (m, 2H), 2.24-2.49 (m, 2H).

Example 91 3-(6-(4-Cyanophenyl)-3H-imidazo[4,5-b]pyridin-2 yl)pyrrolidine-1-carbonitrile: Enantiomer 2

LCMS: Method B, 3.294 min, MS: ES-313.25; Chiral SFC: CHIRALPAK IC 250×4.6 mm 5 μm, mobile phase: (A) Liquid carbon dioxide; (B) MeOH, column flow was 3.0 ml/min and ABPR was 130 bar, isocratic gradient of 45% B over 10 min, RT 5.91 min; $^1$H NMR (400 MHz, CDCl$_3$) δ ppm 12.83-13.15 (m, 1H), 8.70 (s, 1H), 8.33 (br s, 1H), 7.94-8.00 (m, 4H), 3.74-3.87 (m, 3H), 3.50 3.57 (m, 2H), 2.24-2.49 (m, 2H).

The racemic Example 89 was subjected to enantiomeric separation by preparative chiral HPLC to provide the following enantiomers (absolute stereochemistry was not determined):

Example 92 3-(2-(1-Cyanopyrrolidin-3 yl)-3H-imidazo[4,5-b]pyridin-6 yl)-N-methylbenzamide: Enantiomer 1

LCMS: Method B, 2.623 min, MS: ES+347.22; Chiral SFC: CHIRALPAK IC 250×4.6 mm 5 μm, mobile phase: (A) Liquid carbon dioxide; (B) MeOH, column flow was 3.0 ml/min and ABPR was 130 bar, isocratic gradient of 20% B over 3 min, followed by 20% to 50% B over 7 min, followed by isocratic gradient of 50% B over 5 min, RT 11.12 min; $^1$H NMR (400 MHz, CDCl$_3$) δ ppm 12.83 13.15 (m, 1H), 8.68 (s, 1H), 8.59 (d, J=4.4 Hz, 1H), 8.27 (br s, 1H), 8.19 (s, 1H), 7.90 (d, J=8.0 Hz, 1H), 7.84 (d, J=5.6 Hz, 1H), 7.58 (t, J=8.0 Hz, 1H), 4.45-4.48 (m, 1H), 3.79-3.85 (m, 2H), 3.51-3.58 (m, 2H), 2.83 (d, J=4.8 Hz, 3H), 2.36-2.41 (m, 1H), 2.29-2.34 (m, 1H).

Example 93 3-(2-(1-Cyanopyrrolidin-3-yl)-3H-imidazo[4,5-b]pyridin-6-yl)-N-methylbenzamide: Enantiomer 2

LCMS: Method B, 2.621 min, MS: ES+347.22; Chiral SFC: CHIRALPAK IC 250×4.6 mm 5 μm, mobile phase: (A) Liquid carbon dioxide; (B) MeOH, column flow was 3.0 ml/min and ABPR was 130 bar, isocratic gradient of 20% B over 3 min, followed by 20% to 50% B over 7 min, followed by isocratic gradient of 50% B over 5 min, RT 11.59 min; $^1$H NMR (400 MHz, CDCl$_3$) δ ppm 12.83 13.15 (m, 1H), 8.68 (s, 1H), 8.59 (d, J=4.4 Hz, 1H), 8.27 (br s, 1H), 8.19 (s, 1H), 7.90 (d, J=8.0 Hz, 1H), 7.84 (d, J=5.6 Hz, 1H), 7.58 (t, J=8.0 Hz, 1H), 4.45-4.48 (m, 1H), 3.79-3.85 (m, 2H), 3.51-3.58 (m, 2H), 2.83 (d, J=4.8 Hz, 3H), 2.36-2.41 (m, 1H), 2.29-2.34 (m, 1H).

Example 94 (S)-2-(6-Phenyl-1H-benzo[d]imidazol-2-yl)pyrrolidine-1-carbonitrile

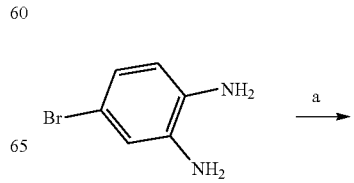

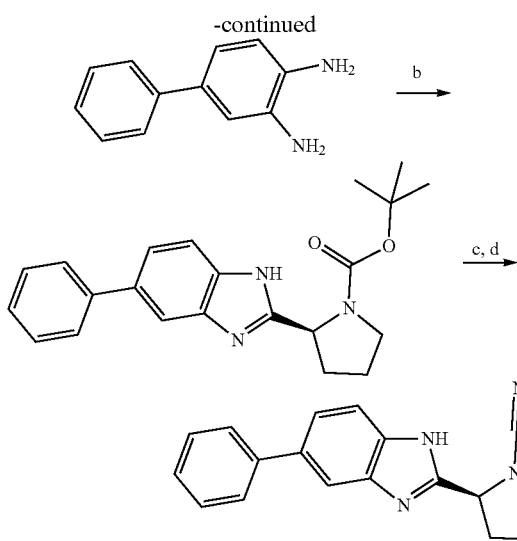

Step a. A mixture of 4-bromobenzene-1,2-diamine (CAS Number 1575-37-7; 0.60 g, 3.21 mmol), phenylboronic acid (0.47 g, 3.85 mmol) and K₂CO₃ (0.89 g, 6.42 mmol) in 1,4-dioxane:water (8:2) (20 ml) was degassed for 30 min at rt before addition of 1,1'-bis(diphenylphosphino)ferrocene-palladium(II)dichloride DCM complex (0.26 g, 0.320 mmol). The reaction mixture was heated at 120° C. for 2 h. The resulting reaction mixture was cooled to rt and poured into water (20 ml). The obtained mixture was extracted with EtOAc (6×10 ml). The combined organic phase was dried over Na₂SO₄, filtered and concentrated under reduced pressure. The resulting residue was purified by flash chromatography (10% EtOAc in hexane) yielding [1,1'-biphenyl]-3,4-diamine (0.22 g, 1.195 mmol). LCMS: Method C, 1.671 min, MS: ES+185.05.

Step b. To a solution of [1,1'-biphenyl]-3,4-diamine (0.22 g, 1.195 mmol) in DMF (3 ml) were added tert-butyl (S)-2-formylpyrrolidine-1-carboxylate (CAS Number 69610-41-9; 0.24 g, 1.195 mmol) and sodium metabisulfite (0.23 g, 1.195 mmol)) at rt. The resulting reaction mixture was heated at 120° C. for 2 h. The resulting reaction mixture was cooled to rt. The resulting reaction mixture was poured into water (20 ml) and extracted with EtOAc (3×10 ml). The combined organic phase was dried over Na₂SO₄, filtered and concentrated under reduced pressure. The resulting residue was purified by flash chromatography (1% MeOH in DCM) yielding tert-butyl (S)-2-(6-phenyl-1H-benzo[d]imidazol-2-yl)pyrrolidine-1-carboxylate (0.16 g, 0.441 mmol). LCMS: Method C, 1.989 min, MS: ES+364.

Step c. To a solution of tert-butyl (S)-2-(6-phenyl-1H-benzo[d]imidazol-2-yl)pyrrolidine-1-carboxylate (0.14 g, 0.385 mmol) in DCM (3 ml) was added TFA (0.50 ml) at rt. The reaction mixture was stirred at rt for 1 h. The resulting reaction mixture was concentrated under reduced pressure. The obtained residue was azeotropically distilled with DCM (3×5 ml), triturated with diethyl ether (5 ml) and finally dried under high vacuum to yield (S)-6-phenyl-2-(pyrrolidin-2-yl)-1H-benzo[d]imidazole TFA salt (0.14 g, 0.371 mmol). LCMS: Method C, 1.747 min, MS: ES+264.27. This material was used directly for the next step without further purification.

Step d. To a solution of (S)-6-phenyl-2-(pyrrolidin-2-yl)-1H-benzo[d]imidazole TFA salt (0.14 g, 0.371 mmol) in THF (3 ml) was added K₂CO₃ (0.10 g, 0.742 mmol) at rt. Cyanogen bromide (0.05 g, 0.445 mmol) was added to the reaction mixture at rt. The reaction mixture was stirred at it for 30 min. The resulting reaction mixture was poured into water (20 ml) and extracted with EtOAc (3×10 ml). The combined organic phase was dried over Na₂SO₄, filtered and concentrated under reduced pressure. The resulting residue was purified by flash chromatography (0.5% MeOH in DCM) yielding the title compound (0.040 g, 0.138 mmol). LCMS: Method A, 3.993 min, MS: ES+288.97; ¹H NMR (400 MHz, DMSO-d6) δ ppm 12.69-12.72 (m, 1H), 7.33-7.77 (m, 8H), 4.97-5.01 (m, 1H), 3.42 3.71 (m, 2H), 2.32-4.41 (m, 1H), 1.98-2.18 (m, 3H). NMR showed duplication of peaks due to plausible tautomers.

Example 95 3-(5-Phenyl-1H-benzo[d]imidazol-2-yl)pyrrolidine-1-carbonitrile

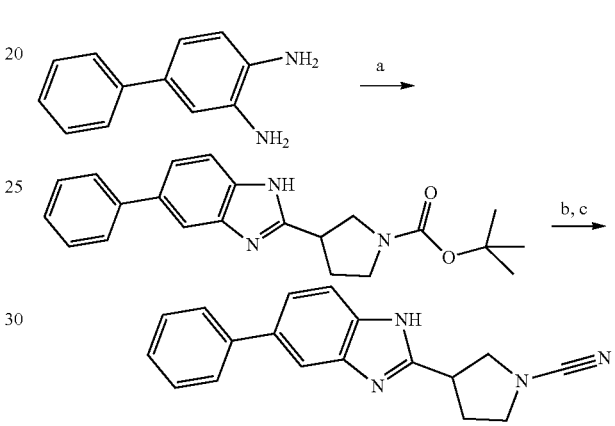

Step a. To a stirred solution of N—BOC-pyrrolidine-3-carboxylic acid (CAS Number 59378-75-5; 0.467 g, 2.17 mmol) and TEA (0.6 ml, 4.35 mmol) in THF (10 ml) was added propylphosphonic anhydride solution (50% in EtOAc) (1.6 ml, 2.61 mmol) at 0° C. The reaction mixture was stirred at 0° C. for 30 min before addition of [1,1'-biphenyl]-3,4-diamine (Example 94, step a; 0.4 g, 2.17 mmol). The reaction mixture was warmed to rt and stirred for 8 h. The resulting reaction mixture was diluted with EtOAc (50 ml) and washed with water (3×50 ml). The organic phase was separated, dried over Na₂SO₄, filtered and concentrated under reduced pressure. The resulting crude material was purified by column chromatography (3 to 5% MeOH in DCM) yielding tert-butyl 3-((3-amino-[1,1'-biphenyl]-4-yl)-carbamoyl)pyrrolidine-1-carboxylate (0.3 g, mmol). LCMS: Method B, 4.178 min, MS: ES+382.28.

Step b. A mixture of tert-butyl 3-((3-amino-[1,1'-biphenyl]-4-yl)carbamoyl)pyrrolidine-1-carboxylate (0.25 g, 0.656 mmol) and concentrated HCl (0.1) ml in MeOH (5 ml) was heated at 90° C. for 2 h. The resulting mixture was cooled to rt and concentrated under vacuum yielding 5-phenyl-2-(pyrrolidin-3-yl)-1H-benzo[d]imidazole (0.115 g, 0.437 mmol). This material was used for the next step without further purification. LCMS: Method D, 6.195 min, MS: ES+264.20.

Step c. To a stirred solution of 5-phenyl-2-(pyrrolidin-3-yl)-1H-benzo[d]imidazole (0.1 g, 0.38 mmol) in DMF (5 ml) was added K₂CO₃ (0.078 g, 0.5703 mmol) at 0° C. The reaction mixture was stirred at 0° C. for 30 min. Cyanogen bromide (0.044 g, 0.418 mmol) was added to the reaction mixture at 0° C. The reaction mixture was stirred at rt for 2 h. The resulting reaction mixture was poured into water (20 ml) and extracted with EtOAc (3×20 ml). The combined organic phase was separated, dried over Na₂SO₄, filtered and concentrated under reduced pressure. The obtained crude material was purified by preparative HPLC; mobile phase: (A) 0.1% formic acid in water and (B) 0.1% formic acid in MeCN, column: YMC Actus C8 250×20 mm, 5 μm, flow rate 20.0 ml/min to provide 3-(5-phenyl-1H-benzo[d]imidazol-2-yl)pyrrolidine-1-carbonitrile formic salt (0.009 g, 0.031 mmol). LCMS: Method D, 6.407 min, MS: ES+289.20; ¹H NMR (400 MHz, DMSO-d6) δ ppm 12.65 (br s, 2H), 8.41 (s, 1H), 7.76 (s, 1H), 7.68 (d, J=7.2 Hz, 2H), 7.58 (d, H=7.6 Hz, 1H), 7.46 (s, 3H), 7.34 (t, J=7.6 Hz, 1H), 3.76-3.84 (m, 3H), 3.41-3.60 (m, 2H), 2.34-2.39 (m, 1H), 2.25-2.30 (m, 1H).

Example 96 (S)-2-(1-Methyl-5-phenyl-1H-benzo[d]imidazol-2-yl)pyrrolidine-1-carbonitrile

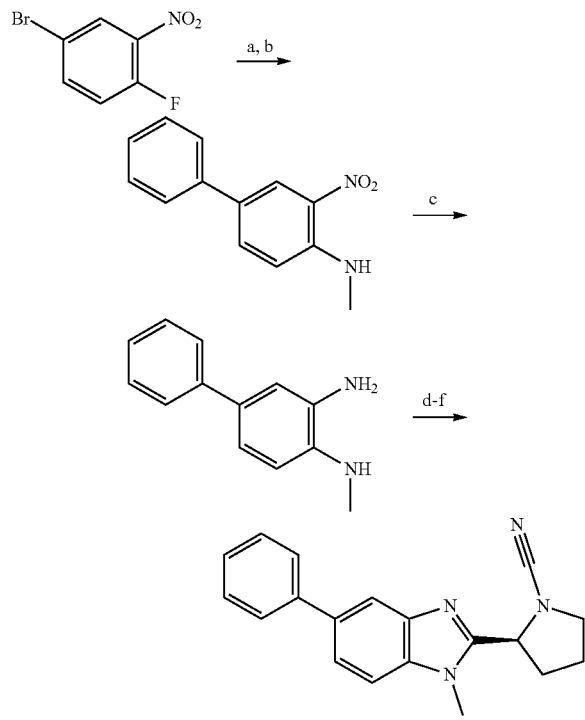

Step a. A mixture of 4-bromo-1-fluoro-2-nitrobenzene (CAS Number 364-73-8; 1.5 g, 6.85 mmol) and methylamine solution (2 M in THF) (9 ml) was stirred at rt for 1 h. The resulting reaction mixture was poured into water (200 ml) and extracted with EtOAc (3×100 ml). The combined organic phase was washed with brine (100 ml), dried over Na₂SO₄, filtered and concentrated under reduced pressure yielding 4-bromo-N-methyl-2-nitroaniline (1.54 g, 6.70 mmol). This material was used directly to the next step without further purification. LCMS: Method C, 2.268 min.

Step b. To a stirred solution of 4-bromo-N-methyl-2-nitroaniline (1.50 g, 6.52 mmol) in 1,2-dimethoxyethane (15 ml) were added phenylboronic acid (0.87 g, 7.18 mmol)) and Cs₂CO₃ (4.3 g, 13.05 mmol) at rt. The reaction mixture was degassed for 15 min before addition of Pd(PPh₃)₄ (0.38 g, 0.33 mmol). The reaction mixture was heated at 80° C. for 3 h. The resulting reaction mixture was cooled to rt, poured into water (200 ml) and extracted with EtOAc (200 ml). The reaction mixture was filtered through celite bed, organic phase was separated and aqueous phase was re-extracted with EtOAc (2×100 ml). The combined organic phase was washed with brine (100 ml). The organic phase was separated, dried over Na₂SO₄, filtered and concentrated under reduced pressure. The resulting crude material was purified by flash chromatography (10% EtOAc in hexane) yielding N-methyl-3-nitro-[1,1'-biphenyl]-4-amine (1.0 g, 4.38 mmol). LCMS: Method C, 2.500 min, MS: ES+229.15.

Step c. To a stirred solution of N-methyl-3-nitro-[1,1'-biphenyl]-4-amine (1.0 g, 4.38 mmol) in MeOH (15 ml) was added 10% dry Pd/C (0.1 g, 0.1 w/w) at rt. The reaction mixture was purged with hydrogen at rt for 2 h. The resulting reaction mixture was carefully filtered through celite hyflow and washed with MeOH (50 ml). The combined filtrate was concentrated under vacuum yielding N4-methyl-[1,1'-biphenyl]-3,4-diamine (0.79 g, 3.99 mmol). This material was used directly to the next step without further purification. LCMS: Method C, 1.872 min, MS: ES+199.13.

Step d. To a stirred solution of N4-methyl-[1,1'-biphenyl]-3,4-diamine (0.79 g, 3.99 mmol) in DMF (7.9 ml) was added (S)—BOC-pyrrolidine-2-carboxaldehyde (CAS Number 69610-41-9) (0.79 g, 3.99 mmol)) and sodium metabisulphite (0.76 g, 3.99 mmol) at rt. The reaction mixture was heated at 110° C. for 2 h. The resulting reaction mixture was cooled to rt and poured into ice water (100 ml). The solid precipitates were filtered and dried under vacuum. The resulting crude material was purified by flash chromatography (35% EtOAc in hexane) yielding tert-butyl (S)-2-(1-methyl-5-phenyl-1H-benzo[d]imidazol-2-yl)pyrrolidine-1-carboxylate (1.2 g, 3.18 mmol). LCMS: Method C, 2.014 min, MS: ES+378.10.

Steps e, f. The title compound was synthesised from the intermediate above using a procedure similar to that described for Example 14, steps d, e. LCMS: Method A, 4.214 min, MS: ES+302.94; ¹H NMR (400 MHz, DMSO-d6) δ ppm 7.92 (d, J=1.2 Hz, 1H), 7.71-7.73 (m, 2H), 7.65-7.67 (m, 1H), 7.58-7.61 (m, 1H), 7.45-7.49 (m, 2H), 7.32-7.36 (m, 1H), 5.30-5.33 (m, 1H), 3.88 (s, 3H), 3.64-3.70 (m, 1H), 3.55-3.60 (m, 1H), 2.33-2.40 (m, 1H), 2.22-2.31 (m, 1H), 2.10-2.18 (m, 1H), 1.98-2.08 (m, 1H).

Example 97 3-(5-Phenyl-3H-imidazo[4,5-b]pyridin-2-yl)pyrrolidine-1-carbonitrile

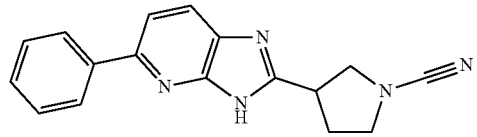 [SMILES: N#CN1CCC(c2nc3ccc(-c4ccccc4)nc3[nH]2)C1]

The title compound was synthesised using a procedure similar to that described for Example 80, using 6-bromopyridine-2,3-diamine (CAS Number 129012-04-0) in step a. LCMS: Method B, 3.184 min, MS: ES+289.90; ¹H NMR (400 MHz, CDCl₃) δ ppm 12.83-13.15 (m, 1H), 8.09-8.11 (m, 2H), 8.03 (d, J=8.4 Hz, 1H), 7.82 (d, J=8.4 Hz, 1H), 7.48-7.52 (m, 2H), 7.39-7.43 (m, 1H), 3.76-3.84 (m, 3H), 3.50-3.58 (m, 2H), 2.28-2.41 (m, 2H).

Example 98 3-(7-Phenyl-3H-imidazo[4,5-b]pyridin-2 yl)pyrrolidine-1-carbonitrile

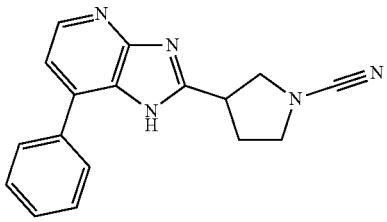 [SMILES: N#CN1CCC(c2nc3nccc(-c4ccccc4)c3[nH]2)C1]

The title compound was synthesised using a procedure similar to that described for Example 80, using 4-bromopyridine-2,3-diamine (CAS Number 1232431-75-2) in step a. LCMS: Method B, 3.23 min, MS: ES-288.16; $^1$H NMR (400 MHz, CDCl$_3$) δ ppm 12.83-13.15 (m, 1H), 8.30-8.33 (m, 2H), 7.47-7.61 (m, 5H), 3.75-3.86 (m, 2H), 3.50-3.61 (m, 3H), 2.27-2.41 (m, 2H).

Example 99 3-(5-Methyl-6-phenyl-3H-imidazo[4,5-b]pyridin-2-yl)pyrrolidine-1-carbonitrile

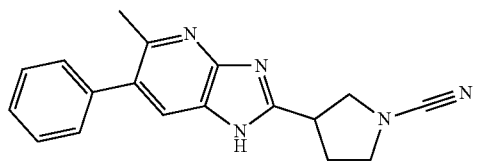 [SMILES: Cc1nc2nc(C3CCN(C#N)C3)[nH]c2cc1-c1ccccc1]

The title compound was synthesised using a procedure similar to that described for Example 80, using 5-bromo-6-methylpyridine-2,3-diamine (CAS Number 59352-90-8) in step a. LCMS: Method A, 3.510 min, MS: ES+304.01; $^1$H NMR (400 MHz, DMSO-d6) δ ppm 12.60-12.90 (m, 1H), 7.72 (br s, 1H), 7.45-7.49 (m, 2H), 7.38-7.41 (m, 3H), 3.73-3.82 (m, 3H), 3.51-3.56 (m, 2H), 2.45 (s, 3H), 2.24-2.38 (m, 2H).

Example 100 3-(7-Methyl-6-phenyl-3H-imidazo[4,5-b]pyridin-2 yl)pyrrolidine-1-carbonitrile

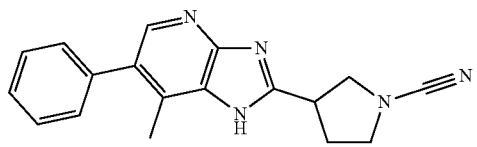 [SMILES: Cc1c(-c2ccccc2)cnc2nc(C3CCN(C#N)C3)[nH]c12]

The title compound was synthesised using a procedure similar to that described for Example 80, using 5-bromo-4-methylpyridine-2,3-diamine (CAS Number 41230-93-7) in step a. LCMS: Method G, 20.301 min, MS: ES+304.01; $^1$H NMR (400 MHz, DMSO-d6) δ ppm 12.68-12.99 (m, 1H), 8.10-8.18 (m, 1H), 7.47-7.51 (m, 2H), 7.39-7.42 (m, 3H), 3.78-3.87 (m, 3H), 3.53-3.59 (m, 2H), 2.47 (s, 3H), 2.25-2.42 (m, 2H).

Example 101 3-(3-Methyl-6-phenyl-3H-imidazo[4,5-b]pyridin-2-yl)pyrolidine-1-carbonitrile

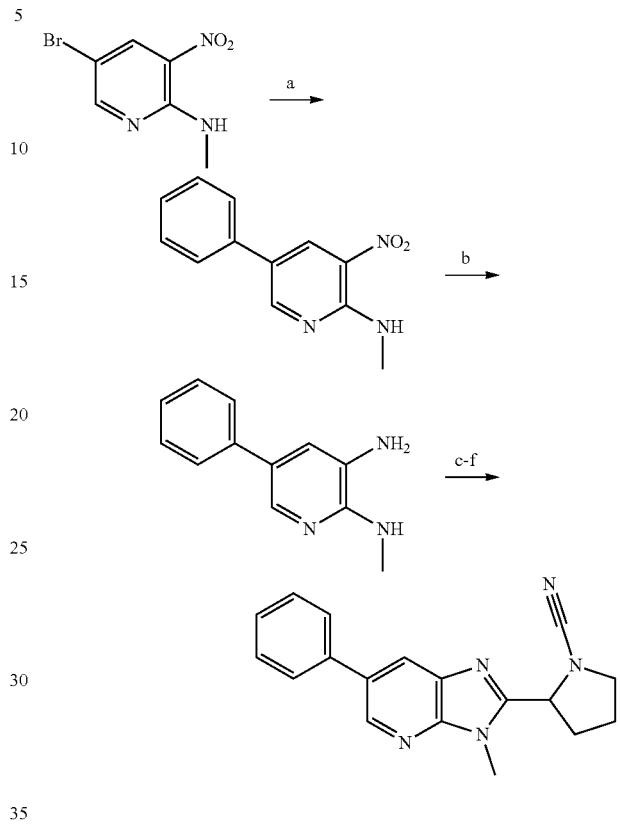

Step a. To a solution of 5-bromo-N-methyl-3-nitropyridin-2-amine (CAS Number 70232-59-6; 0.5 g, 2.16 mmol) in DMF:water (5:1 ml) was added phenylboronic acid (0.52 g, 4.32 mmol) and NaHCO$_3$ (0.54 g, 6.49 mmol) at rt. The reaction mixture was degassed for 15 min before addition of PdCl$_2$(dppf) (0.176 g, 0.216 mmol). The reaction mixture was heated at 120° C. in a microwave for 1 h. The resulting reaction mixture was cooled to rt and poured into water (100 ml). The obtained mixture was extracted with EtOAc (2×75 ml). The combined organic phase was dried over Na$_2$SO$_4$, filtered and concentrated under reduced pressure. The residue was purified by column chromatography (5% MeOH in DCM) to yield N-methyl-3-nitro-5-phenylpyridin-2-amine (0.72 g, 3.14 mmol). LCMS: Method C, 2.357 min, MS: ES+230.13

Step b. To a solution of N-methyl-3-nitro-5-phenylpyridin-2-amine (0.850 g, 3.71 mmol) in THE (5 ml) was added 10% Pd/C (dry basis) (0.1 g) at 0° C. The reaction mixture was purged with hydrogen gas at rt for 1H. The reaction mixture was carefully filtered through celite hyflow and the filtrate was concentrated under reduced pressure yielding N-2-methyl-5-phenylpyridine-2,3-diamine (0.7 g, 3.51 mmol). This material was used directly for the next step without further purification.

Steps c-e. The title compound was synthesised from the intermediate above using a procedure similar to that described for Example 80, steps b-d. LCMS: Method B, 3.557 min, MS: ES+304.18; $^1$H NMR (400 MHz, DMSO-d6) δ ppm 8.63 (d, J=2.0 Hz, 1H), 8.29 (d, J=2.0 Hz, 1H), 7.75 (d, J=7.6 Hz, 1H), 7.50 (t, J=7.6 Hz, 3H), 7.37-7.41 (m, 1H), 3.95-4.00 (m, 1H), 3.87-3.90 (m, 1H), 3.85 (s, 3H), 3.77-3.81 (m, 1H), 3.52-3.65 (m, 2H), 2.36-2.44 (m, 1H), 2.21-2.29 (m, 1H).

(Trans)-3-methyl-4-(6-phenyl-3H-imidazo[4,5-b]pyridin-2-yl)pyrrolidine-1-carbonitrile

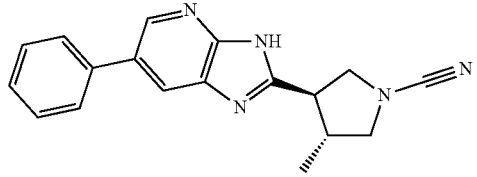 [SMILES: C[C@H]1CN(C#N)C[C@@H]1c1nc2cc(-c3ccccc3)cnc2[nH]1]

The title compound was synthesised using a procedure similar to that described for Example 80 using 1-cyano-4-methylpyrrolidine-3-carboxylic acid. The obtained racemic material was subjected to enantiomeric separation by preparative chiral HPLC to provide the following enantiomers (absolute stereochemistry was not determined):

Example 102 Trans-3-methyl-4-(6-phenyl-3H-imidazo[4,5-b]pyridin-2-yl)pyrrolidine-1-carbonitrile: Enantiomer 1

LCMS: Method B, 3.275 min, MS: ES+304.27; Chiral HPLC: Method Y, 18.85 min; $^1$H NMR (400 MHz, CDCl$_3$) δ ppm 12.83-13.15 (m, 1H), 8.57-8.86 (m, 1H), 8.09-8.24 (m, 1H), 7.73-7.75 (m, 2H), 7.48-7.53 (m, 2H), 7.39-7.42 (m, 1H), 3.89-3.92 (m, 1H), 3.73-3.81 (m, 2H), 3.29-3.32 (m, 1H), 3.16-3.21 (m, 1H), 2.65-2.67 (m, 1H), 1.03-1.08 (m, 3H).

Example 103 Trans-3-methyl-4-(6-phenyl-3H-imidazo[4,5-b]pyridin-2-yl)pyrrolidine-1-carbonitrile: Enantiomer 2

LCMS: Method B, 3.274 min, MS: ES+304.27; Chiral HPLC: Method Y, 21.02 min; $^1$H NMR (400 MHz, CDCl$_3$) δ ppm 12.83-13.15 (m, 1H), 8.61 (s, 1H), 8.19 (s, 1H), 7.74 (d, J=7.2 Hz, 2H), 7.48-7.52 (m, 2H), 7.38-7.41 (m, 1H), 3.90-3.94 (m, 1H), 3.72-3.81 (m, 2H), 3.31-3.38 (m, 1H), 3.17-3.21 (m, 1H), 2.61-2.69 (m, 1H), 1.07 (d, J=6.8 Hz, 3H).

Example 104 Trans-3-methyl-4-(5-phenyl-1H-benzo[d]imidazol-2 yl)pyrrolidine-1-carbonitrile: Enantiomer 1

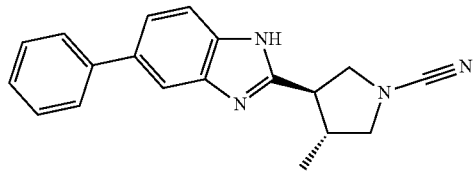 [SMILES: C[C@H]1CN(C#N)C[C@@H]1c1nc2cc(-c3ccccc3)ccc2[nH]1]

The title compound was synthesised using a procedure similar to that described for Example 80, using trans tert-butyl 3-formyl-4-methylpyrrolidine-1-carboxylate (Example 19, steps a-d) and 4-bromobenzene-1,2-diamine in step b and purified by preparative chiral HPLC. LCMS: Method B, 3.283 min, MS: ES+303.27; Chiral HPLC: Method Z, 6.35 min; $^1$H NMR (400 MHz, CDCl$_3$) δ ppm 12.40-12.80 (m, 1H), 7.77 (s, 1H), 7.66-7.68 (m, 2H), 7.59-7.61 (m, 1H), 7.44-7.50 (m, 3H), 7.32-7.36 (m, 1H), 3.88-3.93 (m, 1H), 3.71-3.79 (m, 2H), 3.29-3.31 (m, 1H), 3.16-3.20 (m, 1H), 2.62-2.68 (m, 1H), 1.06 (d, J=6.8 Hz, 3H).

Example 105 3-(5-(Pyridin-2 yl)-4H-1,2,4-triazol-3 yl)pyrrolidine-1-carbonitrile

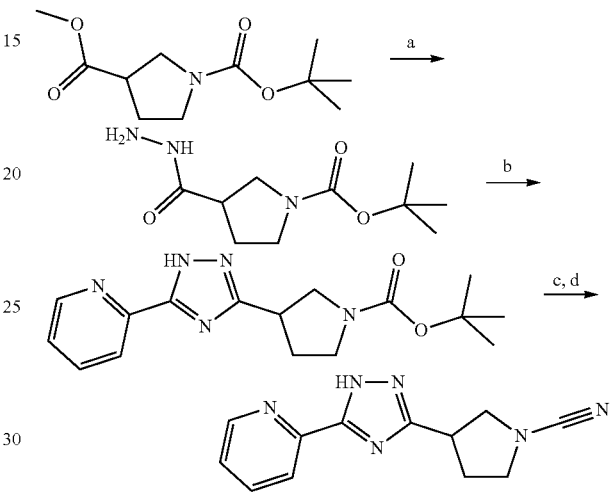

Step a. A mixture of tert-butyl methyl pyrrolidine-1,3-dicarboxylate (CAS Number 122684-33-7) (0.5 g, 1.695 mmol) and hydrazine hydrate (99%) (0.424 g, 8.47 mmol) in EtOH (10 ml) was heated at 80° C. for 3 h. The reaction mixture was cooled to rt, excess of solvent was evaporated under vacuum and the residue was diluted in a mixture of EtOAc:water (1:1; 200 ml). The organic phase was separated, dried over Na$_2$SO$_4$, filtered and concentrated under reduced pressure yielding tert-butyl 3-(hydrazinecarbonyl)pyrrolidine-1-carboxylate (0.5 g, quantitative). This material was used for the next step without further purification. LCMS: Method C, 1.499 min, MS: ES+174.09 (M-56); $^1$H NMR (400 MHz, DMSO-d6) δ ppm 9.13 (s, 1H), 4.22 (s, 2H), 3.34-3.42 (m, 2H), 3.16-3.25 (m, 2H), 2.78-2.86 (m, 1H), 1.85-1.97 (m, 2H), 1.39 (s, 9H).

Step b. To a stirred solution of tert-butyl 3-(hydrazinecarbonyl)pyrrolidine-1-carboxylate (0.5 g, 2.18 mmol) and 2-cyanopyridine (0.25 g, 2.40 mmol) in ethylene glycol (5 ml) was added sodium methoxide (0.058 g, 1.091 mmol) at rt. The reaction mixture was heated at 130° C. for 4 h. The resulting reaction mixture was cooled to rt, poured into water (100 ml) and extracted with EtOAc (2×100 ml). The organic phase was separated, dried over Na$_2$SO$_4$, filtered and concentrated under reduced pressure. The crude material was purified by flash chromatography (50% EtOAc in hexane) yielding tert-butyl 3-(5-(pyridin-2-yl)-4H-1,2,4-triazol-3-yl)pyrrolidine-1-carboxylate (0.7 g, 2.22 mmol). LCMS: Method C, 1.76 min, MS: ES+316.0; $^1$H NMR (400 MHz, DMSO-d6) δ ppm 14.51 (s, 1H), 8.69 (d, J=4.0 Hz, 1H), 8.05 (d, J=7.6 Hz, 1H), 7.98 (t, J=7.2 Hz, 1H), 7.52 (t, J=6.0 Hz, 1H), 3.63-3.69 (m, 1H), 3.48-3.52 (m, 2H), 3.33-3.54 (m, 2H), 2.18-2.24 (m, 1H), 2.12-2.18 (m, 1H), 1.41 (s, 9H).

Step c. To a stirred solution of tert-butyl 3-(5-(pyridin-2-yl)-4H-1,2,4-triazol-3-yl)pyrrolidine-1-carboxylate (0.5 g, 1.59 mmol) in DCM (10 ml) was added to TFA (1 ml) at 0° C. The reaction mixture was stirred at rt for 1.5 h. The resulting reaction mixture was concentrated under vacuum to yield 2-(5-(pyrrolidin-3-yl)-4H-1,2,4-triazol-3-yl)pyridine TFA salt. This material was used directly to the next step without further purification. LCMS: Method C, 0.649 min, MS: ES+216.39.

Step d. To a stirred solution of 2-(5-(pyrrolidin-3-yl)-4H-1,2,4-triazol-3-yl)pyridine TFA salt (0.3 g, 1.395 mmol) in THF (5 ml) was added $K_2CO_3$ (0.962 g, 6.976 mmol) at rt. The reaction mixture was stirred at rt for 10 min. Cyanogen bromide (0.147 g, 1.395 mmol) was added to the reaction mixture at 0° C. The reaction mixture was stirred at rt for 0.5 h. The resultant reaction mixture was poured into water (100 ml) and extracted with EtOAc (2×100 ml). The combined organic phase was separated, dried over $Na_2SO_4$, filtered and concentrated under reduced pressure. The resulting crude material was purified by flash chromatography (80% EtOAc in hexane) yielding 3-(5-(pyridin-2-yl)-4H-1,2,4-triazol-3-yl)pyrrolidine-1-carbonitrile (0.05 g, g, 0.208 mmol). The obtained material was purified by preparative TLC (mobile phase: 50% EtOAc in hexane; 300 ml) yielding 3-(5-(pyridin-2-yl)-4H-1,2,4-triazol-3-yl)pyrrolidine-1-carbonitrile (0.009 g, g, 0.037 mmol). LCMS: Method B, 2.391 min, MS: ES+241.3; $^1$H NMR (400 MHz, DMSO-d6) δ ppm 14.6 (s, 1H), 8.70 (s, 1H), 8.06 (d, J=7.2 Hz, 1H), 7.99 (m, 1H), 7.53 (s, 1H), 3.78-3.81 (m, 1H), 3.62-3.68 (m, 2H), 3.49-3.53 (m, 2H), 2.23-2.33 (m, 1H), 2.15-2.17 (m, 1H).

Example 106 3-(5-Phenyl-4H-1,2,4-triazol-3-yl)pyrrolidine-1-carbonitrile

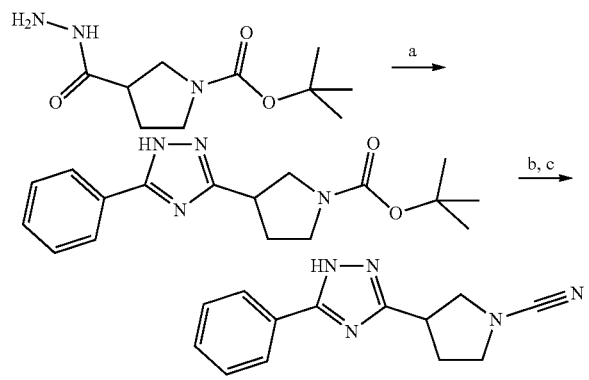

Step a. To a solution of ethyl benzimidate hydrochloride (CAS Number 5333-86-8; 0.13 g, 0.59 mmol) in IPA (5 ml) was added tert-butyl 3-(hydrazinecarbonyl)pyrrolidine-1-carboxylate (Example 105, step a; 0.2 g, 0.87 mmol) and DIPEA (1.05 ml, 6.09 mmol) at rt. The reaction mixture was heated at 130° C. in microwave for 25 min. The resulting reaction mixture was concentrated under reduced pressure. The obtained residue was purified by column chromatography (5% MeOH in DCM) to yield tert-butyl 3-(5-phenyl-4H-1,2,4-triazol-3-yl)pyrrolidine-1-carboxylate (0.09 g, 0.28 mmol). LCMS: Method C, 1.980 min, MS: ES+315.5

Step b. To a solution of tert-butyl 3-(5-phenyl-4H-1,2,4-triazol-3-yl)pyrrolidine-1-carboxylate (0.09 g, 0.28 mmol) in DCM (20 ml) was added TFA (0.22 ml, 2.86 mmol) at rt. The reaction mixture was stirred at rt for 45 min. The resulting reaction mixture was concentrated under reduced pressure. The obtained mixture was azeotropically distilled with DCM (2×10 ml), triturated with diethyl ether (15 ml) and dried under reduced pressure to yield 3-phenyl-5-(pyrrolidin-3-yl)-4H-1,2,4-triazole TFA salt (0.12 g, 0.36, quantitative). LCMS: Method C, 1.355 min, MS: ES+215.28

Step c. To a solution of 3-phenyl-5-(pyrrolidin-3-yl)-4H-1,2,4-triazole (0.12 g, 0.56 mmol) in THF (20 ml) was added $K_2CO_3$ (0.30 g, 2.24 mmol) at −78° C. The reaction mixture was stirred at −78° C. for 15 min. Cyanogen bromide (0.060 g, 0.56 mmol) was added to the reaction mixture at −78° C. The reaction mixture was stirred at rt for 30 min. The resulting reaction mixture was poured into water (35 ml) and extracted with EtOAc (2×35 ml). The combined organic phase dried over $Na_2SO_4$, filtered and concentrated under reduced pressure. The resulting residue was purified by preparative TLC (5% MeOH in DCM) to yield 3-(5-phenyl-4H-1,2,4-triazol-3-yl)pyrrolidine-1-carbonitrile (0.027 g, 0.11 mmol). LCMS: Method B, 3.000 min, MS: ES+240.33; $^1$H NMR (400 MHz, DMSO-d6) δ ppm 14.3 (brs, 1H), 7.98 (m, 2H), 7.43-7.56 (m, 3H), 3.75-3.78 (m, 1H), 3.55-3.62 (m, 2H), 3.40-3.55 (m, 2H), 2.28-2.33 (m, 1H), 2.14-2.22 (m 1H).

Example 107 3-(5-(1H-Benzo[d]imidazol-6-yl)-4H-1,2,4-triazol-3-yl)pyrrolidine-1-carbonitrile

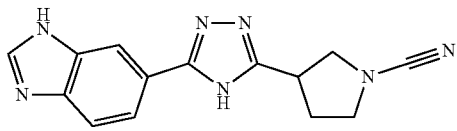 [SMILES: N#CN1CCC(c2nnc(-c3ccc4nc[nH]c4c3)[nH]2)C1]

The title compound was synthesised using a procedure similar to that described for Example 105, using benzimidazole-6-carbonitrile (CAS Number 6287-83-8) in step b. LCMS: Method C, 1.515 min, MS: ES+280.33; $^1$H NMR (400 MHz, DMSO-d6) δ ppm 13.98-14.14 (m, 1H), 12.67 (br s, 1H), 8.25 (s, 1H), 8.14 (s, 1H), 7.94 (br s, 1H), 7.74 (d, J=8.8 Hz, 1H), 3.72-3.79 (m, 1H), 3.63 3.64 (m, 2H), 3.48-3.57 (m, 2H), 2.24-2.30 (m, 1H), 2.17-2.22 (m, 1H).

Example 108 3-(5-(Imidazo[1,2-a]pyridin-6-yl)-4H-1,2,4-triazol-3-yl)pyrrolidine-1-carbonitrile

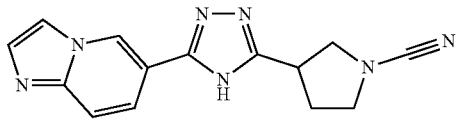 [SMILES: N#CN1CCC(c2nnc(-c3ccc4nccn4c3)[nH]2)C1]

The title compound was synthesised using a procedure similar to that described for Example 105, using 6-cyanoimidazo[1,2-a]pyridine (CAS Number 106850-34-4) in step b. LCMS: Method A, 1.901 min, MS: ES+280.00; $^1$H NMR (400 MHz, DMSO-d6) δ ppm 14.06-14.40 (m, 1H), 9.18-9.24 (m, 1H), 8.10-8.15 (s, 1H), 7.74-7.81 (m, 1H), 7.61-7.66 (m, 2H), 3.45-3.80 (m, 5H), 2.32-2.35 (m, 1H), 2.09-2.18 (m, 1H).

Example 109 3-(5-(4-Phenylpyridin-2-yl)-4H-1,2,4-triazol-3 yl)pyrrolidine-1-carbonitrile

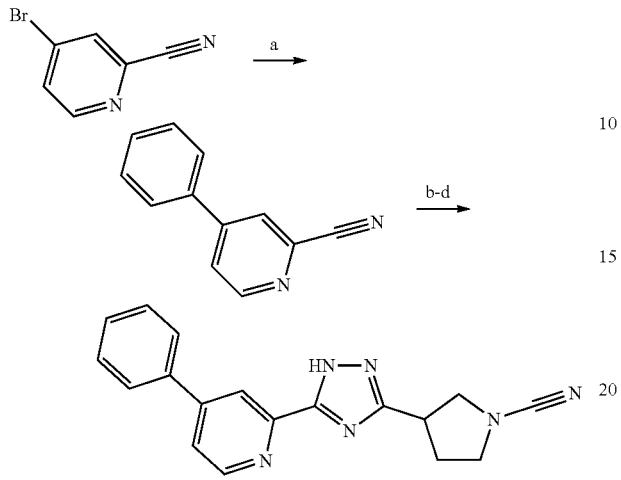

Step a. To a solution of 4-bromopicolinonitrile (CAS Number 62150-45-2; (1400 g, 2.185 mmol) in 1,4-dioxane:water (8:2, 10 ml) were added phenylboronic acid (0.266 g, 2.18 mmol) and $Cs_2CO_3$ (2.137 g, 6.56 mmol) at rt. The resulting reaction mixture was degassed for 30 min before addition of $Pd(PPh_3)_4$ (0.126 g, 0.109 mmol). The reaction mixture was heated at 80° C. for 1 h. The resulting reaction mixture was cooled to rt and concentrated reduce pressure. The obtained residue was diluted with water (10 ml) and extracted with EtOAc (2×20 ml). The combined organic layer was dried over $Na_2SO_4$, filtered and concentrated under reduced pressure. The resulting residue was purified by column chromatography (5% EtOAc in hexane) yielding 4-phenylpicolinonitrile (0.380 g, 2.11 mmol). LCMS: Method C, 2.229 min, MS: ES+181.11.

Steps b-d. The title compound was synthesized from the intermediate above using a procedure similar to that described for steps b-d of Example 105. LCMS: Method B, 3.482 min, MS: ES+317.34; $^1H$ NMR (400 MHz, DMSO-d6) δ ppm 14.15-14.70 (m, 1H), 8.76 (d, J=5.2 Hz, 1H), 8.30 (s, 1H), 7.87-7.89 (m, 3H), 7.51-7.59 (m, 3H), 3.77-3.79 (m, 1H), 3.64-3.67 (m, 2H), 3.48-3.53 (m, 2H), 2.19-2.32 (m, 2H).

Example 110 3-(5-(6-Phenylpyridin-2 yl)-4H-1,2,4-triazol-3 yl)pyrrolidine-1-carbonitrile

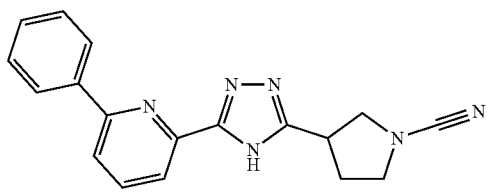 [SMILES: N#CN1CCC(c2nnc(-c3cccc(-c4ccccc4)n3)[nH]2)C1]

The title compound was synthesised using a procedure similar to that described for Example 109, using 6-bromopicolinonitrile (CAS Number 122918-2.5-6) in step a. LCMS: Method A, 2.947 min, MS: ES+317.04; $^1H$ NMR (400 MHz, DMSO-d6) δ ppm 14.20-14.57 (m, 1H), 8.37 (d, J=7.2 Hz, 2H), 7.98-8.13 (m, 3H), 7.49-7.56 (m, 3H), 3.77-3.82 (m, 1H), 3.64-3.67 (m, 2H), 3.50-3.55 (m, 2H), 2.19-2.33 (m, 2H).

Example 111 3-(3-([1,1'-Biphenyl]-3-yl)-1H-1,2,4-triazol-5-yl)pyrrolidine-1-carbonitrile

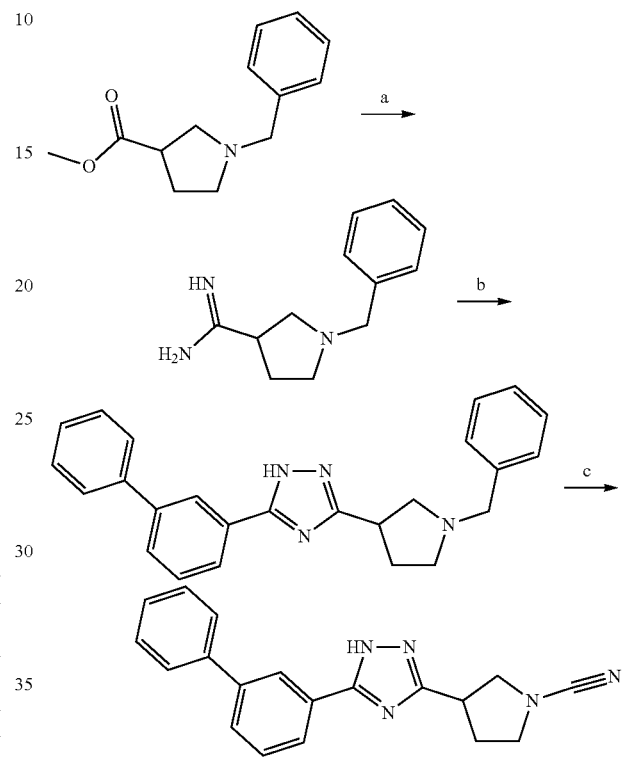

Step a. To a mixture of $NH_4Cl$ (2.46 g, 45.67 mmol) in toluene was added trimethylaluminum solution (2 M in heptane; 22.8 ml, 45.6 mmol) over a period of 2 h at 0° C. under nitrogen atmosphere. The reaction mixture was stirred at rt for 1 h. Methyl N-benzyl-3-pyrrolidinecarboxylate (CAS Number 17012-21-4; 2.0 g, 9.13 mmol) was added to the reaction mixture at rt, which was stirred for 30 min and then heated at 85° C. for 18 h. The resulting reaction mixture was cooled to rt. Cold MeOH (150 ml) was slowly added to the reaction mixture and stirred at rt for 1 h. The resulting mixture was filtered and washed with MeOH (2×50 ml). The filtrate was concentrated under reduced pressure and the residue was triturated with diethyl ether:DCM (1:1) (50 ml) and finally dried under high vacuum yielding 1-benzylpyrrolidine-3-carboximidamide hydrochloride (2.8 g, quantitative). LCMS: Method D, 4.456 min; MS: ES+204.2; $^1H$ NMR (400 MHz, DMSO-d6) δ ppm 7.44-7.48 (m, 1H), 7.32 7.39 (m, 4H), 3.94 (s, 2H), 3.22-3.31 (m, 2H), 2.96-3.05 (m, 3H), 2.29-2.36 (m, 1H), 1.89-2.04 (m, 1H).

Step b. To a stirred solution of 1-benzylpyrrolidine-3-carboximidamide hydrochloride (0.42 g, 1.75 mmol) in EtOH (15 ml) was added sodium methoxide (0.33 g, 6.207 mmol). The reaction mixture was stirred at rt for 45 min and then filtered to remove solid precipitates. 3-Biphenylcarboxylic acid hydrazide (CAS Number 709653-55-4; 0.29 g, 1.39 mmol) was added to the reaction mixture at rt. The reaction mixture was heated at 105° C. for 64 h. The resulting reaction mixture was cooled to rt and concentrated under vacuum and the crude material was purified by flash chromatography (neutral aluminium oxide; 1% MeOH in DCM) yielding 3-([1,1'-biphenyl]-3-yl)-5-(1-benzylpyrrolidin-3-yl)-1H-1,2,4-triazole (0.2 g, 0.53 mmol). LCMS: Method D, 7.095 min, MS: ES+381.2; $^1$H NMR (400 MHz, DMSO-d6) δ ppm 13.73 (br s, 1H), 8.24 (s, 1H), 7.97 (d, J=7.6 Hz, 1H), 7.71 (d, J=7.6 Hz, 3H), 7.49-7.57 (m, 3H), 7.39-7.43 (m, 1H), 7.31-7.35 (m, 4H), 7.23-7.30 (m, 1H), 3.65 (s, 2H), 3.47-3.54 (m, 2H), 2.97-3.01 (m, 1H), 2.65-2.76 (m, 2H), 2.13-2.31 (m, 2H).

Step c. To a stirred solution of 3-([1,1'-biphenyl]-3-yl)-5-(1-benzylpyrrolidin-3-yl)-1H-1,2,4-triazole (0.07 g, 0.184 mmol) in THF (4 ml) was added $K_2CO_3$ (0.025 g, 0.184 mmol) at it Cyanogen bromide (0.039 g, 0.368 mmol) was added to the reaction mixture at rt. The reaction mixture was stirred at rt for 2 h. The reaction mixture was poured into water (20 ml) and extracted with EtOAc (2×15 ml). The combined organic phase was separated, dried over $Na_2SO_4$, filtered and concentrated under reduced pressure. The resulting residue was purified by preparative TLC (3% MeOH in DCM, 300 ml) yielding 3-(3-([1,1'-biphenyl]-3-yl)-1H-1,2,4-triazol-5-yl)pyrrolidine-1-carbonitrile (0.018 g, 0.057 mmol). LCMS: Method B, 4.039 min, MS: ES+316.25; $^1$H NMR (400 MHz, DMSO-d6) δ ppm 14.03 (s, 1H), 8.27 (br s, 1H), 7.98 (br s, 1H), 7.72-7.82 (m, 3H), 7.52-7.63 (m, 3H), 7.35-7.43 (m, 1H), 3.73-3.82 (m, 1H), 3.60-3.71 (m, 2H), 3.48-3.60 (m, 2H) 2.18-2.34 (m, 2H).

Example 199 3-(3-(2-Phenylpyridin-4-yl)-1H-1,2,4-triazol-5-yl)pyrrolidine-1-carbonitrile Step b. To a solution of tert-butyl 2-(5-bromonicotinoyl)hydrazine-1-carboxylate (4.00 g, 12.7 mmol) in DCM (20 ml) was added TFA (2 ml) at rt. The reaction mixture was stirred at rt for 16 h. The resulting reaction mixture was concentrated under reduced pressure. The obtained crude material was co-distilled with DCM (3×50 ml) and resulting crude material was dried under high vacuum yielding 5-bromonicotinohydrazide TFA salt (3.9 g). This material was used directly for the next step without further purification. LCMS: Method C, 1.188 min, MS: ES+21.5.9, 218.1

Step c. To a mixture of 5-bromonicotinohydrazide TFA salt (1.210 g, 3.676 mmol) and 1-benzylpyrrolidine-3-carboximidamide (prepared according to Example 111, step a; 0.886 g, 3.676 mmol) in EtOH (10 ml) was added sodium methoxide (1.190 g, 22.20 mmol) at rt. The reaction mixture was heated at 90° C. for 16 h. The resulting reaction mixture was cooled to rt and concentrated under high vacuum. The obtained residue was co-distilled with DCM (3×20 ml). The resulting residue was diluted with EtOAc (50 ml). The organic layer was washed with water (2×40 ml). The organic layer was dried over $Na_2SO_4$, filtered and concentrated under reduced pressure. The crude material was purified by column chromatography (6% MeOH in DCM) yielding 3-(5-(1-benzyl-pyrrolidin-3-yl)-1H-1,2,4-triazol-3-yl)-5-bromopyridine (0.320 g, 0.832 mmol). LCMS: Method C, 1.748 min, MS: ES+384.13, 386.13

Step d. To a solution of 3-(5-(1-benzylpyrrolidin-3-yl)-1H-1,2,4-triazol-3-yl)-5-bromopyridine (0.500 g, 1.302 mmol) in DMF:water (9:1, 10 ml) were added phenylboronic acid and $Cs_2CO_3$ (1.270 g, 3.906 mmol) at rt. The

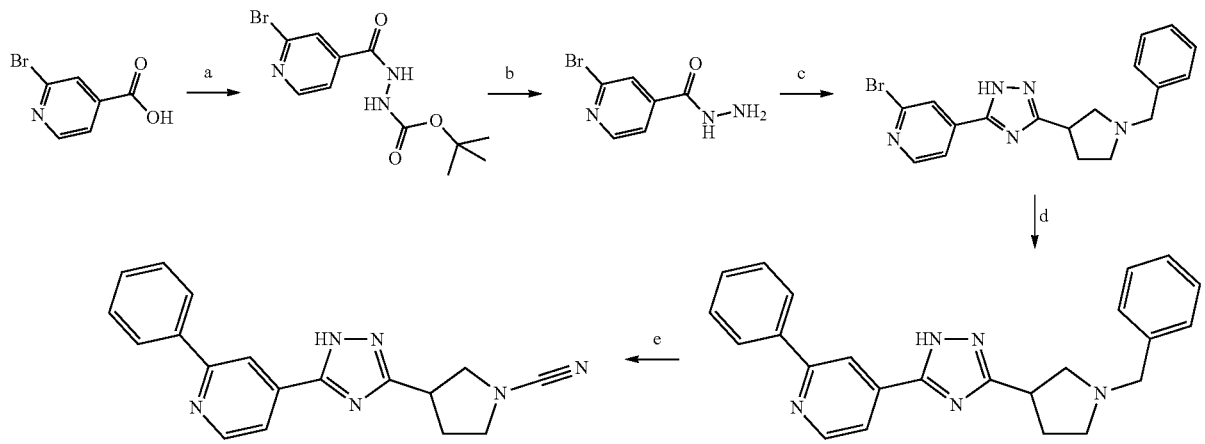

Step a. To a solution of 5-bromonicotinic acid (5.00 g, 24.7 mmol) in DCM (50 ml) was added EDCI (4.727 g, 24.7 mmol) and HOBt (3.787 g, 24.7 mmol) at 0° C. The reaction mixture was stirred at 0° C. for 1 h. DIPEA (15.2 ml, 89.1 mmol) and tert-butyl hydrazinecarboxylate (2.940 g, 22.3 mmol) were added dropwise to the reaction mixture at 0° C. The reaction mixture was stirred at rt for 16 h. The resulting reaction mixture was poured into water (200 ml) and extracted with EtOAc (2×50 ml). The combined organic layer was washed with saturated $NaHCO_3$ solution (2×40 ml), dried over $Na_2SO_4$, filtered and concentrated under reduced pressure. The crude material was purified by flash chromatography (2% MeOH in DCM) yielding tert-butyl 2-(5-bromonicotinoyl)hydrazine-1-carboxylate (4.00 g, 12.7 mmol). LCMS: Method C, 1.783 min, MS: ES+316.22, 318.22 reaction mixture was degassed at rt for 20 min before addition of $PdCl_2$(dppf) (0.095 g, 0.130 mmol). The reaction mixture was heated at 130° C. for 2 h. The resulting reaction mixture was cooled to rt, poured into water (100 ml) and extracted with EtOAc (2×40 ml). The combined organic layer was washed with brine (100 ml), dried over $Na_2SO_4$, filtered and concentrated under reduced pressure. The crude material was purified by column chromatography (7% MeOH in DCM) yielding 3-(5-(1-benzylpyrrolidin-3-yl)-1H-1,2,4-triazol-3-yl)-5-phenylpyridine (0.120 g, 0.314 mmol). LCMS: Method C, 1.824 min, MS: ES+382.38 [M+1]

Step e. To a stirred solution of 3-(5-(1-benzylpyrrolidin-3-yl)-1H-1,2,4-triazol-3-yl)-5-phenylpyridine (0.120 g, 0.314 mmol) in DMF:THF (1:1, 4 ml) was added $K_2CO_3$ (0.130 g, 0.943 mmol) at 0° C. The reaction mixture stirred at 0° C. for 30 min. Cyanogen bromide (0.066 g, 0.629 mmol) was added to the reaction mixture at 0° C. The reaction mixture was stirred at rt for 5 h. The resulting reaction mixture was poured into water (50 ml) and extracted with EtOAc (2×30 ml). The combined organic phase was washed with cold water (3×20 ml), dried over Na$_2$SO$_4$, filtered and concentrated under reduced pressure. The crude material was purified by preparative HPLC: Kinetic Evo C18 250×21.2 mm, 5 μm column, mobile phase: (A) water and (B) 100% MeCN, flow rate 15.0 ml/min to provide the title compound (0.016 g, 0.050 mmol). LCMS: Method A, 2.662 min, MS: ES+316.99 [M+1]; $^1$H NMR (400 MHz, DMSO-d6) δ ppm 14.22 (s, 1H), 9.14 (d, J=1.6 Hz, 1H), 8.95 (d, J=2.0 Hz, 1H), 8.52 (s, 1H), 7.80 (d, J=7.2 Hz, 2H), 7.55 (t, J=7.6 Hz, 2H), 7.45-7.49 (m, 1H), 3.79-3.82 (m, 1H), 3.63 3.73 (m, 2H), 3.48-3.57 (m, 2H), 2.29-2.35 (m, 1H), 2.19-2.25 (m, 1H).

Example 112 3-(3-([1,1'-Biphenyl]-4-yl)-1H-1,2,4-triazol-5-yl)pyrrolidine-1-carbonitrile

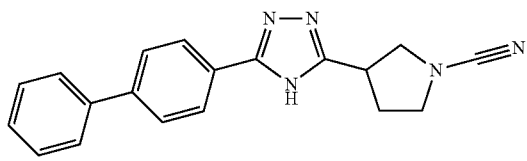 [SMILES: N#CN1CCC(c2nnc(-c3ccc(-c4ccccc4)cc3)[nH]2)C1]

The title compound was synthesised using a procedure similar to that described for Example 111, using 4-biphenylcarboxylic acid hydrazide (CAS Number 18622-23-6) in step b. LCMS: Method B, 4.103 min, MS: ES+316.45; $^1$H NMR (400 MHz, DMSO-d6) δ ppm 13.96 (s, 1H), 8.08 (t, J=7.6 Hz, 2H), 7.72-7.87 (m, 3H), 7.48-7.53 (m, 2H), 7.36-7.43 (m, 2H), 3.73-3.82 (m, 1H), 3.50-3.70 (m, 4H), 2.18-2.39 (m, 2H).

Example 113 Trans 3-methyl-4-(3-phenyl-1H-1,2,4-triazol-5-yl)pyrrolidine-1-carbonitrile

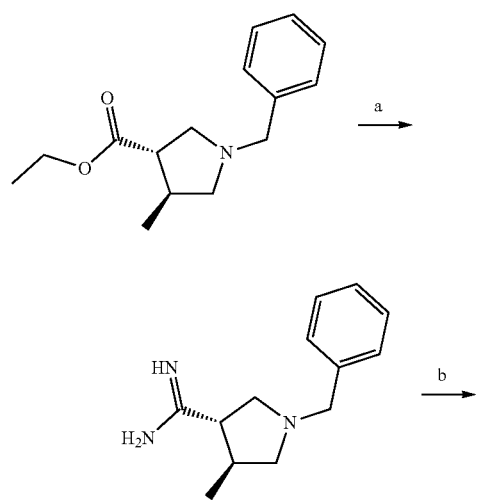

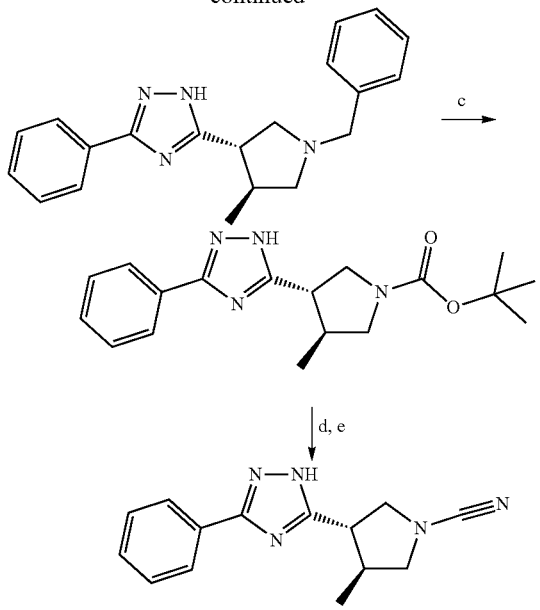

Step a. To a suspension of ammonium chloride (1.6 g, 29.9 mmol) in toluene (50 ml) was added trimethylaluminium (2M in toluene; 15 ml, 30 mmol) drop wise at rt. The resulting reaction mixture was stirred at rt until gas evolution ceased. Trans ethyl 1-benzyl-4-methylpyrrolidine-3-carboxylate (Example 19, step a; 1.5 g, 6.07 mmol) was added to the reaction mixture. The reaction mixture was heated at 80° C. for 24 h. The resulting reaction mixture was combined with one other batch prepared on the same scale by an identical method. The resulting mixture was poured into water (800 ml) and extracted with EtOAc (3×250 ml). The combined organic phase was dried over Na$_2$SO$_4$, filtered and concentrated under reduced pressure yielding trans 1-benzyl-4-methylpyrrolidine-3-carboximidamide (4.1 g, 18.9 mmol). This material was used for the next step without purification. LCMS: Method D, 5.476 min, MS: ES+206.18; $^1$H NMR (400 MHz, DMSO-d6) δ ppm 12.795 (s, 1H), 7.63-7.66 (m, 2H), 7.35-7.39 (m, 2H), 7.12-7.16 (t, 1H), 4.03-4.08 (m, 1H), 3.94-3.98 (m, 1H), 3.32-3.39 (m, 1H), 2.76-2.83 (m, 1H), 2.66-2.77 (m, 1H).

Step b. To a solution of trans 1-benzyl-4-methylpyrrolidine-3-carboximidamide (0.5 g, 2.3 mmol) in DMSO (15 ml) were added benzonitrile (0.166 g, 1.61 mmol), Cs$_2$CO$_3$ (1.49 g, 4.6 mmol) and copper bromide (0.009 g, 0.069 mmol) at rt. The reaction mixture was heated at 120° C. for 2 h. The resulting reaction mixture was combined with one other batch prepared on the same scale by an identical method. The resulting mixture was poured into water (700 ml) and extracted with EtOAc (3×300 ml). The combined organic phase was dried over Na$_2$SO$_4$, filtered and concentrated under reduced pressure. The obtained residue was purified using column chromatography (75% EtOAc in hexane) yielding trans 5-(1-benzyl-4-methylpyrrolidin-3-yl)-3-phenyl-1H-1,2,4-triazole (0.21 g, 0.66 mmol). LCMS: Method C, 1.640 min, MS: ES+319.28

Step c. To a solution of trans 5-(1-benzyl-4-methylpyrrolidin-3-yl)-3-phenyl-1H-1,2,4-triazole (0.08 g, 0.251 mmol) in EtOH (10 ml) was added polymethylhydroxylsiloxane (0.08 g, w/w) at 0° C. The reaction mixture was stirred at 0° C. for 10 min and treated with 20% Pd(OH)$_2$ (dry basis) (0.04 g, w/w). The reaction mixture was stirred at 0° C. for 10 min before addition of BOC anhydride (0.109 g, 0.502 mmol). The reaction mixture was warmed to rt. Hydrogen gas was purged into the reaction mixture at rt for 1 h. The resulting reaction mixture was carefully filtered through celite hyflow and washed with EtOH (5 ml). The obtained filtrate was poured into water (50 ml) and extracted with EtOAc (3×20 ml). The combined organic phase was dried over Na$_2$SO$_4$, filtered and concentrated under reduced pressure. The obtained residue was purified using column chromatography (5% MeOH in DCM) yielding trans tert-butyl 3-methyl-4-(3-phenyl-1H-1,2,4-triazol-5-yl)pyrrolidine-1-carboxylate (0.08 g, 0.243 mmol). LCMS: Method C, 2.895 min, MS: ES+329.33

Steps d, e. The title compound was synthesised from the intermediate above using a procedure similar to that described for Example 14, steps d, c. LCMS: Method A, 2.761 min, MS: ES+253.97

Example 114 Trans-3-(3-([1,1'-biphenyl]-3-yl)-1H-1,2,4-triazol-5-yl)-4-methylpyrrolidine-1-carbonitrile

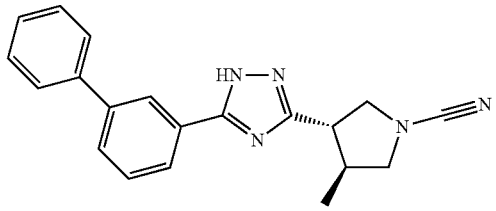 [SMILES: C[C@@H]1CN(C#N)C[C@H]1c1n[nH]c(-c2cccc(-c3ccccc3)c2)n1]

The title compound was synthesised following a procedure similar to Example 111, using trans ethyl 1-benzyl-4-methylpyrrolidine-3-carboxylate (Example 19, step a) in step a. LCMS: Method B, 4.301 min, MS: ES+330.28; $^1$H NMR (400 MHz, DMSO-d6) δ ppm 14.06-14.37 (s, 1H), 8.26 (s, 1H), 7.98 (d, J=6.8 Hz, 1H), 7.70-7.76 (m, 4H), 7.50-7.60 (m, 2H), 7.36-7.44 (m, 1H), 3.84-3.87 (m, 1H), 3.66-3.72 (m, 2H), 3.15-3.17 (m, 2H), 2.40-2.45 (m, 1H), 1.05 (d, J=6.4 Hz, 3H).

The obtained racemic material was subjected to enantiomeric separation by preparative chiral SFC: CHIRALART SA 250×4.6 mm 5 µm, mobile phase: (A) Liquid carbon dioxide; (B) 0.1% DEA in MeOH to provide the following enantiomers (absolute stereochemistry was not determined):

Example 115 Trans-3-(3-([1,1'-biphenyl]-3 yl)-1H-1,2,4-triazol-5-yl)-4-methylpyrrolidine-1-carbonitrile: Enantiomer 1

LCMS: Method B, 4.314 min, MS: ES+330.23; Chiral SFC: CHIRALPAK IC 250×4.6 mm 5 µm, mobile phase: (A) Liquid carbon dioxide; (B) IPA, column flow was 4.0 ml/min and ABPR was 150 bar, isocratic gradient of 40% B over 10 min, RT 2.99 min; $^1$H NMR (400 MHz, DMSO-d6) δ ppm 14.00-14.37 (m, 1H), 8.26 (s, 1H), 7.98 (d, J=8 Hz, 1H), 7.72-7.74 (m, 3H), 7.60-7.61 (m, 1H), 7.50-7.54 (m, 2H), 7.42-7.44 (m, 1H), 3.85-3.89 (m, 1H), 3.66-3.74 (m, 2H), 3.22-3.23 (m, 1H), 3.13-3.17 (m, 1H), 2.40-2.45 (m, 1H), 1.05 (d, J=6.4 Hz, 3H).

Example 116 Trans-3-(3-([1,1'-biphenyl]-3-yl)-1H-1,2,4-triazol-S yl)-4-methylpyrrolidine-1-carbonitrile: Enantiomer 2

LCMS: Method B, 4.314 min, MS: ES+330.23; Chiral SFC: CHIRALPAK IC 250×4.6 mm 5 µm, mobile phase: (A) Liquid carbon dioxide; (B) IPA, column flow was 4.0 ml/min and ABPR was 150 bar, isocratic gradient of 40% B over 10 min, RT 6.36 min; $^1$H NMR (400 MHz, DMSO-d6) δ ppm 14.00-14.37 (m, 1H), 8.26 (s, 1H), 7.98 (d, J=8 Hz, 1H), 7.72-7.74 (m, 3H), 7.59-7.62 (m, 1H), 7.50-7.54 (m, 2H), 7.40-7.44 (m, 1H), 3.85-3.89 (m, 1H), 3.66-3.74 (m, 2H), 3.22-3.23 (m, 1H), 3.13-3.17 (m, 1H), 2.40-2.45 (m, 1H), 1.05 (d, J=6.4 Hz, 3H).

Example 117 3-(3-([1,1'-Biphenyl]-3-yl)isoxazol-5-yl)pyrrolidine-1-carbonitrile

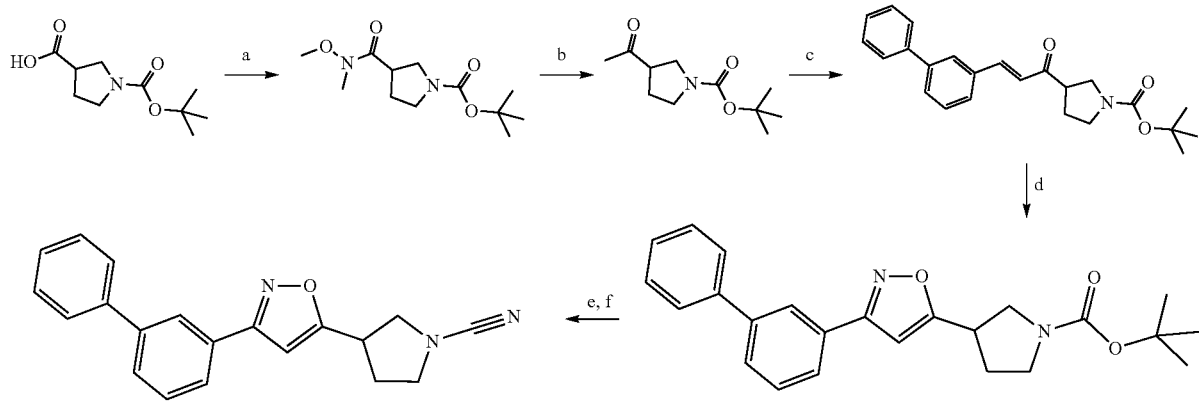

Step a. To a stirred solution of N—BOC-pyrrolidine-3-carboxylic acid (CAS Number 59378-75-5; 3.0 g, 13.9 mmol) in DCM (80 ml) was added CDI (2.26 g, 13.9 mmol) at 0° C. The reaction mixture was stirred at 0° C. for 1 h before addition of N,O-dimethylhydroxylamine HCl (2.03 g, 20.9 mmol). The reaction mixture was stirred at rt for 16 h. The resulting reaction mixture was poured into water (250 ml), basified using solid NaHCO$_3$ and extracted with EtOAc (2×150 ml). The combined organic phase was separated, dried over Na$_2$SO$_4$, filtered and concentrated under reduced pressure yielding tert-butyl 3-(methoxy(methyl)carbamoyl) pyrrolidine-1-carboxylate (3.1 g, 12.0 mmol). This material was used directly to the next step without further purification. LCMS: Method C, 2.018 min, MS: ES+258.9; $^1$H NMR (400 MHz, DMSO-d6) δ ppm 3.69 (s, 3H), 3.44-3.47

(m, 3H), 3.23-3.27 (m, 2H), 3.11 (s, 3H), 2.00-2.06 (m, 1H), 1.85-1.96 (m, 1H), 1.40 (s, 9H).

Step b. To a stirred solution of tert-butyl 3-(methoxy (methyl)carbamoyl)pyrrolidine-1-carboxylate (3.0 g, 11.63 mmol) in THF (50 ml) was added MeMgBr solution (3 M in diethyl ether; 19.3 ml, 57.9 mmol) drop wise at 0° C. The reaction mixture was stirred at 0° C. for 1 h. The resulting reaction mixture was poured into saturated NaHCO$_3$ (500 ml) solution. The obtained solids were filtered and filtrate was extracted with EtOAc (2×300 ml). The combined organic phase was separated, dried over Na$_2$SO$_4$, filtered and concentrated under reduced pressure yielding tert-butyl 3-acetylpyrrolidine-1-carboxylate (1.8 g, 8.4.5 mmol). This material was used directly to the next step without further purification. LCMS: Method C, 1.929 min, MS: ES+158.08 (M-56); $^1$H NMR (400 MHz, DMSO-d6) δ ppm 3.17-3.38 (m, 5H), 2.19 (s, 3H), 2.03-2.11 (m, 1H), 1.85-1.94 (m, 1H) 1.4 (s, 9H).

Step c. To a stirred solution of tert-butyl 3-acetylpyrrolidine-1-carboxylate (0.3 g, 1.408 mmol) in MeOH (7 ml) was added sodium methoxide (0.152 g, 2.82 mmol) at rt. The reaction mixture was stirred for 30 min before addition of 3-phenylbenzaldehyde (CAS Number 1204-60-0; 0.256 g, 1.41 mmol) and the reaction mixture was stirred at rt for 16 h. The resulting reaction mixture was diluted with DCM (100 ml) and poured into water (100 ml). The organic phase was separated and the aqueous phase was extracted with DCM (100 ml). The combined organic phase was separated, dried over Na$_2$SO$_4$, filtered and concentrated under reduced pressure. The resulting crude material was purified by flash chromatography (10% EtOAc in hexane) yielding tert-butyl (E)-3-(3-([1,1'-biphenyl]-3-yl)acryloyl)-pyrrolidine-1-carboxylate (0.22 g, 0.583 mmol). MS: ES+322.0 (M-56); $^1$H NMR (400 MHz, DMSO-d6) δ ppm 8.07 (s, 1H), 7.74-7.78 (m, 5H), 7.48-7.56 (m, 3H), 7.41 (t, J=7.2 Hz, 1H), 7.18 (d, J=16 Hz, 1H), 3.46-3.66 (m, 2H), 3.4-3.44 (m, 1H), 3.29-3.34 (m, 2H), 2.16-2.21 (m, 1H) 1.96-1.98 (m, 1H), 1.4 (s, 9H).

Step d. To a stirred solution of tert-butyl N-hydroxyl-4-toluenesulfonamide (CAS Number 1593-60-8; 0.595 g, 3.18 mmol) in MeOH:water (5:1; 6 ml) was added K$_2$CO$_3$ (0.527 g, 3.82 mmol), followed by tert-butyl (E)-3-(3-([1,1'-biphenyl]-3-yl)acryloyl)pyrrolidine-1-carboxylate (0.12 g, 0.32 mmol). The reaction mixture was heated at 60° C. for 16 h. The resulting reaction mixture was cooled to rt, diluted with DCM (70 ml) and poured into water (100 ml). The organic phase was separated and aqueous phase was extracted with DCM (70 ml). The combined organic phase was separated, dried over Na$_2$SO$_4$, filtered and concentrated under reduced pressure. The resulting crude material was purified by flash chromatography (10% EtOAc in hexane) yielding a mixture of tert-butyl (E)-3-(3-([1,1'-biphenyl]-3-yl)acryloyl)pyrrolidine-1-carboxylate and tut-butyl 3-(3-([1,1'-biphenyl]-3-yl) isoxazol-5-yl)pyrrolidine-1-carboxylate (0.108 g, quantitative). LCMS: Method B, 5.577 min, 5.697 min, MS: ES+335.27 (M-56). This material was used directly to the next step without further purification.

Steps e, f. The title compound was synthesised from the intermediate above using a procedure similar to that described for Example 14, steps d, e. The crude material was purified by preparative HPLC; Phenomenex Kinetex EVO C18 250×21.2 mm, 5 µm, mobile phase: (A) water and (B) MeCN, flow rate 15.0 ml/min to provide 3-(3-([1,1'-biphenyl]-3-yl)isoxazol-5-yl)pyrrolidine-1-carbonitrile. LCMS: Method B, 4.649 min, MS: ES+316.44; Chiral SFC: Chiralpak IC 250×4.6 mm 5 µm, mobile phase: (A) Liquid carbon dioxide; (B) IPA:MeCN (50:50), column flow was 3.0 ml/min and ABPR was 130 bar, isocratic gradient of 25% B over 15 min, RT 8.77 and 10.27 min; $^1$H NMR (400 MHz, DMSO-d6) δ ppm 8.11 (t, J=1.6 Hz, 1H), 7.87 (d, J=8.0 Hz, 1H), 7.81 (d, J=8.4 Hz, 1H), 7.76 (d, J=7.2 Hz, 2H), 7.62 (t, J=8.0 Hz, 1H), 7.52 (t, J=8.0 Hz, 2H), 7.42 (t, J=7.2 Hz, 1H), 7.21 (s, 1H), 3.76-3.85 (m, 2H), 3.54-3.60 (m, 3H), 2.33-2.41 (m, 1H), 2.11-2.18 (m, 1H).

The obtained racemic material was subjected to enantiomeric separation by prep chiral SFC: Chiralpak IC, 250× 21.0 mm, 5 µm, mobile phase: (A) Liquid carbon dioxide; (B) IPA:MeCN (50:50), column flow was 70.0 ml/min and ABPR was 100 bar, which yielded the following enantiomers (absolute stereochemistry was not determined):

Example 118 3-(3-([1,1'-Biphenyl]-3-yl)isoxazol-5-yl)pyrrolidine-1-carbonitrile: Enantiomer 1

LCMS: Method B, 4.890 min, MS: ES+316.40; $^1$H NMR (400 MHz, DMSO-d6) δ ppm 8.11 (s, 1H), 7.87 (d, J=8.0 Hz, 1H), 7.80 (d, J=8.0 Hz, 1H), 7.76 (d, J=7.2 Hz, 2H), 7.62 (t, J=7.6 Hz, 1H), 7.51 (t, J=7.2 Hz, 2H), 7.40-7.44 (m, 1H), 7.20 (s, 1H), 3.76-3.85 (m, 2H) 3.51-3.59 (m, 3H), 2.33-2.41 (m, 1H), 2.11-2.16 (m, 1H).

Example 119 3-(3-([1,1'-Biphenyl]-3 yl)isoxazol-5-yl)pyrrolidine-1-carbonitrile: Enantiomer 2

LCMS: Method B, 4.889 min, MS: ES+315.80; $^1$H NMR (400 MHz, DMSO-d6) δ ppm 8.11 (s, 1H), 7.87 (d, J=8.0 Hz, 1H), 7.80 (d, J=8.0 Hz, 1H), 7.76 (d, J=7.2 Hz, 2H), 7.62 (t, J=7.6 Hz, 1H), 7.51 (t, J=7.2 Hz, 2H), 7.40-7.44 (m, 1H), 7.20 (s, 1H), 3.76-3.85 (m, 2H) 3.51-3.59 (m, 3H), 2.33-2.41 (m, 1H), 2.11-2.16 (in, 1H).

Example 120 3-(6-Oxo-5-phenyl-1,6-dihydropyrimidin-2 yl)pyrrolidine-1-carbonitrile

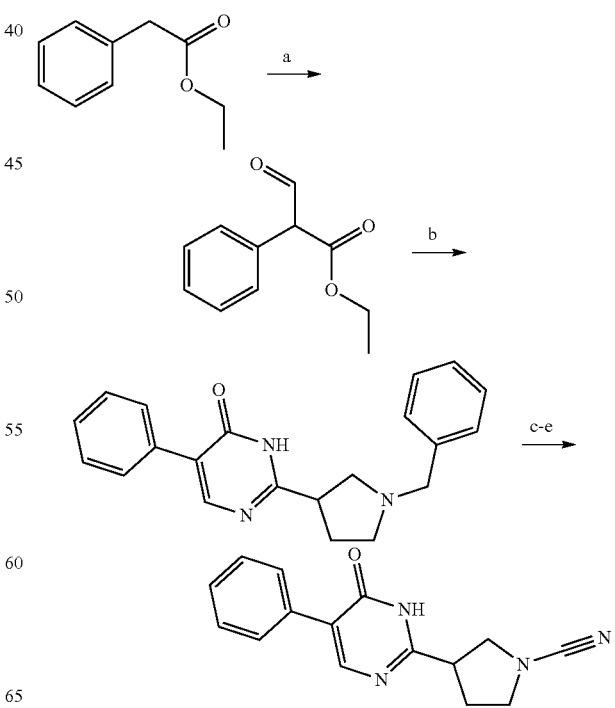

Step a. To a solution of ethyl phenylacetate (1.5 g, 9.15 mmol) and ethyl formate (4.74 g, 64.0 mmol) in THF (15 ml) was slowly added NaH (60% dispersion in mineral oil, 0.73 g, 18.3 mmol) at 0° C. The reaction mixture was stirred at rt for 3 h. The resulting reaction mixture was poured into cold water (50 ml) and adjusted to pH 5 using 1 M HCl. The resulting reaction mixture was extracted with DCM (2×25 ml). The combined organic phase was washed with brine (20 ml), dried over $Na_2SO_4$, filtered and concentrated under reduced pressure yielding ethyl 3-oxo-2-phenylpropanoate (1.8 g, quantitative). LCMS: Method C, 2.062 min; MS: ES+193.19; $^1$H NMR (400 MHz, $CDCl_3$) δ ppm 12.14 (d, J=12.4 Hz, 1H), 7.29-7.38 (m, 6H), 4.31 (q, J=7.2 Hz, 2H), 1.32 (t, J=3.6 Hz, 3H).

Step b. To a solution of ethyl 3-oxo-2-phenylpropanoate (0.8 g, 4.17 mmol) in THF: water (1:1) (10 ml) were added 1-benzylpyrrolidine-3-carboximidamide hydrochloride (Example 111, step a; 1 g, 4.17 mmol) and $Na_2CO_3$ (4.34 g, 41.7 mmol) at rt. The resulting reaction mixture was heated at 70° C. for 8 h. The reaction mixture was cooled to rt and combined with one other batch prepared on the same scale by an identical method. The resulting reaction mixture was concentrated under reduced pressure and poured into water (20 ml). The obtained mixture was extracted with EtOAc (2×25 ml). The combined organic phase was wash with brine (10 nil), dried over $Na_2SO_4$, filtered and concentrated under reduced pressure. The resulting residue was purified by flash chromatography (2% MeOH in DCM) yielding 2-(1-benzylpyrrolidin-3-yl)-5-phenylpyrimidin-4(3H)-one (0.35 g, 1.056 mmol). LCMS: Method C, 1.774 min; MS: ES+332.38.

Step c. To a solution of 2-(1-benzylpyrrolidin-3-yl)-5-phenylpyrimidin-4(3H)-one (0.3 g, 0.91 mmol) in MeOH (10 ml) was added 20% $Pd(OH)_2$ (50% moisture content; 1.0 g) and poly-(methylhydrosiloxane) (1.5 g) at 0° C. and stirred for 5 min. BOC anhydride (0.217 g, 0.996 mmol) was added to the reaction mixture at 0° C. The resulting reaction mixture was stirred at rt for 3 h. The resulting mixture was filtered through celite hyflow and washed with MeOH (50 ml). The resulting filtrate was concentrated under reduced pressure. The resulting residue was dissolved in DCM (20 ml), dried over $Na_2SO_4$, filtered and concentrated under reduced pressure. The resulting residue was purified by flash chromatography (3.5% MeOH in DCM) yielding tert-butyl 3-(6-oxo-5-phenyl-1,6-dihydropyrimidin-2-yl)pyrrolidine-1-carboxylate (0.18 g, 0.527 mmol) LCMS: Method C, 2.199 min; MS: ES+342.38.

Step d. To a solution of tert-butyl 3-(6-oxo-5-phenyl-1,6-dihydropyrimidin-2-yl)pyrrolidine-1-carboxylate (0.1 g, 0.293 mmol) in DCM (5 ml) was added TFA (1.0 ml) at 0° C. The reaction mixture was stirred at rt for 1 h. The resulting reaction mixture was concentrated under reduced pressure. The obtained residue was triturated with diethyl ether: hexane (1:1) (5 ml) and finally dried under high vacuum yielding 5-phenyl-2-(pyrrolidin-3-yl)pyrimidin-4 (3H)-one TFA salt (0.08 g, 0.225 mmol). LCMS: Method C, 1.536 min, MS: ES+242.28.

Step e. To a solution of 5-phenyl-2-(pyrrolidin-3-yl)pyrimidin-4(3H)-one TFA salt (0.08 g, 0.225 mmol) in THF (5 ml) was added $K_2CO_3$ (0.16 g, 1.126 mmol) at 0° C. Cyanogen bromide (0.024 g, 0.225 mmol) was added to the reaction mixture at 0° C. The reaction mixture was stirred at rt for 30 min. The resulting reaction mixture was concentrated under reduced pressure. Water (10 ml) was added to the resulting residue and extracted with DCM (2×15 ml). The combined organic phase was dried over $Na_2SO_4$, filtered and concentrated under reduced pressure. The residue was triturated with diethyl ether and hexane (1:1) (2×2 ml) and finally dried under high vacuum yielding title compound (0.046 g, 0.172 mmol). LCMS: Method A, 2.147 min, MS: ES+267.09; $^1$H NMR (400 MHz, DMSO-d6) δ ppm 13.79 (br s, 1H), 8.14 (s, 1H), 7.68-7.72 (m, 2H), 7.41 (t, J=6.8 Hz, 2H), 7.32-7.37 (m, 1H), 3.64-3.73 (m, 2H), 3.43-3.55 (m 3H), 2.25-2.33 (m, 1H), 2.13-2.20 (m, 1H).

Example 121 (R)-3-(7-(4-Methyl-1H-imidazol-1-yl)-1,6-dioxo-1,3,4,6-tetrahydro-2H-pyrido[1,2-a]pyrazin-2-yl)pyrrolidine-1-carbonitrile

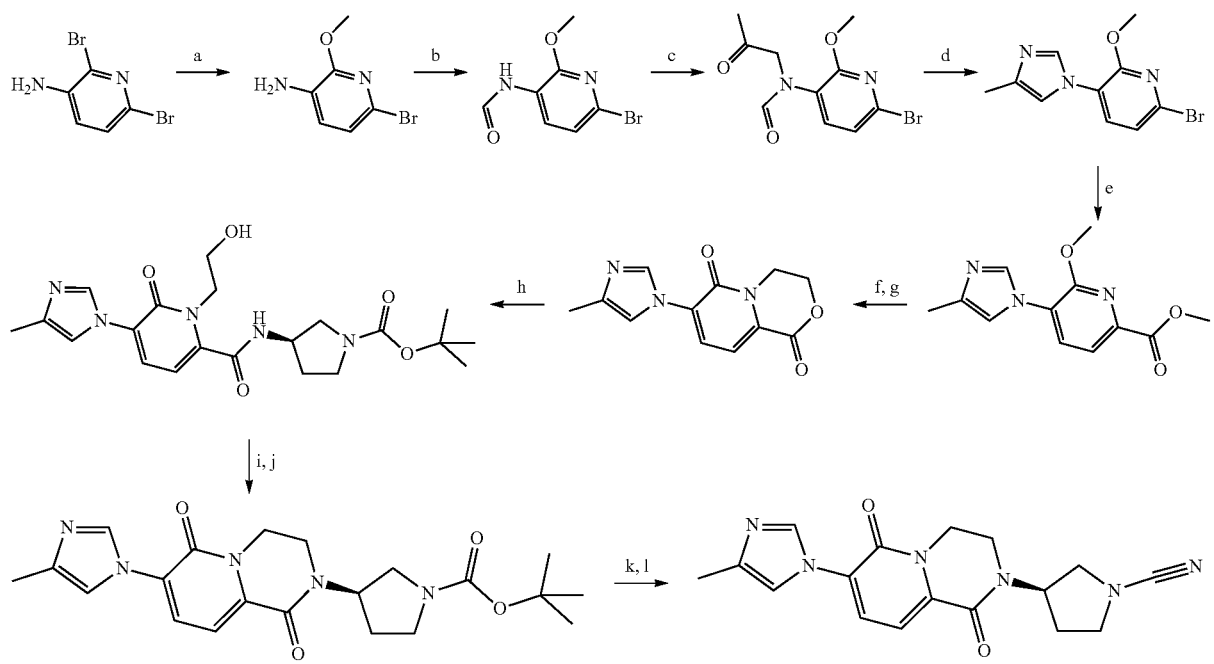

Step a. To a solution of 2,6-dibromopyridin-3-amine (CAS Number 39856-57-0; 5.00 g, 19.84 mmol) in 1,4-dioxane (100 ml) was added sodium methoxide (1.60 g, 29.76 mmol) portion wise at rt. The reaction mixture was heated at 110° C. for 24 h. The resulting reaction mixture was cooled to rt and poured into saturated ammonium chloride (200 ml). The obtained mixture was extracted with EtOAc (3×100 ml). The combined organic phase was dried over $Na_2SO_4$, filtered and concentrated under reduced pressure. The resulting residue was purified by column chromatography (5% EtOAc in hexane) yielding 6-bromo-2-methoxypyridin-3-amine (3.00 g, 14.77 mmol). LCMS: Method C, 2.072 min, MS: ES+203.18

Step b. A mixture of formic acid (7.50 ml, 2.5 vol) and acetic anhydride (5.55 ml, 3.76 mmol) was stirred at rt for 30 min. A solution of 6-bromo-2-methoxypyridin-3-amine (3.00 g, 14.8 mmol) in THF (15.0 nil) was added drop wise to the reaction mixture at rt. The reaction mixture was heated at 60° C. for 16 h. The resulting reaction mixture was cool to rt and poured into ice cold water (200 ml) and stirred for 30 min. The obtained solids were filtered off, washed with water (20 ml) and dried under reduced pressure to yield N-(6-bromo-2-methoxypyridin-3-yl) formamide (2.6 g, 11.25 mmol). This material was used directly for the next step without further purification. LCMS: Method C, 2.019 min, MS: ES+233.08; $^1H$ NMR (400 MHz, DMSO-d6) δ ppm 9.99 (s, 1H), 8.40 (d, J=8 Hz, 1H), 8.34 (d, J=1.2 Hz, 1H), 7.21 (d, J=8 Hz, 1H), 3.94 (s, 3H).

Step c. To a solution of N-(6-bromo-2-methoxypyridin-3-yl)formamide (2.6 g, 11.2 mmol) in DMF (25 ml) were added KI (0.186 g, 1.12 mmol) and $K_2CO_3$ (5.43 g, 39.4 mmol) at rt. Chloroacetone (2.60 g, 28.1 mmol) was added drop wise to the reaction mixture at rt. The reaction mixture was stirred at rt for 16 h. The resulting reaction mixture was poured into ice cold water (200 ml) and stirred for 30 min. The obtained solids were filtered off, washed with water (20 ml) and dried under reduced pressure yielding N-(6-bromo-2-methoxypyridin-3-yl)-N-(2-oxopropyl)formamide (2.5 g, 8.74 mmol). This material was used directly for the next step without further purification. LCMS: Method C, 2.032 min, MS: ES+288; $^1H$ NMR (400 MHz, DMSO-d6) δ ppm 8.28 (s, 1H), 7.60 (d, J=8 Hz, 1H), 7.31 (d, J=8 Hz, 1H), 4.48 (s, 2H), 3.90 (s, 3H), 2.09 (s, 3H).

Step d. To a solution of N-(6-bromo-2-methoxypyridin-3-yl)-N-(2-oxopropyl)formamide (2.5 g, 8.74 mmol) in acetic acid (31.5 ml) was added ammonium acetate (3.55 g, 46.1 mmol) at rt. The reaction mixture was heated at 130° C. for 4 h. The resulting reaction mixture was cooled to rt and poured into ice cold water (150 ml). The obtained mixture was basified with 25% ammonia solution up to pH 8. The aqueous layer was exacted with EtOAc (2×100 ml). The combined organic phase was dried over Na2SO4, filtered and concentrated under reduced pressure. The resulting residue was purified by column chromatography (15% EtOAc in hexane) yielding 6-bromo-2-methoxy-3-(4-methyl-1H-imidazol-1-yl) pyridine (2.3 g, 5.24 mmol). LCMS: Method C, 1.689 min, MS: ES+268, 270; $^1H$ NMR (400 MHz, DMSO-d6) δ ppm 7.88 (s, 1H), 7.82-7.80 (d, J=8 Hz, 1H), 7.39-7.37 (d, J=8 Hz, 1H), 7.22 (s, 1H), 3.93 (s, 3H), 2.14 (s, 3H).

Step e. A solution of 6-bromo-2-methoxy-3-(4-methyl-1H-imidazol-1-yl) pyridine (2.3 g, 5.24 mmol) in MeOH (15 ml) was prepared in an autoclave. TEA (1.45 ml, 10.48 mmol) was added to the reaction mixture at rt. The reaction mixture was degassed for 10 min before addition of $PdCl_2$ (dppf).DCM complex (0.213 g, 0.26 mmol). The reaction mixture was heated at 60° C. under 60 Psi of carbon monoxide for 4 h. The resulting reaction mixture was cooled to rt and concentrated under reduced pressure. The obtained residue was diluted with water (150 ml). The aqueous layer was exacted with DCM (3×100 ml). The combined organic phase was dried over $Na_2SO_4$, filtered and concentrated under reduced pressure. The resulting residue was purified by column chromatography (40% EtOAc in hexane) yielding methyl 6-methoxy-5-(4-methyl-1H-imidazol-1-yl)picolinate (0.90 g, 3.64 mmol). LCMS: Method C, 1.545 min, MS: ES+248; $^1H$ NMR (400 MHz, DMSO-d6) δ ppm 8.04-8.02 (d, J=8 Hz, 2H), 7.81-7.79 (d, J=8 Hz, 1H), 7.35 (s, 1H), 4.01 (s, 3H), 3.89 (s, 3H), 2.17 (s, 3H).

Step f. A mixture of methyl 6-methoxy-5-(4-methyl-1H-imidazol-1-yl)picolinate (0.90 g, 3.64 mmol) in concentrated HCl (3.0 ml) was refluxed for 16 h. The resulting reaction mixture was cooled to rt and concentrated under reduced pressure. The obtained material was azeotropically distilled with DCM (2×10 ml) and dried under vacuum. The obtained residue was triturated with 1,4-dioxane (20 ml), filtered and dried under vacuum yielding 5-(4-methyl-1H-imidazol-1-yl)-6-oxo-5,6-dihydro-pyridine-2-carboxylic acid HCl salt (0.70 g, 2.75 mmol). LCMS: Method C, 0.708 min, MS: ES+220; $^1H$ NMR (400 MHz, DMSO-d6) δ ppm 14.64 (br s, 1H), 12.64 (br s, 1H), 9.53 (s, 1H), 8.04 (d, J=8 Hz, 1H), 7.86 (s, 1H), 7.10 (d, J=8 Hz, 1H), 2.34 (s, 3H).

Step g. To a solution of 5-(4-methyl-1H-imidazol-1-yl)-6-oxo-5,6-dihydropyridine-2-carboxylic acid HCl salt (0.70 g, 2.75 mmol) in DMF were added $Cs_2CO_3$ (1.36 g, 4.19 mmol) and 1,2-dibromoethane (0.579 g, 3.09 mmol) at rt. The reaction mixture was heated at 90° C. for 6 h. The resulting reaction mixture was cooled to rt and filtered through celite hyflow. The celite bed was washed with DCM (20 ml). The obtained filtrate was concentrated under reduced pressure. The resulting residue was diluted with DCM (100 ml) and washed with brine solution (50 ml). The organic phase was dried over $Na_2SO_4$, filtered and concentrated under reduced pressure. The obtained residue was triturated with MeCN (10 ml), filtered and dried under vacuum yielding 7-(4-methyl-1H-imidazol-1-yl)-3,4-dihydropyrido[2,1-c][1,4]oxazine-1,6-dione (0.30 g, 1.224 mmol). LCMS: Method C, 0.522 min, MS: ES+246; $^1H$ NMR (400 MHz, DMSO-d6) δ ppm 8.34 (s, 1H), 7.85-7.83 (d, J=8 Hz 1H), 7.48 (s, 1H), 7.25-7.23 (d, J=8 Hz, 1H), 4.69 (t, J=4 Hz 2H), 4.29 (t, J=8 Hz, 2H), 2.16 (s, 3H).

Step h. To a solution of tert-butyl (R)-3-aminopyrrolidine-1-carboxylate (CAS Number 147081-49-0; 0.273 g, 1.469 mmol) in THF (10 ml) was added bis(trimethylaluminum)-1,4-diazabicyclo[2.2.2]octane adduct (CAS Number 137203-34-0; 0.507 g, 1.98 mmol) at rt. The reaction mixture was heated at 55° C. for 30 min before careful addition of 7-(4-methyl-1H-imidazol-1-yl)-3,4-dihydropyrido[2,1-c][1,4]oxazine-1,6-dione (0.30 g, 1.224 mmol) at 55° C. The reaction mixture was further refluxed for 3 h. The resulting reaction mixture was cooled to and diluted with 0.5 M NaOH solution (100 ml). The obtained mixture was extracted with EtOAc (3×50 ml). The combined organic phase was dried over $Na_2SO_4$, filtered and concentrated under reduced pressure. The residue was purified by column chromatography (2% MeOH in DCM) yielding tert-butyl (R)-3-(1-(2-hydroxyethyl)-5-(4-methyl-1H-imidazol-1-yl)-6-oxo-1,6-dihydropyridine-2-carboxamido) pyrrolidine-1-carboxylate (0.38 g, 0.881 mmol). LCMS: Method C, 1.665 min, MS: ES+432.

Step i. To a solution of tert-butyl (R)-3-(1-(2-hydroxyethyl)-5-(4-methyl-1H-imidazol-1-yl)-6-oxo-1,6-dihydropyridine-2-carboxamido)pyrrolidine-1-carboxylate (0.25 g, 0.580 mmol) in THF (10 ml) were added TEA (0.24 ml, 1.74 mmol) and methanesulphonyl chloride (0.099 g, 0.87 mmol) at 0° C. The reaction mixture was stirred at rt for 16 h. The resulting reaction mixture was diluted with cold water (100 ml) and extracted with EtOAc (3×50 ml). The combined organic phase was dried over Na₂SO₄, filtered and concentrated under reduced pressure. The obtained residue was triturated with diethyl ether (10 ml), filtered and dried under vacuum tert-butyl (R)-3-(1-(2-chloroethyl)-5-(4-methyl-1H-imidazol-1-yl)-6-oxo-1,6-dihydropyridine-2-carboxamido) pyrrolidine-1-carboxylate (0.15 g, 0.334 mmol). LCMS: Method C, 1.813 min, MS: ES+450. This material was used for the next step without purification.

Step j. To a solution of tert-butyl (R)-3-(1-(2-chloroethyl)-5-(4-methyl-1H-imidazol-1-yl)-6-oxo-1,6-dihydropyridine-2-carboxamido)pyrrolidine-1-carboxylate (0.15 g, 0.33 mmol) in THF (3 ml) was added lithium bis(trimethylsilyl) amide (1 M in THF, 0.83 ml, 0.83 mmol) at 0° C. The reaction mixture was stirred at rt for 5 h. The resulting reaction mixture was poured into saturated NH₄Cl solution (100 ml) and extracted with EtOAc (3×50 ml). The combined organic phase was dried over Na₂SO₄, filtered and concentrated under reduced pressure. The obtained residue was triturated with diethyl ether (10 ml), filtered and dried under vacuum yielding tert-butyl (R)-3-(7-(4-methyl-1H-imidazol-1-yl)-1,6-dioxo-1,3,4,6-tetrahydro-2H-pyrido[1,2-a]pyrazin-2-yl)pyrrolidine-1-carboxylate (0.11 g, 0.266 mmol). LCMS: Method C, 1.727 min, MS: ES+414. This material was used for the next step without purification.

Steps k, l. The title compound was synthesized from the intermediate above using a procedure similar to that described for Example 14, steps d, e. LCMS: Method A, 2.662 min, MS: ES+339.20; ¹H NMR (400 MHz, DMSO-d6) δ ppm 8.27 (s, 1H), 7.80 (d, J=7.6 Hz, 1H), 7.42 (s, 1H), 7.09 (d, J=7.6 Hz, 1H), 5.10-5.12 (m, 1H), 4.25-4.30 (m, 1H), 4.17-4.22 (m, 1H), 3.69-3.71 (m, 2H), 3.55-3.61 (m, 2H), 3.50-3.70 (m, 2H), 2.15 (s, 3H), 2.02-2.12 (m, 1H).

Example 122 (S)-2-(1-Cyanopyrrolidin-2-yl)-N-methyl-6-phenylbenzo[d]oxazole-4-carboxamide

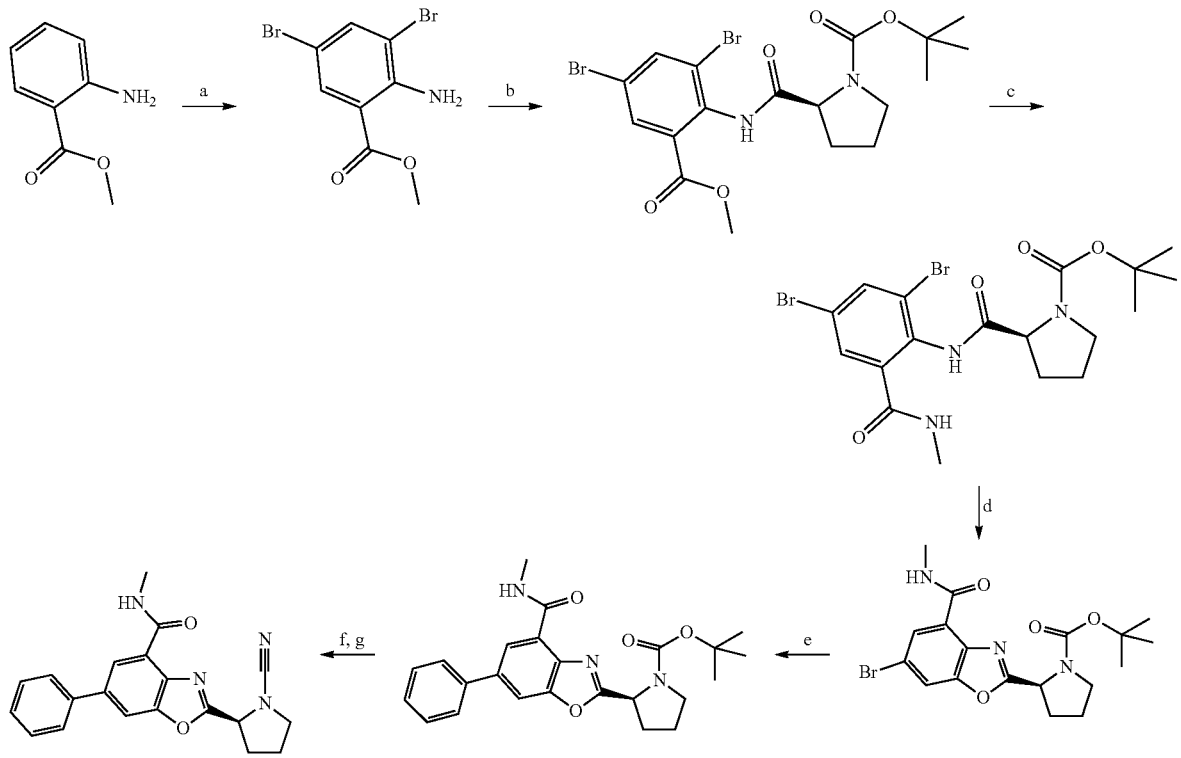

Step a. To a suspension of methyl anthranilate (CAS Number 134-20-3; 2.5 g, 16.54 mmol) in acetic acid (30 ml) was slowly added bromine (7.92 g, 49.6 mmol) at rt over a period of 10 min. The reaction mixture was stirred at rt for 2 h. The resulting reaction mixture was combined with one other batch prepared on the same scale by an identical method. The combined reaction mixture was diluted with DCM (300 ml) and washed with sodium bisulphite solution (3×100 ml) and water (2×100 ml). The resulting organic phase was washed with brine (100 ml), dried over Na₂SO₄, filtered and concentrated under reduced pressure. The resulting residue was purified by column chromatography (2.5% EtOAc in hexane) yielding methyl 2-amino-3,5-dibromobenzoate (7.0 g, 22.8 mmol). LCMS: Method C, 2.792 min, MS: ES+310.3, 312.3; ¹H NMR (400 MHz, CDCl₃) δ ppm 7.99 (d, J=2.4 Hz, 1H), 7.70 (d, J=2.4 Hz, 1H), 6.38 (br s, 2H), 3.91 (s, 3H).

Step b. To a solution of methyl 2-amino-3,5-dibromobenzoate (2.5 g, 8.16 mmol) and (2S)-1-[(tert-butoxy)carbonyl] pyrrolidine-2-carboxylic acid (CAS Number 15761-39-4; 3.51 g, 16.32 mmol) in DCM (30 ml) was added pyridine (19.34 g, 245 mmol) at 0° C. The reaction mixture was stirred at 0° C. for 10 min before drop-wise addition of POCl₃ (12.51 g, 81.6 mmol) at 0° C. The resulting reaction mixture was stirred at rt for 2 h. The resulting reaction mixture was combined with one other batch prepared on the same scale by an identical method. The resulting reaction mixture was quenched by cold citric acid solution (200 ml) and extracted with EtOAc (3×150 ml). The combined organic phase was washed with citric acid solution (200 ml), brine solution (100 ml), dried over Na$_2$SO$_4$, filtered and concentrated under reduced pressure. The resulting residue was purified by column chromatography (20% EtOAc in hexane) yielding tert-butyl (S)-2-((2,4-dibromo-6-(methoxycarbonyl)phenyl)-carbamoyl)pyrrolidine-1-carboxylate (3.0 g, 5.95 mmol). LCMS: Method C, 2.391 min, MS: ES+505.4, 507.4.

Step c. To a solution of tert-butyl (S)-2-((2,4-dibromo-6-(methoxycarbonyl)phenyl)carbamoyl)-pyrrolidine-1-carboxylate (1.5 g, 2.98 mmol) in THF (15 ml) was added 1,5,7-triazabicyclo[4,4,0]-dec-5-ene (CAS Number 5807-14-7; 0.83 g, 5.96 mmol) at rt. The resulting reaction mixture was stirred at rt for 5 min before addition of methylamine (2 M in THF; 3.0 ml, 6.0 mmol). The reaction mixture was stirred at rt for 2 h. The resulting reaction mixture was poured into water (80 ml) and extracted with EtOAc (3×80 ml). The combined organic phase was washed with brine solution (50 ml), dried over Na$_2$SO$_4$, filtered and concentrated under reduced pressure. The resulting residue was purified by flash chromatography (2% MeOH in DCM) yielding tert-butyl (S)-2-((2,4-dibromo-6-(methylcarbamoyl)-phenyl)carbamoyl)pyrrolidine-1-carboxylate (0.8 g, 1.59 mmol). LCMS: Method C, 2.081 min, MS: ES+504.5, 506.5.

Step d. To a solution tert-butyl (S)-2-((2,4-dibromo-6-(methylcarbamoyl)phenyl)carbamoyl) pyrrolidine-1-carboxylate (0.1 g, 0.198 mmol) in DME (1 ml) were added Cs$_2$CO$_3$ (0.096 g, 0.297 mmol), 1,10-phenanthroline (0.0089 g, 0.049 mmol) and CuI (0.0018 g, 0.009 mmol) at rt. The reaction mixture was heated in a microwave at 110° C. for 2 h. The resulting reaction mixture was combined with another 7 batches prepared on the same scale by an identical method. The resulting reaction mixture was quickly poured into water (20 ml) and extracted with EtOAc (3×30 ml). The combined organic phase was washed with brine (2×30 ml), dried over Na$_2$SO$_4$, filtered and concentrated under reduced pressure. The resulting residue was purified by flash chromatography (30% EtOAc in hexane) yielding tert-butyl (S)-2-(6-bromo-4-(methylcarbamoyl)benzo[d]oxazol-2-yl) pyrrolidine-1-carboxylate (0.42 g, 0.992 mmol). LCMS: Method C, 2.363 min, MS: ES+424.4, 426.4.

Step e. To a solution of tert-butyl (S)-2-(6-bromo-4-(methylcarbamoyl)benzo[d]oxazol-2-yl)-pyrrolidine-1-carboxylate (0.42 g, 0.99 mmol) in 1,4-dioxane:water (8:2) (6 ml) was added phenylboronic acid (0.15 g, 1.19 mmol) and Na$_2$CO$_3$ (0.21 g, 1.985 mmol) at rt. The reaction mixture was degassed for 30 min before addition of PdCl$_2$(dppf) (0.036 g, 0.049 mmol) at rt. The reaction mixture was heated at 90° C. for 1 h. The resulting reaction mixture was cooled to rt, poured into water (70 ml) and extracted with EtOAc (3×50 ml). The combined organic phase was dried over Na$_2$SO$_4$, filtered and concentrated under reduced pressure. The resulting residue was purified by flash chromatography (38% EtOAc in hexane) yielding tert-butyl (S)-2-(4-(methylcarbamoyl)-6-phenylbenzo[d]oxazol-2-yl)pyrrolidine-1-carboxylate (0.21 g, 0.498 mmol). LCMS: Method C, 2.549 min, MS: ES+422.65.

Step f. To a solution of tert-butyl (S)-2-(4-(methylcarbamoyl)-6-phenylbenzo[d]oxazol-2-yl)-pyrrolidine-1-carboxylate (0.21 g, 0.498 mmol) in DCM (5 ml) was added TFA (1 ml) at 0° C. The reaction mixture was stirred at 40° C. for 2 h. The resulting reaction mixture was concentrated under reduced pressure. The resulting residue was triturated with the diethyl ether and dried under vacuum to yielding (S)—N-methyl-6-phenyl-2-(pyrrolidin-2-yl)benzo[d]oxazole-4-carboxamide TFA salt (0.2 g, 0.459 mmol). LCMS: Method C, 1.660 min, MS: ES+322.44. This material was used directly for the next step without further purification.

Step g. To a solution of (S)—N-methyl-6-phenyl-2-(pyrrolidin-2-yl)benzo[d]oxazole-4-carboxamide TFA salt (0.2 g, 0.46 mmol) in THF (5 ml) was added K$_2$CO$_3$ (0.32 g, 2.30 mmol) at 0° C. The resulting reaction mixture was stirred for 5 min. Cyanogen bromide (0.06 g, 0.551 mmol) was added to the reaction mixture at 0° C. The reaction mixture was stirred at 40° C. for 30 min. The resulting reaction mixture was poured into water (30 ml) and extracted with EtOAc (3×20 ml). The combined organic phase was washed with brine (20 ml), dried over Na$_2$SO$_4$, filtered and concentrated under reduced pressure. The resulting residue was purified by flash chromatography (60% EtOAc in hexane) yielding the title compound (0.050 g, 0.144 mmol). LCMS: Method A, 4.362 min, MS: ES+346.98; $^1$H NMR (400 MHz, DMSO-d6) δ ppm 8.62-6.69 (m, 1H), 8.32 (d, J=1.6 Hz, 1H), 8.19 (d, J=1.6 Hz, 1H), 7.96 (d, J=7.2 Hz, 2H), 7.53 (t, J=7.6 Hz, 2H), 7.43 (t, J=7.2 Hz, 1H), 5.28-5.31 (m, 1H), 3.67-3.72 (m, 1H), 3.55-3.61 (m, 1H), 2.97 (d, J=4.8 Hz, 3H), 2.37-2.47 (m, 2H), 2.05-2.10 (m, 2H).

Example 123 3-(2-Amino-[1,1'-biphenyl]-3-yl)pyrrolidine-1-carbonitrile

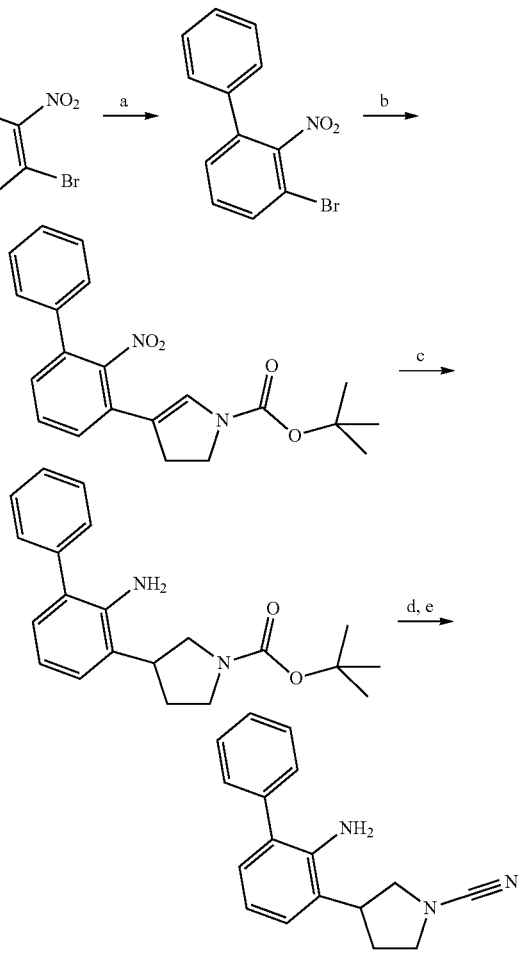

Step a. To a solution of 2-bromo-6-iodonitrobenzene (CAS Number 1126425-84-0; 0.25 g, 0.765 mmol) and phenylboronic acid (0.12 g, 0.994 mmol) in 1,4-dioxane (5 ml) was added a solution of Na$_2$CO$_3$ (0.162 g, 1.532 mmol) in water (1 ml) at rt. The reaction mixture was degassed for 30 min before addition of Pd(PPh$_3$)$_4$ (0.044 g, 0.038 mmol) at rt. The reaction mixture was heated at 90° C. for 15 h. The resulting reaction mixture was cooled to rt, poured into saturated NaHCO$_3$ solution (10 ml) and extracted with EtOAc (2×30 ml). The combined organic phase was dried over Na$_2$SO$_4$, filtered and concentrated under reduced pressure. The resulting residue was purified by flash chromatography (10% EtOAc in hexane) yielding 3-bromo-2-nitro-1,1'-biphenyl (0.13 g, 0.469 mmol). $^1$H NMR (400 MHz, CDCl$_3$) δ ppm 7.68-7.70 (m, 1H), 7.40-7.46 (m, 5H), 7.35-7.39 (m, 2H).

Step b. A mixture of 3-bromo-2-nitro-1,1'-biphenyl (0.13 g, 0.469 mmol), 1-BOC-2,5-dihydro-1H-pyrrole-3-boronic acid, pinacol ester (CAS Number 212127-83-8; 0.7 g, 2.372 mmol) and Na$_2$CO$_3$ (0.09 g, 0.938 mmol) in DMF:water (8:2; 4 ml) was degassed for 30 min before addition of Pd(PPh$_3$)$_4$ (0.027 g, 0.023 mmol) at rt. The reaction mixture was heated at 80° C. for 15 h. The resulting reaction mixture was cooled to rt, poured into water (10 ml) and extracted with EtOAc (2×25 ml). The combined organic phase was dried over Na$_2$SO$_4$, filtered and concentrated under reduced pressure. The resulting residue was purified by flash chromatography (5% EtOAc in hexane) yielding tert-butyl 4-(2-nitro-[1,1'-biphenyl]-3-yl)-2,3-dihydro-1H-pyrrole-1-carboxylate (0.06 g, 0.163 mmol). LCMS: Method C, 2.909 min, MS: ES+311.2 (M-56).

Step c. To a solution of tert-butyl 4-(2-nitro-[1,1'-biphenyl]-3-yl)-2,3-dihydro-1H-pyrrole-1-carboxylate (0.06 g, 0.163 mmol) in MeOH (5 ml) was added 10% Pd/C (50% moisture content; 0.02 g) at rt. The reaction mixture was purged with hydrogen at rt for 3 h. The resulting mixture was carefully filtered through celite hyflow and the celite bed was washed with MeOH (10 ml). The filtrate was concentrated under reduced pressure to provide tert-butyl 3-(2-amino-[1,1'-biphenyl]-3-yl)pyrrolidine-1-carboxylate (0.05 g, 0.147 mmol). LCMS: Method C, 2.792 min, MS: ES+283.4 (M 56).

Step d. To a solution of tert-butyl 3-(2-amino-[1,1'-biphenyl]-3-yl)pyrrolidine-1-carboxylate (0.05 g, 0.147 mmol) in DCM (5 ml) was added TFA (0.5 ml) at rt. The reaction mixture was stirred at rt for 1 h. The resulting reaction mixture was concentrated under reduced pressure. The obtained residue was triturated with DCM (5 ml) and finally dried under high vacuum to yield 3-(pyrrolidin-3-yl)-[1,1'-biphenyl]-2-amine TFA salt (0.05 g, 0.142 mmol). LCMS: Method C, 1.801 min, MS: ES+239.58. This material was used directly for the next step without further purification.

Step e. To a solution of 3-(pyrrolidin-3-yl)-[1,1'-biphenyl]-2-amine TFA salt (0.05 g, 0.142 mmol) in THF (5 ml) was added NaHCO$_3$ (0.059 g, 0.710 mmol) at rt. Cyanogen bromide (0.018 g, 0.170 mmol) was added to the reaction mixture at rt. The reaction mixture was stirred at rt for 1 h. The resulting reaction mixture was poured into water (10 ml) and extracted with EtOAc (2×25 ml). The combined organic phase was dried over Na$_2$SO$_4$, filtered and concentrated under reduced pressure. The resulting residue was purified by flash chromatography (50% EtOAc in hexane) yielding the title compound (0.005 g, 0.019 mmol). LCMS: Method A, 4.807 min, MS: ES+264.30; $^1$H NMR (400 MHz, DMSO-d6) δ ppm 7.47 (t, J=7.6 Hz, 2H), 7.35-7.39 (m, 3H), 7.09 (d, J=6.8 Hz, 1H), 6.88-6.93 (m, 1H), 6.69 (t, J=7.6 Hz, 1H), 4.59 (s, 2H), 3.79 (t, J=7.6 Hz, 1H), 3.42-3.57 (m, 3H), 3.27-3.33 (m, 1H), 2.21-2.29 (m, 1H), 1.95-2.00 (m, 1H).

Example 124 3-(7-Phenylimidazo[1,2-a]pyridin-3-yl)pyrrolidine-1-carbonitrile

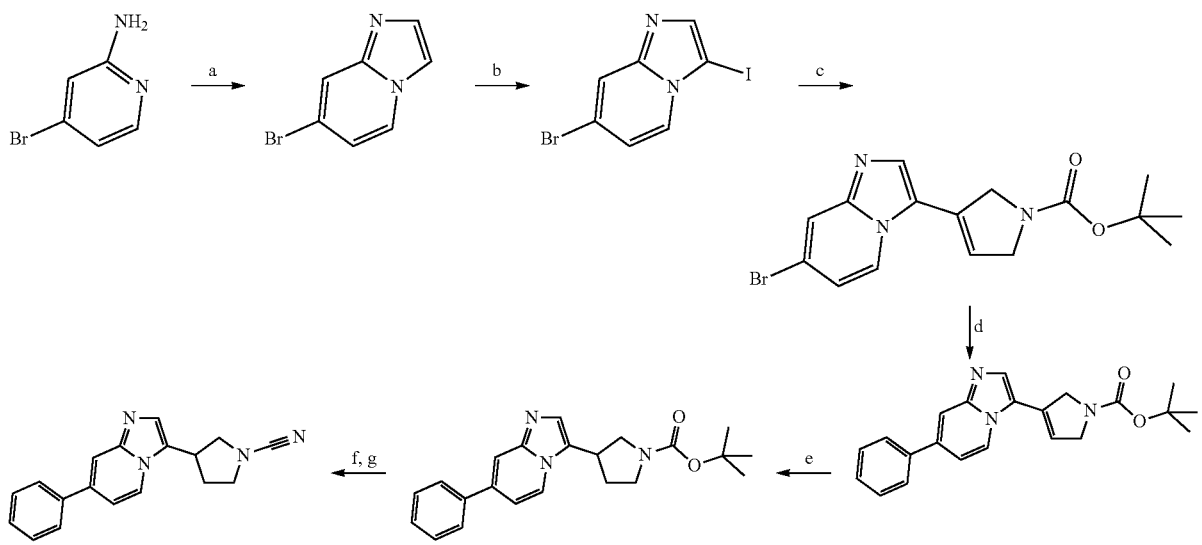

Step a. To a solution of 4-bromopyridin-2-amine (2.500 g, 14.45 mmol) in EtOH (20 ml) was added chloroacetaldehyde (2.55 ml, 36.0 mmol) at rt. The reaction mixture was heated at 100° C. for 8 h. The resulting reaction mixture was cooled to rt and combined with 1 other batch prepared on the same scale by an identical method. The combined reaction mixture was concentrated under reduced pressure. The obtained residue was poured into saturated aqueous NaHCO$_3$ solution (400 ml) and extracted with EtOAc (3×300 ml). The combined organic layer was dried over Na$_2$SO$_4$, filtered and concentrated under reduced pressure. The resulting residue was purified by flash chromatography (30-40% EtOAc in hexane) yielding 7-bromoimidazo[1,2-a]pyridine (4.200 g, 21.54 mmol). LCMS: Method C, 0.418 min, MS: ES+196.92; $^1$H NMR (400 MHz, CDCl$_3$) δ ppm 8.024 (d, J=7.2 Hz, 1H), 7.84 (s, 1H), 7.61 (d, J=16.8 Hz, 2H), 6.90 (dd, J=7.2, 1.6 Hz, 1H).

Step b. To a solution of 7-bromoimidazo[1,2-a]pyridine (4.100 g, 20.9 mmol) in MeOH (70 ml) was added sodium acetate (7.810 g, 57.4 mmol) and iodine (9.200 g, 36.2 mmol) at 0° C. The reaction mixture was stirred at rt for 5 h. The resulting mixture was concentrated under reduced pressure. The resulting residue was purified by flash chromatography (15% EtOAc in hexane) yielding 7-bromo-3-iodoimidazo[1,2-a]pyridine (4.70 g, 14.55 mmol). LCMS: Method C, 1.815 min, MS: ES+324.99; $^1$H NMR (400 MHz, CDCl$_3$) δ ppm 8.02 (dd, J=7.2, 0.4 Hz, 1H), 7.83 (d, J=1.2 Hz, 1H), 7.69 (s, 1H), 7.05 (dd, J=7.2, 1.2 Hz, 1H).

Step c. To a solution of 7-bromo-3-iodoimidazo[1,2-a]pyridine (2.610 g, 8.082 mmol) and tert-butyl 3-(4,4,5,5-tetramethyl-1,3,2-dioxaborolan-2-yl)-2,5-dihydro-1H-pyrrole-1-carboxylate (CAS Number 212127-83-8; 2.820 g, 8.92 mmol) in 1,4-dioxane (100 ml) was added Na$_2$CO$_3$ (2.390 g, 22.55 mmol) at rt. The reaction mixture was degassed for 15 min before addition of Pd(dppf)Cl$_2$ (0.660 g, 0.90 mmol) at rt. The resulting reaction mixture was heated at 9.5° C. for 20 h. The reaction mixture was poured into water (500 ml) and extracted with EtOAc (3×400 ml). The combined organic layer was dried over Na$_2$SO$_4$, filtered and concentrated under reduced pressure. The resulting residue was purified by flash chromatography (33% EtOAc in hexane) yielding tert-butyl 3-(7-bromoindolizin-3-yl)-2,5-dihydro-1H-pyrrole-1-carboxylate (1.800 g, 4.955 mmol). LCMS: Method C, 2.067, MS: ES+364.2, 366.2.

Step d. To a solution of tert-butyl 3-(7-bromoindolizin-3-yl)-2,5-dihydro-1H-pyrrole-1-carboxylate (0.100 g, 0.275 mmol) in 1,4-dioxane:water (2:1, 3 ml) was added phenylboronic acid (0.100 g, 0.820 mmol) and K$_2$CO$_3$ (0.113 g, 0.818 mmol) at rt. The resulting reaction mixture was degassed for 15 min before addition of Pd(PPh$_3$)$_4$ (0.015 g, 0.012 mmol) at rt. The reaction mixture was heated at 75° C. for 1 h. The resulting reaction mixture was cooled to rt and combined with 3 other batches prepared on the same scale by an identical method. The reaction mixture was poured into water (50 ml) and extracted with EtOAc (3×50 ml). The combined organic layer was dried over Na$_2$SO$_4$, filtered and concentrated under reduced pressure. The resulting residue was purified by column chromatography (20-30% EtOAc in hexane) yielding tert-butyl 3-(7-phenylimidazo[1,2-a]pyridin-3-yl)-2,5-dihydro-1H-pyrrole-1-carboxylate (0.082 g, 0.226 mmol). LCMS: Method C, 2.120 min, MS: ES+362.31 Step e. To a solution of tert-butyl 3-(7-phenylimidazo[1,2-a]pyridin-3-yl)-2,5-dihydro-1H-pyrrole-1-carboxylate (0.080 g, 0.221 mmol) in MeOH (4 ml) was added 10% Pd/C (dry; 0.040 g, 50% w/w) at rt. The reaction mixture was purged with hydrogen at rt for 3 h. The resulting reaction mixture was carefully filtered through celite hyflow and washed with MeOH (2×2 ml). The filtrate was concentrated under reduced pressure yielding tert-butyl 3-(7-phenylimidazo[1,2-a]pyridin-3-yl)pyrrolidine-1-carboxylate (0.073 g, 0.200 mmol). LCMS: Method C, 1.870 min, MS: ES+364.29. This material was used directly for the next step without further purification.

Step f. To a solution of tert-butyl 3-(7-phenylimidazo[1,2-a]pyridin-3-yl)pyrrolidine-1-carboxylate (0.070 g, 0.192 mmol) in DCM (3 ml) was added TFA (1.0 ml) at 0° C. The reaction mixture was stirred at rt for 1 h. The resulting reaction mixture was evaporated under reduced pressure. The obtained residue was co-evaporated with DCM (2×2 ml). The obtained material was triturated with diethyl ether (2×2 ml) and dried under high vacuum to yield 7-phenyl-3-(pyrrolidin-3-yl)imidazo[1,2-a]pyridine TFA salt (0.080 g, quantitative). LCMS: Method C, 1.439 min, MS: ES+264.27. This material was used directly for the next step without further purification.

Step g. To a solution 7-phenyl-3-(pyrrolidin-3-yl)imidazo[1,2-a]pyridine TFA salt (0.078 g, 0.296 mmol) in THF (5 ml) was added K$_2$CO$_3$ (0.122 g, 0.889 mmol) at 0° C. Cyanogen bromide (0.031 g, 0.296 mmol) was added to the reaction mixture at 0° C. The reaction mixture was stirred at rt for 1 h.

The resulting reaction mixture was poured into ice cold water (25 ml) and extracted with EtOAc (3×20 ml). The combined organic phase was dried over Na$_2$SO$_4$, filtered and concentrated under reduced pressure. The crude material was purified by preparative HPLC; mobile phase: (A) 0.1% formic acid in water and (B) 100% MeCN, column: YMC Actus Triart C18 250×20 mm, 5 μm, flow rate: 17 ml/min which yielded 3-(7-phenylimidazo[1,2-a]pyridin-3-yl)pyrrolidine-1-carbonitrile (0.010 g, 0.034 mmol). LCMS: Method B, 2.887 min, MS: ES+289.39; $^1$H NMR (400 MHz, DMSO-d6) δ ppm 8.56 (d, J=7.2 Hz, 1H), 7.89 (s, 1H), 7.84 (d, J=7.6 Hz, 2H), 7.57 (s, 1H), 7.49-7.55 (m, 2H), 7.40-7.43 (m, 1H), 7.34-7.36 (m, 1H), 3.88-3.97 (m, 2H), 3.34-3.63 (m, 3H), 2.06-2.11 (m, 2H).

Example 125 3-(7-(3,5-Dimethylisoxazol-4-yl)imidazo[1,2-a]pyridin-3-yl)pyrrolidine-1-carbonitrile

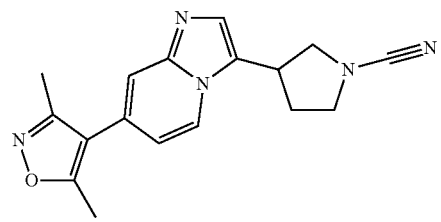 [SMILES: Cc1noc(C)c1-c1ccn2c(C3CCN(C#N)C3)cnc2c1]

The title compound was synthesised using a procedure similar to that described for Example 124, using 3,5-dimethylisoxazole-4-boronic acid (CAS Number 16114-47-9) in step d. LCMS: Method A, 3.347 min, MS: ES+307.93; 1H NMR (400 MHz, DMSO-d6) δ ppm 13.18-13.25 (m, 1H), 8.68 (s, 1H), 8.27-8.34 (m, 2H), 8.12 (d, J=7.6 Hz, 1H), 7.85 (d, J=8.0 Hz, 1H), 7.68-7.76 (m, 1H), 3.80-3.93 (m, 3H), 3.54-3.56 (m, 2H), 2.29-2.37 (m, 2H).

Scheme 6

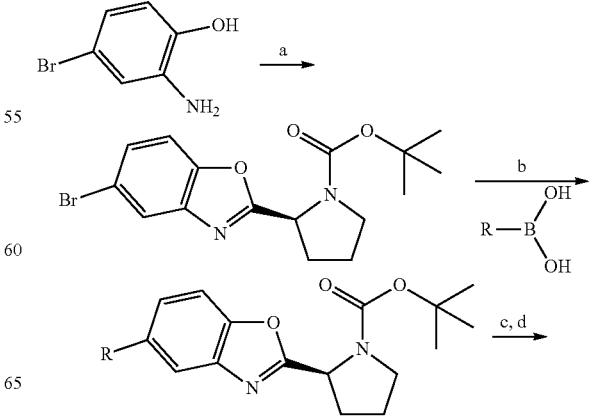

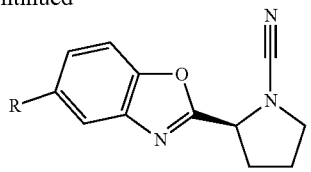

Reagents and conditions: a) (i) (2S)-1-[(tert-butoxy)carbonyl]pyrrolidine-2-carboxylic acid, HOBt, EDCI, DCM, rt, 20 h; (ii) PPh₃, DIAD, THF, rt 24 h; b) PdCl₂(dppf), K₂CO₃, 1, 4-dioxane, 80° C., 4 h; c) TFA/DCM, rt, 1 h; d) cyanogen bromide, K₂CO₃, THF, rt, 1 h.

Example 126 (S)-2-(5-(3-Cyanophenyl)benzo[d]oxazol-2-yl)pyrrolidine-1-carbonitrile (Prepared according to Scheme 6)

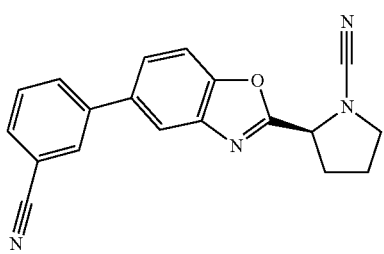 [SMILES: N#Cc1cccc(-c2ccc3oc([C@@H]4CCCN4C#N)nc3c2)c1]

Step a. To a mixture of 2-amino-4-bromophenol (CAS Number 40925-68-6; 1.000 g, 5.31 mmol), (2S)-1-[(tert-butoxy)carbonyl]pyrrolidine-2-carboxylic acid (1.140 g, 5.31 mmol) and HOBT (0.776 g, 5.74 mmol) in DCM (2 ml) was added EDCI (1.100 g, 5.74 mmol) at rt. The reaction mixture was stirred at rt for 20 h. The resulting reaction mixture was diluted water (50 ml) and extracted with DCM (3×15 ml). The combined organic layer was dried over Na₂SO₄, filtered and concentrated under reduced pressure. The resulting residue was dissolved in THF (20 ml) and treated with triphenylphosphine (1.500 g, 5.74 mmol), followed by slow addition of DIAD (1.12 ml, 5.74 mmol) at rt. The reaction mixture was stirred at rt for 24 h. The resulting reaction mixture was concentrated under vacuum. The obtained residue was triturated with diethyl ether (2×10 ml) followed by hexane (2×10 ml). The resulting residue was purified by flash chromatography (10% EtOAc in hexane) yielding tert-butyl (S)-2-(5-bromobenzo[d]oxazol-2-yl)pyrrolidine-1-carboxylate (0.977 g, 2.66 mmol). LCMS: Method C, 2.514, MS: ES+367.20, 369.20

Step b. To a mixture of tert-butyl (S)-2-(5-bromobenzo[d]oxazol-2-yl)pyrrolidine-1-carboxylate (0.300 g, 0.819 mmol) and 3-cyanophenylboronic acid (0.120 g, 0.819 mmol) in 1,4-dioxane (8 ml) was added a solution of K₂CO₃ (0.339 g, 2.40 mmol) in water (2 ml) at rt. The reaction mixture was degassed for 30 min before addition of PdCl₂(dppf) (0.059 g, 0.082 mmol) at rt. The resulting reaction mixture was heated at 80° C. for 4 h. The reaction mixture was cooled to rt, diluted with water (75 ml) and extracted with EtOAc (3×25 ml). The combined organic layer was dried over Na₂SO₄, filtered and concentrated under reduced pressure. The obtained residue was purified by flash column chromatography (22% EtOAc in hexane) yielding tert-butyl (S)-2-(5-(3-cyanophenyl)benzo[d]oxazol-2-yl)pyrrolidine-1-carboxylate (0.236 g, 0.606 mmol). MS: ES+290.20

Step c. To a solution of tert-butyl (S)-2-(5-(3-cyanophenyl)benzo[d]oxazol-2-yl)pyrrolidine-1-carboxylate (0.230 g, 0.591 mmol) in DCM (8 ml) was added TFA (2.3 ml) at 0° C. The reaction mixture was stirred at rt for 2 h. The resulting reaction mixture was evaporated under reduced pressure. The obtained residue was co-distilled with DCM (3×5 ml). The obtained residue was triturated using diethyl ether (2×5 ml) and dried under high vacuum yielding (S)-3-(2-(pyrrolidin-2-yl)benzo[d]oxazol-5-yl)benzonitrile TFA salt (0.247 g, quantitative). This material was used directly for the next step without further purification. LCMS: Method C, 1.680 min, MS: ES+290.25.

Step d. To a solution of (S)-3-(2-(pyrrolidin-2-yl)benzo[d]oxazol-5-yl)benzonitrile TFA salt (0.242 g, 0.600 mmol) in THF (8 ml) was added K₂CO₃ (0.248 g, 1.801 mmol) at rt. The reaction mixture was stirred at rt for 15 min. Cyanogen bromide (0.076 g, 0.720 mmol) was added to the reaction mixture at 0° C. The reaction mixture was stirred at rt for 45 min. The resulting reaction mixture was diluted with ice cold water (75 ml) and extracted with EtOAc (3×25 ml). The combined organic layer was dried over Na₂SO₄, filtered and concentrated under reduced pressure. The resulting residue was purified by flash chromatography (52% EtOAc in hexane) yielding title compound (0.101 g, 0.321 mmol). LCMS: Method A, 4.614, MS: ES+314.99; NMR (400 MHz, DMSO-d6) δ ppm 8.24 (s, 1H), 8.19 (d, J=1.2 Hz, 1H), 8.09-8.11 (m, 1H), 7.81-7.90 (m, 3H), 7.69 (t, J=8.0 Hz, 1H), 5.20-5.23 (m, 1H), 3.65-3.69 (m, 1H), 3.53-3.63 (m, 1H), 2.28-2.43 (m, 2H), 2.02-2.08 (m, 2H).

Example 127 (S)-6-(2-(1-Cyanopyrrolidin-2-yl)benzo[d]oxazol-5-yl)picolinonitrile

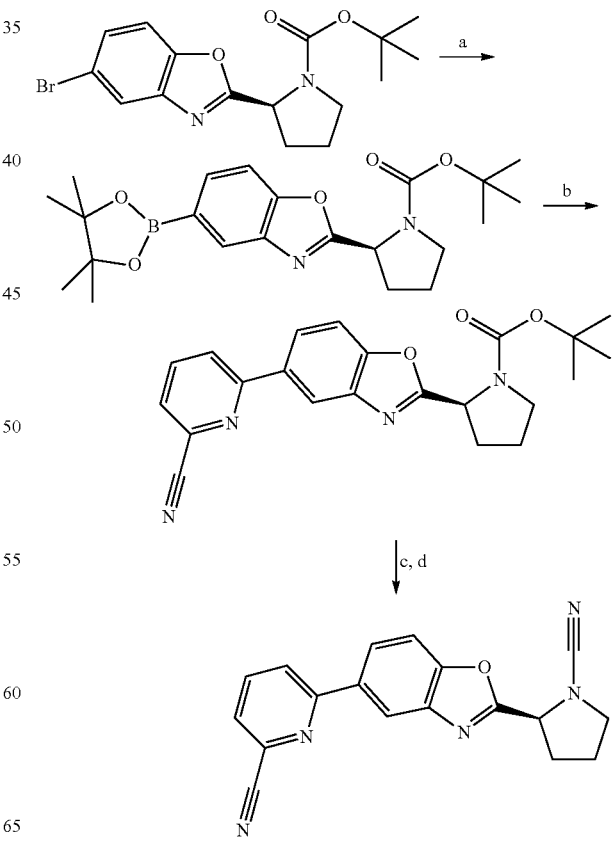

Step a. To a mixture of tert-butyl (S)-2-(5-bromobenzo[d]oxazol-2-yl)pyrrolidine-1-carboxylate (Example 126, step a; 0.300 g, 0.82 mmol) and bis(pinacolato)diboron (0.416 g, 1.64 mmol) in DMF (8 ml) was added a solution of potassium acetate (0.160 g, 1.64 mmol) in water (2 ml) at rt. The reaction mixture was degassed for 15 min before addition of PdCl$_2$(dppf) (0.089 g, 0.122 mmol) at rt. The resulting reaction mixture was heated at 100° C. for 16 h. The reaction mixture was cooled to rt, diluted with water (75 ml) and extracted with EtOAc (3×25 ml). The combined organic layer was dried over Na$_2$SO$_4$, filtered and concentrated under reduced pressure. The obtained residue was purified by flash column chromatography (53% EtOAc in hexane) yielding tert-butyl (S)-2-(5 (4,4,5,5-tetramethyl-1,3,2-dioxaborolan-2-yl)benzo[d]oxazol-2-yl)pyrrolidine-1-carboxylate (0.311 g, 0.75 mmol). LCMS: Method C, 2.812 min, MS: ES+415.52

Step b. To a mixture of tert-butyl (S)-2-(5-(4,4,5,5-tetramethyl-1,3,2-dioxaborolan-2-yl)-benzo[d]oxazol-2-yl)pyrrolidine-1-carboxylate (0.300 g, 0.724 mmol) and 6-bromopicolinonitrile (CAS Number 122918-25-6; 0.132 g, 0.724 mmol) in 1,4-dioxane:water (4:1, 10 ml) was added Cs$_2$CO$_3$ (0.706 g, 2.173 mmol) at rt. The reaction mixture was degassed for 30 min before addition of PdCl$_2$(dppf) (0.052 g, 0.072 mmol) at rt. The resulting reaction mixture was heated at 80° C. for 4 h. The reaction mixture was cooled to rt and diluted with water (100 ml). The resulting mixture was extracted with EtOAc (3×50 ml). The combined organic layer was dried over Na$_2$SO$_4$, filtered and concentrated under reduced pressure. The obtained residue was purified by flash column chromatography (52% EtOAc in hexane) yielding tert-butyl (S)-2-(5-(6-cyanopyridin-2-yl)benzo[d]oxazol-2-yl)pyrrolidine-1-carboxylate (0.095 g, 0.243 mmol). LCMS: Method C, 2.398 min, MS: ES+391.40

Step c. To a solution of tert-butyl (S)-2-(5-(6-cyanopyridin-2-yl)benzo[d]oxazol-2-yl)pyrrolidine-1-carboxylate (0.090 g, 0.230 mmol) in DCM (5 ml) was added TFA (0.9 ml) at 0° C. The reaction mixture was stirred at rt for 1.5 h. The resulting reaction mixture was evaporated under reduced pressure. The obtained residue was co-distilled with DCM (3×5 ml). The obtained residue was triturated using diethyl ether (2×5 ml) and dried under high vacuum yielding (S)-6-(2-(pyrrolidin-2-yl)benzo[d]oxazol-5-yl)picolinonitrile TFA salt (0.099 g, quantitative). This material was used directly for the next step without further purification. LCMS: Method C, 1.600 min, MS: ES+291.28

Step d. To a solution of (S)-6-(2-(pyrrolidin-2-yl)benzo[d]oxazol-5-yl)picolinonitrile TFA salt (0.098 g, 0.242 mmol) in THF (5 ml) was added K$_2$CO$_3$ (0.100 g, 0.727 mmol) at rt. The reaction mixture was stirred at rt for 5 min. Cyanogen bromide (0.030 g, 0.291 mmol) was added to the reaction mixture at 0° C. The reaction mixture was stirred at rt for 1 h. The resulting reaction mixture was diluted with water (50 ml) and extracted with EtOAc (3×15 ml). The combined organic layer was dried over Na$_2$SO$_4$, filtered and concentrated under reduced pressure. The resulting residue was purified by flash chromatography (63% EtOAc in hexane) yielding title compound (0.037 g, 0.117 mmol). LCMS: Method A, 4.258, MS: ES+315.92; $^1$H NMR (400 MHz, DMSO-d6) δ ppm 8.52 (s, 1H), 8.44 (d, J=8.4 Hz, 1H), 8.22-8.22 (m, 1H), 8.17 (t, J=8.0 Hz, 1H), 8.02 (d, J=7.6 Hz, 1H), 7.93 (d, J=8.8 Hz, 1H), 5.21-5.24 (m, 1H), 3.63-3.69 (m, 1H), 3.53-3.59 (m, 1H), 2.29-2.43 (m, 2H), 2.02-2.08 (m, 2H).

Example 128 (S)-2-(6-(3-Cyanophenyl)benzo[d]oxazol-2-yl)pyrrolidine-1-carbonitrile

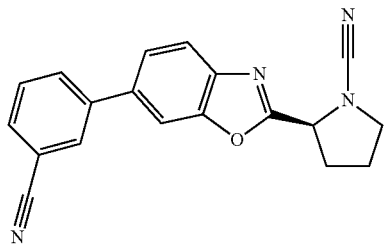 [SMILES: N#Cc1cccc(-c2ccc3nc([C@@H]4CCCN4C#N)oc3c2)c1]

The title compound was synthesised using a procedure similar to that described for Example 126, using 2-amino-5-bromophenol (CAS Number 38191-34-3) in step a. LCMS: Method A, 4.516 min, MS: ES+314.99; $^1$H NMR (400 MHz, DMSO-d6) δ ppm 8.27 (s, 1H), 8.22 (d, J=1.6 Hz, 1H), 8.12 (d, J=8.0 Hz, 1H), 7.85-7.90 (m, 2H), 7.80-7.82 (m, 1H), 7.70 (d, J=8.0 Hz, 1H), 5.21-5.24 (m, 1H), 3.63-3.68 (m, 1H), 3.53-3.59 (m, 1H), 2.28-2.43 (m, 2H), 2.01-2.08 (m, 2H).

Example 129 (S)-2-(5-(3-Ethylphenyl)benzo[d]oxazol-2 yl)pyrrolidine-1-carbonitrile

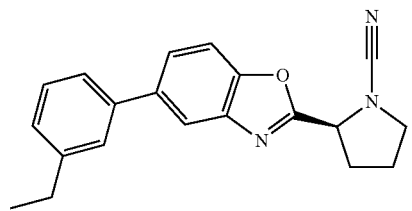 [SMILES: CCc1cccc(-c2ccc3oc([C@@H]4CCCN4C#N)nc3c2)c1]

The title compound was synthesised using a procedure similar to that described for Example 126. LCMS: Method A, 5.483 min, MS: ES+318.05; $^1$H NMR (400 MHz, DMSO-d6) δ ppm 8.04 (d, J=1.2 Hz, 1H), 7.83 (d, J=8.1 Hz, 1H), 7.72 (dd, J=8.4, 1.2 Hz, 1H), 7.55 (s, 1H), 7.52 (d, J=8.0, 1 H), 7.39 (t, J=7.6 Hz, 1H), 7.23 (d, J=7.2 Hz, 1H), 5.18-5.22 (m, 1H), 3.63-3.68 (m, 1H), 3.53-3.59 (m, 1H), 2.66-2.71 (m, 2H), 2.27-2.42 (m, 2H), 2.01-2.08 (m, 2H), 1.24 (t, J=7.6 Hz, 3H).

Example 130 (S)-2-(6-(3-Ethylphenyl)benzo[d]oxazol-2-yl)pyrrolidine-1-carbonitrile

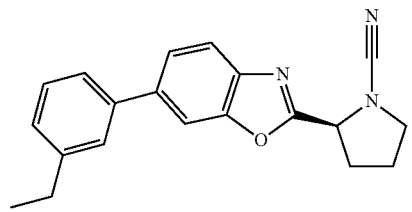 [SMILES: CCc1cccc(-c2ccc3nc([C@@H]4CCCN4C#N)oc3c2)c1]

The title compound was synthesised using a procedure similar to that described for Example 128. LCMS: Method A, 5.207 min, MS: ES+318.20; $^1$H NMR (400 MHz, DMSO-d6) δ ppm 8.07 (d, J=1.2 Hz, 1H), 7.84 (d, J=8.0 Hz, 1H), 7.71 (dd, J=8.4, 1.6 Hz, 1H), 7.59 (s, 1H), 7.55 (d, J=8.0 Hz, 1H), 7.40 (t, J=7.6 Hz, 1H), 7.24 (d, J=7.6 Hz, 1H), 5.18-5.22 (m, 1H), 3.62-3.68 (m, 1H), 3.53-3.59 (m, 1H), 2.66-2.72 (m, 2H), 2.37-2.43 (m, 1H), 2.29-2.35 (m, 1H), 2.01-2.08 (m, 2H), 1.24 (t, J=7.6 Hz, 3H).

Example 131 (S)-2-(1-Cyanopyrrolidin-2 yl)-6-(3-ethylphenyl)-N-methylbenzo[d]oxazole-4-carboxamide

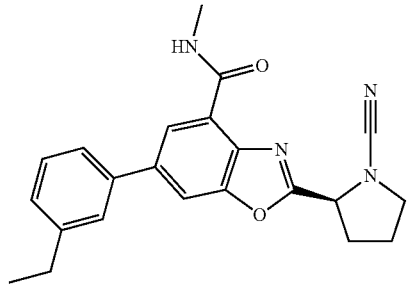 [SMILES: CCc1cccc(-c2cc(C(=O)NC)c3nc([C@@H]4CCCN4C#N)oc3c2)c1]

The title compound was synthesised using a procedure similar to that described for Example 122. LCMS: Method A, 5.005 min, MS: ES+375.05; ¹H NMR (400 MHz, DMSO-d6) δ ppm 8.65 (d, J=4.4 Hz, 1H), 8.30 (d, J=1.2 Hz, 1H), 8.18 (d, J=1.2 Hz, 1H), 7.61 (s, 1H), 7.58 (d, J=7.6, 1H), 7.43 (t, J=8.0 Hz, 1H), 7.28 (d, J=7.6 Hz, 1H), 5.28-5.31 (m, 1H), 3.67-3.72 (m, 1H), 3.55-3.61 (m, 1H), 2.97 (d, J=3.6 Hz, 3H), 2.68-2.73 (m, 2H), 2.33-2.43 (m, 2H), 2.04-2.10 (m, 2H), 1.25 (t, J=8.0 Hz, 3H).

Example 132 (S)-6-(2-(1-Cyanopyrrolidin-2 yl)benzo[d]oxazol-6 yl)picolinonitrile

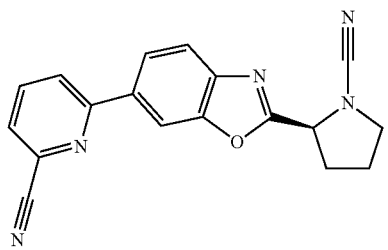 [SMILES: N#Cc1cccc(-c2ccc3nc([C@@H]4CCCN4C#N)oc3c2)n1]

The title compound was synthesised using a procedure similar to that described for Example 127. LCMS: Method A, 3.923 min, MS: ES+316.20; ¹H NMR (400 MHz, DMSO-d6) δ ppm 8.51 (d, J=1.2 Hz, 1H), 8.44 (d, J=7.6 Hz, 1H), 8.16-8.22 (m, 2H), 8.03 (d, J=7.2 Hz, 1H), 7.93 (d, J=7.6 Hz, 1H), 5.22-5.25 (m, 1H), 3.63-3.69 (m, 1H), 3.53-3.59 (m, 1H), 2.29-2.43 (m, 2H), 2.02-2.08 (m, 2H).

Compounds in Table 7 were synthesised using a procedure similar to that described for Example 126.

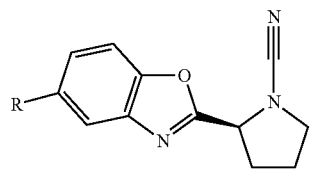

TABLE 7

| Ex | R | Name | LCMS Method | LCMS RT (min) | MS (ES+) |
|---|---|---|---|---|---|
| 133 | F₃C-O-phenyl | (S)-2-(5-(3-(Trifluoromethoxy)phenyl)-benzo[d]oxazol-2-yl)pyrrolidine-1-carbonitrile | K | 3.199 | 374.0 |
| 134 | 3-methyl-1H-indazol-6-yl | (S)-2-(5-(3-Methyl-1H-indazol-6-yl)-benzo[d]oxazol-2-yl)pyrrolidine-1-carbonitrile | H | 2.731 | 344.2 |
| 135 | 1-methyl-1H-indazol-5-yl | (S)-2-(5-(1-Methyl-1H-indazol-5-yl)-benzo[d]oxazol-2-yl)pyrrolidine-1-carbonitrile | H | 2.796 | 344.1 |
| 136 | O₂N-phenyl | (S)-2-(5-(3-Nitrophenyl)benzo[d]oxazol-2-yl)pyrrolidine-1-carbonitrile | I | 3.006 | 335.0 |
| 137 | NC-(2-F-phenyl) | (S)-2-(5-(3-Cyano-2-fluorophenyl)-benzo[d]oxazol-2-yl)pyrrolidine-1-carbonitrile | H | 3.092 | 333.0 |

TABLE 7-continued

| Ex | R | Name | LCMS Method | LCMS RT (min) | MS (ES+) |
|---|---|---|---|---|---|
| 138 | (structure: 3-cyano-5-fluorophenyl) | (S)-2-(5-(3-Cyano-5-fluorophenyl)-benzo[d]oxazol-2-yl)pyrrolidine-1-carbonitrile | H | 3.147 | 333.0 |
| 139 | (structure: N-benzyl-4-methylbenzenesulfonamide) | (S)-N-Benzyl-3-(2-(1-cyanopyrrolidin-2-yl)-benzo[d]oxazol-5-yl)-4-methyl-benzenesulfonamide | K | 3.090 | 473.0 |

Example 140 2-(5-([1,1'-Biphenyl]-3 yl)-1,3,4-oxa-diazol-2 yl)pyrrolidine-1-carbonitrile

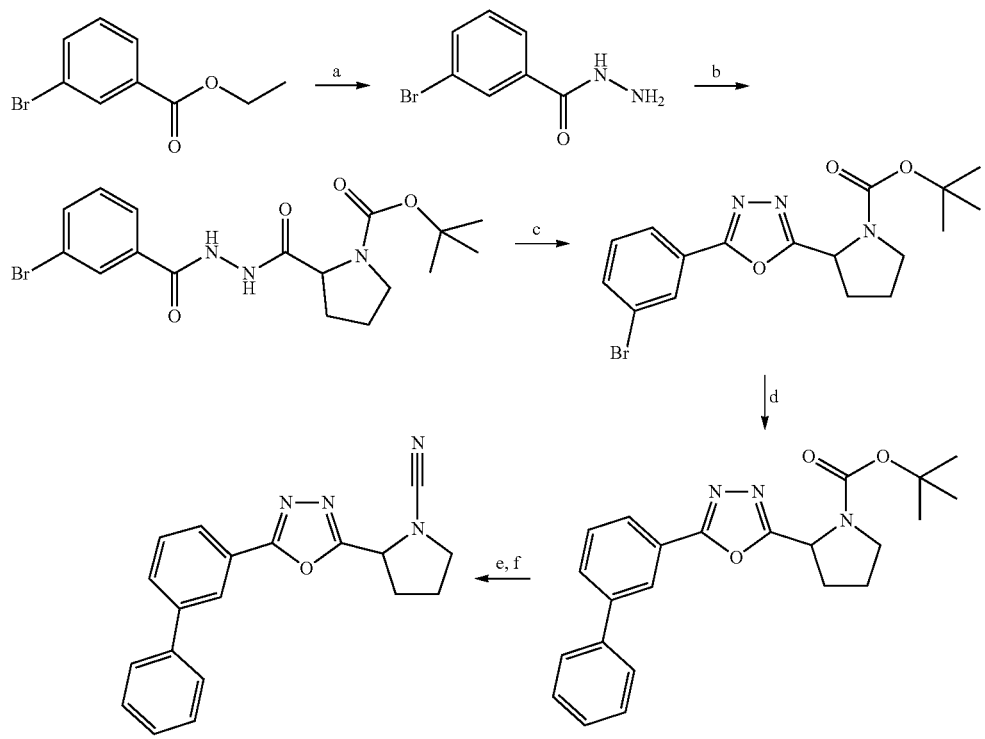

Step a. To a solution of ethyl 3-bromobenzoate (0.750 g, 3.270 mmol) in EtOH (10 ml) was added hydrazine hydrate (0.982 g, 19.6 mmol check this) at rt. The reaction mixture was heated at 80° C. for 2 h. The resulting reaction mixture was concentrated under vacuum and the residue was re-distilled from DCM (2×5 ml). The resulting residue was dried under high vacuum yielding 3-bromobenzohydrazide (0.500 g, 2.325 mmol). This material was used directly for the next step without further purification. LCMS: Method C, 1.564, MS: ES+215.10, 217.10

Step b. To a solution of 1-[(tert-butoxy)carbonyl]pyrrolidine-2-carboxylic acid (0.450 g, 2.09 mmol) in THF (10 ml) were added TBTU (1.000 g, 3.14 mmol) followed by DIPEA (0.539 g, 4.19 mmol) at 0° C. The reaction mixture was stirred at rt for 30 min before addition of 3-bromobenzohydrazide (0.450 g, 2.093 mmol) at 0° C. The reaction mixture was stirred at rt for 2 h. The resulting reaction mixture was diluted with saturated NaHCO$_3$ solution (20 ml) and extracted with EtOAc (2×20 ml). The combined organic layer was dried over Na$_2$SO$_4$, filtered and concentrated under reduced pressure. The resulting residue was purified by flash chromatography (40% EtOAc in hexane) yielding tert-butyl 2-(2-(3-bromobenzoyl)hydrazine-1-carbonyl)pyrrolidine-1-carboxylate (0.425 g, 1.031 mmol). LCMS: Method C, 1.987, MS: ES+412.20, 414.20

Step c. To a mixture of tert-butyl 2-(2-(3-bromobenzoyl)hydrazine-1-carbonyl)pyrrolidine-1-carboxylate (0.420 g, 1.02 mmol) in DCM (5 ml) were added DIPEA (0.394 g, 3.06 mmol), p-toluene sulphonyl chloride (0.290 g, 1.53 mmol) and Na₂SO₄ (0.289 g, 2.04 mmol) at rt. The reaction mixture was stirred at rt for 30 min. The resulting reaction mixture was diluted with water (20 ml) and extracted with DCM (2×20 ml). The combined organic layer was dried over Na₂SO₄, filtered and concentrated under reduced pressure yielding tert-butyl 2-(5-(3-bromophenyl)-1,3,4-oxadiazol-2-yl)pyrrolidine-1-carboxylate (0.360 g, 0.913 mmol). LCMS: Method C, 2.514, MS: ES+394.20, 396.20

Step d. To a mixture of tert-butyl 2-(5-(3-bromophenyl)-1,3,4-oxadiazol-2-yl)pyrrolidine-1-carboxylate (0.350 g, 0.888 mmol) and phenylboronic acid (0.162 g, 1.93 mmol) in 1,4-dioxane:water (4:1, 10 ml) was added K₂CO₃ (0.367 g, 2.66 mmol) at rt. The reaction mixture was degassed for 30 min before addition of Pd(PPh₃)₄ (0.051 g, 0.044 mmol) at rt. The resulting reaction mixture was heated at 90° C. for 2 h. The reaction mixture was cooled to rt, diluted with water (25 ml) and extracted with EtOAc (2×25 ml). The combined organic layer was dried over Na₂SO₄, filtered and concentrated under reduced pressure. The obtained residue was purified by flash column chromatography (20% EtOAc in hexane) yielding tert-butyl 2-(5-([1,1'-biphenyl]-3-yl)-1,3,4-oxadiazol-2-yl)pyrrolidine-1-carboxylate (0.285 g, 0.728 mmol). LCMS: Method C, 2.675 min, MS: ES+392.41 Step e. To a solution of tert-butyl 2-(5-([1,1'-biphenyl]-3-yl)-1,3,4-oxadiazol-2-yl)pyrrolidine-1-carboxylate (0.280 g, 0.715 mmol) in DCM (5 ml) was added TFA (1 ml) at 0° C. The reaction mixture was stirred at rt for 2 h. The resulting mixture was evaporated under reduced pressure. The obtained residue was triturated using mixture of diethyl ether:hexane (1:1, 5 ml) and dried under high vacuum yielding 2-([1,1'-biphenyl]-3-yl)-5-(pyrrolidin-2-yl)-1,3,4-oxadiazole TFA salt (0.250 g, 0.617 mmol). This material was used directly for the next step without further purification. LCMS: Method C, 1.792 min, MS: ES+292.27 Step f. To a solution of 2-([1,1'-biphenyl]-3-yl)-5-(pyrrolidin-2-yl)-1,3,4-oxadiazole TFA salt (0.250 g, 0.617 mmol) in THF (5 ml) was added K₂CO₃ (0.255 g, 1.850 mmol) at 0° C., followed by cyanogen bromide (0.065 g, 0.617 mmol). The reaction mixture was stirred at rt for 30 min. The resulting reaction mixture was diluted with water (20 ml) and extracted with EtOAc (2×20 ml). The combined organic layer was dried over Na₂SO₄, filtered and concentrated under reduced pressure. The resulting residue was purified by flash chromatography (30% EtOAc in hexane) yielding title compound (0.120 g, 0.379 mmol). LCMS: Method A, 4.791, MS: ES+316.99; ¹H NMR (400 MHz, DMSO-d6) δ ppm 8.23 (s, 1H), 8.02 (d, J=7.6 Hz, 1H), 7.96 (d, J=8.0 Hz, 1H), 7.70-7.76 (m, 3H), 7.51-7.55 (m, 2H), 7.42-7.46 (m, 1H), 5.25-5.28 (m, 1H), 3.63-3.68 (m, 1H), 3.51-3.57 (m, 1H), 2.32-2.41 (m, 2H), 2.02-2.09 (m, 2H).

Example 141 (S)-2-(3-([1,1'-Biphenyl]-3-yl)-1,2,4-oxadiazol-5-yl)pyrrolidine-1-carbonitrile

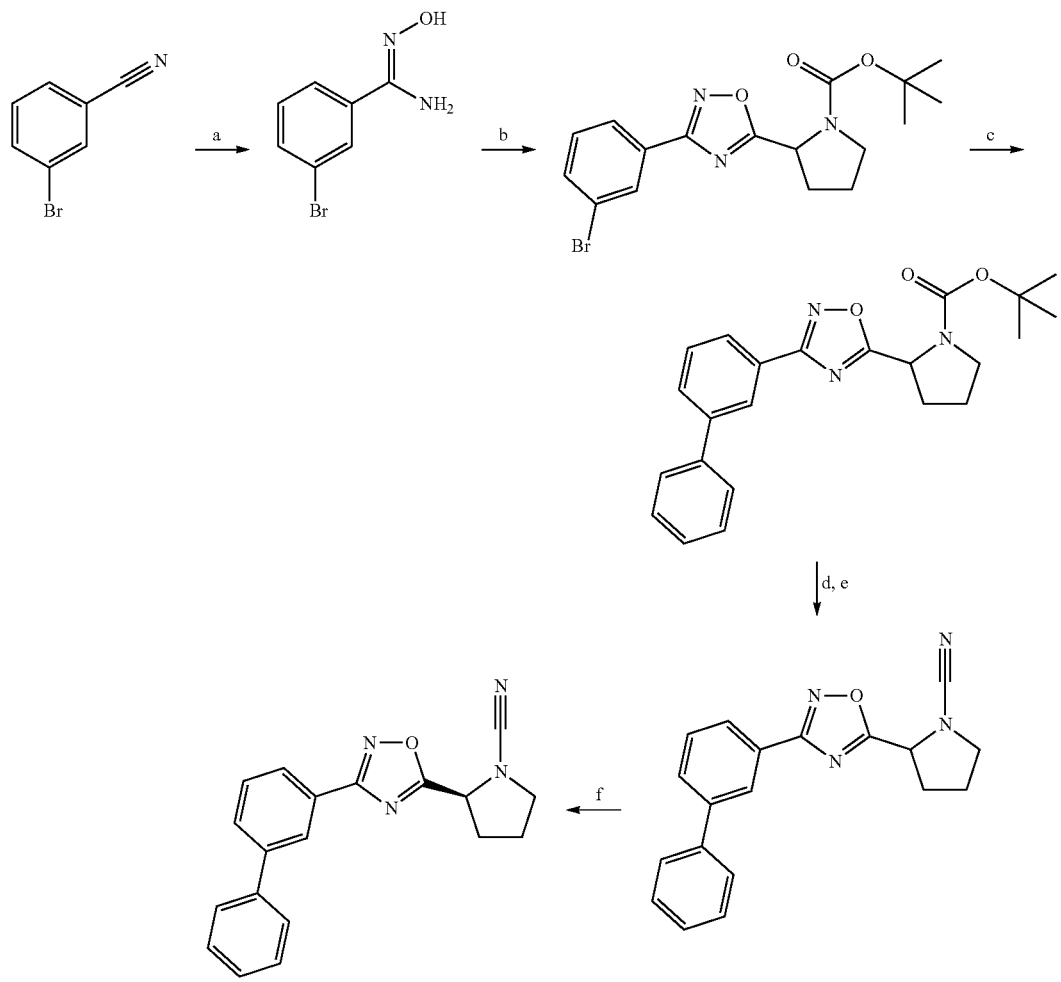 [SMILES: N#Cc1cccc(Br)c1 ; N/C(=N\O)c1cccc(Br)c1 ; CC(C)(C)OC(=O)N1CCCC1c1nc(-c2cccc(Br)c2)no1 ; CC(C)(C)OC(=O)N1CCCC1c1nc(-c2cccc(-c3ccccc3)c2)no1 ; N#CN1CCC[C@H]1c1nc(-c2cccc(-c3ccccc3)c2)no1 ; N#CN1CCCC1c1nc(-c2cccc(-c3ccccc3)c2)no1]

Step a. To a solution of 3-bromobenzonitrile (1.00 g, 5.49 mmol) in MeOH (10 ml) was added NaHCO₃ (1.840 g, 22.0 mmol) followed by NH₂OH·HCl (0.750 g, 11.0 mmol) at rt. The reaction mixture was heated at 70° C. for 1 h. The resulting reaction mixture was concentrated under vacuum. The obtained residue was diluted with ice cold water (50 ml). The resulting precipitates were collected by filtration and washed with water (25 ml). The resulting solid material was dried under high vacuum yielding 3-bromo-N'-hydroxybenzimidamide (1.050 g, 4.88 mmol). This material was used directly for the next step without further purification. LCMS: Method C, 1.386, MS: ES+215.10, 217.10

Step b. To a solution of 1-[(tert-butoxy)carbonyl]pyrrolidine-2-carboxylic acid (0.950 g, 4.418 mmol) in DMF (10 ml) were added EDCI (1.270 g, 6.627 mmol) and HOBt (0.895 g, 6.627 mmol) at 0° C. The reaction mixture was stirred at rt for 30 min before addition of 3-bromo-N'-hydroxybenzimidamide (0.950 g, 4.42 mmol) at 0° C. The reaction mixture was stirred at rt for 30 min and then heated at 90° C. for 18 h. The resulting reaction mixture was cooled to rt, diluted with saturated NaHCO₃ solution (50 ml) and extracted with EtOAc (3×25 ml). The combined organic layer was dried over Na₂SO₄, filtered and concentrated under reduced pressure. The resulting residue was purified by flash chromatography (18% EtOAc in hexane) yielding tert-butyl 2-(3-(3-bromophenyl)-1,2,4-oxadiazol-5-yl)pyrrolidine-1-carboxylate (0.580 g, 1.472 mmol). LCMS: Method C, 2.869, MS: ES+394.30, 396.30

Step c. To a mixture of tert-butyl 2-(3-(3-bromophenyl)-1,2,4-oxadiazol-5-yl)pyrrolidine-1-carboxylate (0.550 g, 1.39 mmol) and phenylboronic acid (0.255 g, 2.09 mmol) in 1,4-dioxane:water (4:1, 15 ml) was added K₂CO₃ (0.577 g, 4.18 mmol) at rt. The reaction mixture was degassed for 30 min before addition of Pd(PPh₃)₄ (0.080 g, 0.069 mmol) at rt. The reaction mixture was heated at 90° C. for 2 h. The resulting mixture was cooled to rt, diluted with water (25 ml) and extracted with EtOAc (2×25 ml). The combined organic layer was dried over Na₂SO₄, filtered and concentrated under reduced pressure. The resulting residue was purified by flash chromatography (18% EtOAc in hexane) yielding tert-butyl 2-(3-([1,1'-biphenyl]-3-yl)-1,2,4-oxadiazol-5-yl)pyrrolidine-1-carboxylate (0.500 g, 1.278 mmol). LCMS: Method C, 2.972, MS: ES+336.20 [M-56]

Step d. To a solution of tert-butyl 2-(3-([1,1'-biphenyl]-3-yl)-1,2,4-oxadiazol-5-yl)pyrrolidine-1-carboxylate (0.500 g, 1.28 mmol) in DCM (5 ml) was added TFA (2 ml) at 0° C. The reaction mixture was stirred at rt for 2 h. The resulting reaction mixture was evaporated under reduced pressure. The obtained residue was triturated using mixture of diethyl ether:hexane (1:1, 5 ml) and dried under high vacuum yielding 3-([1,1'-biphenyl]-3-yl)-5-(pyrrolidin-2-yl)-1,2,4-oxadiazole TFA salt (0.500 g, 1.23 mmol). This material was used directly for the next step without further purification. LCMS: Method C, 1.883 min, MS: ES+292.31

Step e. To a solution of 3-([1,1'-biphenyl]-3-yl)-5-(pyrrolidin-2-yl)-1,2,4-oxadiazole TFA salt (0.500 g, 1.23 mmol) in THF (10 ml) was added K₂CO₃ (0.510 g, 3.70 mmol) at 0° C., followed by cyanogen bromide (0.129 g, 1.23 mmol). The reaction mixture was stirred at rt for 30 min. The mixture was diluted with water (25 ml) and extracted with EtOAc (2×25 ml). The combined organic layer was dried over Na₂SO₄, filtered and concentrated under reduced pressure. The resulting residue was purified by flash chromatography (30% EtOAc in hexane) yielding title compound (0.250 g, 0.791 mmol). LCMS: Method A, 5.337, MS: ES+316.90; ¹H NMR (400 MHz, DMSO-d6) δ ppm 8.23 (s, 1H), 8.03 (d, J=7.6 Hz, 1H), 7.91-7.93 (m, 1H), 7.67-7.75 (m, 3H), 7.50-7.54 (m, 2H), 7.42-7.45 (m, 1H), 5.34-5.37 (m, 1H), 3.64-3.70 (m, 1H), 3.52-3.58 (m, 1H), 2.39-2.43 (m, 1H), 2.27-2.33 (m, 1H), 2.05-2.08 (m, 2H).

Step f. The isolated racemic material was subjected to enantiomeric separation by preparative chiral SFC Purification: Chiralcel OX-H 250×21.0 mm, 5 μm, mobile phase: (A) Liquid carbon dioxide; (B) IPA:MeCN (30:70), column flow was 70.0 ml/min and ABPR was 100 bar. LCMS: Method A, 5.328 min, MS: ES+316.90; Chiral SFC: Chiralcel OX-H 250×4.6 mm 5 μm, mobile phase: (A) Liquid carbon dioxide; (B) IPA:MeCN (30:70), column flow was 3.0 ml/min and ABPR was 130 bar, isocratic gradient of 15% B over 10 min, RT 6.35 min; ¹H NMR (400 MHz, DMSO-d6) δ ppm 8.23 (s, 1H), 8.03 (d, J=7.6 Hz, 1H), 7.91-7.93 (m, 1H), 7.67-7.75 (m, 3H), 7.50-7.54 (m, 2H), 7.42-7.45 (m, 1H), 5.34-5.37 (m, 1H), 3.64-3.70 (m, 1H), 3.52-3.58 (m, 1H), 2.39-2.43 (m, 1H), 2.27-2.33 (m, 1H), 2.05-2.08 (m, 2H).

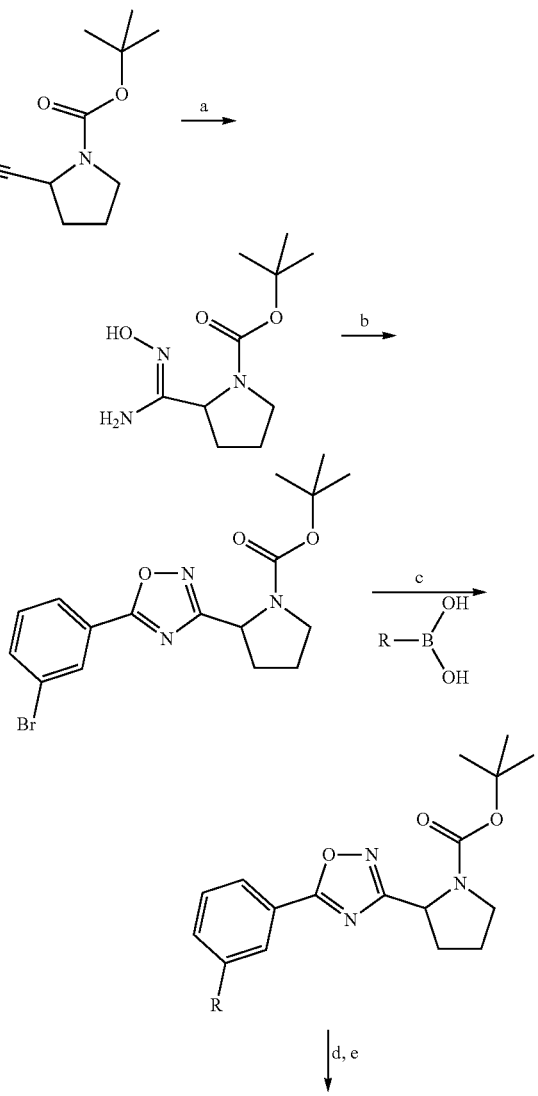

Scheme 7

-continued

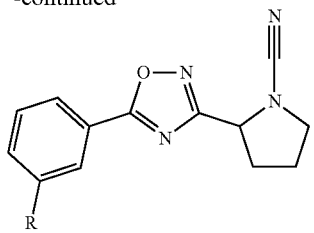

Reagents and conditions: a) NH₂OH•HCl, EtOH, 90° C., 4 h;
b) ArCO₂H, CDI, DMF, rt to 90° C., 3 h; c) PdCl₂(dppf), NaHCO₃, DMF, water, 100° C., 1 h; d) TFA, DCM, rt, 1 h; e) cyanogen bromide, K₂CO₃, THF, rt, 1 h.

Example 142 2-(5-(6-Phenylpyridin-2-yl)-1,2,4-oxadiazol-3-yl)pyrrolidine-1-carbonitrile (Prepared according to Scheme 7)

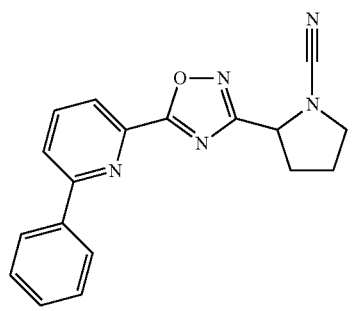 [SMILES: N#CN1CCCC1c1noc(-c2cccc(-c3ccccc3)n2)n1]

Step a. To a solution of tert-butyl 2-cyanopyrrolidine-1-carboxylate (1.000 g, 5.095 mmol) in EtOH (8 ml) were added NH₂OH·HCl (0.708 g, 10.19 mmol) followed by DIPEA (2.6 ml, 15.3 mmol) at rt. The reaction mixture was heated at 90° C. for 4 h. The resulting reaction mixture was cooled and concentrated under vacuum. The obtained residue was diluted with water (20 ml). The resulting precipitates were collected by filtration and washed with hexane (10 ml). The resulting solid material was dried under high vacuum yielding tert-butyl 2-(N'-hydroxycarbamimidoyl)pyrrolidine-1-carboxylate (0.630 g, 2.751 mmol). This material was used directly for the next step without further purification. LCMS: Method C, 1.502, MS: ES+230.28

Step b. To a solution of 6-bromopicolinic acid (CAS Number 21190-87-4; 0.200 g, 0.990 mmol) in DMF (3 ml) was added CDI (0.176 g, 1.09 mmol) at 0° C. The reaction mixture was stirred at rt for 30 min before addition of tert-butyl 2-(N'-hydroxycarbamimidoyl)pyrrolidine-1-carboxylate (0.273 g, 1.19 mmol) at rt. Then reaction mixture was cooled to 0° C. and CDI (0.176 g, 1.09 mmol) was added. The reaction mixture was heated at 120° C. for 3 h. The resulting reaction mixture was cooled to rt and diluted with ice cold water (30 nil). The resulting precipitates were collected by filtration and dried under high vacuum yielding tert-butyl 2-(5-(6-bromopyridin-2-yl)-1,2,4-oxadiazol-3-yl)pyrrolidine-1-carboxylate (0.235 g, 0.594 mmol). This material was used directly for the next step without further purification. LCMS: Method C, 2.413, MS: ES+395.13, 397.13

Step c. To a mixture of tert-butyl 2-(5-(6-bromopyridin-2-yl)-1,2,4-oxadiazol-3-yl)pyrrolidine-1-carboxylate (0.180 g, 0.456 mmol) and phenylboronic acid (0.111 g, 0.913 mmol) in DMF:water (4:1, 4 ml) was added NaHCO₃ (0.115 g, 1.37 mmol) at rt. The reaction mixture was degassed for 10 min before addition of PdCl₂(dppf) (0.033 g, 0.045 mmol) at rt. The resulting reaction mixture was heated at 100° C. for 1 h. The reaction mixture was cooled to rt. Precipitation observed in the reaction mixture at rt. The obtained precipitates were collected by filtration and purified by flash column chromatography (35% EtOAc in hexane) yielding tert-butyl 2-(5-(6-phenylpyridin-2-yl)-1,2,4-oxadiazol-3-yl)-pyrrolidine-1-carboxylate (0.160 g, 0.408 mmol). LCMS: Method C, 2.622 min, MS: ES+393.40

Step d. To a solution of tert-butyl 2-(5-(6-phenylpyridin-2-yl)-1,2,4-oxadiazol-3-yl)pyrrolidine-1-carboxylate (0.150 g, 0.382 mmol) in DCM (2 ml) was added TFA (1 ml) at 0° C. The reaction mixture was stirred at rt for 1 h. The resulting reaction mixture was evaporated under reduced pressure. The obtained residue was triturated using diethyl ether (10 ml) and dried under high vacuum yielding 5-(6-phenylpyridin-2-yl)-3-(pyrrolidin-2-yl)-1,2,4-oxadiazole TFA salt (0.145 g, 0.357 mmol). This material was used directly for the next step without further purification. LCMS: Method A, 4.431 min, MS: ES+292.92.

Step e. To a solution of 5-(6-phenylpyridin-2-yl)-3-(pyrrolidin-2-yl)-1,2,4-oxadiazole TFA salt (0.145 g, 0.357 mmol) in THF (4 ml) was added K₂CO₃ (0.147 g, 1.071 mmol) at rt. The reaction mixture was stirred at rt for 10 min before addition of cyanogen bromide (0.056 g, 0.535 mmol) at 0° C. The reaction mixture was stirred at 0° C. for 1 h. The resulting reaction mixture was diluted with ice cold water (15 ml) and extracted with EtOAc (5×10 ml). The combined organic layer was dried over Na₂SO₄, filtered and concentrated under reduced pressure. The resulting residue was purified by flash chromatography (50% EtOAc in hexane) yielding title compound (0.090 g, 0.283 mmol). LCMS: Method A, 4.819, MS: ES+317.92; ¹H NMR (400 MHz, DMSO-d6) δ ppm 8.31-8.33 (m, 1H), 8.17-8.23 (m, 4H), 7.51-7.60 (m, 3H), 5.13-5.16 (m, 1H), 3.62-3.68 (m, 1H), 3.53-3.59 (m, 1H), 2.33-2.43 (m, 1H), 2.20-2.23 (m, 1H), 2.02-2.17 (m, 2H).

Compounds in Table 8 were synthesised using a procedure similar to that described for Example 142.

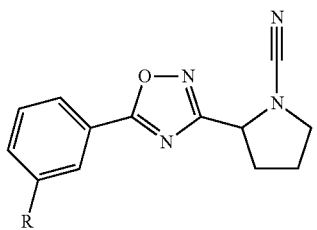

TABLE 8

| Ex | R | Name | LCMS Method | LCMS RT (min) | MS (ES+) |
|---|---|---|---|---|---|
| 143 | 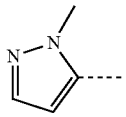 | 2-(5-(3-(1-Methyl-1H-pyrazol-5-yl)phenyl)-1,2,4-oxadiazol-3-yl)pyrrolidine-1-carbonitrile | H | 2.518 | 321.0 |
| 144 | 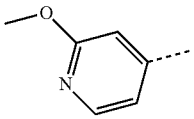 | 2-(5-(3-(2-Methoxypyridin-4-yl)phenyl)-1,2,4-oxadiazol-3-yl)pyrrolidine-1-carbonitrile | H | 2.765 | 348.0 |
| 145 | 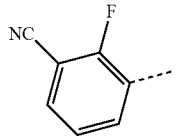 | 2-(5-(3'-Cyano-2'-fluoro-[1,1'-biphenyl]-3-yl)-1,2,4-oxadiazol-3-yl)pyrrolidine-1-carbonitrile | I | 2.931 | 377.0 |
| 146 | 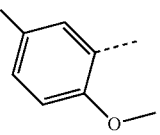 | 2-(5-(5'-Cyano-2'-methoxy-[1,1'-biphenyl]-3-yl)-1,2,4-oxadiazol-3-yl)pyrrolidine-1-carbonitrile | I | 2.910 | 389.0 |
| 147 | 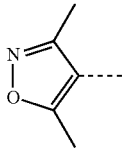 | 2-(5-(3-(3,5-Dimethylisoxazol-4-yl)phenyl)-1,2,4-oxadiazol-3-yl)pyrrolidine-1-carbonitrile | H | 2.937 | 336.1 |
| 148 |  | 2-(5-(3-(1-Methyl-1H-pyrazol-4-yl)phenyl)-1,2,4-oxadiazol-3-yl)pyrrolidine-1-carbonitrile | H | 2.687 | 321.1 |
| 149 | 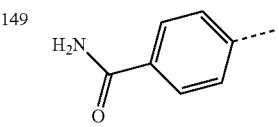 | 3'-(3-(1-Cyanopyrrolidin-2-yl)-1,2,4-oxadiazol-5-yl)-[1,1-biphenyl]-4-carboxamide | H | 2.605 | 360.1 |
| 150 | 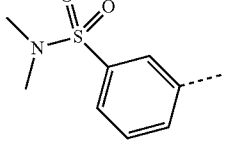 | 3'-(3-(1-Cyanopyrrolidin-2-yl)-1,2,4-oxadiazol-5-yl)-N,N-dimethyl-[1,1'-biphenyl]-3-sulfonamide | H | 3.108 | 424.0 |
| 151 | 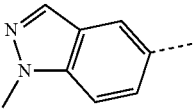 | 2-(5-(3-(1-Methyl-1H-indazol-5-yl)phenyl)-1,2,4-oxadiazol-3-yl)pyrrolidine-1-carbonitrile | H | 3.091 | 371.1 |
| 152 | 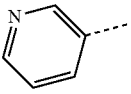 | 2-(5-(3-(Pyridin-3-yl)phenyl)-1,2,4-oxadiazol-3-yl)pyrrolidine-1-carbonitrile | H | 2.054 | 318.2 |
| 153 | 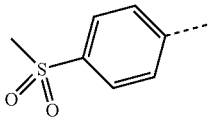 | 2-(5-(4'-(Methylsulfonyl)-[1,1'-biphenyl]-3-yl)-1,2,4-oxadiazol-3-yl)pyrrolidine-1-carbonitrile | H | 2.861 | 395.0 |

TABLE 8-continued

| Ex | R | Name | LCMS Method | LCMS RT (min) | MS (ES+) |
|---|---|---|---|---|---|
| 154 | 6-methylpyridin-3-yl | 2-(5-(3-(6-Methylpyridin-3-yl)phenyl)-1,2,4-oxadiazol-3-yl)pyrrolidine-1-carbonitrile | H | 2.077 | 332.1 |
| 155 | 2-cyanophenyl | 2-(5-(2'-Cyano-[1,1'-biphenyl]-3-yl)-1,2,4-oxadiazol-3-yl)pyrrolidine-1-carbonitrile | H | 3.088 | 342.1 |
| 156 | 2-(methoxycarbonyl)phenyl | Methyl 3'-(3-(1-cyanopyrrolidin-2-yl)-1,2,4-oxadiazol-5-yl)-[1,1'-biphenyl]-2-carboxylate | H | 3.202 | 375.0 |
| 157 | 4-nitrophenyl | 2-(5-(4'-Nitro-[1,1'-biphenyl]-3-yl)-1,2,4-oxadiazol-3-yl)pyrrolidine-1-carbonitrile | I | 2.976 | 362.0 |
| 158 | 6-methoxypyridin-3-yl | 2-(5-(3-(6-Methoxypyridin-3-yl)phenyl)-1,2,4-oxadiazol-3-yl)pyrrolidine-1-carbonitrile | H | 3.081 | 348.1 |
| 159 | pyrimidin-5-yl | 2-(5-(3-(Pyrimidin-5-yl)phenyl)-1,2,4-oxadiazol-3-yl)pyrrolidine-1-carbonitrile | I | 2.236 | 319.1 |
| 160 | furan-3-yl | 2-(5-(3-(Furan-3-yl)phenyl)-1,2,4-oxadiazol-3-yl)pyrrolidine-1-carbonitrile | H | 3.045 | 307.1 |
| 161 | 3-nitrophenyl | 2-(5-(3'-Nitro-[1,1'-biphenyl]-3-yl)-1,2,4-oxadiazol-3-yl)pyrrolidine-1-carbonitrile | I | 3.160 | 379.2 |
| 162 | 2-methoxypyridin-3-yl | 2-(5-(3-(2-Methoxypyridin-3-yl)phenyl)-1,2,4-oxadiazol-3-yl)pyrrolidine-1-carbonitrile | H | 3.052 | 348.2 |
| 163 | 3-cyano-5-fluorophenyl | 2-(5-(3'-Cyano-5'-fluoro-[1,1'-biphenyl]-3-yl)-1,2,4-oxadiazol-3-yl)pyrrolidine-1-carbonitrile | H | 3.170 | 360.1 |
| 164 | 5-methylpyridin-3-yl | 2-(5-(3-(5-Methylpyridin-3-yl)phenyl)-1,2,4-oxadiazol-3-yl)pyrrolidine-1-carbonitrile | H | 2.164 | 332.1 |

TABLE 8-continued

| Ex | R | Name | LCMS Method | LCMS RT (min) | MS (ES+) |
|---|---|---|---|---|---|
| 165 | 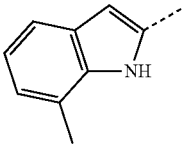 | 2-(5-(3-(7-Methyl-1H-indol-2-yl)phenyl)-1,2,4-oxadiazol-3-yl)pyrrolidine-1-carbonitrile | K | 3.056 | 370.2 |
| 166 | 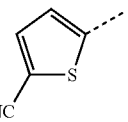 | 2-(5-(3-(5-Cyanothiophen-2-yl)phenyl)-1,2,4-oxadiazol-3-yl)pyrrolidine-1-carbonitrile | H | 3.171 | 348.0 |

Compounds in Table 9 were synthesised using a procedure similar to that described for Example 142.

Compounds in Table 10 were synthesised using a procedure similar to that described for Example 142, using (S)-tert-butyl 2-cyanopyrrolidine-1-carboxylate (CAS Number 228244-04-0) in step a.

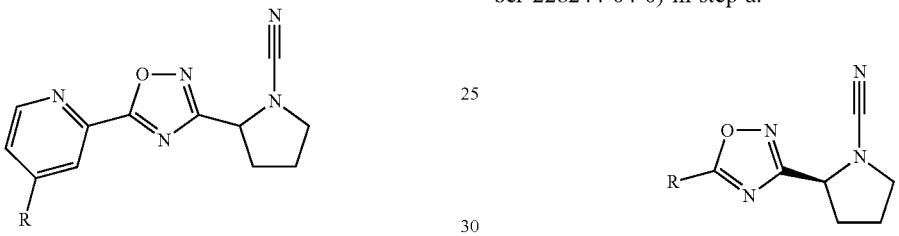

TABLE 9

| Ex | R | Name | LCMS Method | LCMS RT (min) | MS (ES+) | $^1$H NMR (400 MHz, DMSO-d6) δ ppm |
|---|---|---|---|---|---|---|
| 167 | 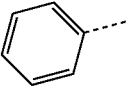 | 2-(5-(2-Phenylpyridin-4-yl)-1,2,4-oxadiazol-3-yl)pyrrolidine-1-carbonitrile | A | 4.625 | 317.99 | 8.98 (dd, J = 4.8, 0.8 Hz, 1 H), 8.50 (s, 1 H), 8.19-8.21 (m, 2 H), 8.00 (dd, J = 9.2, 1.2 Hz, 1 H), 7.50-7.58 (m, 3 H), 5.15-5.18 (m, 1 H), 3.64-3.68 (m, 1 H), 3.54-3.59 (m, 1 H), 2.35-2.44 (m, 1 H), 2.15-2.22 (m, 1 H), 2.03-2.13 (m, 2 H) |
| 168 | 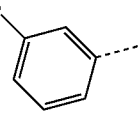 | 2-(5-(2-(3-(Trifluoromethoxy)phenyl)-pyridin-4-yl)-1,2,4-oxadiazol-3-yl)pyrrolidine-1-carbonitrile | A | 5.368 | 402.06 | 9.00 (dd, J = 4.8, 0.8 Hz, 1 H), 8.62 (s, 1 H), 8.28 (d, J = 8.0 Hz, 1 H), 8.21 (s, 1 H), 8.08 (dd, J = 4.8, 1.2 Hz, 1 H), 7.70 (t, J = 8.0 Hz, 1 H), 7.53 (d, J = 8.0 Hz, 1 H), 5.15-5.18 (m, 1 H), 3.63-3.69 (m, 1 H), 3.54-3.60 (m, 1 H), 2.33-2.43 (m, 1 H), 2.15-2.21 (m, 1 H), 2.03-2.13 (m, 2 H) |
| 169 | 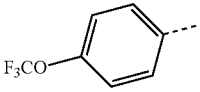 | 2-(5-(2-(4-(Trifluoromethoxy)phenyl)-pyridin-4-yl)-1,2,4-oxadiazol-3-yl)pyrrolidine-1-carbonitrile | C | 2.416 | 402.53 | 8.97 (d, J = 8.8 Hz, 1 H), 8.53 (s, 1 H), 8.32 (d, J = 8.8 Hz, 2 H), 8.01 (dd, J = 5.2, 1.2 Hz, 1 H), 7.52 (d, J = 8.4 Hz, 2 H), 5.12-5.15 (m, 1 H), 3.62-3.65 (m, 1 H), 3.53-3.56 (m, 1 H), 2.30-2.43 (m, 1 H), 2.12-2.19 (m, 1 H), 2.00-2.10 (m, 2 H) |
| 170 | 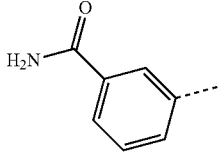 | 3-(4-(3-(1-Cyanopyrrolidin-2-yl)-1,2,4-oxadiazol-5-yl)pyridin-2-yl)benzamide | B | 3.254 | 361.58 | 9.01 (d, J = 4.8 Hz, 1 H), 8.67 (s, 1 H), 8.63 (s, 1 H), 8.37 (d, J = 7.6 Hz, 1 H), 8.24 (s, 1 H), 8.00-8.05 (m, 2 H), 7.64 (t, J = 7.6 Hz, 1 H), 7.53 (s, 1 H), 5.15-5.18 (m, 1 H), 3.63-3.69 (m, 1 H), 3.54-3.59 (m, 1 H), 2.33-2.43 (m, 1 H), 2.15-2.23 (m, 1 H), 2.03-2.13 (m, 2 H) |
| 171 | 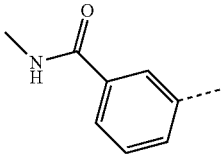 | 3-(4-(3-(1-Cyanopyrrolidin-2-yl)-1,2,4-oxadiazol-5-yl)pyridin-2-yl)-N-methylbenzamide | B | 3.391 | 375.68 | 9.01 (d, J = 5.2 Hz, 1 H), 8.68 (d, J = 4.4 Hz, 1 H), 8.61 (d, J = 8.4 Hz, 2 H), 8.36 (d, J = 8.0 Hz, 1 H), 8.06 (d, J = 4.8 Hz, 1 H), 7.97 (d, J = 8.0 Hz, 1 H), 7.65 (t, J = 7.6 Hz, 1 H), 5.15-5.18 (m, 1 H), 3.63-3.69 (m, 1 H), 3.54-3.60 (m, 1 H), 2.85 (d, J = 4.4 Hz, 3 H), 2.36-2.43 (m, 1 H), 2.15-2.22 (m, 1 H), 2.04-2.12 (m, 2 H) |

TABLE 9-continued

| Ex | R | Name | LCMS Method | LCMS RT (min) | MS (ES+) | $^1$H NMR (400 MHz, DMSO-d6) δ ppm |
|---|---|---|---|---|---|---|
| 172 | NC-phenyl (3-cyanophenyl) | 2-(5-(4-(3-Cyanophenyl)pyridin-2-yl)-1,2,4-oxadiazol-3-yl)pyrrolidine-1-carbonitrile | A | 3.908 | 343.10 | 8.95 (d, J = 5.2 Hz, 1 H), 8.60 (s, 1 H), 8.51 (s, 1 H), 8.29 (d, J = 7.6 Hz, 1 H), 8.16 (d, J = 7.6 Hz, 1 H), 8.02 (d, J = 7.6 Hz, 1 H), 7.91 (t, J = 7.6 Hz, 1 H), 5.13-5.16 (m, 1 H), 3.63-3.68 (m, 1 H), 3.54-3.59 (m, 1 H), 2.33-2.42 (m, 1 H), 2.16-2.21 (m, 1 H), 2.03-2.13 (m, 2 H) |
| 173 | NC-pyridine | 4'-(3-(1-Cyanopyrrolidin-2-yl)-1,2,4-oxadiazol-5-yl)-[2,2'-bipyridine]-4-carbonitrile | A | 4.000 | 344.05 | 9.03-9.06 (m, 2 H), 8.97 (s, 1 H), 8.75 (s, 1 H), 8.20 (dd, J = 5.2, 2.0 Hz, 1 H), 8.05 (dd, J = 4.8, 1.6 Hz, 1 H), 5.15-5.18 (m, 1 H), 3.63-3.72 (m, 1 H), 3.55-3.59 (m, 1 H), 2.37-2.43 (m, 1 H), 2.17-2.21 (m, 1 H), 2.05-2.09 (m, 2 H) |

TABLE 10

| Ex | R | Name | LCMS Method | LCMS RT (min) | MS (ES+) | $^1$H NMR (400 MHz, DMSO-d6) δ ppm |
|---|---|---|---|---|---|---|
| 174 | NC-biphenyl | (S)-2-(5-(4'-Cyano-[1,1'-biphenyl]-3-yl)-1,2,4-oxadiazol-3-yl)pyrrolidine-1-carbonitrile | A | 4.771 | 342.06 | 8.40 (s, 1 H), 8.20 (d, J = 8.0 Hz, 1 H), 8.11 (d, J = 8.0 Hz, 1 H), 7.98-8.02 (m, 4 H), 7.80 (t, J = 7.6 Hz, 1 H), 5.09-5.12 (m, 1 H), 3.61-3.67 (m, 1 H), 3.54-3.58 (m, 1 H), 2.35-2.40 (m, 1 H), 2.11-2.19 (m, 1H), 1.99-2.09 (m, 2 H) |
| 175 | NC-phenyl-pyridine | (S)-2-(5-(6-(4-Cyanophenyl)pyridin-2-yl)-1,2,4-oxadiazol-3-yl)pyrrolidine-1-carbonitrile | A | 3.887 | 343.10 | 8.39-8.45 (m, 2 H), 8.24-8.31 (m, 2 H), 8.05 (d, J = 8.4 Hz, 2 H), 5.13-5.17 (m, 1 H), 3.62-3.68 (m, 1 H), 3.54-3.59 (m, 1 H), 2.33-2.44 (m, 1 H), 2.15-2.22 (m, 1 H), 2.02-2.13 (m, 2 H) |
| 176 | NC-phenyl-pyridine | (S)-2-(5-(4-(4-Cyanophenyl)pyridin-2-yl)-1,2,4-oxadiazol-3-yl)pyrrolidine-1-carbonitrile | B | 3.737 | 343.53 | 8.96 (d, J = 5.2 Hz, 1 H), 8.55 (s, 1 H), 8.14-8.17 (m, 3 H), 8.05-8.07 (m, 2 H), 5.13-5.16 (m, 1 H), 3.62-3.66 (m, 1 H), 3.55-3.59 (m, 1 H), 2.37-2.42 (m, 1 H), 2.16-2.21 (m, 1 H), 2.05-2.11 (m, 2 H) |
| 177 | NC-phenyl-pyridine | (S)-2-(5-(2-(4-Cyanophenyl)pyridin-4-yl)-1,2,4-oxadiazol-3-yl)pyrrolidine-1-carbonitrile | A | 4.004 | 343 | 9.04 (d, J = 5.2 Hz, 1 H), 8.64 (s, 1 H), 8.42 (d, J = 8.4 Hz, 2 H), 8.11 (dd, J = 5.2, 1.2 Hz, 1 H), 8.03 (d, J = 8.4 Hz, 2 H), 5.15-5.18 (m, 1 H), 3.63-3.68 (m, 1 H), 3.54-3.59 (m, 1 H), 2.33-2.44 (m, 1 H), 2.15-2.22 (m, 1 H), 2.02-2.14 (m, 2 H) |
| 200 | NC-phenyl-pyridine | (S)-2-(5-(2-(3-cyanophenyl)pyridin-4-yl)-1,2,4-oxadiazol-3-yl)pyrrolidine-1-carbonitrile | A | 3.925 | 384.10 | 9.01 (d, J = 4.8 Hz, 1 H), 8.70 (d, J = 5.6 Hz, 2 H), 8.57 (d, J = 8.0 Hz, 1 H), 8.09 (d, J = 5.2 Hz, 1 H), 7.99 (d, J = 5.6 Hz, 1 H), 7.77 (t, J = 8.0 Hz, 1 H), 5.15-5.18 (m, 1 H), 3.44-3.68 (m, 2 H), 2.36-2.44 (m, 1 H), 2.04-2.22 (m, 3 H) |

Example 178 (S)-2-(5-(7-Cyanonaphthalen-2-yl)-1,2,4-oxadiazol-3-yl)pyrrolidine-1-carbonitrile

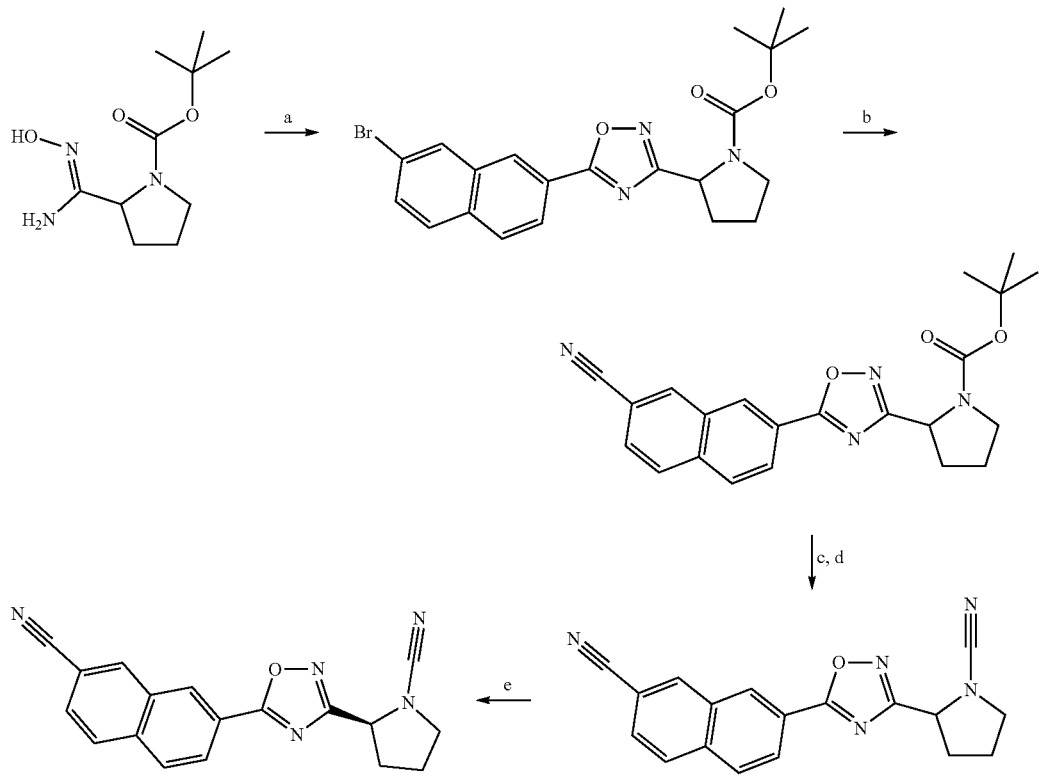

Step a. To a mixture of tert-butyl 2-(N'-hydroxycarbamimidoyl)pyrrolidine-1-carboxylate (Example 142, step a; 0.300 g, 1.31 mmol) and 7-bromo-2-naphthoic acid (CAS Number 5043-14-1; 0.328 g, 1.31 mmol) in DMF (12 ml) were added HATU (0.746 g, 1.96 mmol) and DIPEA (0.337 g, 2.62 mmol) at rt. The reaction mixture was heated at 100° C. for 16 h. The resulting reaction mixture was cooled to rt, diluted with ice cold water (100 ml) and extracted with EtOAc (5×100 ml). The combined organic layer was dried over $Na_2SO_4$, filtered and concentrated under reduced pressure. The resulting residue was purified by flash chromatography (8% EtOAc in hexane) yielding tert-butyl 2-(5-(7-bromonaphthalen-2-yl)-1,2,4-oxadiazol-3-yl)pyrrolidine-1-carboxylate (0.630 g, quantitative yield). LCMS: Method C, 2.930, MS: ES+444.40, 446.50

Step b. To a solution of tert-butyl 2-(5-(7-bromonaphthalen-2-yl)-1,2,4-oxadiazol-3-yl)pyrrolidine-1-carboxylate (0.300 g, 0.677 mmol) in DMA (3 ml) was added zinc dust (0.017 g, 0.27 mmol) and $Zn(CN)_2$ (0.159 g, 1.35 mmol) at rt in microwave tube. The reaction mixture was degassed for 20 min before addition of $Pd_2(dba)_3$ (0.062 g, 0.067 mmol) and dppf (0.037 g, 0.060 mmol). The resulting reaction mixture was heated at 160° C. for 220 min under microwave condition. The resulting reaction mixture was cooled to rt, diluted with ice cold water (200 ml) and extracted with EtOAc (5×100 ml). The combined organic layer was dried over $Na_2SO_4$, filtered and concentrated under reduced pressure. The resulting residue was purified by flash chromatography (7.5% EtOAc in hexane) yielding tert-butyl 2-(5-(7-cyanonaphthalen-2-yl)-1,2,4-oxadiazol-3-yl)pyrrolidine-1-carboxylate (0.130 g, 0.333 mmol). LCMS: Method C, 2.493, MS: ES+391.48

Step c. To a solution of tert-butyl 2-(5-(7-cyanonaphthalen-2-yl)-1,2,4-oxadiazol-3-yl)pyrrolidine-1-carboxylate (0.190 g, 0.428 mmol) in DCM (2 ml) was added TFA (0.4 ml) at 0° C. The reaction mixture was stirred at rt for 3 h. The resulting reaction mixture was evaporated under reduced pressure. The residue was triturated using hexane (3×50 ml) and dried under high vacuum yielding 7-(3-(pyrrolidin-2-yl)-1,2,4-oxadiazol-5-yl)-2-naphthonitrile TFA salt (0.170 g, 0.420 mmol). This material was used directly for the next step without further purification. LCMS: Method C, 1.510 min, MS: ES+291.33

Step d. To a solution of 7-(3-(pyrrolidin-2-yl)-1,2,4-oxadiazol-5-yl)-2-naphthonitrile TFA salt (0.165 g, 0.407 mmol) in THF (15 ml) were added $K_2CO_3$ (0.449 g, 3.25 mmol) followed by cyanogen bromide (0.051 g, 0.49 mmol) at 0° C. The reaction mixture was stirred at rt for 1.2 h. The resulting reaction mixture was diluted with water (100 ml) and extracted with EtOAc (5×50 ml). The combined organic layer was dried over $Na_2SO_4$, filtered and concentrated under reduced pressure. The residue was purified by flash chromatography (34% EtOAc in hexane) yielding title compound (0.060 g, 0.190 mmol). LCMS: Method A, 4.308, MS: ES+316.2; $^1$H NMR (400 MHz, DMSO-$d_6$) δ ppm 8.98 (s, 1H), 8.89 (s, 1H), 8.32-8.35 (m, 2H), 8.26-8.30 (m, 1H), 8.00 (dd, J=8.8, 1.2 Hz, 1H), 5.11-5.15 (m, 1H), 3.63-3.68 (m, 1H), 3.53-3.63 (m, 1H), 2.32-2.42 (m, 1H), 2.15-2.23 (m, 1H), 2.02-2.12 (m, 2H).

Step e. The isolated racemic material was subjected to enantiomeric separation by preparative chiral SFC Purification: Chiralpak AD-H 250×21.0 mm, 5 μm, mobile phase: (A) Liquid carbon dioxide; (B) IPA:MeCN (50:50), column flow was 70.0 ml/min and ABPR was 100 bar, isocratic gradient of 20% B over 12 minutes. LCMS: Method B, 4.281, MS: ES+316.48; Chiral SFC: Chiralpak AD-H 250× 4.6 mm, 5 μm, mobile phase: (A) Liquid carbon dioxide; (B) IPA:MeCN (50:50), column flow was 3.0 ml/min and ABPR was 150 bar, isocratic gradient of 25% B over 9 minutes, RT 5.16 min; $^1$H NMR (400 MHz, DMSO-d6) δ ppm 8.98 (s, 1H), 8.89 (s, 1H), 8.32-8.35 (m, 2H), 8.26-8.30 (m, 1H), 8.00 (dd, J=8.8, 1.2 Hz, 1H), 5.11-5.15 (m, 1H), 3.63-3.68 (m, 1H), 3.53-3.63 (m, 1H), 2.32-2.42 (m, 1H), 2.15-2.23 (m, 1H), 2.02-2.12 (m, 2H).

Example 179 7-(3-(1-Cyanopyrrolidin-2-yl)-1,2,4-oxadiazol-5-yl)quinoline-2-carbonitrile

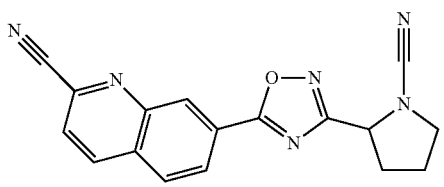 [SMILES: N#Cc1ccc2ccc(-c3nc(C4CCCN4C#N)no3)cc2n1]

The title compound was synthesised using a procedure similar to that described for Example 178, using 2-chloroquinoline-7-carboxylic acid (CAS Number 1092287-40-5) in step a. LCMS: Method A, 4.223 min, MS: ES+317.06; $^1$H NMR (400 MHz, DMSO-d6) δ ppm 8.83-8.85 (m, 2H), 8.41-8.43 (m, 2H), 8.23 (d, J=8.4 Hz, 1H), 5.14-5.17 (m, 1H), 3.56-3.67 (m, 2H), 2.38-2.42 (m, 1H), 2.17-2.22 (m, 1H), 2.05-2.11 (m, 2H).

Example 180 4'-(3-(1-Cyanopyrrolidin-2-yl)-1,2,4-oxadiazol-5-yl)-[2,2'-bipyridine]-6-carbonitrile

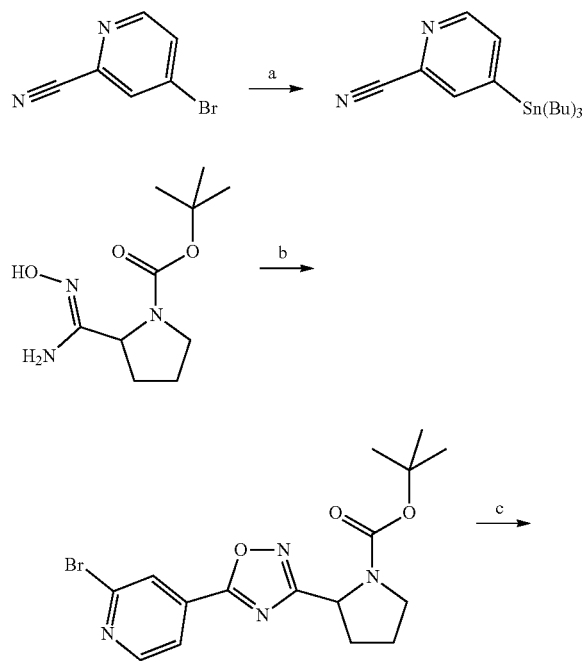

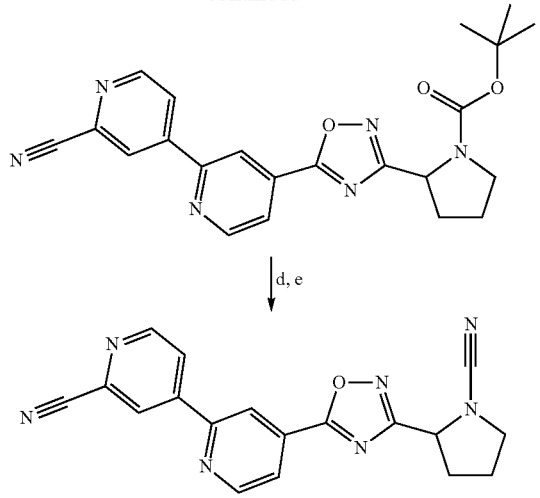

Step a. To a solution of 6-bromopicolinonitrile (CAS Number 122918-25-6; 0.400 g, 2.18 mmol) in DME:DMF (8:1, 9 ml) was added hexabutylditin (1.90 g, 3.28 mmol) at rt. The reaction mixture was degassed for 30 min before addition of Pd(PPh$_3$)$_4$ (0.224 g, 0.194 mmol) at rt. The resulting reaction mixture was heated at 100° C. for 8 h. The reaction mixture was cooled to rt, diluted with ice cold water (100 ml) and extracted with EtOAc (2×100 ml). The combined organic layer was dried over Na$_2$SO$_4$, filtered and concentrated under reduced pressure. The obtained residue was purified by flash column chromatography (10% EtOAc in hexane) yielding 6-(tributylstannyl)picolinonitrile (0.350 g, 0.888 mmol). LCMS: Method C, 3.515 min, MS: ES+395.58

Step b. To a solution of 2-bromoisonicotinic acid (CAS Number 66572-56-3; 5.00 g, 24.8 mmol) in DMF (100 ml) was added CDI (4.30 g, 27.2 mmol) at rt. The reaction mixture was stirred at rt for 1 h before addition of tert-butyl (Z)-2-(N'-hydroxycarbamimidoyl)pyrrolidine-1-carboxylate (Example 142, step a; 11.30 g, 49.5 mmol) and molecular sieves at rt. A second portion of CDI (4.30 g, 27.2 mmol) was added and then heated to 90° C. for 16 h. The resulting mixture was to cooled to rt, diluted with ice cold water (500 ml) and extracted with EtOAc (2×400 ml). The combined organic layer was dried over Na$_2$SO$_4$, filtered and concentrated under reduced pressure. The obtained residue was purified by flash column chromatography (10% EtOAc in hexane) yielding tert-butyl 2-(5-(2-bromopyridin-4-yl)-1,2,4-oxadiazol-3-yl)pyrrolidine-1-carboxylate (3.70 g, 9.37 mmol). LCMS: Method C, 2.258 min, MS: ES+395.40, 397.40

Step c. To a solution of tert-butyl 2-(5-(2-bromopyridin-4-yl)-1,2,4-oxadiazol-3-yl)pyrrolidine-1-carboxylate (0.280 g, 0.71 mmol) in DMF (6 ml) was added 6-(tributylstannyl)picolinonitrile (0.252 g, 0.639 mmol) and CsF (0.270 g, 1.776 mmol) at rt. The reaction mixture was degassed for 15 min before addition of Pd$_2$(dba)$_3$ (0.032 g, 0.035 mmol), CuI (0.013 g, 0.071 mmol) and bis[tris(tert-butyl)-phosphine] palladium (0.036 g, 0.071 mmol) at rt. The resulting reaction mixture was heated at 90° C. for 1.5 h. The resulting reaction mixture was cooled to rt, diluted with water (100 ml) and extracted with EtOAc (2×100 ml). The combined organic layer was dried over Na$_2$SO$_4$, filtered and concentrated under reduced pressure. The residue was purified by flash chromatography (10% EtOAc in hexane) yielding tert-butyl 2-(5-(2'-cyano-[2,4'-bipyridin]-4-yl)-1,2,4-oxadiazol-3-yl)pyrrolidine-1-carboxylate (0.180 g, 0.430 mmol). LCMS: Method C, 2.308, MS: ES+419.60 Steps d, e. The title compound was synthesized from the intermediate above using a procedure similar to that described for Example 14, steps d, e. LCMS: Method A, 4.290 min, MS: ES+344.10; $^1$H NMR (400 MHz, DMSO-d$_6$) δ ppm 9.02 (d, J=4.8 Hz, 1H), 8.87 (s, 1H), 8.71 (d, J=8.0 Hz, 1H), 8.27 (t, J=8.0 Hz, 1H), 8.17-8.18 (m, 2H), 5.13-5.16 (m, 1H), 3.62-3.67 (m, 1H), 3.51-3.57 (m, 1H), 2.34-2.41 (m, 1H), 2.13-2.19 (m, 1H), 2.04-2.06 (m, 2H).

Example 181 (S)-4-(3-(J-Cyanopyrrolidin-2-yl)-1,2,4-oxadiazol-5-yl)-[2,4'-bipyridine]-2'-carbonitrile

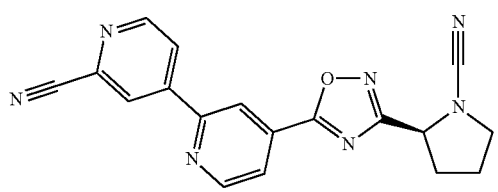 [SMILES: N#Cc1cc(-c2cc(-c3nc([C@@H]4CCCN4C#N)no3)ccn2)ccn1]

The title compound was synthesised using a procedure similar to that described for Example 180, using 4-chloropyridine-2-carbonitrile (CAS Number 19235-89-3) in step a. LCMS: Method B, 3.774 min, MS: ES+344.38; $^1$H NMR (400 MHz, DMSO-d6) δ ppm 9.09 (d, J=5.2 Hz, 1H), 8.94 (d, J=4.8 Hz, 1H), 8.89 (s, 1H), 8.85 (s, 1H), 8.55 (dd, J=5.2, 1.6 Hz, 1H), 8.21 (dd, J=4.8, 1.2 Hz, 1H), 5.16-5.18 (m, 1H), 3.63-3.69 (m, 1H), 3.54-3.60 (m, 1H), 2.38-2.45 (m, 1H), 2.15-2.20 (m, 1H), 2.04-2.14 (m, 2H).

Example 182 (S)-2'-(3-(1-Cyanopyrrolidin-2 yl)-1,2,4-oxadiazol-5-yl)-[4,4'-bipyridine]-2-carbonitrile

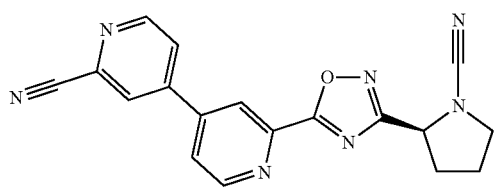 [SMILES: N#Cc1cc(-c2ccnc(-c3nc([C@@H]4CCCN4C#N)no3)c2)ccn1]

The title compound was synthesised using a procedure similar to that described for Example 180, using 4-chloropyridine-2-carbonitrile in step a. LCMS: Method A, 3.212 min, MS: ES+344.00; $^1$H NMR (400 MHz, DMSO-d6) δ ppm 8.94-9.03 (m, 2H), 8.71-8.74 (m, 2H), 8.26-8.34 (m, 2H), 5.18-5.22 (m, 1H), 3.63-3.66 (m, 1H), 3.54-3.59 (m, 1H), 2.36-2.45 (m, 1H), 2.14-2.20 (m, 1H), 2.05-2.09 (m, 2H).

Example 183 (S)-6-(3-(1-Cyanopyrrolidin-2-yl)-1,2,4-oxadiazol-5-yl)-[2,4'-bipyridine]-2'-carbonitrile

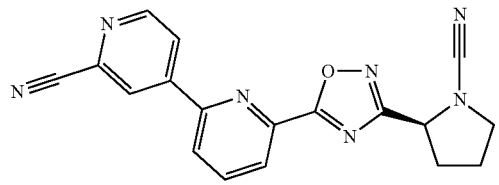 [SMILES: N#Cc1cc(-c2cccc(-c3nc([C@@H]4CCCN4C#N)no3)n2)ccn1]

The title compound was synthesised using a procedure similar to that described for Example 180, using 4-chloropyridine-2-carbonitrile in step a. LCMS: Method A, 3.526 min, MS: ES+344.00; $^1$H NMR (400 MHz, DMSO-d6) δ ppm 8.97 (d, J=5.2 Hz, 1H), 8.77 (s, 1H), 8.57 (d, J=7.2 Hz, 1H), 8.50-8.51 (m, 1H), 8.32-8.40 (m, 2H), 5.14-5.17 (m, 1H), 3.63-3.68 (m, 1H), 3.54-3.60 (m, 1H), 2.36-2.45 (m, 1H), 2.16-2.23 (m, 1H), 2.04-2.13 (m, 2H).

Example 184 2-(5-(2-(3-(Trifluuoromethoxy)phenyl)pyrimidin-4 yl)-1,2,4-oxadiazol-3 yl)pyrrolidine-1-carbonitrile

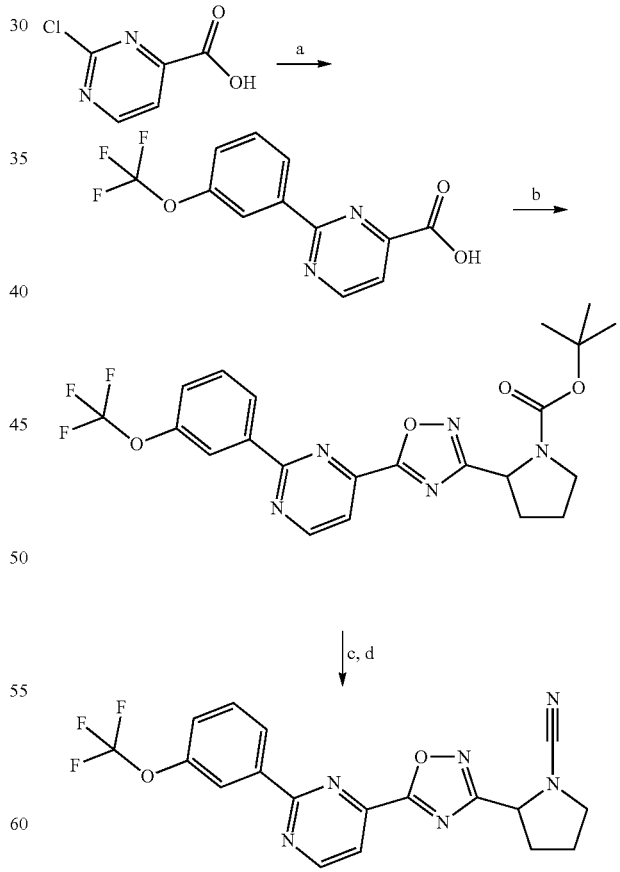

Step a. To a mixture of 2-chloropyrimidine-4-carboxylic acid (CAS Number 14984-92-3; 0.300 g, 1.89 mmol) and 3-(trifluoromethoxy)benzeneboronic acid (CAS Number 179113-90-7; 0.506 g, 2.46 mmol) in DME (15 ml) was added a solution of Na₂CO₃ (0.601 g, 5.68 mmol) in water (4 ml) at rt. The reaction mixture was degassed for 20 min before addition of PdCl₂(dppf)·DCM complex (0.077 g, 0.094 mmol) at rt. The reaction mixture was heated at 110° C. for 3 h. The resulting mixture was cooled to rt, diluted with water (50 ml) and washed with EtOAc (2×20 ml). The aqueous layer was acidified using dilute HCl (10 ml) and extracted into EtOAc (2×20 ml). The combined organic layer was dried over Na₂SO₄, filtered and concentrated under reduced pressure yielding 2-(3-(trifluoromethoxy)phenyl)-pyrimidine-4-carboxylic acid (0.330 g, 1.16 mmol). This material was used directly for the next step without further purification. LCMS: Method C, 1.883, MS: ES+283.33

Step b. To a solution of 2-(3-(trifluoromethoxy)phenyl) pyrimidine-4-carboxylic acid (0.300 g, 1.055 mmol) in DMF (10 ml) was added CDI (0.205 g, 1.27 mmol) at rt. The reaction mixture was stirred at rt for 1 h before addition of tert-butyl (Z)-2-(N'-hydroxycarbamimidoyl) pyrrolidine-1-carboxylate (Example 142, step a; 0.483 g, 2.11 mmol) at rt. The reaction mixture was heated at 100° C. for 3 h. The resulting mixture was cooled to rt, diluted with water (50 ml) and extracted with EtOAc (2×20 ml). The combined organic layer was dried over Na₂SO₄, filtered and concentrated under reduced pressure. The residue was purified by flash column chromatography (20% EtOAc in hexane) yielding tert-butyl 2-(5-(2-(3-(trifluoromethoxy)phenyl)pyrimidin-4-yl)-1,2,4-oxadiazol-3-yl)pyrrolidine-1-carboxylate (0.180 g, 0.377 mmol). LCMS: Method C, 2.686 min, MS: ES+478.70

Steps c, d. The title compound was synthesized from the intermediate above using a procedure similar to that described for Example 14, steps d, e. LCMS: Method B, 4.747 min, MS: ES+403.63; ¹H NMR (400 MHz, DMSO-d₆) δ ppm 9.30 (d, J=5.2 Hz, 1H), 8.51 (d, J=8.0 Hz, 1H), 8.35 (s, 1H), 8.24 (d, J=5.2 Hz, 1H), 7.77 (t, J=8.0 Hz, 1H), 7.64-7.66 (m, 1H), 5.18-5.21 (m, 1H), 3.63-3.68 (m, 1H), 3.54-3.60 (m, 1H), 2.36-2.43 (m, 1H), 2.15-2.22 (m, 1H), 2.06-2.12 (m, 2H).

Example 201 (S)-5-(4-(3-(1-Cyanopyrrolidin-2-yl)-1,2,4-oxadiazol-5-yl)pyrimidin-2-yl)picolinonitrile

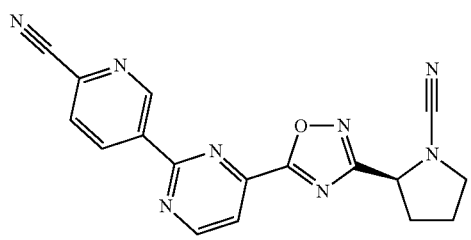 [SMILES: N#Cc1ccc(-c2nccc(-c3nc([C@@H]4CCCN4C#N)no3)n2)cn1]

The title compound was synthesised using a procedure similar to that described for Example 184. LCMS: Method B, 3.667 min, MS: ES+345.33; ¹H NMR (400 MHz, DMSO-d6) δ ppm 9.68 (s, 1H), 9.37 (d, J=5.2 Hz, 1H), 8.94-8.96 (m, 1H), 8.28-8.33 (m, 2H), 5.19-5.22 (m, 1H), 3.63-3.68 (m, 1H), 3.54-3.60 (m, 1H), 2.37-2.44 (m, 1H), 2.15-2.21 (m, 1H), 2.06-2.09 (m, 2H).

Example 185 (S)-2-(5-(2-(4-Cyanophenyl)pyrimidin-4-yl)-1,2,4-oxadiazol-3-yl)pyrrolidine-1-carbonitrile

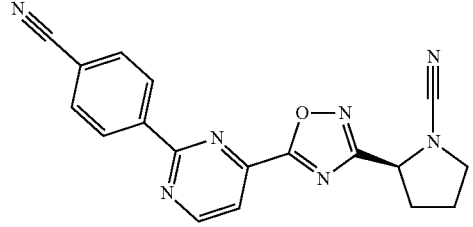 [SMILES: N#Cc1ccc(-c2nccc(-c3nc([C@@H]4CCCN4C#N)no3)n2)cc1]

The title compound was synthesised using a procedure similar to that described for Example 184. LCMS: Method B, 4.008 min, MS: ES+344.58; ¹H NMR (400 MHz, DMSO-d6) δ ppm 9.33 (d, J=4.8 Hz, 1H), 8.63 (d, J=8.4 Hz, 2H), 8.27 (d, J=4.8 Hz, 1H), 8.09 (d, J=8.0 Hz, 2H), 5.18-5.21 (m, 1H), 3.63-3.68 (m, 1H), 3.54-3.60 (m, 1H), 2.37-2.44 (m, 1H), 2.15-2.22 (m, 1H), 2.06-2.09 (m, 2H).

Example 186 (S)-2-(5-(2-(3-Cyanophenyl)pyrimidin-4-yl)-1,2,4-oxadiazol-3-yl)pyrrolidine-1-carbonitrile

The title compound was synthesised using a procedure similar to that described for Example 184. LCMS: Method A, 4.429 min, MS: ES+344.00; ¹H NMR (400 MHz, DMSO-d6) δ ppm 9.32 (d, J=4.8 Hz, 1H), 8.76-8.77 (m, 2H), 8.26 (d, J=4.8 Hz, 1H), 8.11 (d, J=7.6 Hz, 1H), 7.83-7.87 (m, 1H), 5.18-5.22 (m, 1H), 3.63-3.69 (m, 1H), 3.54-3.60 (m, 1H), 2.37-2.44 (m, 1H), 2.15-2.23 (m, 1H), 2.06-2.11 (m, 2H).

Example 187 (S)-1-(4-(3-(1-Cyanopyrrolidin-2-yl)-1,2,4-oxadiazol-5-yl)pyrimidin-2 yl)-1H-pyrazole-4-carbonitrile

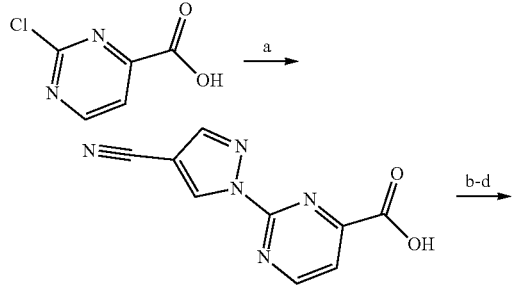

-continued

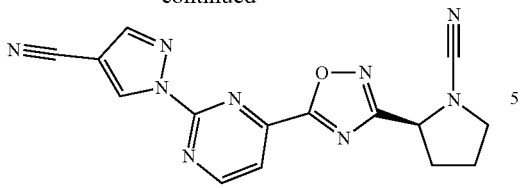

Step a. To a solution of 2-chloropyrimidine-4-carboxylic acid (CAS Number 149849-92-3; 0.350 g, 2.21 mmol) in DMF (9 ml) was added 4-cyanopyrazole (CAS Number 31108-57-3; 0.410 g, 4.42 mmol) and $K_2CO_3$ (0.914 g, 6.62 mmol) at rt. The reaction mixture was degassed for 15 min before addition of KI (0.549 g, 3.31 mmol). The resulting mixture was heated at 110° C. for 5 h. The reaction mixture was cooled to rt, diluted with water (150 ml) and acidified using diluted HCl. The obtained precipitates were collected by filtration and washed with water (20 ml) followed by hexane (50 ml). The resulting solid material was purified by trituration using hexane (4×20 ml) and dried under high vacuum yielding 2-(4-cyano-1H-pyrazol-1-yl)pyrimidine-4-carboxylic acid (0.440 g, 2.0.5 mmol). This material was directly used for the next step without any further purification. LCMS: Method C, 1.259, MS: ES+216.28

Steps b-d. The title compound was synthesized from the intermediate above using a procedure similar to that described for Example 184, steps b-d. LCMS: Method B, 3.210 min, MS: ES+334.33; 1H NMR (400 MHz, DMSO-d6) δ ppm 9.59 (s, 1H), 9.28 (d, J=4.8 Hz, 1H), 8.52 (s, 1H), 8.31 (d, J=4.8 Hz, 1H), 5.18-5.22 (m, 1H), 3.63-3.66 (m, 1H), 3.54-3.59 (m, 1H), 2.36-2.45 (m, 1H), 2.14-2.20 (m, 1H), 2.05-2.09 (m, 2H).

Example 202 (S)-1-(6-(3-(1-Cyanopyrrolidin-2-yl)-1,2,4-oxadiazol-5-yl)pyrazin-2-yl)-1H-pyrazole-4-carbonitrile

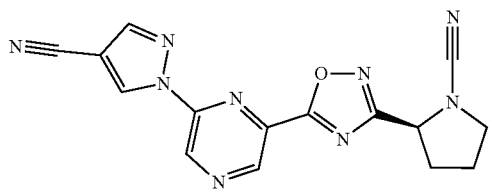 [SMILES: N#Cc1cnn(-c2cncc(-c3nc([C@@H]4CCCN4C#N)no3)n2)c1]

The title compound was synthesised using a procedure similar to that described for Example 187. LCMS: Method B, 3.569 min, MS: ES+334.30; ¹H NMR (400 MHz, DMSO-d6) δ ppm 9.55 (s, 1H), 9.52 (s, 1H), 9.44 (s, 1H), 8.58 (s, 1H), 5.16-5.19 (m, 1H), 3.54-3.64 (m, 2H), 2.37-2.42 (m, 1H), 2.04-2.18 (m, 3H).

Example 188 (S)-4-(4-(3-(1-Cyanopyrrolidin-2 yl)-1,2,4-oxadiazol-5-yl)pyrimidin-2-yl)picolinonitrile

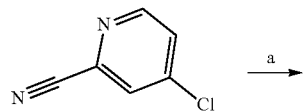

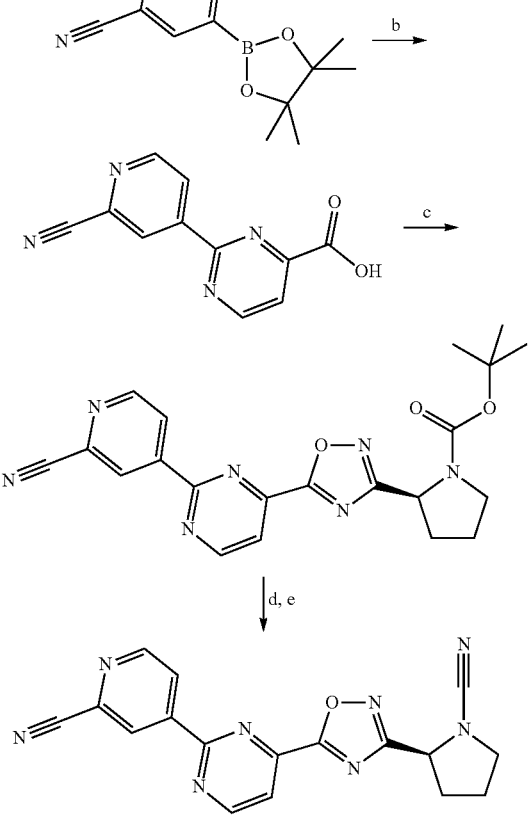

Step a. To a solution of 4-chloro-2-pyridinecarbonitrile (0.700 g, 5.05 mmol) in 1,4-dioxane (14 ml) were added dis(pinacolato)diboron (1.920 g, 7.57 mmol) and potassium acetate (1.53 g, 15.7 mmol) at rt. The reaction mixture was degassed for 15 min before addition of $Pd(dppf)Cl_2$ (0.184 g, 0.252 mmol). The reaction was heated at 100° C. for 2 h. The resulting reaction mixture was cooled to rt, combined with one other batch prepared on the same scale by an identical method, diluted with water (40 ml) and extracted with EtOAc (2×40 ml). The combined organic layer was dried over $Na_2SO_4$, filtered and concentrated under reduced pressure. The residue was purified by flash chromatography (5% EtOAc in hexane) yielding 4-(4,4,5,5-tetramethyl-1,3,2-dioxaborolan-2-yl)picolinonitrile (1.200 g, 5.22 mmol). LCMS: Method C, 1.136, MS: ES+149.20 [M-81]

Step b. To a mixture of 2-chloropyrimidine-4-carboxylic acid (0.110 g, 0.694 mmol) and 4-(4,4,5,5-tetramethyl-1,3,2-dioxaborolan-2-yl)picolinonitrile (0.478 g, 2.08 mmol) in DMF:water (4:1, 5 ml) was added $NaHCO_3$ (0.174 g, 2.08 mmol) at rt. The reaction mixture was degassed for 15 min before addition of $Pd(dppf)Cl_2$ (0.051 g, 0.069 mmol). The resulting mixture was heated at 110° C. for 2 h. The reaction was cooled to rt, diluted with water (30 ml) and washed with EtOAc (2×20 ml). The aqueous layer was acidified with diluted HCl and extracted with EtOAc (2×30 ml). The combined organic layer was dried over $Na_2SO_4$, filtered and concentrated under reduced pressure yielding 2-(2-cyano-pyridin-4-yl)pyrimidine-4-carboxylic acid (0.130 g, 0.575 mmol). This material was directly used for the next step without any further purification. LCMS: Method C, 1.473, MS: ES-225.20

Steps b-d. The title compound was synthesized from the intermediate above using a procedure similar to that described for Example 184, steps b-d. LCMS: Method B, 3.851 min, MS: ES+345.33; $^1$H NMR (400 MHz, DMSO-d6) δ ppm 9.40 (d, J=5.2 Hz, 1H), 9.04 (dd, J=4.8, 0.8 Hz, 1H), 8.81 (s, 1H), 8.65 (dd, J=5.2, 2.0 Hz, 1H), 8.38 (d, J=5.2 Hz, 1H), 5.19-5.22 (m, 1H), 3.63-3.70 (m, 1H), 3.56-3.60 (m, 1H), 2.35-2.42 (m, 1H), 2.15-2.21 (m, 1H), 2.04-2.10 (m, 2H).

Example 203 (S)-4-(6-(3-(1-Cyanopyrrolidin-2-yl)-1,2,4-oxadiazol-5-yl)pyrazin-2-yl)picolinonitrile

The title compound was synthesised using a procedure similar to that described for Example 188. LCMS: Method B, 3.382 min, MS: ES+345.28; $^1$H NMR (400 MHz, DMSO-d6) δ ppm 9.76 (s, 1H), 9.55 (s, 1H), 9.00 (d, J=4.8 Hz, 1H), 8.48 (s, 1H), 8.53 (dd, J=5.2, 1.6 Hz, 1H), 5.16-5.19 (m, 1H), 3.61-3.67 (m, 1H), 3.52-3.58 (m, 1H), 2.35-2.42 (m, 1H), 2.04-2.21 (m, 3H).

Example 204 (5)-4-(5-(3-(1-Cyanopyrrolidin-2 yl)-1,2,4-oxadiazol-5 yl)pyridazin-3 yl)picolinonitrile

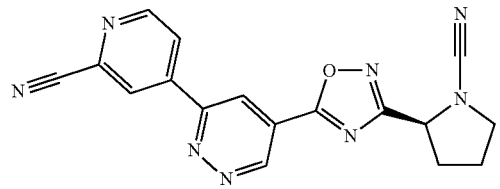 [SMILES: N#Cc1cc(-c2cc(-c3nc([C@@H]4CCCN4C#N)no3)cnn2)ccn1]

The title compound was synthesised using a procedure similar to that described for Example 188. LCMS: Method A, 3.324 min, MS: ES+345.00; $^1$H NMR (400 MHz, DMSO-d6) δ ppm 9.93 (d, J=1.6 Hz, 1H), 9.10 (d, J=2.0 Hz, 1H), 8.98-8.99 (m, 2H), 8.65 (dd, J=4.8, 1.6 Hz, 1H), 5.19-5.22 (m, 1H), 3.61-3.67 (m, 1H), 3.53-3.58 (m, 1H), 2.36-2.42 (m, 1H), 2.03-2.19 (m, 3H).

Example 189 2-(5-(6-(3-Cyanophenyl)pyrimidin-4-yl)-1,2,4-oxadiazol-3-yl)pyrrolidine-1-carbonitrile

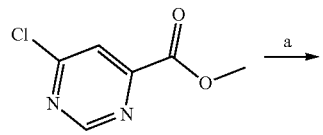

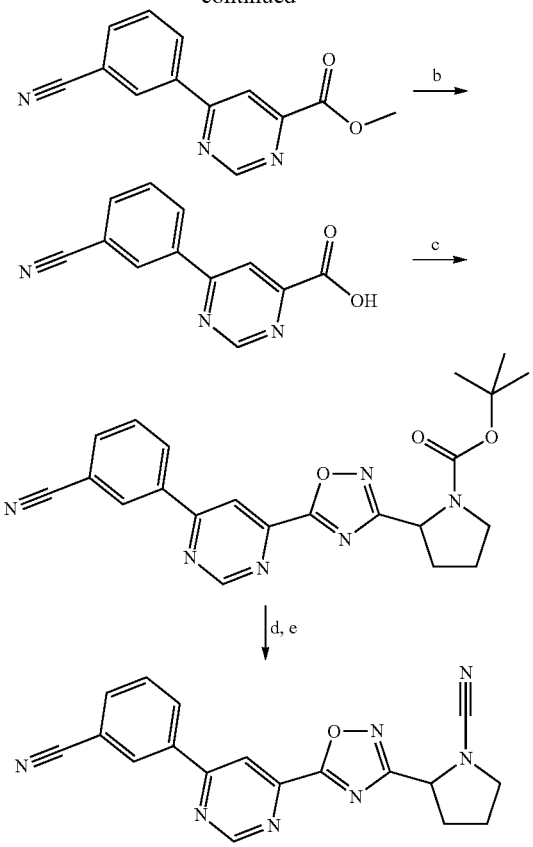

Step a. To a mixture of methyl 6-chloropyrimidine-4-carboxylate (CAS Number 6627-22-1; 0.500 g, 2.90 mmol) and 3-cyanophenylboronic acid (CAS Number 150255-96-2; 0.510 g, 3.48 mmol) in DMF (5 ml) was added K$_3$PO$_4$ (0.921 g, 4.35 mmol) in at rt. The reaction mixture was degassed for 15 min before addition of PdCl$_2$(dppf) (0.106 g, 0.144 mmol) at rt. The reaction mixture was heated at 60° C. for 3 h. The resulting mixture was cooled to rt, diluted with water (100 ml) and extracted with EtOAc (3×25 ml). The combined organic layer was washed with water (50 ml), dried over Na$_2$SO$_4$, filtered and concentrated under reduced pressure. The obtained residue was purified by flash column chromatography (30% EtOAc in hexane) yielding methyl 6-(3-cyanophenyl)pyrimidine-4-carboxylate (0.497 g, 2.08 mmol). This material was used directly for the next step without further purification. LCMS: Method C, 1.674, MS: ES+240.60

Step b. To a solution of methyl 6-(3-cyanophenyl)pyrimidine-4-carboxylate (0.330 g, 1.38 mmol) in THF (15 ml) was added a solution of LiOH·H$_2$O (0.232 g, 5.52 mmol) in water (5 ml) at rt. The reaction mixture was stirred at rt for 1.5 h. The resulting mixture was acidified using 1M HCl (15 ml) and extracted into EtOAc (3×25 ml). The combined organic layer was dried over Na$_2$SO$_4$, filtered and concentrated under reduced pressure yielding 2-(3-(trifluoromethoxy)phenyl)pyrimidine-4-carboxylic acid (0.350 g, quantitative yield). This material was used directly for the next step without further purification. LCMS: Method C, 1.479, MS: ES+226.33

Step c. To a solution of 2-(3-(trifluoromethoxy)phenyl)pyrimidine-4-carboxylic acid (0.350 g, 1.55 mmol) in DMF (4 ml) was added CDI (0.277 g, 1.71 mmol) at rt. The reaction mixture was stirred at rt for 30 min before addition of tert-butyl 2-(N'-hydroxycarbamimidoyl) pyrrolidine-1-carboxylate (Example 142, step a; 0.712 g, 3.11 mmol) and molecular sieves (0.1 g) at rt. A second portion of CDI (0.277 g, 1.71 mmol) was added to the reaction mixture and then heated to 80° C. for 3 h. The resulting reaction mixture was cooled to rt, filtered through a celite bed, washing with EtOAc (20 ml). The combined filtrate was diluted with water (100 ml) and extracted with EtOAc (3×50 ml). The combined organic layer was washed with water (100 ml), dried over Na$_2$SO$_4$, filtered and concentrated under reduced pressure. The residue was purified by flash column chromatography (33% EtOAc in hexane) yielding tert-butyl 2-(5-(6-(3-cyanophenyl)pyrimidin-4-yl)-1,2,4-oxadiazol-3-yl) pyrrolidine-1-carboxylate (0.099 g, 0.24 mmol). LCMS: Method C, 2.220 min, MS: ES+419.60

Steps d, e. The title compound was synthesized from the intermediate above using a procedure similar to that described for Example 14, steps d, e. LCMS: Method B, 3.967 min, MS: ES+344.50; $^1$H NMR (400 MHz, DMSO-d$_6$) δ ppm 9.59 (s, 1H), 8.94 (s, 1H), 8.88 (s, 1H), 8.70 (d, J=8.0 Hz, 1H), 8.12 (d, J=7.6 Hz, 1H), 8.83 (t, J=7.6 Hz, 1H), 5.18-5.21 (m, 1H), 3.64-3.69 (m, 1H), 3.57-3.61 (m, 1H), 2.36-2.43 (m, 1H), 2.16-2.22 (m, 1H), 2.05-2.12 (m, 2H).

Example 190 (S)-1-(3-(3-(1-Cyanopyrrolidin-2-yl)-1,2,4-oxadiazol-5-yl)phenyl)-1H-pyrazole-4-carbonitrile

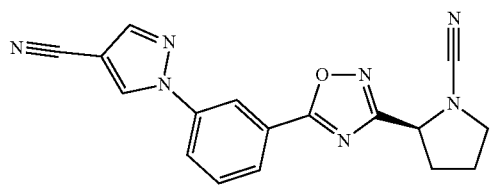 [SMILES: N#Cc1cnn(-c2cccc(-c3nc([C@@H]4CCCN4C#N)no3)c2)c1]

Step a. To a mixture of 4-cyanopyrazole (0.500 g, 5.38 mmol) and 3-methoxycarbonylphenylboronic acid (CAS Number 99769-19-4; 1.161 g, 6.45 mmol) in pyridine (10 ml) was added K$_2$CO$_3$ (1.112 g, 8.06 mmol) at rt. The reaction mixture was degassed for 30 min before addition of Cu(OAc)$_2$ (1.450 g, 8.06 mmol). The resulting mixture was heated at 80° C. for 16 h. The resulting reaction mixture was cooled to rt, combined with one other batch prepared on the same scale by an identical method, diluted with ice cold water (200 ml) and extracted with EtOAc (2×100 ml). The combined organic layer was dried over Na$_2$SO$_4$, filtered and concentrated under reduced pressure. The resulting residue was purified by flash chromatography 18% EtOAc in hexane) yielding methyl 3-(4-cyano-1H-pyrazol-1-yl)benzoate (0.850 g, 3.74 mmol). LCMS: Method C, 1.916, MS: ES+228.31

Steps b-e. The title compound was synthesized from the intermediate above using a procedure similar to that described for Example 189, steps b-e. LCMS: Method A, 3.861 min, MS: ES+350.15; $^1$H NMR (400 MHz, DMSO-d6) δ ppm 9.56 (s, 1H), 8.58 (s, 1H), 8.45 (s, 1H), 8.24 (d, J=8.4 Hz, 1H), 8.17 (d, J=8.0 Hz, 1H), 7.85 (t, J=8.0 Hz, 1H), 5.10-5.13 (m, 1H), 3.62-3.67 (m, 1H), 3.53-3.58 (m, 1H), 2.34-2.43 (m, 1H), 2.15-2.21 (m, 1H), 1.99-2.13 (m, 2H).

Example 191 (S)-1-(2-(3-(1-Cyanopyrrolidin-2 yl)-1,2,4-oxadiazol-5-yl)pyridin-4 yl)-1H-pyrazole-4-carbonitrile

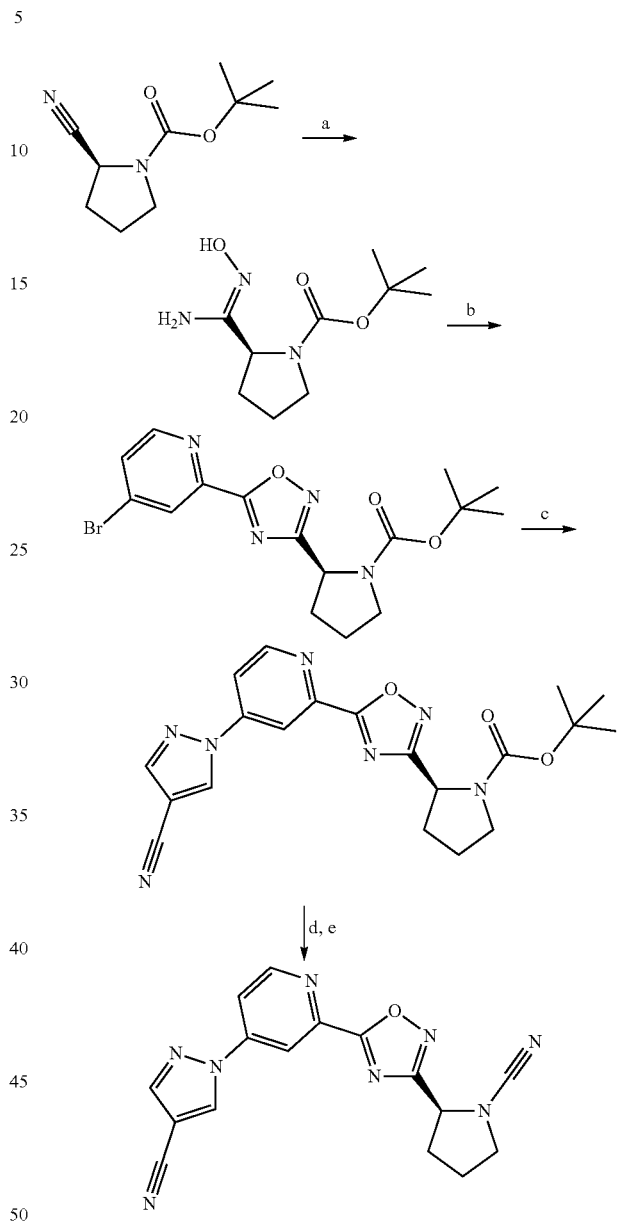

Step a. To a solution of (S)-1-Boc-2-cyanopyrrolidine (CAS Number 228244-04-0; 4.00 g, 20.4 mmol) in EtOH (20 ml) was added NH$_2$OH·HCl (2.80 g, 40.8 mmol) followed by TEA (8.5 ml, 61.2 mmol) at rt. The reaction mixture was heated at 80° C. for 16 h. The resulting reaction mixture was concentrated under vacuum and the residue was triturated with EtOH (2×50 ml). The resulting solid material was dried under high vacuum yielding tert-butyl (S)-2-(N'-hydroxy-carbamimidoyl)pyrrolidine-1-carboxylate (9.200 g, quantitative yield). This material was used directly for the next step without further purification. LCMS: Method C, 1.464, MS: ES+230.31

Step b. To a solution of 4-bromopicolinic acid (CAS Number 30766-03-1; 0.500 g, 2.47 mmol) in DMF (10 ml) was added CDI (0.441 g, 2.72 mmol) at rt. The reaction mixture was stirred at rt for 1 h before addition of tert-butyl (S)-2-(N'-hydroxycarbamimidoyl)pyrrolidine-1-carboxylate (1.130 g, 4.95 mmol) and molecular sieves (300 mg). A second portion of CDI (0.441 g, 2.72 mmol) was added and the reaction mixture was heated at 90° C. for 16 h. The resulting mixture was cooled to rt, diluted with ice cold water (100 ml) and extracted with EtOAc (2×100 ml). The combined organic layer was dried over Na$_2$SO$_4$, filtered and concentrated under reduced pressure. The obtained residue was purified by flash column chromatography (10% EtOAc in hexane) yielding tert-butyl (S)-2-(5-(4-bromopyridin-2-yl)-1,2,4-oxadiazol-3-yl)pyrrolidine-1-carboxylate (0.460 g, 1.17 mmol). LCMS: Method C, 2.159 min, MS: ES+395.50, 397.50

Step c. To a mixture of tert-butyl (S)-2-(5-(4-bromopyridin-2-yl)-1,2,4-oxadiazol-3-yl)pyrrolidine-1-carboxylate (0.300 g, 0.761 mmol) and 4-cyanopyrazole (0.212 g, 2.28 mmol) in DMF (5 ml) was added K$_2$CO$_3$ (0.315 g, 2.28 mmol) at rt. The reaction mixture was degassed for 10 min before addition of KI (0.189 g, 1.14 mmol). The resulting reaction mixture was heated at 110° C. for 16 h. The mixture was cooled to rt, diluted with ice cold water (100 ml) and extracted with EtOAc (2×100 ml). The combined organic layer was dried over Na$_2$SO$_4$, filtered and concentrated under reduced pressure. The resulting residue was purified by flash chromatography (40% EtOAc in hexane) yielding tert-butyl (S)-2-(5-(4-(4-cyano-1H-pyrazol-1-yl)pyridin-2-yl)-1,2,4-oxadiazol-3-yl)pyrrolidine-1-carboxylate (0.265 g, 0.65 mmol). LCMS: Method C, 2.010, MS: ES+408.50

Steps d, e. The title compound was synthesized from the intermediate above using a procedure similar to that described for Example 14, steps d, e. LCMS: Method A, 3.627 min, MS: ES+333.10; 1H NMR (400 MHz, DMSO-d6) δ ppm 9.77 (s, 1H), 8.99 (d, J=5.6 Hz, 1H), 8.70 (d, J=1.6 Hz, 1H), 8.55 (s, 1H), 8.23 (dd, J=5.6, 2.0 Hz, 1H), 5.14-5.17 (m, 1H), 3.63-3.68 (m, 1H), 3.54-3.59 (m, 1H), 2.33-2.44 (m, 1H), 2.18-2.22 (m, 1H), 2.09-2.16 (m, 2H).

Example 192 (S)-1-(6-(3-(1-Cyanopyrrolidin-2-yl)-1,2,4-oxadiazol-5-yl)pyridin-2-yl)-1H-pyrazole-4-carbonitrile

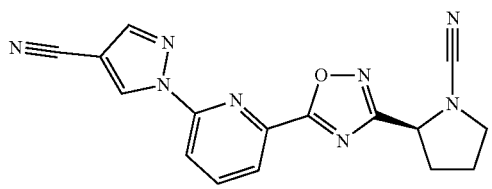 [SMILES: N#Cc1cnn(-c2cccc(-c3nc([C@@H]4CCCN4C#N)no3)n2)c1]

The title compound was synthesised using a procedure similar to that described for Example 191. LCMS: Method A, 3.598 min, MS: ES+333.00; 1H NMR (400 MHz, DMSO-d6) δ ppm 9.49 (s, 1H), 8.51 (s, 1H), 8.28-8.39 (m, 3H), 5.14-5.17 (m, 1H), 3.62-3.68 (m, 1H), 3.54-3.59 (m, 1H), 2.33-2.44 (m, 1H), 2.13-2.22 (m, 1H), 2.03-2.11 (m, 2H).

Example 193 (S)-1-(4-(3-(1-Cyanopyrrolidin-2 yl)-1,2,4-oxadiazol-5 yl)pyridin-2 yl)-1H-pyrazole-4-carbonitrile

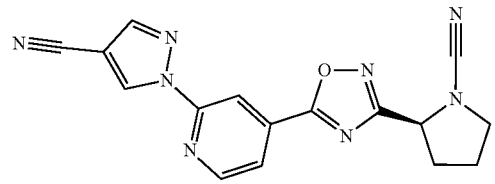 [SMILES: N#Cc1cnn(-c2cc(-c3nc([C@@H]4CCCN4C#N)no3)ccn2)c1]

The title compound was synthesised using a procedure similar to that described for Example 191. LCMS: Method B, 3.863 min, MS: ES+333.43; 1H NMR (400 MHz, DMSO-d6) δ ppm 9.53 (s, 1H), 8.85 (d, J=4.8 Hz, 1H), 8.52 (s, 1H), 8.49 (s, 1H), 8.13 (d, J=5.2 Hz, 1H), 5.15-5.18 (m, 1H), 3.62-3.68 (m, 1H), 3.53-3.59 (m, 1H), 2.3.5-2.42 (m, 1H), 2.14-2.20 (m, 1H), 2.05-2.08 (m, 2H).

Biological Activity of Compounds of the Invention

Abbreviations

TAMRA carboxytetramethylrhodamine
PCR polymerase chain reaction
PBS phosphate buffered saline
EDTA ethylenediaminetetraacetic acid
Tris 2-amino-2-(hydroxymethyl)-1,3-propanediol
NP-40 Nonidet P-40, octylphenoxypolyethoxyethanol
BSA bovine serum albumin
PNS peripheral nervous system
BH3 Bcl-2 homology domain 3
PTEN phosphatase and tensin homologue In Vitro USP30 Inhibition Assay USP30 biochemical kinetic assay. Reactions were performed in duplicate in black 384 well plates (small volume, Greiner 784076) in a final reaction volume of 21 µl. USP30 CD (57-517, #64-0057-050 Ubiquigent) was diluted in reaction buffer (40 mM Tris, pH 7.5, 0.005% Tween 20, 0.5 mg/ml BSA, 5 mM beta-mercaptoethanol) to the equivalent of 0, 0.005, 0.01, 0.05, 0.1 and 0.5 µl/well. Buffer was optimised for optimal temperature, pH, reducing agent, salts, time of incubation, and detergent. Reactions were initiated by the addition of 50 nM of TAMRA labelled peptide linked to ubiquitin via an iso-peptide bond as fluorescence polarisation substrate. Reactions were incubated at room temperature and read every 2 min for 120 min. Readings were performed on a Pherastar Plus (BMG Labtech). λ Excitation 540 nm; λ Emission 590 nm.

USP30 Biochemical IC50 Assay

Dilution plates were prepared at 21 times the final concentration (2100 µM for a final concentration of 100 µM) in 50% DMSO in a 96-well polypropylene V-bottom plate (Greiner #651201). A typical 8-point dilution series would be 100, 30, 10, 3, 1, 0.3, 0.1, 0.03 µM final. Reactions were performed in duplicate in black 384 well plates (small volume, Greiner 784076) in a final reaction volume of 21 µl. Either 1 µl of 50% DMSO or diluted compound was added to the plate. USP30 was diluted in reaction buffer (40 mM Tris, pH 7.5, 0.005% Tween 20, 0.5 mg/ml BSA, 5 mM beta-mercaptoethanol) to the equivalent of 0.05 µl/well and 10 µl of diluted USP30 was added to the compound. Enzyme and compound were incubated for 30 min at room temp. Reactions were initiated by the addition of 50 nM of TAMRA labelled peptide linked to ubiquitin via an isopeptide bond as fluorescence polarisation substrate. Reactions were read immediately after addition of substrate and following a 2 h incubation at room temperature. Readings were performed on a Pherastar Plus (BMG Labtech). λ Excitation 540 nm; λ Emission 590 nm.

Activity of Exemplary Compounds in USP30 Biochemical IC50 Assay

Ranges:
- A<0.1 µM;
- 0.1<B<1 µM;
- 1<C<10 µM;
- 10<D<100 µM

| Example | IC50 range |
| --- | --- |
| 1 | B |
| 2 | C |
| 3 | C |
| 4 | C |
| 5 | B |
| 6 | C |
| 7 | C |
| 8 | B |
| 9 | C |
| 10 | C |
| 11 | C |
| 12 | B |
| 13 | C |
| 14 | B |
| 15 | A |
| 16 | B |
| 17 | A |
| 18 | B |
| 19 | B |
| 20 | B |
| 21 | B |
| 22 | A |
| 23 | B |
| 24 | B |
| 25 | B |
| 26 | B |
| 27 | C |
| 28 | B |
| 29 | B |
| 30 | B |
| 31 | C |
| 32 | C |
| 33 | B |
| 34 | C |
| 35 | B |
| 36 | B |
| 37 | B |
| 38 | B |
| 39 | B |
| 40 | B |
| 41 | B |
| 42 | B |
| 43 | B |
| 44 | C |
| 45 | B |
| 46 | B |
| 47 | B |
| 48 | C |
| 49 | C |
| 50 | B |
| 51 | B |
| 52 | C |
| 53 | B |
| 54 | B |
| 55 | A |
| 56 | C |
| 57 | B |
| 58 | C |
| 59 | C |
| 60 | C |
| 61 | C |
| 62 | C |
| 63 | B |
| 64 | C |
| 65 | C |
| 66 | B |
| 67 | C |
| 68 | B |
| 69 | B |
| 70 | B |
| 71 | B |
| 72 | B |
| 73 | B |
| 74 | B |
| 75 | B |
| 76 | A |
| 77 | B |
| 78 | C |
| 79 | B |
| 80 | B |
| 81 | B |
| 82 | C |
| 83 | B |
| 84 | B |
| 85 | B |
| 86 | B |
| 87 | B |
| 88 | C |
| 89 | C |
| 90 | B |
| 91 | B |
| 92 | C |
| 93 | B |
| 94 | C |
| 95 | B |
| 96 | D |
| 97 | C |
| 98 | C |
| 99 | B |
| 100 | B |
| 101 | B |
| 102 | B |
| 103 | B |
| 104 | B |
| 105 | C |
| 106 | C |
| 107 | C |
| 108 | C |
| 109 | B |
| 110 | B |
| 111 | A |
| 112 | B |
| 113 | C |
| 114 | A |
| 115 | A |
| 116 | B |
| 117 | A |
| 118 | A |
| 119 | A |
| 120 | C |
| 121 | C |
| 122 | D |
| 123 | B |
| 124 | B |
| 125 | C |
| 126 | B |
| 127 | C |
| 128 | B |
| 129 | B |
| 130 | B |
| 131 | C |
| 132 | C |
| 133 | B |
| 134 | C |
| 135 | C |
| 136 | B |
| 137 | C |
| 138 | B |

-continued

| Example | IC50 range |
|---|---|
| 139 | C |
| 140 | C |
| 141 | B |
| 142 | C |
| 143 | C |
| 144 | C |
| 145 | A |
| 146 | B |
| 147 | C |
| 148 | C |
| 149 | C |
| 150 | C |
| 151 | B |
| 152 | B |
| 153 | B |
| 154 | B |
| 155 | B |
| 156 | B |
| 157 | A |
| 158 | C |
| 159 | C |
| 160 | B |
| 161 | A |
| 162 | B |
| 163 | A |
| 164 | C |
| 165 | B |
| 166 | A |
| 167 | B |
| 168 | B |
| 169 | C |
| 170 | C |
| 171 | C |
| 172 | B |
| 173 | C |
| 174 | A |
| 175 | A |
| 176 | B |
| 177 | B |
| 178 | B |
| 179 | C |
| 180 | B |
| 181 | A |
| 182 | B |
| 183 | A |
| 184 | A |
| 185 | B |
| 186 | A |
| 187 | B |
| 188 | A |
| 189 | B |
| 190 | B |
| 191 | C |
| 192 | A |
| 193 | C |
| 194 | A |
| 195 | A |
| 196 | B |
| 197 | B |
| 198 | B |
| 199 | B |
| 200 | A |
| 201 | B |
| 202 | B |
| 203 | A |
| 204 | B |

The invention claimed is:

1. A compound, having the formula (IB):

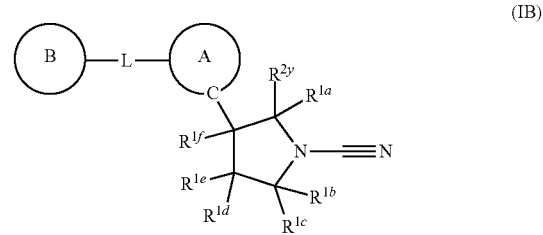

(IB)

a tautomer thereof, or a pharmaceutically acceptable salt of said compound or tautomer, wherein:

$R^{1a}$, $R^{1b}$, $R^{1c}$, $R^{1d}$, $R^{1e}$ and $R^{1f}$ each independently represent hydrogen, optionally substituted $C_1$-$C_6$ alkyl or optionally substituted $C_3$-$C_4$ cycloalkyl;

$R^{2y}$ represents hydrogen or optionally substituted $C_1$-$C_6$ alkyl;

A represents a 9 to 10-membered bicyclic ring selected from a heteroaryl, heterocyclyl and aryl ring;

L represents a covalent bond, an oxygen atom, a sulphur atom, -$OR^8$—, —SO—, —$SO_2$—, —CO—, —C(O)O—, $C_0$-$C_3$ alkylene-$CONR^6$—$C_0$-$C_3$ alkylene-, —$C_0$-$C_3$ alkylene-$NR^6$—$C_0$-$C_3$ alkylene, —$C_0$-$C_3$ alkylene-$NR^6CO$—$C_0$-$C_3$ alkylene, —$C_0$-$C_3$ alkylene-$NR_6CONR^7$—$C_0$-$C_3$ alkylene, —$C_0$-$C_3$ alkylene-$SO_2NR^6$—$C_0$-$C_3$ alkylene, —$C_0$-$C_3$ alkylene-$NR^6SO^2$—$C_0$-$C_3$ alkylene, —$C_0$-$C_3$ alkylene-$NR^6SO_2NR^7$—$C_0$-$C_3$ alkylene, —$C_0$-$C_3$ alkylene-$NR^6C(O)O$—$C_0$-$C_3$ alkylene, —$C_0$-$C_3$ alkylene-$NR^6C(O)OR^7$—$C_0$-$C_3$ alkylene, optionally substituted —$C_1$-$C_6$ alkylene or optionally substituted —$C_2$-$C_6$ alkenylene;

B represents a 3 to 10-membered monocyclic or bicyclic heterocyclyl, heteroaryl, cycloalkyl or aryl ring;

wherein A is optionally substituted with one to four substituents, each independently selected from halogen, cyano, oxo, nitro, hydroxyl, —$SR^3$, —$NR^3R^4$, —$CONR^3R^4$, —$NR^3COR^4$, —$NR^3CONR^4R^5$, —$COR^5$, —$C(O)OR^3$, —$SO_2R^3$, —$SO_2NR^3R^4$, —$NR^3SO_2R^4$, $NR^3SO_2NR^4R^5$, —$NR^3C(O)OR^4$, optionally substituted —$C_1$-$C_6$ alkyl, optionally substituted —$C_1$-$C_6$ alkoxy, optionally substituted —$C_2$-$C_6$ alkenyl, optionally substituted —$C_2$-$C_6$ alkynyl and $C_3$-$C_4$ cycloalkyl;

wherein B is optionally substituted with one to four substituents independently, each selected from halogen, cyano, oxo, nitro, hydroxyl, —$SR^9$, optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, -$Q^{1a}$-$NR^9CONR^{10}R^{11}$, -$Q^{1a}$-$NR^9R^{10}$, -$Q^{1a}$-$COR^9$, -$Q^{1a}$-$NR^9COR^{10}$, -$Q^{1a}$-$NR^9C(O)OR^{10}$, -$Q^{1a}$-$SO_2R^9$, -$Q^{1a}$-$CONR^9R^{10}$, -$Q^{1a}$-$CO_2R^9$, -$Q^{1a}$-$SO_2NR^9R^{10}$, -$Q^{1a}$-$SO_2R^9$, -$Q^{1a}$-$CONR^9R^{10}$, -$Q^{1a}$-$CO_2R^9$, -$Q^{1a}$-$SO_2NR^9R^{10}$, -$Q^{1a}$-$NR^9SO_2R^{10}$ and -$Q^{1a}$-$NR^9SO_2NR^{10}R^{11}$;

$Q^{1a}$ represents a covalent bond, optionally substituted $C_1$-$C_6$ alkylene or optionally substituted $C_2$-$C_6$ alkenylene;

$R^3$, $R^4$ and $R^5$ each independently represent hydrogen or optionally substituted $C_1$-$C_6$ alkyl;

$R^6$ and $R^7$ each independently represent hydrogen or optionally substituted $C_1$-$C_6$ alkyl;

R⁸ represents optionally substituted C₁-C₆ alkylene or optionally substituted C₂-C₆ alkenylene;

R⁹, R¹⁰ and R¹¹ each independently represent hydrogen or optionally substituted C₁-C₆ alkyl; and wherein C₁-C₆ alkyl, C₁-C₆ alkoxy, C₂-C₆ alkenyl, C₂-C₆ alkynyl, C₁-C₆ alkylene and C₂-C₆ alkenylene of R¹ᵃ, R¹ᵇ, R¹ᶜ, R¹ᵈ, R¹ᵉ, R¹ᶠ, R²ʸ, R³, R₄, R⁵, R⁶, R⁷, R⁸, R⁹, R¹⁰, R¹¹, A, B, L and Q¹ᵃ and C₃-C₄ cycloalkyl of R¹ᵃ, R¹ᵇ, R¹ᶜ, R¹ᵈ, R¹ᵉ and R¹ᶠ, are each optionally substituted with one to four substituents independently selected from halogen, hydroxyl, thiol, cyano, amino, amido, nitro and SF₅;

with the proviso that:

(i) A cannot be triazolopyridazinyl, triazolopyridinyl, imidazotriazinyl, imidazopyrazinyl, pyrrolopyrimidinyl or [1,2,4]triazolo[1,5-a]pyrazinyl, (ii) B cannot be substituted with phenoxyl, and (iii) B cannot be cyclopentyl when L is an oxygen atom.

2. The compound according to claim 1, wherein A, which is optionally substituted, is selected from indolyl, indolizinyl, isoindolyl, purinyl, indazolyl, benzofuranyl, isobenzofuranyl, benzothiophenyl, isobenzothiophenyl, benzimidazolyl, benzothiazolyl, benzoxazolyl, naphthyridinyl, pteridinyl, quinolinyl, isoquinolinyl, cinnolinyl, phthalazinyl, quinazolinyl, imidazopyridinyl, pyrazolopyridinyl, thiazolopyridinyl, dihydropyrrolopyridinyl, quinoxalinyl, dihydrobenzoxazinyl, tetrahydropyridopyrazinyl, tetrahydroquinolinyl and tetrahydroisoquinolinyl.

3. The compound according to claim 1, wherein A, which is optionally substituted, is selected from benzimidazolyl, imidazopyridinyl, tetrahydropyridopyrazinyl, and benzoxazolyl.

4. The compound according to claim 1, wherein A is optionally substituted with one to four substituents, each independently selected from halogen, oxo, optionally substituted C₁-C₆ alkyl, —NR³R⁴ and —CONR³R⁴.

5. The compound according to claim 1, wherein L represents a covalent bond or —C₀-C₃ alkylene-NR⁶CO—C₀-C₃ alkylene.

6. The compound according to claim 1, wherein B, which is optionally substituted, is selected from phenyl, pyridinyl, pyridazinyl, pyrazinyl, pyrimidinyl, indazolyl, quinolinyl, benzothiazolyl, pyrazolyl, isoxazolyl, piperidinyl, pyrrolidinyl, imidazopyridinyl, benzoimidazolyl, imidazolyl, azetidinyl and naphthalenyl.

7. The compound according to claim 1, wherein B is optionally substituted with one to four substituents, each independently selected from halogen, cyano, nitro, optionally substituted C₁-C₆ alkyl, optionally substituted C₁-C₆ alkoxy, -Q¹ᵃ-CONR⁹R¹⁰, -Q¹ᵃ—NR⁹COR¹⁰.

8. The compound according to claim 1, wherein R¹ᵃ, R¹ᵇ, R¹ᶜ, R¹ᵈ, R¹ᵉ and R¹ᶠ are each hydrogen.

9. The compound according to claim 1, wherein one of R¹ᵃ, R¹ᵇ, R₁𝒸, R¹ᵈ, R¹ᵉ and R¹ᶠ presents methyl, ethyl or cyclopropyl; and the others are each hydrogen.

10. The compound according to claim 1, wherein R¹ᵃ is optionally substituted C₁-C₆ alkyl, and R¹ᵇ, R¹ᶜ, R¹ᵈ, R¹ᵉ and R¹ᶠ are each hydrogen.

11. The compound according to claim 1, wherein R¹ᵇ is optionally substituted C₁-C₆ alkyl, and R¹ᵃ, R¹ᶜ, R¹ᵈ, R¹ᵉ and R¹ᶠ are each hydrogen.

12. The compound according to claim 1, wherein R¹ᵈ is optionally substituted C₁-C₆ alkyl or optionally substituted C₃-C₄ cycloalkyl, and R¹ᵃ, R¹ᵇ, R¹ᶜ, R¹ᵉ and R¹ᶠ are each hydrogen.

13. A pharmaceutical composition, comprising a compound according to claim 1, a tautomer thereof, or a pharmaceutically acceptable salt of said compound or tautomer, together with one or more pharmaceutically acceptable excipients.

14. A compound, selected from the group consisting of:
3-(6-(3-cyanophenyl)-1H-benzo[d]imidazol-2-yl)pyrrolidine-1-carbonitrile;
4-(2-(1-cyanopyrrolidin-3-yl)-1H-benzo[d]imidazol-6-yl)benzamide;
4-(2-(1-cyanopyrrolidin-3-yl)-1H-benzo[d]imidazol-6-yl)-N-methylbenzamide;
3-(6-(2-fluoro-5-methylphenyl)-1H-benzo[d]imidazol-2-yl)pyrrolidine-1-carbonitrile;
3-(6-(6-isopropoxypyridin-3-yl)-1H-benzo[d]imidazol-2-yl)pyrrolidine-1-carbonitrile;
3-(6-(1-isobutyl-1H-pyrazol-4-yl)-1H-benzo[d]imidazol-2-yl)pyrrolidine-1-carbonitrile;
3-(6-(pyridin-4-yl)-3H-imidazo[4,5-b]pyridin-2-yl)pyrrolidine-1-carbonitrile;
(S)-3-(6-(pyridin-4-yl)-3H-imidazo[4,5-b]pyridin-2-yl)pyrrolidine-1-carbonitrile;
(R)-3-(6-(pyridin-4-yl)-3H-imidazo[4,5-b]pyridin-2-yl)pyrrolidine-1-carbonitrile;
3-(6-phenyl-3H-imidazo[4,5-b]pyridin-2-yl)pyrrolidine-1-carbonitrile;
3-(6-(4-cyanophenyl)-3H-imidazo[4,5-b]pyridin-2-yl)pyrrolidine-1-carbonitrile;
3-(6-(3-cyanophenyl)-3H-imidazo[4,5-b]pyridin-2-yl)pyrrolidine-1-carbonitrile;
3-(6-(6-methoxypyridin-3-yl)-3H-imidazo[4,5-b]pyridin-2-yl)pyrrolidine-1-carbonitrile;
3-(6-(1H-indazol-5-yl)-3H-imidazo[4,5-b]pyridin-2-yl)pyrrolidine-1-carbonitrile;
3-(6-(1H-pyrazol-4-yl)-3H-imidazo[4,5-b]pyridin-2-yl)pyrrolidine-1-carbonitrile;
3-(2-(1-cyanopyrrolidin-3-yl)-3H-imidazo[4,5-b]pyridin-6-yl)-N-methylbenzamide;
3-(6-(4-cyanophenyl)-3H-imidazo[4,5-b]pyridin-2-yl)pyrrolidine-1-carbonitrile: Enantiomer 1;
3-(6-(4-cyanophenyl)-3H-imidazo[4,5-b]pyridin-2-yl)pyrrolidine-1-carbonitrile: Enantiomer 2;
3-(2-(1-cyanopyrrolidin-3-yl)-3H-imidazo[4,5-b]pyridin-6-yl)-N-methylbenzamide: Enantiomer 1;
3-(2-(1-cyanopyrrolidin-3-yl)-3H-imidazo[4,5-b]pyridin-6-yl)-N-methylbenzamide: Enantiomer 2;
(S)-2-(6-phenyl-1H-benzo[d]imidazol-2-yl)pyrrolidine-1-carbonitrile;
3-(5-phenyl-1H-benzo[d]imidazol-2-yl)pyrrolidine-1-carbonitrile;
(S)-2-(1-methyl-5-phenyl-1H-benzo[d]imidazol-2-yl)pyrrolidine-1-carbonitrile;
3-(5-phenyl-3H-imidazo[4, 5-b]pyridin-2-yl)pyrrolidine-1-carbonitrile;
3-(7-phenyl-3H-imidazo[4, 5-b]pyridin-2-yl)pyrrolidine-1-carbonitrile;
3-(5-methyl-6-phenyl-3H-imidazo[4, 5-b]pyridin-2-yl)pyrrolidine-1-carbonitrile;
3-(7-methyl-6-phenyl-3H-imidazo[4, 5-b]pyridin-2-yl)pyrrolidine-1-carbonitrile;
3-(3-methyl-6-phenyl-3H-imidazo[4, 5-b]pyridin-2-yl)pyrrolidine-1-carbonitrile;
trans-3-methyl-4-(6-phenyl-3H-imidazo[4, 5-b] pyridin-2-yl)pyrrolidine-1-carbonitrile: Enantiomer 1;
trans-3-methyl-4-(6-phenyl-3H-imidazo [4, 5-b]pyridin-2-yl)pyrrolidine-1-carbonitrile: Enantiomer 2;
trans-3-methyl-4-(5-phenyl-1H-benzo[d]imidazol-2-yl)pyrrolidine-1-carbonitrile: Enantiomer 1;

(R)-3-(7-(4-methyl-1H-imidazol-1-yl)-1,6-dioxo-1,3,4,6-tetrahydro-2H-pyrido[1,2-a]pyrazin-2-yl)pyrrolidine-1-carbonitrile;

(S)-2-(1-cyanopyrrolidin-2-yl)-N-methyl-6-phenylbenzo[d]oxazole-4-carboxamide;

3-(7-phenylimidazo[1,2-a]pyridin-3-yl)pyrrolidine-1-carbonitrile;

3-(7-(3,5-dimethylisoxazol-4-yl)imidazo[1,2-a]pyridin-3-yl)pyrrolidine-1-carbonitrile;

(S)-2-(5-(3-cyanophenyl)benzo[d]oxazol-2-yl)pyrrolidine-1-carbonitrile;

(S)-6-(2-(1-cyanopyrrolidin-2-yl)benzo[d]oxazol-5-yl)picolinonitrile;

(S)-2-(6-(3-cyanophenyl)benzo[d]oxazol-2-yl)pyrrolidine-1-carbonitrile;

(S)-2-(5-(3-ethylphenyl)benzo[d]oxazol-2-yl)pyrrolidine-1-carbonitrile;

(S)-2-(6-(3-ethylphenyl)benzo[d]oxazol-2-yl)pyrrolidine-1-carbonitrile;

(S)-2-(1-cyanopyrrolidin-2-yl)-6-(3-ethylphenyl)-N-methylbenzo[d]oxazole-4-carboxamide;

(S)-6-(2-(1-cyanopyrrolidin-2-yl)benzo[d]oxazol-6-yl)picolinonitrile;

(S)-2-(5-(3-(trifluoromethoxy)phenyl)benzo[d]oxazol-2-yl)pyrrolidine-1-carbonitrile;

(S)-2-(5-(3-methyl-1H-indazol-6-yl)benzo[d]oxazol-2-yl)pyrrolidine-1-carbonitrile;

(S)-2-(5-(1-methyl-1H-indazol-5-yl)benzo[d]oxazol-2-yl)pyrrolidine-1-carbonitrile;

(S)-2-(5-(3-nitrophenyl)benzo[d]oxazol-2-yl)pyrrolidine-1-carbonitrile;

(S)-2-(5-(3-cyano-2-fluorophenyl)benzo[d]oxazol-2-yl)pyrrolidine-1-carbonitrile; and (S)-2-(5-(3-cyano-5-fluorophenyl)benzo[d]oxazol-2-yl)pyrrolidine-1-carbonitrile;

a tautomer thereof, or a pharmaceutically acceptable salt of said compound or tautomer.

15. A pharmaceutical composition, comprising a compound according to claim 14, a tautomer thereof, or a pharmaceutically acceptable salt of said compound or tautomer, together with one or more pharmaceutically acceptable excipients.

* * * * *